US006448390B1

(12) United States Patent
Albritton et al.

(10) Patent No.: US 6,448,390 B1
(45) Date of Patent: Sep. 10, 2002

(54) STABLE ENVELOPE PROTEINS FOR RETROVIRAL, VIRAL AND LIPOSOME VECTORS AND USE IN GENE DRUG THERAPY

(75) Inventors: Lorraine Moore Albritton; Tatiana Zavorotinskaya, both of Memphis, TN (US)

(73) Assignee: The University of Tennessee Research Corporation, Knoxville, TN (US)

( * ) Notice: Subject to any disclaimer, the term of this patent is extended or adjusted under 35 U.S.C. 154(b) by 0 days.

(21) Appl. No.: 09/315,127

(22) Filed: May 20, 1999

Related U.S. Application Data

(60) Provisional application No. 60/086,149, filed on May 20, 1998.

(51) Int. Cl.[7] .................. C07H 21/04; C07H 21/02; C12N 7/00
(52) U.S. Cl. ............... 536/23.72; 536/23.1; 435/235.1
(58) Field of Search ................... 536/23.4, 23.5, 536/237.1, 21.1; 435/320.1, 235.1; 424/143.1, 93.2

(56) References Cited

U.S. PATENT DOCUMENTS

| | | | |
|---|---|---|---|
| 5,512,421 A | 4/1996 | Burns et al. ............... 435/320.1 |
| 5,554,524 A | 9/1996 | Temin et al. ............... 435/235.1 |
| 5,624,820 A | 4/1997 | Cooper ....................... 435/69.1 |
| 5,641,508 A | 6/1997 | Li et al. ..................... 424/450 |
| 5,643,756 A | 7/1997 | Kayman et al. ............ 435/69.7 |
| 5,654,195 A | 8/1997 | Sodroski et al. .......... 435/320.1 |
| 5,670,354 A | 9/1997 | Burns et al. ............... 435/172.3 |
| 5,672,510 A | 9/1997 | Englitis et al. ............. 435/325 |
| 5,693,509 A | 12/1997 | Cotton et al. ............. 435/172.3 |
| 5,707,618 A | 1/1998 | Armentano et al. ........ 424/93.2 |
| 5,710,037 A | 1/1998 | Vanin et al. ............... 435/240.2 |
| 5,711,964 A | 1/1998 | Dattagupta et al. ......... 424/450 |
| 5,716,826 A | 2/1998 | Gruber et al. ............. 435/320.1 |
| 5,718,914 A | 2/1998 | Foldvari ..................... 424/450 |
| 5,718,915 A | 2/1998 | Virtanen et al. ............. 424/450 |
| 5,723,287 A | 3/1998 | Russell et al. ................... 435/5 |
| 5,728,379 A | 3/1998 | Martuza et al. ............ 424/93.2 |
| 5,731,190 A | 3/1998 | Wickham et al. ......... 435/320.1 |
| 5,736,155 A | 4/1998 | Bally et al. ................. 424/450 |
| 5,736,387 A | 4/1998 | Paul et al. ................. 435/320.1 |
| 5,739,271 A | 4/1998 | Sridhar et al. ............... 530/300 |
| 5,744,158 A | 4/1998 | Mayer et al. ................ 424/450 |
| 5,830,458 A | 11/1998 | Gruber et al. ............. 424/93.2 |

FOREIGN PATENT DOCUMENTS

| | | |
|---|---|---|
| WO | WO 94/27643 | 12/1994 |
| WO | WO 98/00541 | 1/1998 |
| WO | WO 98/11243 | 3/1998 |
| WO | WO 98/16240 | 4/1998 |

OTHER PUBLICATIONS

Bae et al., "Functional Dissection of the Moloney Murine Leukemia Virus Envelope Protein gp70," J. Virol., 71(3):2092–2099, 1997.
MacKrell et al., "Identification of a Subdomain in the Moloney Murine Leukemia Virus Envelope Protein Involved in Receptor Binding," J. Virol., 70(3):1768–1774, 1996.
Masuda et al., "Analysis of the Unique Hamster Cell Tropism of Ecotropic Murine Leukemia Virus PVC–211," J. Virol., 70(12):8534–8539, 1996.
Skov et al., "Mutational Analysis of Moloney Murine Leukaemia Virus Surface Protein gp70," J. General Virology, 74:707–714, 1993.
International Search Report of Feb. 18, 2000 in Applicants' Application No. PCT/US99/11155.
Anderson et al., *Nature* (Suppl) (1998) 392:25–30.
Bae et al., *J Virol* (1997) 71(3):2092–2099.
Battini et al., *J Virol* (1998) 72(1):428–435.
Coffin et al., *Retroviruses* (1997) Cold Spring Harbor Press, pp. 55–58.
Cosset et al., *J Virol* (1995) 69(10):6314–6322.
Dass et al., *Drug Deliv: J Deliv & Targeting Ther Agents* (1997) 4:151–165.
Dzau et al., *Proc Natl Acad Sci USA* (1996) 93:11421–11425.
Etiene–Julan et al., *J Gen Virol* (1992) 73:3251–3255.
Freed et al., *J Virol* (1987) 61:2852–2856.
Han et al., *Proc Natl Acad Sci USA* (1995) 92:9747–9751.
Heard et al., *J Virol* (1991) 65(8):4026–4032.
Kasahara et al., *Science* (1994) 266:1373–1376.
Kemble et al., *Cell* (1994) 76:383–391.
Lasic et al., *Adv Drug Deliv Rev* (1996) 20:221–266.
Linder et al., *J Virol* (1994) 68(8):5133–41.
MacKrell et al., *J Virol* (1996) 70:1768–1774.
Marin et al., *J Virol* (1996) 70(5):2957–2962.
Masuda et al., *J Virol* (1996) 70:8534–8539

(List continued on next page.)

*Primary Examiner*—Deborah Crouch
*Assistant Examiner*—Eleanor Sorbello
(74) *Attorney, Agent, or Firm*—Morgan, Lewis & Bockius LLP

(57) ABSTRACT

This invention includes retrovirus envelope mutants into which heterologous peptide or glycopeptide sequences can be linked for expression and stable presentation on retroviral vectors. The envelope mutants are characterized by the ability to restore the target penetration capability that is lost or greatly diminished upon fusion of heterologous sequences to the wild type envelope protein and the ability to increase the fusion envelope protein stability and decrease envelope shedding from virus particles. The envelope mutants are created by rotating residues in at least one of 7 motifs. The disclosed envelope proteins also can be used in liposome or pseudotype-virus compositions for delivery of agents including nucleic acid molecules. Methods of preparing and utilizing these envelope mutants in gene therapy are also described.

13 Claims, 42 Drawing Sheets

OTHER PUBLICATIONS

Malhotra et al., *J. Virol* (1996) 70(1):321–326.
McCune et al., *Cell* (1988) 53:55–67.
Melikyan et al., *Cell Bio* (1997) 136(5):995–1005.
Okamoto et al., *Gene Ther* (1997) 4:969–976.
Peredo et al. *J Virol* (1996) 70(5):3142–3152.
Rein et al., *J Virol* (1998) 72(4):3432–3435.
Skov et al., *J Gen Virol* (1993) 74:707–714.
Somia et al. *Proc Natl Acad Sci USA* (1995) 92:7570–7574.
Valsesia–Wittman et al., *J Virol* (1996) 70(3):2059–2064.
Young et al., *Science* (1990) 250:1421–1423.
Zhao et al., *J Virol* (1997) 72(9):6967–6972.

FIG. 1A

```
  1 marstlskpl knkvnprgpl iplillmlrg vstaspgssp hqvynitwev tngdretvwa
 61 tsgnhplwtw wpdltpdlcm lahhgpsywg leyqspfssp pgppccsggs spgcsrdcee
121 pltsltprcn tawnrlkldq tthksnegfy vcpgphrpre skscggpdsf ycaywgcett
181 graywkpsss wdfitvnnnl tsdqavqvck dnkwcnplvi rftdagrrvt swttghywgl
241 rlyvsgqdpg ltfgirlryq nlgprvpigp npvladqqpl skpkpvksps vtkppsgtpl
301 sptqlppagt enrllnlvdg ayqalnltsp dktqecwlcl vagppyyegv avlgtysnht
361 sapancsvas qhkltlsevt gqglcigavp kthqalcntt qtssrgsyyl vaptgtmwac
421 stgltpcist tilnlttdyc vlvelwprvt yhspsyvygl fersnrhkre pvsltlalll
481 ggltmggiaa gigtgttalm atqqfqqlqa avqddlreve ksisnleksl tslsevvlqn
541 rrgldllflk egglcaalke eccfyadhtg lvrdsmaklr erlnqrqklf estqgwfegl
601 fnrspwfttl istimgpliv llmillfgpc ilnrlvqfvk drisvvqalv ltqqyhqlkp
661 ieyep
```

FIG. 1B-1

```
   1 gcgccagtcc tccgattgac tgagtcgccc gggtacccgt gtatccaata aaccctcttg
  61 cagttgcatc cgacttgtgg tctcgctgtt ccttgggagg gtctcctctg agtgattgac
 121 tacccgtcag cgggggtctt tcatttgggg gctcgtccgg gatcgggaga cccctgccca
 181 gggaccaccg acccaccacc gggaggtaag ctggccagca acttatctgt gtctgtccga
 241 ttgtctagtg tctatgactg attttatgcg cctgcgtcgg tactagttag ctaactagct
 301 ctgtatctgg cggacccgtg gtggaactga cgagttcgga acacccggcc gcaaccctgg
 361 gagacgtccc agggacttcg ggggccgttt ttgtggcccg acctgagtcc aaaaatcccg
 421 atcgttttgg actctttggt gcaccccct tagaggaggg atatgtggtt ctggtaggag
 481 acgagaacct aaaacagttc ccgcctccgt ctgaattttt gctttcggtt tgggaccgaa
 541 gccgcgccgc gcgtcttgtc tgctgcagca tcgttctgtg ttgtctctgt ctgactgtgt
 601 ttctgtattt gtctgagaat atgggccaga ctgttaccac tcccttaagt ttgaccttag
 661 gtcactggaa agatgtcgag cggatcgctc acaaccagtc ggtagatgtc aagaagagac
 721 gttgggttac cttctgctct gcagaatggc caacctttaa cgtcggatgg ccgcgagacg
 781 gcacctttaa ccgagacctc atcacccagg ttaagatcaa ggtcttttca cctggcccgc
 841 atggacaccc agaccaggtc ccctacatcg tgacctggga agccttggct tttgaccccc
 901 ctccctgggt caagcccttt gtacacccta agcctccgcc tcctcttcct ccatccgccc
 961 cgtctctccc ccttgaacct cctcgttcga ccccgcctcg atcctccctt tatccagccc
1021 tcactccttc tctaggcgcc aaacctaaac ctcaagttct ttctgacagt gggggggccgc
1081 tcatcgacct acttacagaa gaccccccgc cttatagggaa cccaagacca ccccctcccg
1141 acagggacgg aaatggtgga gaagcgaccc ctgcgggaga ggcaccggac ccctccccaa
1201 tggcatctcg cctacgtggg agacgggagc cccctgtggc cgactccact acctcgcagg
1261 cattcccct ccgcgcagga ggaaacggac agcttcaata ctggccgttc tcctcttctg
```

FIG. 1B-2

```
1321 acctttacaa ctggaaaaat aataaccctt cttttctga agatccaggt aaactgacag
1381 ctctgatcga gtctgttctc atcacccatc agcccacctg ggacgactgt cagcagctgt
1441 tggggactct gctgaccgga gaagaaaaac aacgggtgct cttagaggct agaaaggcgg
1501 tgcggggcga tgatgggcgc cccactcaac tgcccaatga agtcgatgcc gcttttcccc
1561 tcgagcgccc agactgggat tacaccaccc aggcaggtag gaaccaccta gtccactatc
1621 gccagttgct cctagcgggt ctccaaaacg cgggcagaag ccccaccaat ttggccaagg
1681 taaaaggaat aacacaaggg cccaatgagt ctccctcggc cttcctagag agacttaagg
1741 aagcctatcg caggtacact ccttatgacc ctgaggaccc agggcaagaa actaatgtgt
1801 ctatgtcttt catttggcag tctgccccag acattgggag aaagttagag aggttagaag
1861 atttaaaaaa caagacgctt ggagatttgg ttagagaggc agaaaagatc tttaataaac
1921 gagaaacccc ggaagaaaga gaggaacgta tcaggagaga aacagaggaa aaagaagaac
1981 gccgtaggac agaggatgag cagaaagaga aagaaagaga tcgtaggaga catagagaga
2041 tgagcaagct attggccact gtcgttagtg gacagaaaca ggatagacag ggaggagaac
2101 gaaggaggtc ccaactcgat cgcgaccagt gtgcctactg caaagaaaag gggcactggg
2161 ctaaagattg tccaagaaa ccacgaggac ctcggggacc aagacccag acctccctcc
2221 tgaccctaga tgactaggga ggtcagggtc aggagccccc ccctgaaccc aggataaccc
2281 tcaaagtcgg ggggcaaccc gtcaccttcc tggtagatac tggggcccaa cactccgtgc
2341 tgacccaaaa tcctggaccc ctaagtgata agtctgcctg ggtccaaggg gctactggag
2401 gaaagcggta tcgctggacc acggatcgca aagtacatct agctaccggt aaggtcaccc
2461 actctttcct ccatgtacca gactgtccct atcctctgtt aggaagagat ttgctgacta
2521 aactaaaagc ccaaatccac tttgagggat caggagctca ggttatggga ccaatggggc
2581 agcccctgca agtgttgacc ctaaatatag aagatgagca tcggctacat gagacctcaa
2641 aagagccaga tgtttctcta gggtccacat ggctgtctga ttttcctcag gcctgggcgg
```

FIG. 1B-3

```
2701 aaaccggggg catgggactg gcagttcgcc aagctcctct gatcatacct ctgaaagcaa
2761 cctctacccc cgtgtccata aaacaatacc ccatgtcaca agaagccaga ctggggatca
2821 agccccacat acagagactg ttggaccagg gaatactggt accctgccag tccccctgga
2881 acacgcccct gctacccgtt aagaaaccag ggactaatga ttataggcct gtccaggatc
2941 tgagagaagt caacaagcgg gtggaagaca tccaccccac cgtgcccaac ccttacaacc
3001 tcttgagcgg gctcccaccg tccaccagt ggtacactgt gcttgattta aaggatgcct
3061 ttttctgcct gagactccac cccaccagtc agcctctctt cgcctttgag tggagagatc
3121 cagagatggg aatctcagga caattgacct ggaccagact cccacagggt ttcaaaaaca
3181 gtcccaccct gtttgatgag gcactgcaca gagacctagc agacttccgg atccagcacc
3241 cagacttgat cctgctacag tacgtggatg acttactgct ggccgccact tctgagctag
3301 actgccaaca aggtactcgg gccctgttac aaaccctagg gaacctcggg tatcgggcct
3361 cggccaagaa agcccaaatt tgccagaaac aggtcaagta tctggggtat cttctaaaag
3421 agggtcagag atggctgact gaggccagaa aagagactgt gatggggcag cctactccga
3481 agacccctcg acaactaagg gagttcctag ggacggcagg cttctgtcgc ctctggatcc
3541 ctgggtttgc agaaatggca gccccttgt accctctcac caaaacgggg actctgttta
3601 attggggccc agaccaacaa aaggcctatc aagaaatcaa gcaagctctt ctaactgccc
3661 cagccctggg gttgccagat ttgactaagc cctttgaact ctttgtcgac gagaagcagg
3721 gctacgccaa aggtgtccta acgcaaaaac tgggaccttg gcgtcggccg gtggcctacc
3781 tgtccaaaaa gctagaccca gtagcagctg ggtggccccc ttgcctacgg atggtagcag
3841 ccattgccgt actgacaaag gatgcaggca agctaaccat gggacagcca ctagtcattc
3901 tggcccccca tgcagtagag gcactagtca acaaccccc cgaccgctgg ctttccaacg
3961 cccggatgac tcactatcag gccttgcttt tggacacgga ccgggtccag ttcggaccgg
4021 tggtagccct gaacccggct acgctgctcc cactgcctga ggaagggctg caacacaact
```

FIG. 1B-4

```
4081 gccttgatat cctggccgaa gcccacggaa cccgacccga cctaacggac cagccgctcc
4141 cagacgccga ccacacctgg tacacggatg gaagcagtct cttacaagag ggacagcgta
4201 aggcgggagc tgcggtgacc accgagaccg aggtaatctg ggctaaagcc ctgccagccg
4261 ggacatccgc tcagcgggct gaactgatag cactcaccca ggccctaaag atggcagaag
4321 gtaagaagct aaatgtttat actgatagcc gttatgcttt tgctactgcc catatccatg
4381 gagaaatata cagaaggcgt gggttgctca catcagaagg caaagagatc aaaaataaag
4441 acgagatctt ggccctacta aaagccctct ttctgcccaa aagacttagc ataatccatt
4501 gtccaggaca tcaaaaggga cacagcgccg aggctagagg caaccggatg gctgaccaag
4561 cggcccgaaa ggcagccatc acagagactc cagacacctc taccctcctc atagaaaatt
4621 catcacccta cacctcagaa catttcatt acacagtgac tgatataaag gacctaacca
4681 agttgggggc catttatgat aaaacaaaga agtattgggt ctaccaagga aaacctgtga
4741 tgcctgacca gtttactttt gaattattag actttcttca tcagctgact cacctcagct
4801 tctcaaaaat gaaggctctc ctagagagaa gccacagtcc ctactacatg ctgaaccggg
4861 atcgaacact caaaaatatc actgagacct gcaaagcttg tgcacaagtc aacgccagca
4921 agtctgccgt taaacaggga actagggtcc gcgggcatcg gcccggcact cattgggaga
4981 tcgatttcac cgagataaag cccggattgt atggctataa atatcttcta gtttttatag
5041 ataccttttc tggctggata gaagccttcc caaccaagaa agaaaccgcc aaggtcgtaa
5101 ccaagaagct actagaggag atcttcccca ggttcggcat gcctcaggta ttgggaactg
5161 acaatgggcc tgccttcgtc tccaaggtga gtcagacagt ggccgatctg ttggggattg
5221 attggaaatt acattgtgca tacagacccc aaagctcagg ccaggtagaa agaatgaata
5281 gaaccatcaa ggagacttta actaaattaa cgcttgcaac tggctctaga gactgggtgc
5341 tcctactccc cttagccctg taccgagccc gcaacacgcc gggcccccat ggcctcaccc
5401 catatgagat cttatatggg gcaccccgc cccttgtaaa cttccctgac cctgacatga
```

FIG. 1B-5

```
5461 caagagttac taacagcccc tctctccaag ctcacttaca ggctctctac ttagtccagc
5521 acgaagtctg gagacctctg gcggcagcct accaagaaca actggaccga ccggtggtac
5581 ctcaccctta ccgagtcggc gacacagtgt gggtccgccg acaccagact aagaacctag
5641 aacctcgctg gaaaggacct tacacagtcc tgctgaccac ccccaccgcc ctcaaagtag
5701 acggcatcgc agcttggata cacgccgccc acgtgaaggc tgccgacccc gggggtggac
5761 catcctctag actgacatgg cgcgttcaac gctctcaaaa cccctaaaaa ataaggttaa
5821 cccgcgaggc cccctaatcc ccttaattct tctgatgctc agaggggtca gtactgcttc
5881 gcccggctcc agtcctcatc aagtctataa tatcacctgg gaggtaacca atggagatcg
5941 ggagacggta tgggcaactt ctggcaacca cctctgtgg acctggtggc ctgaccttac
6001 cccagattta tgtatgttag cccaccatgg accatcttat tgggggctag aatatcaatc
6061 cccttttcct tctccccgg ggccccttg ttgctcaggg ggcagcagcc caggctgttc
6121 cagagactgc gaagaacctt taacctccct caccctcgg tgcaacactg cctggaacag
6181 actcaagcta gaccagacaa ctcataaatc aaatgaggga ttttatgttt gccccgggcc
6241 ccaccgcccc cgagaatcca agtcatgtgg gggtccagac tccttctact gtgcctattg
6301 gggctgtgag acaaccggta gagcttactg gaagccctcc tcatcatggg atttcatcac
6361 agtaaacaac aatctcacct ctgaccaggc tgtccaggta tgcaaagata ataagtggtg
6421 caaccccta gttattcggt ttacagacgc cgggagacgg gttacttcct ggaccacagg
6481 acattactgg ggcttacgtt tgtatgtctc cggacaagat ccagggctta catttgggat
6541 ccgactcaga taccaaaatc taggaccccg cgtcccaata gggccaaacc ccgttctggc
6601 agaccaacag ccactctcca agcccaaacc tgttaagtcg ccttcagtca ccaaaccacc
6661 cagtgggact cctctctccc ctacccaact tccaccggcg ggaacggaaa ataggctgct
6721 aaacttagta gacggagcct accaagccct caacctcacc agtcctgaca aaacccaaga
6781 gtgctggttg tgtctagtag cgggaccccc ctactacgaa ggggttgccg tcctgggtac
6841 ctactccaac catacctctg ctccagccaa ctgctccgtg gcctcccaac acaagttgac
```

FIG. 1B-6

```
6901 cctgtccgaa gtgaccggac agggactctg cataggagca gttcccaaaa cacatcaggc
6961 cctatgtaat accacccaga caagcagtcg agggtcctat tatctagttg cccctacagg
7021 taccatgtgg gcttgtagta ccgggcttac tccatgcatc tccaccacca tactgaacct
7081 taccactgat tattgtgttc ttgtcgaact ctggccaaga gtcacctatc attcccccag
7141 ctatgtttac ggcctgtttg agagatccaa ccgacacaaa agagaaccgg tgtcgttaac
7201 cctggcccta ttattgggtg gactaaccat ggggggaatt gccgctggaa taggaacagg
7261 gactactgct ctaatggcca ctcagcaatt ccagcagctc aagccgcag tacaggatga
7321 tctcagggag gttgaaaaat caatctctaa cctagaaaag tctctcactt ccctgtctga
7381 agttgtccta cagaatcgaa ggggcctaga cttgttattt ctaaaagaag gagggctgtg
7441 tgctgctcta aaagaagaat gttgcttcta tgcggaccac acaggactag tgagagacag
7501 catggccaaa ttgagagaga ggcttaatca gagacagaaa ctgtttgagt caactcaagg
7561 atggtttgag ggactgttta acagatcccc ttggtttacc accttgatat ctaccattat
7621 gggacccctc attgtactcc taatgatttt gctcttcgga ccctgcattc ttaatcgatt
7681 agtccaattt gttaaagaca ggatatcagt ggtccaggct ctagttttga ctcaacaata
7741 tcaccagctg aagcctatag agtacgagcc atagataaaa taaaagattt tatttagtct
7801 ccagaaaaag gggggaatga agaccccac ctgtaggttt ggcaagctag cttaagtaac
7861 gccatttgc aaggcatgga aaaatacata actgagaata gagaagttca gatcaaggtc
7921 aggaacagat ggaacagctg aatatgggcc aaacaggata tctgtggtaa gcagttcctg
7981 ccccggctca gggccaagaa cagatggaac agctgaatat gggccaaaca ggatatctgt
8041 ggtaagcagt tcctgccccg gctcagggcc aagaacagat ggtccccaga tgcggtccag
8101 ccctcagcag tttctagaga accatcagat gtttccaggg tgccccaagg acctgaaatg
8161 accctgtgcc ttatttgaac taaccaatca gttcgcttct cgcttctgtt cgcgcgcttc
8221 tgctccccga gctcaataaa agagcccaca acccctcact cggggcgcca gtcctccgat
8281 tgactgagtc gcccgggtac ccgtgtatcc aataaaccct cttgcagttg ca
```

FIG. 2A

```
  1 mvllpgsmll tsnlhhlrhq mspgswkrli illscvfggg gtslqnknph qpmtltwqvl
 61 sqtgdvvwdt kavqppwtww ptlkpdvcal aasleswdip gtdvssskrv rppdsdytaa
121 ykqitwgaig csyprartrm asstfyvcpr dgrtlsearr cggleslyck ewdcettgtg
181 ywlsksskdl itvkwdqnse wtqkfqqchq tgwcnplkid ftdkgklskd witgktwglr
241 fyvsghpgvq ftirlkitnm pavavgpdlv lveqgpprts lalppplppr eapppslpds
301 nstalatsaq tptvrktivt lntpppttgd rlfdlvqgaf ltlnatnpga tescwlclam
361 gppyyeaias sgevaystdl drcrwgtqgk ltltevsghg lcigkvpfth qhlcnqtlsi
421 nssgdhqyll psnhswwacs tgltpclsts vfnqtrdfci qvqlipriyy ypeevllqay
481 dnshprtkre avsltlavll glgitagigt gstalikgpi dlqqgltslq iaidadlral
541 qdsvskleds ltslsevvlq nrrgldllfl kegglcaalk eeccfyidhs gavrdsmkkl
601 kekldkrqle rqksqnwyeg wfnnspwftt llstiagpll llllllilgp ciinklvqfi
661 ndrisac
```

FIG. 2B-1

```
   1 gcgccagtcc ttagagagac tgagccgccc gggtacccgt gtgtccaata aaacctcttg
  61 ctgattgcat ccggagccgt ggtctcgttg ttccttggga gggtttctcc taactattga
 121 ccgcccactt cggggtctc acatttgggg gctcgtccgg gatcggaaac cccacccagg
 181 gaccaccgac ccaccaacgg gaggtaagct ggccagcgac cgttgtgtgt ctcgcttctg
 241 tgtctaagtc cgtaattctg actgtccttg tgtgtctcgc ttctgtgtct gagaccgtaa
 301 ctctgactgc ccttgtaagt gcgcgcattt ttttggtttc agtctgttcc gggtgaatca
 361 ctctgcgagt gacgtgtgag tagcgaacag acgtgttcgg ggctcaccgc ctggtaatcc
 421 agggagacgt cccaggatca ggggaggacc agggacgcct ggtggacccc tcggtaacgg
 481 gtcgttgtga cccgatttca tcgcccgtct ggtaagacgc gctctgaatc tgattctctc
 541 tctcggtcgc ctcgccgccg tctctggttt cttttttgttt cgttctgga aagcctctgt
 601 gtcacagtct ttctctccca aatcatcaat atgggacaag ataattctac ccctatctcc
 661 ctcactctaa atcactggag agatgtgaga acaagggctc acaatctatc cgtggaaatc
 721 aaaaagggaa aatggcagac tttctgttcc tccgagtggc ccacattcgg cgtggggtgg
 781 ccaccggagg gaactttaa tctctctgtc attttgcag ttaaaaagat tgtctttcag
 841 gagaacgggg gacatccgga ccaagttcca tatatcgtgg tatggcagga cctcgcccag
 901 aatcccccac catgggtgcc agcctccgcc aaggtcgctg ttgtctctga tacccgaaga
 961 ccagttgcgg ggaggccatc agctcctccc cgaccccca tctacccggc aacagacgac
1021 ttactcctcc tctctgaacc cacgccccg ccctatccgg cggcactgcc accccctctg
1081 gcccctcagg cgatcggacc gccgtcaggc cagatgcccg atagtagcga tcctgagggg
1141 ccagccgctg ggaccaggag tcgccgtgcc cgcagtccag cagacaactc gggtcctgac
1201 tccactgtga ttttgcccct ccgagccata ggaccccggg ccgagcccaa tggcctggtc
1261 cctctacaat attggccttt ttcctcagca gatctttata attggaaatc taatcatccc
1321 tcttttcctg aaaacccagc aggtctcacg gggctccttg agtctcttat gttctcccat
```

FIG. 2B-2

```
1381 cagcccactt gggacgattg ccaacagctc ctacagattc ttttcaccac tgaggaacgg
1441 gaaagaattc tcctggaggc ccgcaaaaat gtccttgggg acaatggggc ccctacacag
1501 ctcgagaacc tcattaatga ggccttcccc ctcaatcgac ctcactggga ttacaacaca
1561 gccgcaggta gggagcgtct tctggtctac cgccggactc tagtggcagg tctcaaaggg
1621 gcagctcggc gtcctaccaa tttggctaag gtaagagagg tcttgcaggg accggcagaa
1681 cccccttcgg ttttcttaga acgcctgatg gaggcctata ggagatacac tccgtttgat
1741 ccctcttctg agggacaaca ggctgcggtc gccatggcct ttatcggaca gtcagcccca
1801 gatatcaaga aaaagttaca gaggctagag gggctccagg actattcctt acaagattta
1861 gtaaaagagg cagaaaaggt gtaccataag agagagacag aagaagaaag acaagaaaga
1921 gaaaaaaagg aggcagaaga aaaggagagg cggcgcgata ggccgaagaa aaaaaacttg
1981 actaaaattc tggccgcagt agtaagtaga gaagggtcca caggtaggca gacagggaac
2041 ctgagcaacc aggcaaagaa gacacctagg gatggaagac ctccactaga caaagaccag
2101 tgcgcatact gtaaagagaa gggccattgg gcaagagaat gtccccgaaa aaaacacgtc
2161 agagaagcca aggttctagc cctagataac tagggagtc agggttcgga cccccctcccc
2221 gaacctaggg taacactgac tgtggagggg accccccattg agttcctggt cgacaccgga
2281 gctgaacatt cagtattgac ccaacccatg ggaaaagtag gtccagacg gacggtcgtg
2341 gaaggagcga caggcagcaa ggtctacccc tggaccacaa aaagactttt aaaaattgga
2401 cataaacaag tgacccactc cttcctggtc atacccgagt gccctgctcc tctgttgggc
2461 agggacctcc taaccaaact aaaggcccag atccagtttt ccgctgaggg cccacaggta
2521 acatggggag aacgccctac tatgtgcctg gtcctaaacc tggaagaaga ataccgacta
2581 catgaaaagc cagtaccctc ctctatcgac ccatcctggc tccagctttt ccccactgta
2641 tgggcagaaa gagccggcat gggactagcc aatcaagtcc caccagtggt agtagagcta
2701 agatcaggtg cctcaccagt ggctgttcga caatatccaa tgagcaaaga agctcgggaa
```

FIG. 2B-3

```
2761 ggtatcagac cccacatcca gaagttccta gacctagggg tcttggtgcc ctgtcggtcg
2821 ccctggaata cccctctgct acctgtaaaa aagccaggga ccaatgacta tcggccagtt
2881 caagacctga gagaaattaa taaaagggta caggatattc atcccacagt cccaaaccct
2941 tacaatcttc tgagttccct tccgcctagc tatacttggt actcagtctt agatctcaag
3001 gatgcctttt tctgcctcag gctacatccc aacagccagc cgctgttcgc gttcgagtgg
3061 aaagacccag aaaaaggtaa cacaggtcag ctgacctgga cgcggctacc acaagggttc
3121 aagaactctc ccactctctt cgacgaggcc ctccaccgag atttggctcc ctttagggcc
3181 ctcaaccccc aggtggtgtt actccaatat gtggacgacc tcttggtggc cgcccccaca
3241 tatgaagact gcaaaaaagg aacacagaag ctcttacagg agttaagtaa gttggggtac
3301 cgggtatcgg ctaagaaggc ccagctctgc cagagagaag tcacctatct ggggtaccta
3361 ctcaaggaag gaaaaagatg gctaaccccca gcccgaaagg ctactgttat gaaaatccct
3421 gttcctacga cccccagaca ggtccgtgaa tttctaggca ctgccggatt ctgcaggctc
3481 tggatccctg ggtttgcttc cctggctgca cccttgtacc ccctaacaaa agagagcatc
3541 ccttttattt ggactgagga acatcagcag gcttttgacc acataaaaaa agccttgctg
3601 tcagcccctg cattggccct cccagacctc accaagccat tcactctata tatagatgag
3661 agagccggcg tggcccgggg agtgctcact cagactttag gaccctggcg gcggccagta
3721 gcatatctat caaaaaaact ggatccggtg ccagcgggt ggccaacctg cctgaaagcg
3781 gttgcagcag tagcactcct tctcaaagac gctgataagt taaccttggg acaaaatgtg
3841 actgtgattg cttcccatag cctcgaaagc atcgtgcggc aaccccccga ccggtggatg
3901 accaatgcca gaatgactca ttaccagagc ctgctgttaa atgaaagggt atcgtttgcg
3961 ccccctgctg tcctaaaccc agctacccta cttccagtcg agtcggaagc cacccagtg
4021 cacaggtgct cagaaatcct cgccgaagaa actggaactc gacgagacct agaagaccaa
4081 ccattgcccg gggtgccaac ctggtataca gacggtagca gtttcatcac ggaaggtaaa
```

FIG. 2B-4

```
4141 cggagagcag gggccccgat cgtagatggc aagcggacgg tatgggctag cagcctgcca
4201 gaaggtacgt cagcccagaa ggctgaacta gtagccttga cgcaggcatt acgcctggcc
4261 gaaggaaaaa acatcaacat ctacacggac agcaggtatg cttttgccac tgctcatatt
4321 catggggcaa tatataagca gagggggctg ctcacttctg ctggaaaaga tatcaaaaac
4381 aaagaggaaa ttttggccct gctagaggcc atccatctcc ctaggcgggt cgccattatc
4441 cactgtcctg gccaccagag gggaagtaac cctgtggcca ctgggaaccg gagggccgac
4501 gaggctgcaa agcaagccgc cctgtcgacc agagtgctgg caggaactac aaaacctcaa
4561 gagccaatcg agcccgctca agaaaagacc aggccgaggg agctcaccc tgaccgggga
4621 aaagaattca ttaagcggtt acatcagtta actcacttag gaccagaaaa gcttctccaa
4681 ctagtgaacc gtaccagcct cctcatcccg aacctccaat ctgcagttcg cgaagtcacc
4741 agtcagtgtc aggcttgtgc catgactaat gcggtcacca cctacagaga gaccggaaaa
4801 aggcaacgag gagatcgacc cggcgtgtac tgggaggtag acttcacaga aataaagcct
4861 ggtcggtatg gaaacaagta tctgttagta ttcatagata ctttctccgg atgggtagaa
4921 gcttttccta ccaaaactga acggcccta atcgtctgta aaaaaatatt agaagaaatt
4981 ctaccccgct cgggatccc taaggtactc gggtcagaca atggcccggc ctttgttgct
5041 caggtaagtc agggactggc cactcaactg gggataaatt ggaagttaca ttgtgcgtat
5101 agaccccaga gctcaggtca ggtagaaaga atgaacagaa caattaaaga gaccttgacc
5161 aaattagcct tagagaccgg tggaaaagac tgggtgaccc tccttccctt agcgctgctt
5221 agggccagga ataccctgg ccggtttggt ttaactcctt atgaaattct ctatggagga
5281 ccaccccca tacttgagtc tggagaaact ttgggtcccg atgatagatt tctccctgtc
5341 ttatttactc acttaaaggc tttagaaatt gtaaggaccc aaatctggga ccagatcaaa
5401 gaggtgtata agcctggtac cgtaacaatc cctcacccgt tccaggtcgg ggatcaagtg
5461 cttgtcagac gccatcgacc cagcagcctt gagcctcggt ggaaaggccc atacctggtg
```

FIG. 2B-5

```
5521 ttgctgacta ccccgaccgc ggtaaaagtc gatggtattg ctgcctgggt ccatgcttct
5581 cacctcaaac ctgcaccacc ttcggcacca gatgagtcct gggagctgga aaagactgat
5641 catcctctta agctgcgtat tcggcggcgg cgggacgagt ctgcaaaata agaaccccca
5701 ccagcccatg accctcactt ggcaggtact gtcccaaact ggagacgttg tctgggatac
5761 aaaggcagtc cagccccctt ggacttggtg gcccacactt aaacctgatg tatgtgcctt
5821 ggcggctagt cttgagtcct gggatatccc gggaaccgat gtctcgtcct ctaaacgagt
5881 cagacctccg gactcagact atactgccgc ttataagcaa atcacctggg gagccatagg
5941 gtgcagctac cctcgggcta ggactagaat ggcaagctct accttctacg tatgtccccg
6001 ggatggccgg acccttcag aagctagaag gtgcggggggg ctagaatccc tatactgtaa
6061 agaatgggat tgtgagacca cggggaccgg ttattggcta tctaaatcct caaaagacct
6121 cataactgta aaatgggacc aaaatagcga atggactcaa aaatttcaac agtgtcacca
6181 gaccggctgg tgtaaccccc ttaaaataga tttcacagac aaaggaaaat tatccaagga
6241 ctggataacg ggaaaaacct ggggattaag attctatgtg tctggacatc caggcgtaca
6301 gttcaccatt cgcttaaaaa tcaccaacat gccagctgtg gcagtaggtc ctgacctcgt
6361 ccttgtggaa caaggacctc ctagaacgtc cctcgctctc ccacctcctc ttcccccaag
6421 ggaagcgcca ccgccatctc tccccgactc taactccaca gccctggcga ctagtgcaca
6481 aactcccacg gtgagaaaaa caattgttac cctaaacact ccgcctccca ccacaggcga
6541 cagactttt gatcttgtgc aggggggcctt cctaacctta aatgctacca acccaggggc
6601 cactgagtct tgctggcttt gtttggccat gggccccccct tattatgaag caatagcctc
6661 atcaggagag gtcgcctact ccaccgacct tgaccggtgc cgctgggggga cccaaggaaa
6721 gctcaccctc actgaggtct caggacacgg gttgtgcata ggaaaggtgc cctttaccca
```

FIG. 2B-6

```
6781 tcagcatctc tgcaatcaga ccctatccat caattcctcc ggagaccatc agtatctgct
6841 cccctccaac catagctggt gggcttgcag cactggcctc accccttgcc tctccacctc
6901 agtttttaat cagactagag atttctgtat ccaggtccag ctgattcctc gcatctatta
6961 ctatcctgaa gaagttttgt tacaggccta tgacaattct caccccagga ctaaaagaga
7021 ggctgtctca cttaccctag ctgttttact ggggttggga atcacggcgg gaataggtac
7081 tggttcaact gccttaatta aaggacctat agacctccag caaggcctga caagcctcca
7141 gatcgccata gatgctgacc tccgggccct ccaagactca gtcagcaagt tagaggactc
7201 actgacttcc ctgtccgagg tagtgctcca aaataggaga ggccttgact tgctgtttct
7261 aaaagaaggt ggcctctgtg cggccctaaa ggaagagtgc tgtttttaca tagaccactc
7321 aggtgcagta cgggactcca tgaaaaaact caaagaaaaa ctggataaaa gacagttaga
7381 gcgccagaaa agccaaaact ggtatgaagg atggttcaat aactcccctt ggttcactac
7441 cctgctatca accatcgctg ggccccctatt actcctcctt ctgttgctca tcctcgggcc
7501 atgcatcatc aataagttag ttcaattcat caatgatagg ataagtgcat gttaaaattc
7561 tggtccttag acaaaatatc aggccctaga gaacgaaggt aacctttaat tttgctctaa
7621 gattagagct attcacaaga gaaatggggg aatgaaagaa gtgttttttt ttagccaact
7681 gcagtaacgc cattttgcta ggcacaccta aaggatagga aaaatacagc taagaacagg
7741 gccaaacagg atatctgtgg tcatgcacct gggccccggc ccaggccaag gacagagggt
7801 tcccagaaat agatgagtca acagcagttt ccagcaagga cagagggttc ccagaaatag
7861 atgagtcaac agcagtttcc agggtgcccc tcaaccgttt caaggactcc catgaccggg
7921 aattcacccc tggccttatt tgaactaacc aattaccttg cctctcgctt ctgtacccgc
7981 gctttttgct ataaataag ctcagaaact ccacccggag cgccagtcct tagagagact
8041 gagccgcccg ggtacccgtg tgtccaataa aacctcttgc tgattgca
```

FIG. 3A

```
  1 megpafskpl kdkinpwksl mvmgvylrvg maesphqvfn vtwrvtnlmt grtanatsll
 61 gtvqdafprl yfdlcdlvge ewdpsdqepy vgygckypgg rkrtrtfdfy vcpghtvksg
121 cggpregycg ewgcettgqa ywkptsswdl islkrgntpw dtgcskmacg pcydlskvsn
181 sfqgatrggr cnplvleftd agkkanwdgp kswglrlyrt gtdpitmfsl trqvlnigpr
241 ipigpnpvit gqlppsrpvq irlprppqpp ptgaasivpe tappsqqpgt gdrllnlveg
301 ayqalnltnp dktqecwlcl vsgppyyegv avvgtytnhs tapasctats qhkltlsevt
361 gqglcmgalp kthqalcntt qsagsgsyyl aapagtmwac stgltpclst tmlnlttdyc
421 vlvelwprii yhspdymygq leqrtkykre pvsltlalll ggltmggiaa gigtgttali
481 ktqqfeqlha aiqtdlneve ksitnleksl tslsevvlqn rrgldllflk egglcaalke
541 eccfyadhtg lvrdsmaklr erlnqrqklf esgqgwfegq fnrspwfttl istimgpliv
601 lllillfgpc ilnrlvqfvk drisvvqalv ltqqyhqlkp ieyep
```

FIG. 3B

```
   1 ggatccacgc cgctcacgta aaggcggcga caaccccctcc ggccggaaca gcatcaggac
  61 cgacatggaa ggtccagcgt tctcaaaacc ccttaaagat aagattaacc cgtggaagtc
 121 cttaatggtc atgggggtct atttaagagt agggatggca gagagccccc atcaggtctt
 181 taatgtaacc tggagagtca ccaacctgat gactgggcgt accgccaatg ccacctccct
 241 tttaggaact gtacaagatg ccttcccaag attatatttt gatctatgtg atctggtcgg
 301 agaagagtgg gacccttcag accaggaacc atatgtcggg tatggctgca aatacccccgg
 361 agggagaaag cggacccgga cttttgactt ttacgtgtgc cctgggcata ccgtaaaatc
 421 ggggtgtggg gggccaagag agggctactg tggtgaatgg ggttgtgaaa ccaccggaca
 481 ggcttactgg aagcccacat catcatggga cctaatctcc cttaagcgcg gtaacacccc
 541 ctgggacacg ggatgctcca aaatggcttg tggcccctgc tacgacctct ccaaagtatc
 601 caattccttc aaggggcta ctcgaggggg cagatgcaac cctctagtcc tagaattcac
 661 tgatgcagga aaaaaggcta attgggacgg gcccaaatcg tggggactga gactgtaccg
 721 gacaggaaca gatcctatta ccatgttctc cctgacccgc caggtcctca atatagggcc
 781 ccgcatcccc attgggccta atcccgtgat cactggtcaa ctacccccct cccgacccgt
 841 gcagatcagg ctccccaggc ctcctcagcc tcctcctaca ggcgcagcct ctatagtccc
 901 tgagactgcc ccaccttctc aacaacctgg gacgggagac aggctgctaa acctggtaga
 961 aggagcctat caggcgctta acctcaccaa tcccgacaag acccaagaat gttggctgtg
1021 cttagtgtcg ggacctcctt attacgaagg agtagcggtc gtgggcactt ataccaatca
1081 ttctaccgcc ccggccagct gtacggccac ttcccaacat aagcttaccc tatctgaagt
1141 gacaggacag ggcctatgca tgggagcact acctaaaact caccaggcct tatgtaacac
1201 cacccaaagt gccggctcag gatcctacta ccttgcagca cccgctggaa caatgtgggc
1261 ttgtagcact ggattgactc cctgcttgtc caccacgatg ctcaatctaa ccacagacta
1321 ttgtgtatta gttgagctct ggcccagaat aatttaccac tcccccgatt atatgtatgg
1381 tcagcttgaa cagcgtacca aatataagag ggagccagta tcgttgaccc tggcccttct
1441 gctaggagga ttaaccatgg gagggattgc agctggaata gggacgggga ccactgccct
1501 aatcaaaacc cagcagtttg agcagcttca cgccgctatc cagacagacc tcaacgaagt
1561 cgaaaaatca attaccaacc tagaaaagtc actgacctcg ttgtctgaag tagtcctaca
1621 gaaccgaaga ggcctagatt tgctcttcct aaaagaggga ggtctctgcg cagccctaaa
1681 agaagaatgt tgtttttatg cagaccacac gggactagtg agagacagca tggccaaact
1741 aagggaaagg cttaatcaga gacaaaaact atttgagtca ggccaaggtt ggttcgaagg
1801 gcagtttaat agatcccct ggtttaccac cttaatctcc accatcatgg gacctctaat
1861 agtactctta ctgatcttac tctttggacc ctgcattctc aatcgattgg tccaatttgt
1921 taaagacagg atctcagtgg tccaggctct ggttttgact caacaatatc accagctaaa
1981 acctatagag tacgagccat ga
```

FIG. 4A

```
  1 marstlskpp qdkinpwkpl ivmgvllgvg maesphqvfn vtwrvtnlmt grtanatsll
 61 gtvqdafpkl yfdlcdlvge ewdpsdqepy vgygckypag rqrtrtfdfy vcpghtvksg
121 cggpgegycg kwgcettgqa ywkptsswdl islkrgntpw dtgcskvacg pcydlskvsn
181 sfqgatrggr cnplvleftd agkkanwdgp kswglrlyrt gtdpitmfsl trqvlnvgpr
241 vpigpnpvlp dqrlpsspie ivpapqppsp lntsyppstt stpstsptsp svpqpppgtg
301 drllalvkga yqalnltnpd ktqecwlclv sgppyyegva vvgtytnhst apanctatsq
361 hkltlsevtg qglcmgavpk thqalcnttq sagsgsyyla apagtmwacs tgltpclstt
421 vlnlttdycv lvelwprviy hspdymygql eqrtkykrep vsltlalllg gltmggiaag
481 igtgttalik tqqfeqlhaa iqtdlnevek sitnlekslt slsevvlqnr rgldllflke
541 gglcaalkee ccfyadhtgl vrdsmaklre rlnqrqklfe tgqgwfeglf nrspwfttli
601 stimgplivl llillfgpci lnrlvqfvkd risvvqalvl tqqyhqlkpi eyep
```

FIG. 4B

```
   1 ggccgacacc cagagtggac catcctctgg acggacatgg cgcgttcaac gctctcaaaa
  61 cccccctcaag ataagattaa cccgtggaag cccttaatag tcatgggagt cctgttagga
 121 gtagggatgg cagagagccc ccatcaggtc tttaatgtaa cctggagagt caccaacctg
 181 atgactgggc gtaccgccaa tgccacctcc ctcctgggaa ctgtacaaga tgccttccca
 241 aaattatatt ttgatctatg tgatctggtc ggagaggagt gggacccttc agaccaggaa
 301 ccgtatgtcg ggtatggctg caagtacccc gcagggagac agcggacccg gacttttgac
 361 ttttacgtgt gccctgggca taccgtaaag tcggggtgtg ggggaccagg agagggctac
 421 tgtggtaaat gggggtgtga aaccaccgga caggcttact ggaagcccac atcatcgtgg
 481 gacctaatct cccttaagcg cggtaacacc ccctgggaca cgggatgctc taaagttgcc
 541 tgtggcccct gctacgacct ctccaaagta tccaattcct tccaaggggc tactcgaggg
 601 ggcagatgca accctctagt cctagaattc actgatgcag gaaaaaaggc taactgggac
 661 gggcccaaat cgtggggact gagactgtac cggacaggaa cagatcctat taccatgttc
 721 tccctgaccc ggcaggtcct taatgtggga ccccgagtcc catagggcc caacccagta
 781 ttacccgacc aaagactccc ttcctcacca atagagattg taccggctcc acagccacct
 841 agcccctca ataccagtta cccccttcc actaccagta caccctcaac ctcccctaca
 901 agtccaagtg tcccacagcc accccagga actggagata gactactagc tctagtcaaa
 961 ggagcctatc aggcgcttaa cctcaccaat cccgacaaga cccaagaatg ttggctgtgc
1021 ttagtgtcgg gacctcctta ttacgaagga gtagcggtcg tgggcactta taccaatcat
1081 tccaccgctc cggccaactg tacggccact tccaacata agcttaccct atctgaagtg
1141 acaggacagg gcctatgcat gggggcagta cctaaaactc accaggcctt atgtaacacc
1201 acccaaagcg ccggctcagg atcctactac cttgcagcac ccgccggaac aatgtgggct
1261 tgcagcactg gattgactcc ctgcttgtcc accacggtgc tcaatctaac cacagattat
1321 tgtgtattag ttgaactctg gcccagagta atttaccact ccccgatta tatgtatggt
1381 cagcttgaac agcgtaccaa atataaaga gagccagtat cattgaccct ggcccttcta
1441 ctaggaggat taaccatggg agggattgca gctggaatag ggacggggac cactgcctta
1501 attaaaaccc agcagtttga gcagcttcat gccgctatcc agacagacct caacgaagtc
1561 gaaaagtcaa ttaccaacct agaaaagtca ctgacctcgt tgtctgaagt agtcctacag
1621 aaccgcagag gcctagattt gctattccta aaggagggag gtctctgcgc agccctaaaa
1681 gaagaatgtt gttttatgc agaccacacg gggctagtga gagacagcat ggccaaatta
1741 agagaaaggc ttaatcagag acaaaaacta tttgagacag gccaaggatg gttcgaaggg
1801 ctgtttaata gatcccccct gtttaccacc ttaatctcca ccatcatggg acctctaata
1861 gtactcttac tgatcttact ctttggacct tgcattctca atcgattggt ccaatttgtt
1921 aaagacagga tctcagtggt ccaggctctg gttttgactc agcaatatca ccagctaaaa
1981 cccatagagt acgagccatg a
```

FIG. 5
A. Virus titers on NIH3T3 (☐) and 293 / wild type receptor (■)
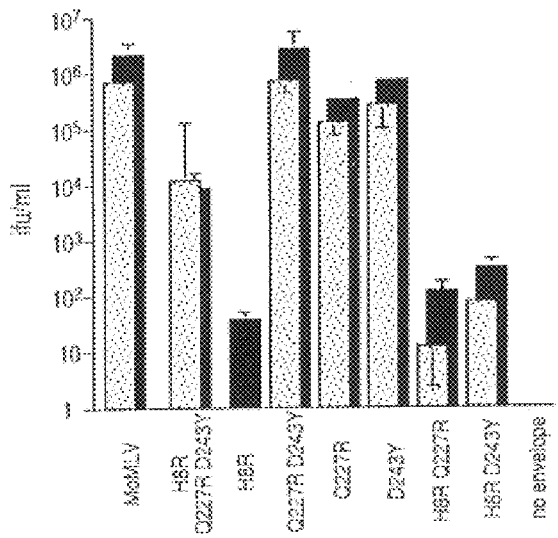
B. Envelope proteins in the virions
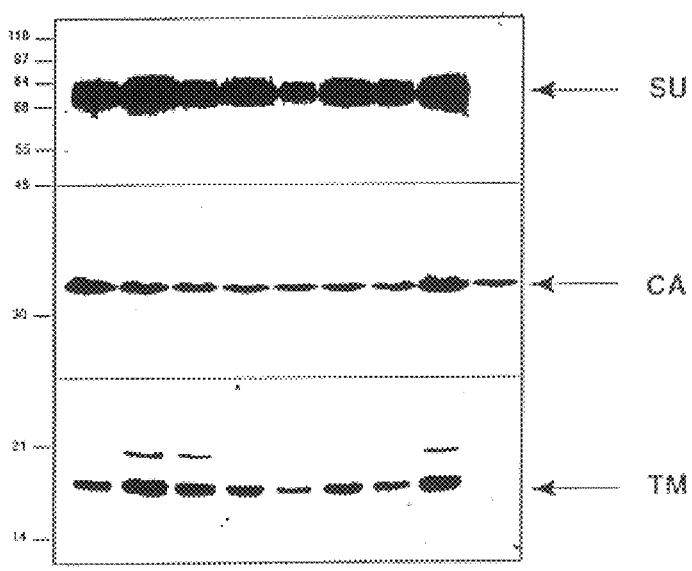
← SU
← CA
← TM
C. Envelope proteins in the cell lysates.
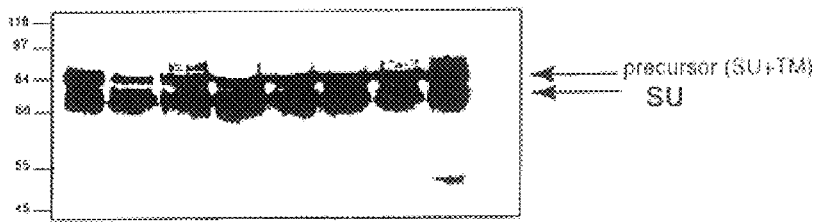
← precursor (SU+TM)
← SU

FIG. 7

| Virus | | Human 293 | | Titer on Host cells (ifu/ml) Human 293+ecotropic receptor | Mouse NIH 3T3 |
|---|---|---|---|---|---|
| | Amphotropic receptor | + | | + | + |
| | Ecotropic receptor | – | | + | + |
| MoMLV | | 0 | | $(9.0 \pm 8.0) \times 10^5$ | $(7.0 \pm 2.0) \times 10^5$ |
| 4070A | | $(9.3 \pm 7.7) \times 10^4$ | | $(2.2 \pm 1.8) \times 10^5$ | $(4.6 \pm 1.8) \times 10^4$ |
| ampho-eco | | 0 | | $(3.0 \pm 1.5) \times 10^2$ | $(4.6 \pm 1.9) \times 10^2$ |
| ampho-eco +Q227R D243Y | | $(1.5 \pm 0.5) \times 10^3$ | | $(1.3 \pm 0.7) \times 10^3$ | $(5.3 \pm 2.5) \times 10^3$ |

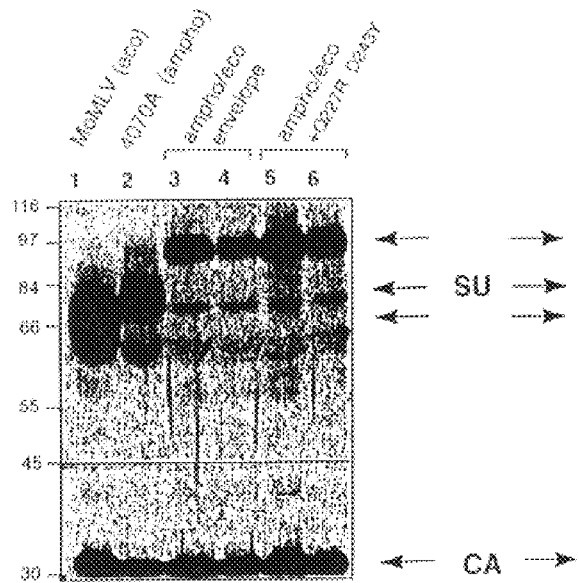
FIG. 8 A. Virions pelleted without sucrose
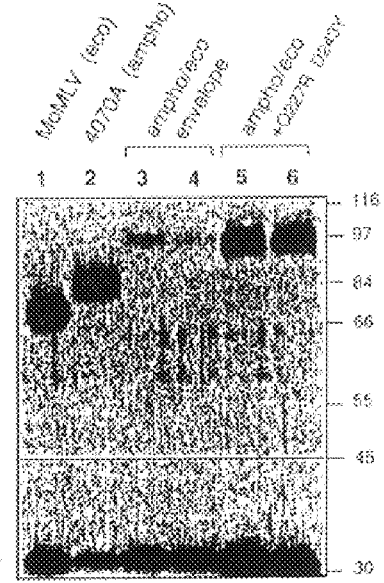
FIG. 8 B. Virions pelleted through sucrose cushion
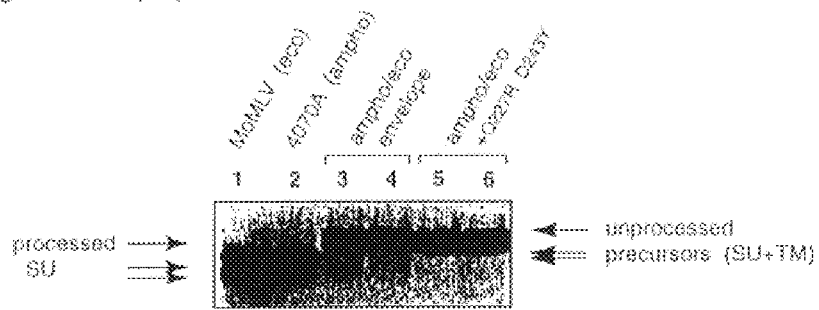
FIG. 8 C. Processing of envelope proteins FIG. 9
A. Virus titers on NIH3T3 (☐) and 293/wild type receptor (■)
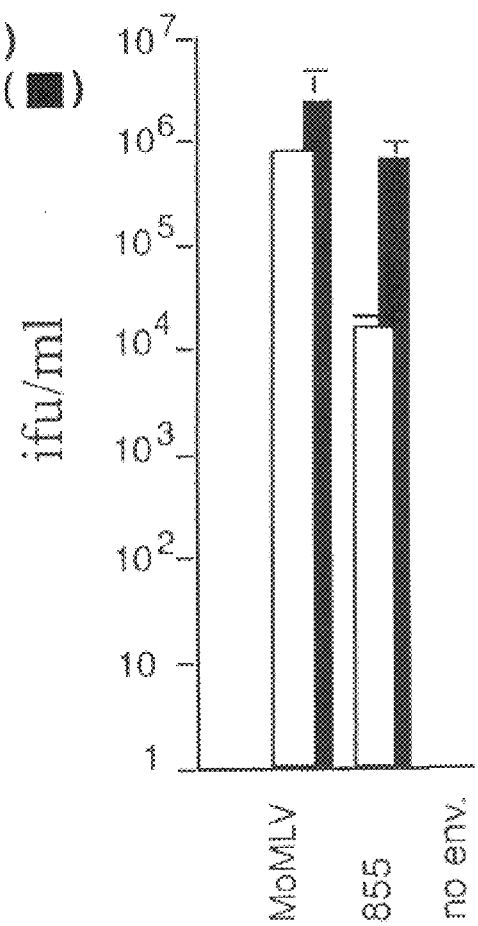
B. Envelope protein in the virions
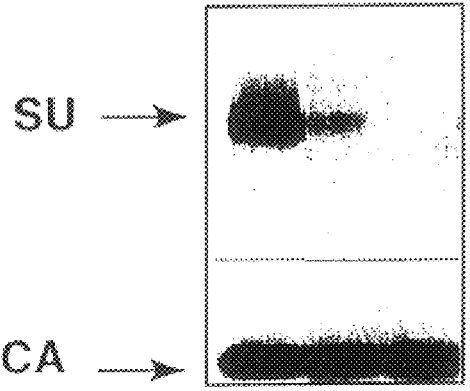
C. Envelope proteins in the cell lysates.
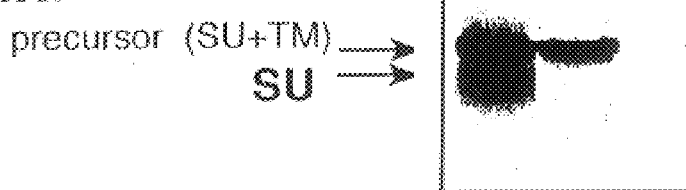

FIG. 10
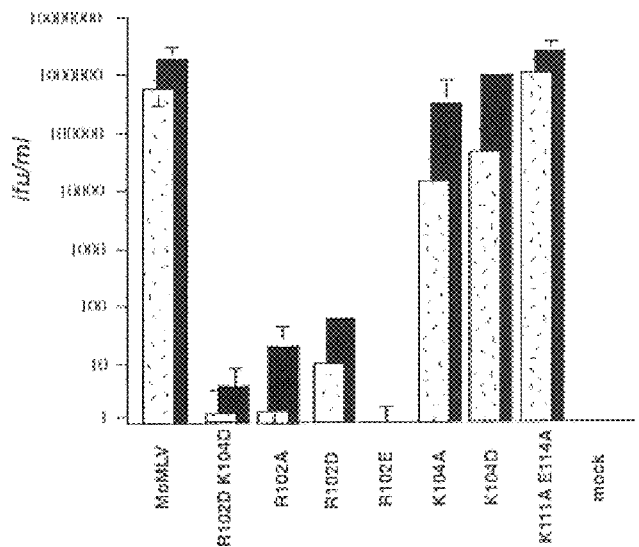
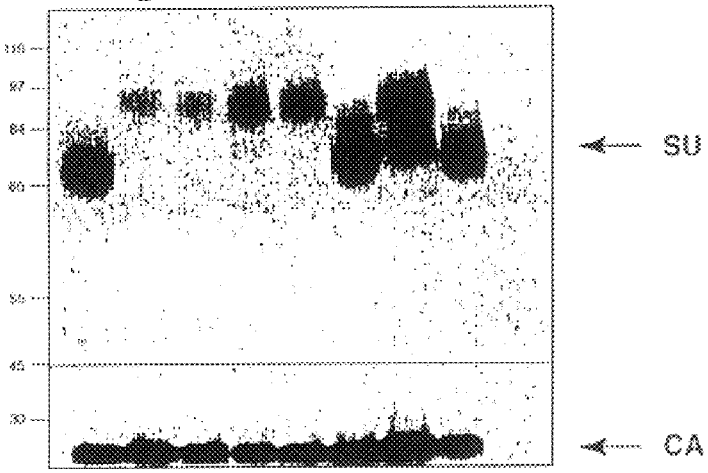
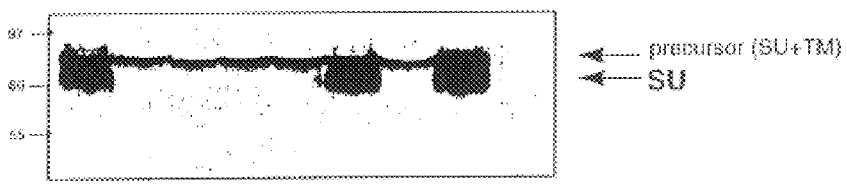

FIG. 11
A. Virus titers on NIH3T3 (☐) and 293/mCAT (■)
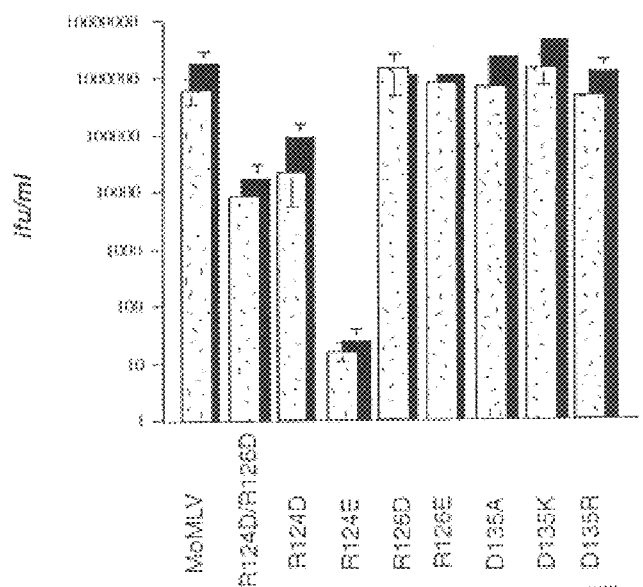
B. Envelope protein in the virions
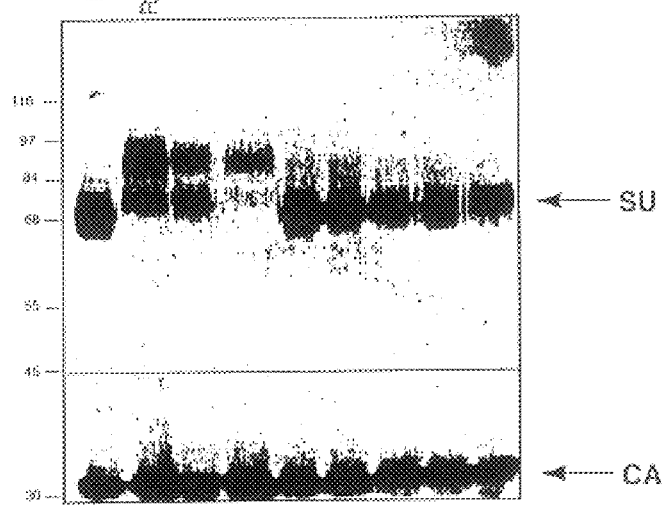
C. Envelope proteins in the cell lysates.

FIG. 12
A. Virus titers on NIH3T3 (☐) and 293/mCAT (■)
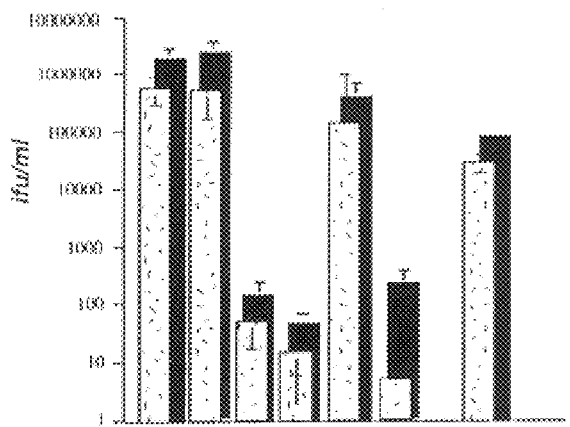
B. Envelope protein in the virions
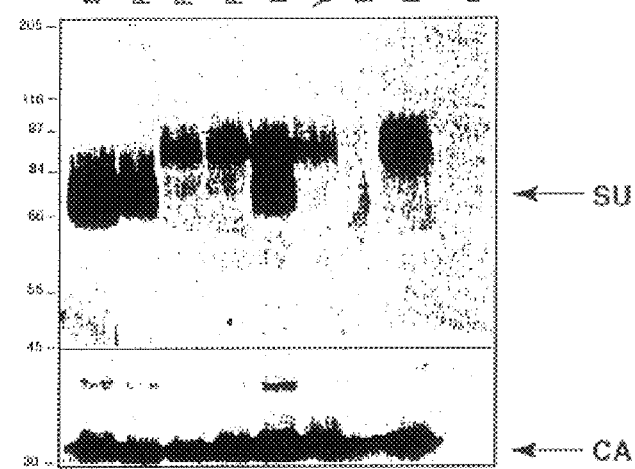
← SU
← CA
C. Envelope proteins in the cell lysates.
← precursor (SU+TM)
← SU

FIG. 14
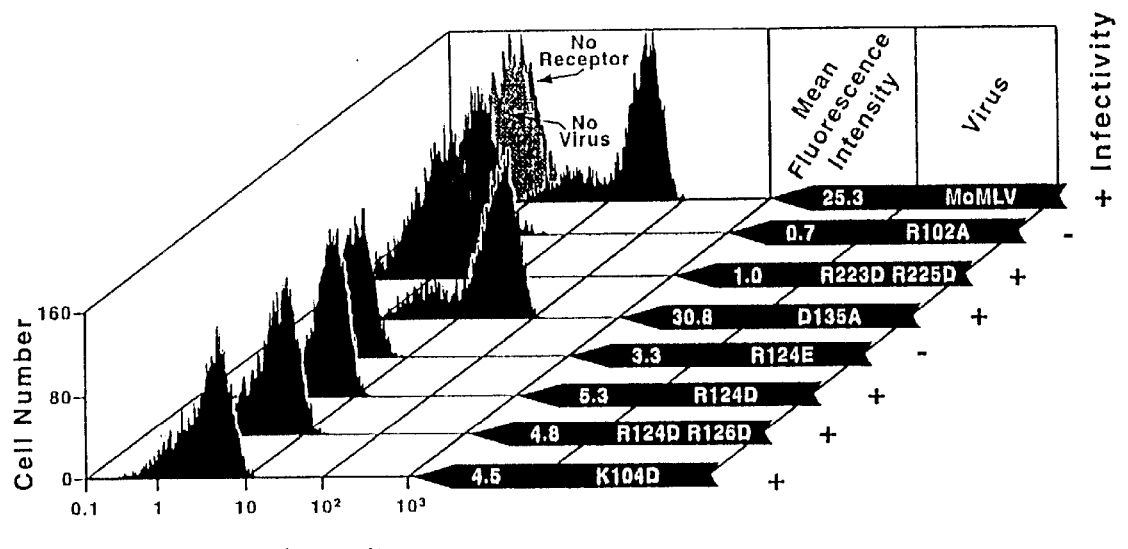
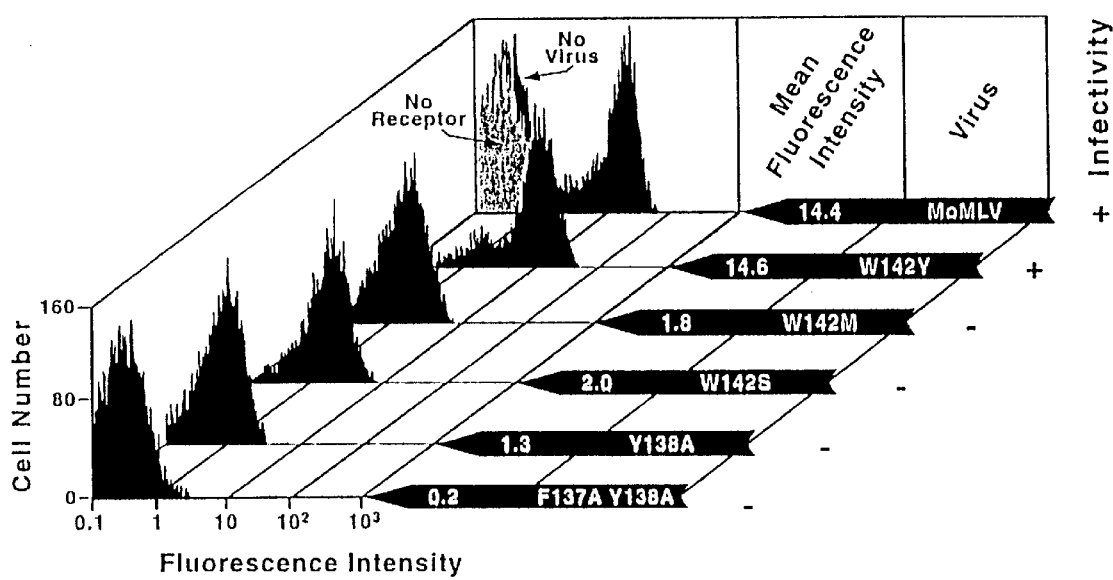

FIG. 15A

```
                                  11      4        5
                               8 16       2       3 8
                               1 18       4       5 8
Moloney   ASPG-SSPHQVYNITWEVTN---GDRETVWATSGNHP-LWT-WWPDLTPDLCMLAHHGPS  54
Friend    AAPG-SSPHQVYNITWEVTN---GDRETVWAISGNHP-LWT-WWPVLTPDLCMLALSGPP  54
4070A     MA---ESPHQVFNVTWRVTNLMTGRTANATSLLGT----VQDAFPKLYFDLCDLV--GEE  51
GALV SEATO -SLQNKNPHQPWTLTWQVLS-QTGD--VVWDTKAVQPP-WT-WWPTLKPDVCALAASLES  54
                     1β           2β          3β     Aα

90    102 104 107 108
Moloney   YWGLEYQSPFSSPPGPPCCSG--GSSPGCSRDCEEPLTSLT-PRCNTAWNRKLDQTHK  111
Friend    HWGLEYQAPYSSPPGPPCCSGSSGSSAGCSRDCDEPLTSLT-PRCNTAWNRKLDQVTHK 113
4070A     -WDP-----------------------SDQEPYVGYG---CKYPAGRQRTR--TFD    78
GALV SEATO -WDIPGTD--------VSSSKRVRPPDSDYTAAYKQIN-WGAIGCSYP--RARTREASST 102
          B3₁₀                        C3α                  Dα

121    128  133  137 138 141 142       151 152   158 160
                        124                 139 140                       159
Moloney   SNEGFYVCP--GPHRPR---ESKSCGGP-DGYCAYWGCETTGRAYWKPSSSWDFITVNN 165
Friend    SSEGFYVCP--GSHRPR---EAKSCGGP-DGFYCASWGCETTGRVYWKPSSSWDYITVDN 167
4070A     ----FYVCP--G-H----TVKSGCGGPGEG-VCGKWGCETTGQAYWKPTSSWDLISLKR 125
GALV SEATO ----FYVCPRDG-RTL--SEARRCGGL-EGLYCKEWDCETTGTGYWLSKSSKDLITVKW 153
               4β          Eα    F3₁₀         5β          6β

196 197 198   203
                                                          199
Moloney   NLTS------DQAVQVC-KDNKW------CNPLVIRFTDAGRRVTSWTTGHYW 205
Friend    NLTT------SQAVQVC-KDNKW------CNPLAIQFTNAGKQVTSWTTGHYW 207
4070A     GNTPWDTGCSKVA-CGPCYDLSKVSNSFQGATRGGRCNPLVLEFTDAGKKATSWDGPKSW 183
GALV SEATO DQNSEWTQKFQQ----CHQTG-W------CNPLKIDFTDKGKLSKDWITGKTW 195
          Gα                         7β         I3₁₀

208 210    217   223 224 225 226 227  233 235    240 241 243
                                                                   242
Moloney   GLRLYVS-GQDPGGTFGIRLRYQNLGPRVPIGPNPVLADQQPLSKPKPVKSPSVTKPPSG 264
Friend    GLRLYVS-GRDPGGTFGIRLRYQNLGPRVPIGPNPVLADQLSLPRPNPLPKPAKSPPASN 266
4070A     GLRLYRT-GTDPIIMFSLRQVLNVGPRVPIGPNPVLPDQRLPSSPIEIVPAPQPPSPLN 242
GALV SEATO GLRFYVS-GH-PGGQFTIRLKITNM-PAVAVGPDLVLVEQGPP-RTSLALPPPLPPREAP 251
          8β         9β

Moloney   -------TPLSPTQ---------LPPAGTENRLLNLVDGAYQALNLTSPDKTQE 302
Friend    STPTLISPSPTPTQ---------PPPAGTGDRLLNLVQGAYQALNLTNPDKTQE 311
4070A     TSYPPSTTSTPSTS---------PTSPSVPQPPGTGDRLLALVKGAYQALNLTNPDKTQE 294
GALV SEATO PPSLPDSNSTALATSAQTPTVRKTIVTLNTPPPTTGDRLFDLVQGAFLTLNATNPGATES 311

Moloney   CWLCLVAGPPYYEGVAVLGTYSNHTSAPANCSVASQHKLTLSEVTGQGLCIGAVPKTHQA 362
Friend    CWLCLVSGPPYYEGVAVLGTYSNHTSAPANCSVASQHKLTLSEVTGRGLCIGTVPKTHQA 371
4070A     CWLCLVSGPPYYEGVAVVGTYTNHSTAPANCTATSQHKLTLSEVTGQGLCMGAVPKTHQA 354
GALV SEATO CWLCLAMGPPYYEAIASSGE-VAYSTDLDRCRWGTQGKLTLTEVSGHGLCIGKVPFTHQH 370
```

FIG. 15B

```
Moloney     LCNTTQTSSRGS-Y-YLVAPTGTMWACSTGLTPCISTTILNLTTDYCVLVELWPRVTYHS  420
Friend      LCNTTLKIDKGS-Y-YLVAPTGTTWACNTGLTPCLSATVLNRTTDYCVLVELWPRVTYHP  429
4070A       LCNTTQSAGSGS-Y-YLAAPAGTMWACSTGLTPCLSTTVLNLTTDYCVLVELWPRVIYHS  412
GALV SEATO  LCNQTLSINSSGDHQYLLPSNHSWWACSTGLTPCLSTSVFNQTRDFCIQVQLIPRIYYY-  430
```

```
                             Precursor
                             Cleavage
                        SU ──→│──→ TM
Moloney     PSYVYGLFERSN--RHKR│EPVSLTLALLLGGLTMGGIAAGIGTGTTALMAT----QQ-FQ  473
Friend      PSYVYSQFEKSY--RHKR│EPVSLTLALLLGGLTMGGIAAGVGTGTTALVAT----QQ-FQ  482
4070A       PDYMYGQLEQRT--KYKR│EPVSLTLALLLGGLTMGGIAAGIGTGTTALIKT----QQ-FE  465
GALV SEATO  PEEVLLQAYDNSHPRTKR│EAVSLTLAVLL-GL---GITAGIGTGSTALIKGPIDLQQGLT  485
```

```
Moloney     QLQAAVQDDLREVEKSISNLEKSLTSLSEVVLQNRRGLDLLFLKEGGLCAALKEECCFYA  533
Friend      QLHAAVQDDLKEVEKSITNLEKSLTSLSEVVLQNRRGLDLLFLKEGGLCAALKEECCFYA  542
4070A       QLHAAIQTDLNEVEKSITNLEKSLTSLSEVVLQNRRGLDLLFLKEGGLCAALKEECCFYA  525
GALV SEATO  SLQIAIDADLRALQDSVSKLEDSLTSLSEVVLQNRRGLDLLFLKEGGLCAALKEECCFYI  545
```

```
Moloney     DHTGLVRDSMAKLRERLNQRQKLFESTQGWFEGLFNRSPWFTTLISTIMGPLIVLLMILL  593
Friend      DHTGLVRDSMAKLRERLTQRQKLFESSQGWFEGLFNRSPWFTTLISTIMGPLIILLLILL  602
4070A       DHTGLVRDSMAKLRERLNQRQKLFETGQGWFEGLFNRSPWFTTLISTIMGPLIVLLLILL  585
GALV SEATO  DHSGAVRDSMKKLKEKLDKRQLERQKSQNWYEGWFNNSPWFTTLLSTIAGPLLLLLLLLI  605
```

```
Moloney     FGPCILNRLVQFVKDRISVVQALVLTQQYHQLKPIEYEP                      632
Friend      FGPCILNRLVQFVKDRISVVQALVLTQQYHQLKPLEYEP                      641
4070A       FGPCILNRLVQFVKDRISVVQALVLTQQYHQLKPIEYEP                      624
GALV SEATO  LGPCIINKLVQFINDRISAC                                         625
```

FIG. 16A

```
                            8   11 16 18       24         35 38
Consensus      AAPG-DSPHQVFNVTWEVTNLMTGDTANATSLLGT----WTDWFPDLYFDLCDLA--GPS
Moloney        ASPG-SSPHQVYNITWEVIN---GDRETVWATSGNHP-LWT-WWPDLTPDLCMLAHHGPS  54
Friend         AAPG-SSPHQVYNITWEVIN---GDRETVWAISGNHP-LWT-WWPVLTPDLCMLASGPS  54
AKV            VTLG-NSPHQVFNLTWEVIN---GDRETVWAITGNHP-LWT-WWPDLTPDLCMLALHGPS  54
CasBrE         LASR-DNPHQVYNITWEVIN---GEQDTVWAVTGNHP-LWT-WWPDLTPDLCMLAHGPT  54
RadLV          VALG-NSPHQVFNLSWEVIN---EDRETVWAITGNHP-LWT-WWPDLTPDLCMLAHGPS  54
10A1           MA---ESPHQVFNVTWRVINLMTGRTANATSLLGT----VQDAFPRLYFDLCDLV--GEE  51
4070A          MA---ESPHQVFNVTWRVINLMTGRTANATSLLGT----VQDAFPKLYFDLCDLV--GEE  51
MCF1233        -SVQDSPHQVFNVTWRVINLMTGQTANATSLLGT----MTDAFPKLYFDLCDLI--GDD  53
Xeno CWM       --VQRDSPHQVFNVTWRVINLMTGQTANATSLLGT----MTDTFPKLYFDLCDLV--GD-  52
Xeno NZB       ASVQRDSPHQIFNVTWRVINLMTGQTANATSLLGT----MTDTFPKLYFDLCDLV--GD-  54
FeLV-A         ANP---SPHQIYNVTWTVITNVQTNTQANATSMLGT----LTDAYPTLHVDLCDLV--GNT  51
FeLV-B         ANP---SPHQVYNVTWTIITNLVTGTKANATSMLGT----LTDAFPTMYFDLCDII--GNT  51
GALV SEATO     -SLQNKNPHQFMTLTWQVLS-QTGD--VVWDTKAVQPP-WT-WWPTLKPDVCALAASLES  54
                             1β              2β            3β       Aα
```

```
                            -W  -  -           -DCE -  -L-G -   -C- -G -L- R-  -THD
                                                                102 104 107 108
                                               90
Consensus       -WDLE------------------DCEEPLTGYG---CNTPWGRLRLR--THD
Moloney         YWGLEYQSPFSSPPGPPCCSG--GSSPGCSRDCEEPLTSLT-PRCNTAWNRLKLDQTTHK  111
Friend          HWGLEYQAPYSSPPGPPCCSGSSGSSAGCSRDCDEPLTSLT-PRCNTAWNRLKLDQVTHK  113
AKV             YWGLEYRAPFSPPPGPPCCSGSSDSTPGCSRDCEEPLTSYT-PRCNTAWNRLKLSKVTHA  113
CasBrE          HWGLDNHPPYSSPPGPPCCSGDAGAVSGCARDCEPLTSYS-PRCNTAWNRLKLARVTHA  113
RadLV           YWGLEYQAPFSPPPGPPCCSRSSGSTPGCSRDCEEPLTSYT-PRCNTAWNRLKLSKVTHA  113
10A1            -WDP--------------------SDQEPYVGYG---CKYPGGRKRTR--TFD  78
4070A           -WDP--------------------SDQEPYVGYG---CKYPAGRQRTR--TFD  78
MCF1233         -WD---------------------ET-GLG---CRTPGGRKRAR--TFD  74
Xeno CWM        HWDDP-------------------EPDIGDG---CRSPGGKRSR--LYD  77
Xeno NZB        YWDDP-------------------EPDIGDG---CRTPGGRRRTR--LYD  79
FeLV-A          -WEPIVL-----------------DPTNVKHGARYSSSKYG-CKTT-DRKKQQQ--TYP  88
FeLV-B          -WNPS-------------------DQEPFPGYG---CDQPM-R-RWQQRNTP  78
GALV SEATO      -WDIPGTD--------VSSSKRVRPPDSDYTAAYKQIT-WGAIGCSYP--RARTRMASST 102
                 B3₁₀                   C3α                    Dα
```

```
                                   121 124  128  133 136 137 138 141 142    151 152   158 160
Consensus       ----FYVCP--G-HRP---TVARGCGP-EG-YCASWGCETTGQ-AYWKPSSSWDL-ITVKR
Moloney         SNEGFYVCP--GPHRPR---ESKSCGP-DS-YCAYWGCETTGRAYWKPSSSWDFITVNN  165
Friend          SSEGFYVCP--GSHRPR---EAKSCGP-DS-YCASWGCETTGRVYWKPSSSWDYITVDN  167
AKV             HNGGFYVCP--GPHRPR---WARSCGP-ES-YCASWGCETTGRASWKPSSSWDYITVSN  167
CasBrE          PKEGFYICP--GSHRPR---WARSCGL-DA-YCASWGCETTGRAAWNPTSSSWDYITVSN  167
RadLV           HNEGFYVCP--GPHRPR---WARSCGP-ES-YCASWGCETTGRASWKPSSSWDYITVSN  167
10A1            ----FYVCP--G-H----TVSGCGPREG-YCGIWGCETTGQAYWKPTSSWDLISLKR  125
4070A           ----FYVCP--G-H----TVSGCGPGEG-YCGKWGCETTGQAYWKPTSSWDLISLKR  125
MCF1233         ----FYVCP--G-H----TVPTGCGPREG-YCGKWGCETTGQAYWKPSSSWDLISLKR  121
Xeno CWM        ----FYVCP--G-H----TVPIGCGPGEG-YCGKWGCETTGQAYWKPSSSWDLISLKR  124
Xeno NZB        ----FYVCP--G-H----TVPIGCGPGEG-YCGKWGCETTGQAYWKPSSSWDLISLKR  126
FeLV-A          ----FYVCP--G-HKPSLGPKGTHCGGAQDG-FCAAWGCETTGEAWWKPSSSWDYITVKR  140
FeLV-B          ----FYVCP--G-HK----ANRKQCGGPQDG-FCAVWGCETTGETYWRPTSSYDYITVKK  125
GALV SEATO      ----FYVCPRDG-RTL---SEARRCGGESLYCKEWDCETTGTGYWLSKSSSDLITVKW  153
                     4β              Dα   F3₁₀        5β           6β
```

FIG. 16B

```
                                                                        196
                                                                        198
                                                                        199      203
Consensus   GLTS-------Q---PCYDSSKW---------GGRCNPLVLEFTDAGKQA-SWDTPKVW
Moloney     NLTS-------DQAVQVC-KDNKW---------CNPLVIRFTDAGRRVTSWTTGHYW  205
Friend      NLTT-------SQAVQVC-KDNKW---------CNPLAIQFTNAGKQVTSWTTGHYW  207
AKV         NLTS-------DQATPVC-KGNEW---------CNSLTIRFTSFGKQATSWVTGHWW  207
CasBrE      NLTS-------SQATKAC-KNNGW---------CNPLVIRFTGPGKRATSWTTGHFW  207
RadLV       NLTS-------GQATPVC-KNNTW---------CNSLTIRFTSLGKQATSWVTGHWW  207
10A1        GNTPWDTGCSKMA-CGPCYDLSKVSNSFQGATRGGRCNPLVLEFTDAGKKA-NWDGPKSW  183
4070A       GNTPWDTGCSKVA-CGPCYDLSKVSNSFQGATRGGRCNPLVLEFTDAGKKA-NWDGPKSW  183
MCF1233     GNTPQNQG-------PCYDSSAVSSDIKGATPGGRCNPLVLEFTDAGKKA-SWDGPKVW  172
Xeno CWM    GNTPKDQG-------PCYLSS-VSSGVQGATPGGRCNPLVLEFTDAGKKA-SWDAPKVW  174
Xeno NZB    GNTPKDQG-------PCYDSS-VSSGVQGATPGGRCNPLVLEFTDAGRKA-SWDAPKVW  176
FeLV-A      GSSQD---------NSC-------------EGKCNPLILQFTQKGRQA-SWDGPKMW  174
FeLV-B      GVTQGIYQCSGGGWCGPCYDKAVHSSTT-GASEGGRCNPLILQFTQKGRQT-SWDGPKSW  183
GALV SEATO  DQNSEWTQKFQQ-----CHQTG-W----------CNPLKIDFTDKGKLSKDWITGKTW  195
               Gα                              7β       13₁₀
```

```
                208                      235        241
                210       217    223-227  234       243
Consensus   GLRLYRS-GHDPGLTFSIRRQVLNIGPRVPTGPNPVLADQLPPSRPVQIRSPPPPQPPPN
Moloney     GLRLYVS-GQDPGLTFGIRLRYQNLGPRVPIGPNPVLADQQPLSKPKPVKSPSVTKPPSG  264
Friend      GLRLYVS-GRDPGLTFGIRLRYQNLGPRVPIGPNPVLADQLSLPRPNPLPKPAKSPPASN  266
AKV         GLRLYVS-GHDPGLIFGIRLKITDSGPRVPIGPNPVLSDRRPPSRPRPTRSPPPS----N  262
CasBrE      GLRLYIS-GHDPGLTFGIRLKVTDLGPRVPIGPNPVLSDQRPPSRPVPARPPPPSASP--  265
RadLV       GLRLYVS-GHDPGLIFGIRLKITDSGPRVPIGPNPVLSDQRPPSQPR---SPPH----SN  259
10A1        GLRLYRT-GTDPITMFSLTRQVLNIGPRIPIGPNPVITGQLPPSRPVQIRLPRPPQPPPT  242
4070A       GLRLYRT-GTDPITMFSLTRQVLNVGPRVPIGPNPVLPDQRLPSSPIEIVPAPQPPSPLN  242
MCF1233     GLRLVRPTGTDPVTRFSLTRRVLNIGPRVPIGPNPVIADQLPPSRPVQIMLPRPPQPPPP  232
Xeno CWM    GLRLYRSTGADPVTRFSLTRQVLNVGPRVPIGPNPVITEQLPPSQPVQIMLPRPPHPPPS  234
Xeno NZB    GLRLYRSTGADPVTRFSLTRQVLNVGPRVPIGPNPVITDQLPPSQPVQIMLPRPPHPPPS  236
FeLV-A      GLRLYRT-GYDPIALFTVSRQVITPPQAMGPNLVLDQKPPSRQSQTGSKVATQRLQT  233
FeLV-B      GLRLYRS-GYDPIALFSVSRQVMTITPPQAMGPNLVLDQKPPSRQSQIESRVTPHHSQG  242
GALV SEATO  GLRFYVS-GH-PGVQFTIRLKITNM-PAVAVGPDLVLVEQGPP-RTSLALPPPLPPREAP  251
                8β         9β
```

```
Consensus   GTPTIVPTTL----------------PPPPGTGDRLLNLVQGAYQALNLTSPDKTQE
Moloney     -------TPLSPTQ--------------LPPAGTENRLLNLVDGAYQALNLTSPDKTQE  302
Friend      STPTLISPSPTPTQ--------------PPPAGTGDRLLNLVQGAYQALNLTNPDKTQE  311
AKV         STPTETPLTLPE----------------PPPAGVENRLLNLVKGAYQALNLTSPDRTQE  305
CasBrE      STPTI-----------------------PPQQGTGDRLLNLVQGAYLTLNMTDPTRTQE  300
RadLV       STPTETPLTLPE----------------PPPAGVENRLLNLVKGAYQALNLTSPDRTQE  302
10A1        GAASIVPETA------------------PPSQQPGTGDRLLNLVEGAYQALNLTNPDKTQE  285
4070A       TSYPPSTTSTPSTS--------PTSPSVPQPPPGTGDRLLALVKGAYQALNLTNPDKTQE  294
MCF1233     GASSIVPETA------------------PPSQQPGTGDRLLNLVDGAYQALNLTSPDKTQE  275
Xeno CWM    GAASMVPGA-------------------PPPSQQPGTGDRLLNLVKGAYQALNLTSPDRTQE  277
Xeno NZB    GTVSMVPGA-------------------PPPSQQPGTGDRLLNLVEGAYQALNLTSPDKTQE  279
FeLV-A      NESASRSVAPTTVV--------------PKRIGTGDRLINLVQGTYLALNATDPNKTKD  278
FeLV-B      NGGTPGITLVNASIAPLSTPVT----PASPKRIGTGDRLINLVQGTYLALNATDPNRTKD  298
GALV SEATO  PPSLPDSNSTALATSAQTPTVRKTIVTLNTPPPTTGDRLFDLVQGAFLTLNATNPGATES  311
```

FIG. 16C

```
Consensus   CWLCLVSGPPYYEGVAVLGTYSNHTSAPANCSVASQHKLTLSEVTGQGLCIGAVPKTHQA

Moloney     CWLCLVAGPPYYEGVAVLGTYSNHTSAPANCSVASQHKLTLSEVTGQGLCIGAVPKTHQA 362
Friend      CWLCLVSGPPYYEGVAVLGTYSNHTSAPANCSVASQHKLTLSEVTGRGLCIGTVPKTHQA 371
AKV         CWLCLVSGPPYYEGVAVLGTYSNHTSAPANCSVASQHKLTLSEVTGQGLCIGAVPKTHQV 365
CasBrE      CWLCLVSEPPYYEGVAVLREYTSHETAPANCSSGSQHKLTLSEVTGQGRCLGTVPKTHQA 360
RadLV       CWLCLVSGPPYYEGVAVLGTYSNHTSAPANCSVASQHKLTLSEVTGRGLCVGAVPKTHQA 362
10A1        CWLCLVSGPPYYEGVAVVGTYTNHSTAPASCTATSQHKLTLSEVTGQGLCMGALPKTHQA 345
4070A       CWLCLVSGPPYYEGVAVVGTYTNHSTAPANCTATSQHKLTLSEVTGQGLCMGAVPKTHQA 354
MCF1233     CWLCLVAGPPYYEGVAVLGTYSNHTSAPTNCSVASQHKLTLSEVTGQGLCVGAVPKTHQA 335
Xeno CWM    CWLCLVSGPPYYEGVAVLGTYSNHTSAPANCSVASQHKLTLSEVTGQGLCVGAVPKTHQA 337
Xeno NZB    CWLCLVSGPPYYEGVAVLGTYSNHTSAPANCSVASQHKLTLSEVTGQGLCVGAVPKTHQA 339
FeLV-A      CWLCLVSRPPYYEGIAILGNYSNQTNPPPSCLSTPQHKLTISEVSGQGLCIGTVPKTHQA 338
FeLV-B      CWLCLVSRPPYYEGIAILGNYSNQTNPPPSCLSIPQHKLTISEVSGQGLCIGTVPKTHQA 358
GALV SEATO  CWLCLAMGPPYYEAIASSGE-VAYSTDLDRCRWGTQGKLTLTEVSGHGLCIGKVPFTHQH 370

Consensus   LCNTTQKTSSGS-Y-YLAAPAGTIWACNTGLTPCLSTTVLNLTTDYCVLVELWPRVTYHS

Moloney     LCNTTQTSSRGS-Y-YLVAPTGTMWACSTGLTPCISTTILNLTTDYCVLVELWPRVTYHS 420
Friend      LCNTTLKIDKGS-Y-YLVAPTGTTWACNTGLTPCLSATVLNRTTDYCVLVELWPRVTYHP 429
AKV         LCNTTQKTSDGS-Y-YLAAPTGTTWACSTGLTPCISTTILDLTTDYCVLVELWPRVTYHS 423
CasBrE      LCNRTEPTVSGS-N-YLVAPEGTLWACSTGLTPCLSTTVLNLTTDYCVLVELWPKVTYHS 418
RadLV       LCNTTQNTSGGS-Y-YLAAPAGTIWACNTGLTPCLSTTVLNLTTDYCVLVELWPRVTYHS 420
10A1        LCNTTQSAGSGS-Y-YLAAPAGTMWACSTGLTPCLSTTMLNLTTDYCVLVELWPRIIYHS 403
4070A       LCNTTQSAGSGS-Y-YLAAPAGTMWACSTGLTPCLSTTVLNLTTDYCVLVELWPRVIYHS 412
MCF1233     LCNTTQKTSDGS-Y-YLAAPAGTIWACNTGLTPCLSTTVLDLTTDYCVLVELWPKVTYHS 393
Xeno CWM    LCNTTQKASDGS-Y-YLAAPAGTIWACNTGLTPCLSTTVLNLTTDYCVLVELWPKVTYHS 395
Xeno NZB    LCNTTQKTSDGS-Y-YLAAPAGTIWACNTGLTPCLSTTVLNLTTDYCVLVELWPKVTYHS 397
FeLV-A      LCNETQQGHTGA-H-YLAAPNGTYWACNTGLTPCISMAVLNWTSDFCVLIELWPRVTYHQ 396
FeLV-B      LCNETQQGHTGA-H-YLAAPNGTYWACNTGLTPCISMAVLNWTSDFCVLIELWPRVTYHQ 416
GALV SEATO  LCNQTLSINSSGDHQYLLPSNHSWWACSTGLTPCLSTSVFNQTRDFCIQVQLIPRIYYY- 430

Precursor
                      Cleavage
                  SU ──→ │ ──→ TM
Consensus   PSYVYGQFEKRT--KYKR│EPVSLTLALLLGGLTMGGIAAGVGTGTTALVAT----QQ-FQ Moloney     PSYVYGLFERSN--RHKR│EPVSLTLALLLGGLTMGGIAAGIGTGTTALMAT----QQ-FQ 473
Friend      PSYVYSQFEKSY--RHKR│EPVSLTLALLLGGLTMGGIAAGVGTGTTALVAT----QQ-FQ 482
AKV         PSYVYHQFERRA--KYKR│EPVSLTLALLLGGLTMGGIAAGVGTGTTALVAT----QQ-FQ 476
CasBrE      PDYVYTQFEPGA--RFRR│EPVSLTLALLPEGLTMGGIAAGVGTGTTALVAT----QQ-FQ 471
RadLV       PSYVYHQFEGRA--KYKR│EPVSLTLALLLGGLTMGGIAAGVGTGTTALVAT----QQ--- 472
10A1        PDYMYGQLEQRT--KYKR│EPVSLTLALLLGGLTMGGIAAGIGTGTTALIKT----QQ-FE 456
4070A       PDYMYGQLEQRT--KYKR│EPVSLTLALLLGGLTMGGIAAGIGTGTTALIKT----QQ-FE 465
MCF1233     PGYVYDQFERKT--KYKR│EPVSLTLALLLGGLTMGGIAAGVGTGTTALVAT----QQ-FQ 446
Xeno CWM    PGYVYDQFERKT--KYKR│EPVSLTLALLLGGLTMGGIAAGVGTGTTALVAT----KQ-FE 448
Xeno NZB    PDYVYGQFEKKT--KYKR│EPVSLTLALLLGGLTMGGIAAGVGTGTTALVAT----KQ-FE 450
FeLV-A      PEYVYTHFAKAV--RFRR│EPISLTVALMLGGLTVGGIAAGVGTGTKALLET----AQ-FR 449
FeLV-B      PEYVYTHFAKAA--RFRR│EPISLTVALMLGGLTVGGIAAGVGTGTKALIET----AQ-FR 469
GALV SEATO  PEEVLLQAYDNSHPRTKR│EAVSLTLAVLL-GL---GITAGIGTGSTALIKGPIDLQQGLT 485
```

STABLE ENVELOPE PROTEINS FOR RETROVIRAL, VIRAL AND LIPOSOME VECTORS AND USE IN GENE DRUG THERAPY

This application claims priority of copending provisional application(s) No. 60/086,149 filed on May 20, 1998.

FEDERAL SUPPORT

This invention arose from research funded by the following NIH grant: R01 A133410.

FIELD OF THE INVENTION

This invention includes retrovirus envelope mutants into which heterologous peptide or glycopeptide sequences can be fused for expression and stable presentation on retroviral, viral and liposome vectors. The invention further relates to methods of making and using these retrovirus envelopes for gene and drug therapy.

I. BACKGROUND

1. Gene Therapy Vectors

Numerous gene therapy vectors have been created. These vectors are constantly being engineered to overcome problems caused by tropism, infectivity and virus stability. Engineered gene therapy virus vectors include adenoviruses (see as examples, D. Armentano et al., 1998 U.S. Pat. No. 5,707,618; T. J. Wickham et al., 1998 U.S. Pat. No. 5,731,190; and M. Cotten et al., 1997 U.S. Pat. No. 5,693,509), herpes simplex viruses (R. L. Martuza et al., 1998 U.S. Pat. No. 5,728,379) and retrovirus vectors. Non-viral vectors include episomal and liposomal vectors such as those described in M. J. Cooper, 1997 U.S. Pat. No. 5,624,820; and L. Li et al., 1997 U.S. Pat. No. 5,641,508.

Retroviruses have been preferred vectors for gene therapy based on their ability to integrate retroviral DNA into the genome of the host cell. Retroviral gene therapy patents include vectors with multiple cloning sites (M. Eglitis et al., 1997 U.S. Pat. No. 5,672,510), retroviruses with mixed LTRs (H. M. Temin et al., 1996 U.S. Pat. No. 5,554,524), retroviruses that deliver genetic elements that stimulate an immune response (H. E. Gruber et al., 1998 U.S. Pat. Nos. 5,716,826 and 5,716,426), and vectors with specific envelope proteins (E. F. Vanin et al., 1998 U.S. Pat. No. 5,710,037).

2. Retroviral Envelope Mutations and Gene Therapy

The retrovirus envelope protein is the viral element that allows a gene therapy vector to recognize and bind to the target, typically a host cell. The native or wild-type retrovirus envelope protein has a natural tropism for certain target cells, which typically must be overcome if the virus is to be used as a gene therapy vector. However, the envelope protein engineered to overcome wild type tropisms must nevertheless maintain the characteristics of: (1) surface (SU) protein stability such that it is not shed from the virus particle too quickly; and (2) infectivity wherein the virion can infect the host cell and introduce the genetic material it is carrying.

The envelope protein in all retroviruses is produced as a glycoprotein precursor that matures into two cleavage products: the surface protein (SU) and transmembrane protein (TM). TM and SU are held together by disulfide bonds and perhaps other non-covalent interactions (J. N. Coffin et al., 1997 *Retroviruses* Cold Spring Harbor Press). Envelope shedding, in Moloney murine leukemia virus (MoMLV) for example, occurs as result of the weak linkage created by the disulfide bonds between the TM (p15E) and the SU (gp70). Although mutations have been made to prevent cleavage of the envelope precursor protein in MoMLV gp80 into SU and TM, typically there has been an associated loss of incorporation into virions observed with these mutants making them undesirable vectors (E. O. Freed et al., 1987 *J. Virol.* 61: 2852–6). Finally, in HIV, the endoproteolytic cleavage of the envelope precursor protein has been demonstrated to be required for the activation of HIV (J. M. McCune et al., 1988 *Cell* 53: 55–67).

Envelope proteins also are known to possess highly conserved functional domains. In MoMLV, amino acid residues 1–33 constitute the leader sequence; amino acids 34–263 constitute the receptor binding domain; amino acids 264–312 comprise the hinge region; and residues 313–469 constitute the body portion of the surface protein (J. M. Mason et al., 1997 U.S. Pat. No. 6,643,770). Mutagenesis analysis of the envelope protein has led to the discovery of other amino acid residues that appear responsible for receptor binding (A. J. MacKrell et al., 1996 *J. Virol.* 70: 1768–74) and fusion events (Y. Bae et al., 1997 *J. Virol.* 71: 2092–9). Although at least one group has proposed that the N-terminal 72 residues of the amphotropic 4070A isolate are not required, for amphotropic receptor usage (C. Peredo et al., 1996 *J. Virol.* 70: 3142–52), other researchers have demonstrated that the N-terminus of the envelope protein is required especially when preparing fusion envelope proteins (see for examples, F-L. Cosset et al., 1995 *J. Virol.* 69: 6314–22; S. Valsesia-Wittmann et al., 1996 *J. Virol.* 70: 2059–64; and J. M. Heard et al., 1991 *J. Virol.* 65: 4026–32). Additional mutagenic analysis of retrovirus (e.g., in PVC-211 murine leukemia virus and MoMLV) envelope proteins has been described and is discussed in the following: M. Masuda et al., 1996 *J. Virol.* 70: 8534–9; and A. J. MacKrell et al., 1996; and H. Skov et al., 1993 *J. Gen. Virol.* 74:707–14).

3. Fusion Glycoproteins

One method of overcoming the retrovirus' natural tropism is by expressing an envelope fusion glycoprotein. A fusion glycoprotein contains the retroviral envelope (env) protein, e.g., the SU protein, linked to a selected peptide or glycopeptide. For examples, see R. W. Paul et al., 1998 U.S. Pat. No. 5,736,387 and S. J. Russell et al., 1998 U.S. Pat. No. 5,723,287. Many of the engineered envelope proteins created to target the retrovirus particle to other cells comprise insertions of heterologous peptides into the amino terminus of SU (F-L Cosset et al., 1995 *J. Virol.* 69: 6314–22). Fusion glycoproteins have been developed to compensate for the folding problems created due to changes in the glycosylated pattern. (S. Kayman et al., 1997 U.S. Pat. No. 5,643,756).

SUMMARY OF THE INVENTION

The inventors disclose novel mutant envelope proteins which when linked or fused to a heterologous peptide or glycopeptide have enhanced stability and maintain retrovirus virion titer and infectivity levels comparable to that observed for wild type retrovirus envelope proteins. Due to the ability to restore the target penetration capability that is lost or greatly diminished upon fusion of a heterologous sequence into the envelope protein, vectors containing these mutant envelope proteins have an increased ability to penetrate targets, typically cells, and a correspondingly increased ability to deliver nucleic acids or drugs. Further, due to the increased association between SU and TM the mutant envelope proteins are more stable and vectors containing these mutant envelope proteins are less likely to shed off of the vector or infective particle. Decreased envelope shedding increases the life span of a virion so it can survive such mechanical stressors as freezing and thawing or vascular shearing forces. Correspondingly, vectors containing these mutant envelope proteins would be extremely useful as nucleic acid and drug delivery vehicles. Methods of identifying retrovirus mutant envelope proteins possessing these desirable characteristics based on three-dimensional structural motifs are also disclosed.

This invention discloses isolated nucleic acid molecules encoding retrovirus envelope proteins or polypeptide fragments thereof having decreased shedding of binding sequences through the suppression of envelope protein cleavage comprising an amino acid substitution in at least one amino acid of at least one of seven motifs or corresponding amino acid residues in other retrovirus envelope proteins. The first five (5) motifs as described for MoMuLV which exhibit this function comprise the following amino acids: (1) $^{104}$Lys, $^{107}$Glu, $^{90}$Thr, $^{102}$Arg and $^{108}$Thr; (2) $^{124}$Arg, $^{138}$Tyr, $^{128}$Ser, $^{132}$Gly, $^{134}$Pro, $^{121}$Gly, and $^{133}$Gly; (3) $^{223}$Arg, $^{225}$Arg, $^{224}$Leu, $^{16}$Glu, $^{24}$Thr, and $^{201}$Thr; (4) $^{137}$Phe, $^{135}$Asp, $^{136}$Ser, $^{208}$Arg, and $^{217}$Gly; and (5) $^{142}$Trp, $^{152}$Trp, $^{210}$Tyr, $^{141}$Tyr and $^{151}$Tyr. For motif 6, which comprises $^{227}$Gln, $^{228}$Asn, and $^{243}$Asp, the isolated nucleic acid molecule encodes a retrovirus envelope protein or polypeptide fragment thereof having increased penetration capability through restoration of the function of residue 8His and decreased shedding of binding sequences through stabilization of SU:TM interaction comprising an amino acid substitution in at least one of the listed amino acid residues. For the seventh motif, the envelope protein encoded by the nucleic acid molecule has increased penetration capability arising from a substitution in at least one of the residues comprising the motif containing: $^{198}$Ser, $^{11}$Tyr, $^{226}$Tyr, $^{35}$Trp, $^{38}$Trp, $^{196}$Val, $^{197}$Thr, $^{160}$Tyr, $^{158}$Trp, $^{123}$His, $^{203}$His, $^{233}$Val, $^{235}$Ile, $^{240}$Val, $^{241}$Leu, and $^{8}$His. The amino acid substitutions contemplated for the residues of these seven motifs are listed in Table I. A short hand form for delimiting said motifs 1–7 is denoted by amino acids $^{104}$Lys, $^{124}$Arg, $^{223}$Arg, $^{137}$Phe, $^{142}$Trp, $^{227}$Gln and $^{198}$Ser, respectively. Substitution of amino acids comprising other retroviral envelope proteins which are in alignment with the above amino acids comprising the 7 motifs are also contemplated. Such an alignment of amino acids comprised in the retroviral envelope proteins for a variety of retroviruses are displayed in the alignments as set forth in FIGS. 15–17.

The inventors also disclose a retrovirus envelope protein that is encoded by the described nucleic acid molecules.

The retrovirus envelope proteins and fragments thereof and the nucleic acid molecules encoding said envelope proteins described above are derived from: Moloney MLV; Friend MLV; MLV 10A1; MLV 4070A; AKV MLV; CasBrE; RadLV; MCF1233; Xeno CWM; Xeno NZB; feline leukemia virus types A and B (FeLV-A and FeLV-B); avian leukosis retrovirus; GALV (gibbon ape leukemia viruses) SEATO strain; and human immunodeficiency virus type 1 (HIV-1). The residue or residues in one or more of the motifs to be altered are determined by alignment of the MoMLV envelope protein sequence with one of these other retrovirus sequences. Alignment of the residues of each of the motifs for these retroviruses is depicted in FIGS. 15–17. Similar alignments can be generated for human immunodeficiency virus type 2 (HIV-2) and simian immunodeficiency virus (SIV) envelope proteins using the Megalign software of DNASTAR.

The invention also discloses recombinant retrovirus particles that infect eukaryotic cells comprising one of the mutant envelope proteins or polypeptide fragments described above and a nucleic acid encoding said envelope protein or polypeptide fragment thereof. Eukaryotic cells contemplated for infection include vertebrate cells, mammalian cells and human cells. The envelope proteins of these recombinant retrovirus particles may further comprise a heterologous polypeptide displayed on the external surface of the particle wherein the heterologous peptide is fused to the retroviral envelope protein or polypeptide fragment thereof.

The invention contemplates a producer cell line transduced with one of the above described retrovirus particles, as well as retroviruses particles produced from said producer cell line. These retrovirus particles can also be utilized to transduce eukaryotic cells, such as vertebrate cells, mammalian cells and human cells.

The inventors also disclose packaging cell lines comprising one of the described nucleic acid molecules.

The inventors further disclose methods of delivering a nucleic acid molecule to treat a disease or condition comprising the step of administering to a subject a retrovirus particle or liposomal particle which comprises at least a retrovirus mutant envelope protein or polypeptide fragment thereof as described above.

The mutant envelope proteins and polypeptide fragments described above can be utilized in liposome compositions, pseudotype viruses, and pseudotype retroviruses, including combinations with lipid destabilizers. A method of administering these compositions to directly and selectively deliver an agent to a target cell is also contemplated.

DESCRIPTION OF THE FIGURES

FIG. 1. The Protein Sequence of Moloney Murine Leukemia Virus (MoMLV)

FIG. 1A is the 665 amino acid envelope protein sequence (GenBank Accession No. J02255). It was first described in the reference by T. M. Shinnick et al., 1981 *Nature* 293: 543–8. FIG. 1B is the complete nucleotide sequence of MoMLV, which includes the envelope encoding sequences (nucleotides 5777–7774).

FIG. 2. The Protein Sequence of Gibbon Ape Leukemia Virus, SEATO Strain

FIG. 2A is the 667 amino acid sequence (GenBank Accession No. M26927) of the envelope protein and was described in S. Delassus et al., 1989 *Virology* 173: 205–13.

FIG. 2B depicts the nucleotide sequence of the entire GALV SEATO strain genome, including the envelope protein (nucleotides 5552–7555).

FIG. 3. The Protein Sequence of Murine Leukemia Virus 10A1

FIG. 3A is the 645 residue long envelope protein described by D. E. Ott et al., 1990 *J. Virol.* 64: 757–66. The DNA sequence encoding it (GenBank Accession No. M33470) is depicted in FIG. 3B.

FIG. 4. The Protein and Nucleic Acid Sequence of Amphotropic Murine Leukemia Virus 4070A FIG. 4A depicts the envelope protein (GenBank Accession No. M33469). FIG. 4B shows the nucleic acid sequence encoding this protein as described in Ott et al., (1990) and in GenBank Accession No. M33469.

FIG. 5. A $^8$His→Arg Mutation Introduces a Defect in Virus Entry That is Overcome By the Synergistic Action of Amino Acid Substitutions at Both Glutamine 227 and Aspartate 243

(A) Infectious titers on NIH3T3 cells (gray bars) and human 293 expressing exogenous wild type receptor (black bars). Titers were calculated from the end-point dilution (n=4) after exposure to virions pseudotyped with envelope proteins containing the indicated substitutions. Each value is the average from at least five independent experiments. (B) Western blot analysis of virions containing mutant env genes. Proteins were separated on a 12% SDS-polyacrylamide gel. The membrane was cut into three parts at the positions indicated by the black lines, roughly that of the 45 kDa and 25 kDa molecular weight standards. The top portion was incubated with anti-SU antisera, the middle portion with anti-capsid (CA) antisera, and the bottom part with anti-TM antisera. (C) Western blot analysis of virus producer cell lysates. Proteins were separated on 8% SDS-polyacrylamide gels then blotted with anti-SU antisera.

Figure 6:
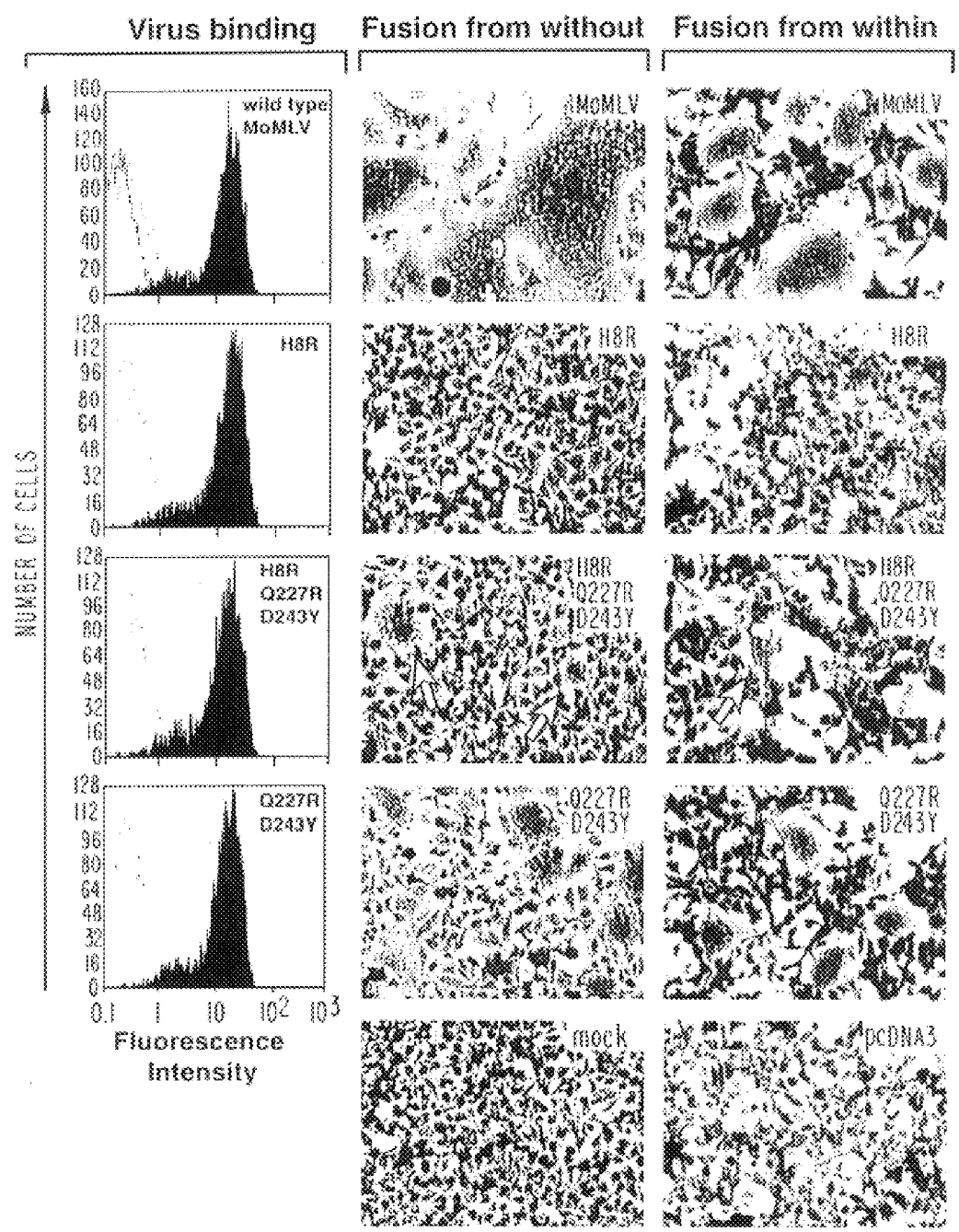

FIG. 6. The $^8$His→Arg Substitution Results in a Defect in Envelope Fusion Function That is Overcome By the Synergistic Actions of Amino Acid Substitutions at Both Glutamine 227 and Aspartate 243

Replacement of histidine 8 with arginine results in a defect in envelope fusion function that is suppressed by glutamine-227-to-arginine and aspartate-243-to-tyrosine mutations. (Left panels) Virus binding. Dashed line, binding of wild-type virus to 293 cells lacking receptor; dotted line, nonspecific binding of antisera in the absence of virus to 293 cells stably expressing receptor. Shaded area represents binding of wild-type or mutant viruses to the 293 cells expressing the receptor. (Middle panels) Fusion from without. XC rat sarcoma cells were exposed to virions pseudotyped with the envelope protein indicated. Induced syncytia were stained with methylene blue and basic fuchsin. (Right panels) XC cells were cocultivated with 293 cells expressing the indicated Env. Mock, mock-infected XC cells; pcDNA3, XC cells cocultivated with 293 cells expressing vector pcDNA3. Arrow in H8R Q227R D243Y panels point to syncytium. H8R, histidine to arginine; Q227R glutamine to arginine; D243Y, aspartate 243 to tyrosine.

FIG. 7. Infectivity of Heterologous 208 Amino Acid Protein Fused to Q227R/D243Y Envelope Mutant Fusion of a 208 amino acid peptide from a heterologous binding peptide in ecotropic MoMLV envelope protein mutant Q227R/D243Y increases infection by at least 1,000-fold in cells expressing the cognate receptor for the heterologous binding protein over infection directed by a wild type MoMLV envelope protein fused to the same heterologous peptide. Human 293 cells expressing only the amphotropic retrovirus receptor were not infected by retroviral vectors pseudotyped with fusion envelope protein in which the amphotropic receptor-binding peptide was linked to the wild type ecotropic envelope protein. However, infection of the 293 cells by retroviral vectors pseudotyped with fusion envelope protein in which the same amphotropic peptide was linked to the Q227R/D243Y mutant envelope protein was comparable to their infection by virions pseudotyped with wild type amphotropic envelope protein. Naive NIH3T3 cells, human 293 cells, and human 293 cells stably expressing the wild type ecotropic receptor were exposed to ten-fold serial dilutions of virus stocks containing virions pseudotyped with envelope proteins containing the indicated substitutions. Titers were calculated from end-point dilution (n=4) as infectious units per ml (ifu/ml) virus-containing stock. Each value is the mean from at least five independent experiments. Retroviral particles were pseudotyped with the following envelope proteins: MoMLV (eco), wild type ecotropic Moloney MLV; 4070A (ampho), wild type amphotropic 4070A MLV; ampho/eco, residues 1–208 of amphotropic 4070A envelope protein encoding the amphotropic retrovirus receptor-binding domain fused between Serine 6 and Proline 7 in the wild type ecotropic Moloney MLV envelope protein; ampho/eco+Q227R/D243Y, the above described residues 1–208 of amphotropic 4070A fused in mutant envelope protein Q227R/D243Y between Serine 6 and Proline 7.

FIG. 8. Stabilization of a Fusion Envelope Protein

In addition to restoring penetration function lost upon fusion of heterologous peptide, mutant Q227R/D243Y envelope protein stabilizes the association of the fused SU protein with TM protein against mechanical stress. Wild type ecotropic (lane 1) and amphotropic (lane 2) envelope SU migrated at 70 and 80 kDa, respectively. The two fusion SUs migrate at 97 kDa (lanes 3–6). Lanes 3 and 4 contain extracts from two different preparations of the ampho/eco retroviral vector and lanes 5 and 6 contain extracts from two different preparations of the ampho/eco+Q227R/D243Y retroviral vector.

In FIG. 8A, virions were analyzed by Western blot analysis. Virions were pelleted by direct high speed centrifugation after one cycle of freezing followed by thawing. Wild type and fusion envelope proteins were associated with virus particles. The membrane was cut into two parts at the position indicated by the black line (approximately at 45 kD). The top portion of the membrane was incubated with anti-SU antisera (Quality Biotech) which recognizes a broad range of retroviral surface proteins, the bottom part with anti-capsid (CA) antisera.

In FIG. 8B, virions were pelleted by high speed centrifugation under conditions of mechanical stress (pelleting through a 25% sucrose cushion) after one cycle of freezing and thawing. Fusion envelope proteins containing the Q227R/D243Y substitutions remain as stably associated with virus particles as do the wild type envelope proteins, whereas fusion envelope proteins lacking these substitutions are shed due to mechanical stress. The top portion was incubated with anti-SU antisera (Quality Biotech) that recognizes a broad range of retroviral surface proteins, the bottom part with anti-capsid (CA) antisera.

In FIG. 8C, cell lysates were prepared from virus producing cells. Cleavage of envelope proteins is not affected by the presence of the fused peptide fragment or by the presence of the Q227R/D243Y substitutions. The increase in size of envelope protein indicated in lanes 3–6 was due to the increase in molecular weight upon fusion of the 208 amino acid peptide into the envelope protein. Membrane was incubated with anti-SU sera.

Figure 8D:
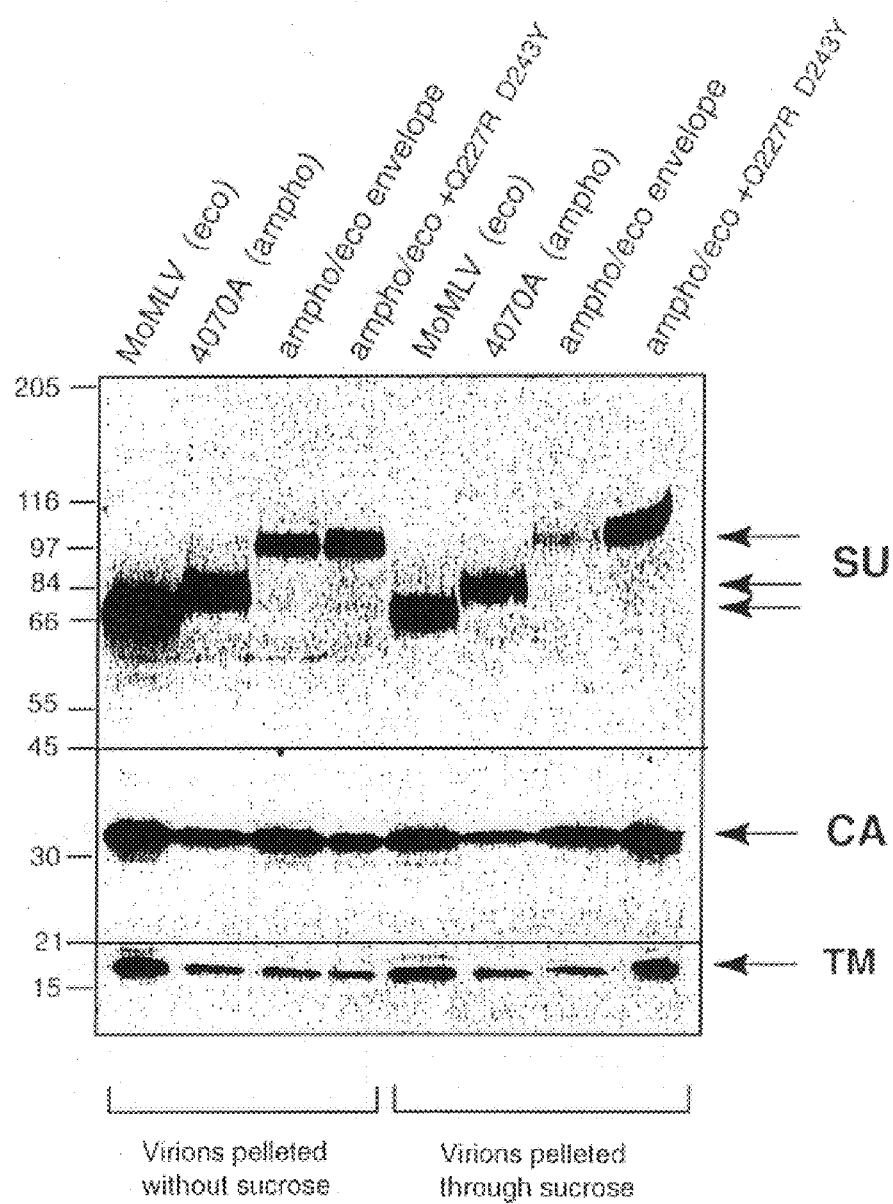

In FIG. 8D, envelope containing the fused heterologous peptide stably associates with retroviral vectors only in the presence of the Q227R/D243Y substitutions. Virions were purified in the presence or absence of mechanical stress resulting from pelleting through a 25% sucrose gradient after one cycle of freezing and thawing. The first four lanes and the last four lanes contain extracts from two different preparations of retroviral vectors. The membrane was cut into three parts at the positions indicated by the black lines (approximately at 45 kDa and 21 kDa). The top portion of the membrane was incubated with anti-SU antisera (Quality Biotech) that recognizes a broad range of retroviral surface proteins, the middle part with anti-capsid (CA) antisera, and the bottom portion with anti-TM (monoclonal anti-p15E 372; ATCC). The amounts of capsid protein present were roughly the same for all samples, indicating that the production of viruses containing the mutant envelope proteins was comparable to that of wild type virus.

Proteins were separated on 8% SDS-polyacrylamide gel, except in FIG. 8D where separation was on an SDS-polyacrylamide 6%–15% gradient gel. Retroviral vectors were pseudotyped with the following envelope proteins: MoMLV (eco), wild type ecotropic Moloney MLV; 4070A (ampho), wild type amphotropic 4070A MLV; ampho/eco, residues 1–208 of amphotropic 4070A envelope protein encoding the amphotropic retrovirus receptor-binding domain fused between Serine 6 and Proline 7 in the wild type ecotropic Moloney MLV envelope protein; ampho/eco+Q227R/D243Y, the above described residues 1–208 of amphotropic 4070A fused in mutant envelope protein Q227R/D243Y between Serine 6 and Proline 7.

FIG. 9. Substitution of Serine 198 By Tyrosine Plus Valine 233 By Isoleucine (S198Y/V233I) Restores Infectivity to Virions Coated With Envelope Protein That Contains a Serine 337 to Proline Substitution Mutant envelope containing the S198Y/V233I substitutions conferred infectivity on virions containing a Serine 337 to proline substitution that almost completely abolishes envelope protein incorporation into virions. In FIG. 9A, virus titers on NIH3T3 cells are indicated by gray bars, and human 293 expressing exogenous wild type receptors are indicated by black bars. Titers were calculated from the end-point dilution (n=4) after exposure to virions pseudotyped with envelope proteins containing the indicated substitutions. Each value is the average of five independent experiments. MoMLV, wild type Moloney-MLV; mock, supernatant or lysate of cells transfected with pcDNA3.

FIG. 9B is a Western blot analysis of virions containing mutant env genes. Proteins were separated on 8% SDS-polyacrylamide gel. The membrane was cut into two parts at the position indicated by the black line (approximately at 45 kD). The top portion was incubated with anti-SU antisera, the bottom part with anti-capsid (CA) antisera.

In FIG. 9C, virus producer cell lysates were analyzed using Western blot analysis. Proteins were separated on an 8% SDS-polyacrylamide gel, membrane was probed with anti-SU antisera. The amounts of capsid protein present were roughly the same for all samples, indicating that the production of viruses containing the mutant envelope proteins was comparable to that of wild type virus.

FIG. 10. Virus Coated With Uncleaved Lysine 104 Changed to Aspartate (K104D) Envelope Protein is Highly Infectious Substitution of amino acids at positions 102 and 104 of the MoMLV-E envelope protein suppressed envelope protein cleavage but did not preclude incorporation of the uncleaved precursor into virions. Arginine 102 ($^{102}$Arg) substitution abolished virus infectivity. Substitutions at positions 111 and 114 do not influence envelope protein processing or virus infectivity. (A) Naive NIH3T3 cells (stippled bars) and human 293 cells stably expressing the wild type ecotropic receptor (black bars) were exposed to ten-fold serial dilutions of virus stocks containing virions pseudotyped with envelope proteins containing the indicated substitutions. Titers were calculated from end-point dilution (n=4). Each value is the average from at least five independent experiments. MoMLV, wild type Moloney-MLV-E; mock, supernatant or lysate of cells transfected with pcDNA3. (B) Western blot analysis of virions containing mutant env proteins genes. Proteins were separated on 8% SDS-poly acrylamide gel. The membrane was cut into two parts at the position indicated by the black line (approximately at 45 kD). The top portion was incubated with anti-SU antisera, the bottom part with anti-capsid (CA) antisera. (C) Western blot analysis of virus producer cell lysates. Proteins were separated on 8% SDS-polyacrylamide gel, membrane was probed with anti-SU antisera. The amounts of capsid protein present were roughly the same for all samples, indicating that the production of viruses containing the mutant envelope proteins was comparable to that of wild type virus.

FIG. 11. Substitution of Arginine 124 With Aspartate Suppressed Envelope Protein Cleavage, Resulting in Incorporation of Precursor Protein Into Highly Infectious Virions Substitution of glutamate at this position produced non-infectious particles coated with uncleaved envelope protein. Mutations at positions 126 and 135 did not affect protein maturation and virus entry. (A) Virus titers on NIH3T3 cells (stippled bars) and human 293 expressing exogenous wild type receptor (black bars). Titers were calculated from the end-point dilution (n=4) after exposure to virions pseudotyped with envelope proteins containing the indicated substitutions. Each value is the average of five independent experiments. MoMLV, wild type Moloney-MLV-E. (B) Western blot analysis of virions containing mutant env genes. Proteins were separated on an 8% SDS-polyacrylamide gel. The membrane was cut into two parts at the position indicated by the black line (approximately at 45 kD). The top portion was incubated with anti-SU antisera, the bottom part with anti-capsid (CA) antisera. (C) Western blot analysis of virus producer cell lysates. Proteins were separated on an 8% SDS-polyacrylamide gel and transferred to the membrane, which was a probed with anti-SU antisera. The amounts of capsid protein present were roughly the same for all samples, indicating that the production of viruses containing the mutant envelope proteins was comparable to that of wild type virus.

FIG. 12. Highly Infectious Virions Coated With Envelope Precursor Protein also Resulted From Substitutions of Residues at Positions 137 and 223 Plus 225

Substitution of Tyrosine 138 abolished precursor cleavage and resulted in noninfectious virions bearing uncleaved envelope. Mutation of Proline 134 did not affect protein maturation or virus infectivity. (A) Virus titers on NIH3T3 cells (stippled bars) and human 293 expressing exogenous wild type receptor (black bars). Titers were calculated from the end-point dilution (n=4) after exposure to virions pseudotyped with envelope proteins containing the indicated substitutions. Each value is the average of five independent experiments. MoMLV, wild type Moloney-MLV-E; ENV-, supernatant or lysate of cells transfected with virus genome lacking env gene; mock, supernatant or lysate of cells transfected with pcDNA3. (B) Western blot analysis of virions containing mutant env genes. Proteins were separated on an 8% SDS-polyacrylamide gel. The membrane was cut into two parts at the position indicated by the black line (approximately at 45 kD). The top portion was incubated with anti-SU antisera, the bottom part with anti-capsid (CA) antisera. (C) Western blot analysis of virus producer cell lysates. Proteins were separated on an 8% SDS-polyacrylamide gel and the proteins transferred to a membrane. The membrane was probed with anti-SU antisera. The amounts of capsid protein present were roughly the same for all samples, indicating that the production of virus particles containing the mutant envelope proteins was comparable to that of wild type virus.

Figure 13:
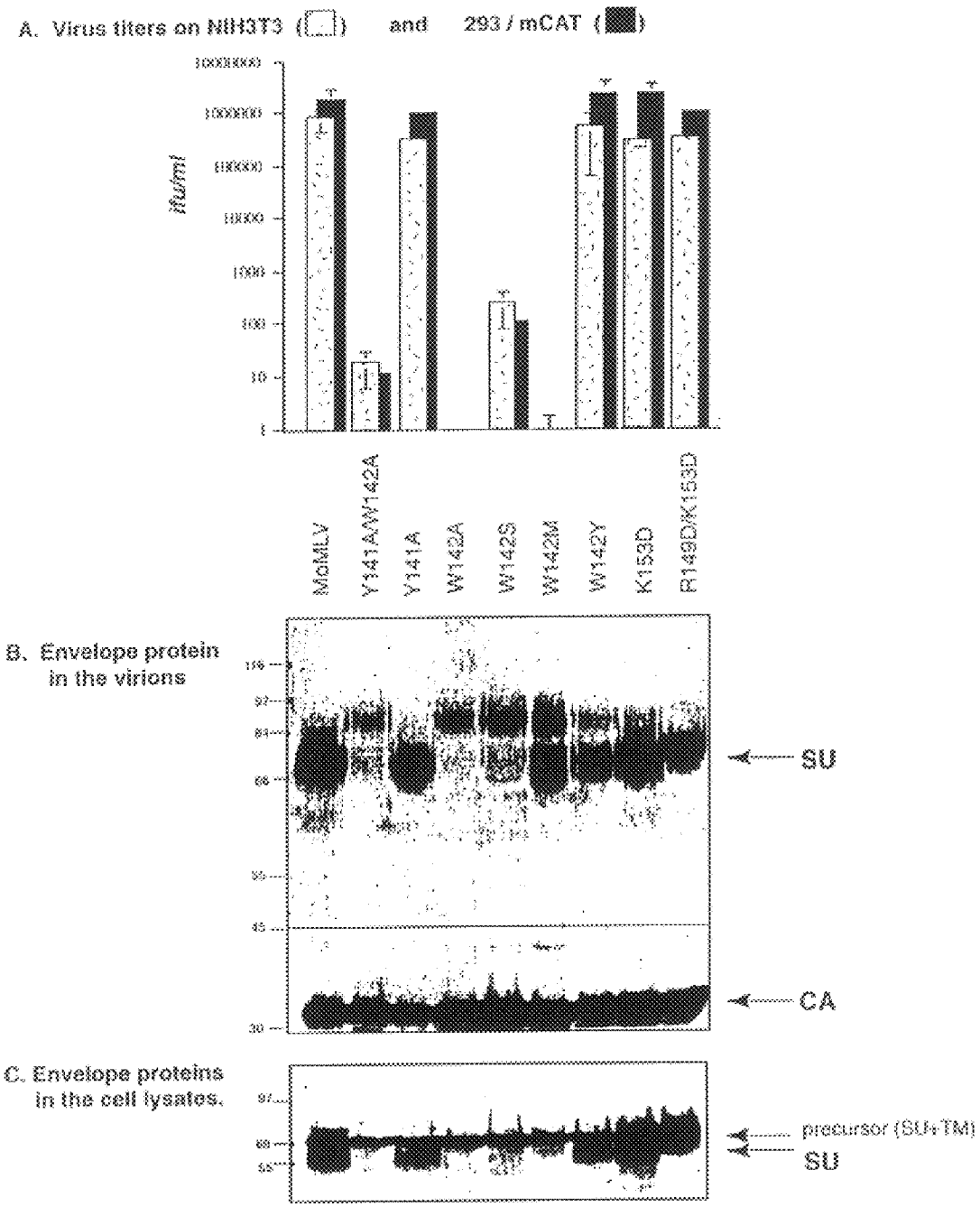

FIG. 13. Substitution of an Aromatic Residue for Tryptophan 142 Does Not Affect Envelope Protein Processing and Virus Infectivity, But Replacement of That Position With an Alanine or Serine Residue Interfered With Precursor Cleavage and Virus Entry Viruses containing a Tryptophan$^{142}$ ($^{142}$Trp) to methionine substitution (W142M) contained appreciable amounts of cleaved SU, but the presence of this mature SU did not rescue their infectivity. Mutation of residues 149 or 153 did not affect protein maturation and virus infectivity. (A) Virus titers on NIH3T3 cells (stippled bars) and human 293 expressing exogenous wild type receptor (black bars). Titers were calculated from the end-point dilution (n=4) after exposure to virions pseudotyped with envelope proteins containing the indicated substitutions. Each value is the average of five independent experiments. MoMLV, wild type Moloney-MLV-E. (B) Western blot analysis of virions containing mutant env genes. Proteins were separated on 8% SDS-poly acrylamide gel. The membrane was cut into two parts at the position indicated by the black line (approximately at 45 kD). The top portion was incubated with anti-SU antisera, the bottom part with anti-capsid (CA) antisera. (C) Western blot analysis of virus producer cell lysates. Proteins were separated using an 8% SDS-polyacrylamide gel. Proteins were transferred to a membrane which was probed with anti-SU antisera. The amounts of capsid protein present were roughly the same for all samples, indicating that the production of viruses containing the mutant envelope proteins was comparable to that of wild type virus.

Numbering of the SU and TM proteins described are according to the MoMLV sequence reported by Shinnick et al. (1981) beginning with the alanine on the amino terminus of the mature SU after cleavage of the signal peptide. For TM, numbering begins with the glutamate on the amino terminus after cleavage of the precursor.

FIG. 14. Virus Binding

Binding assays were performed essentially as described (Cosset et al., J Virol (1995) 69:6315–6322 and Kadan et al., J Virol (1992) 66:2281–2287). Briefly, $10^6$ 293 cells stably expressing ecotropic receptor or parental 293 cells were incubated with 1 ml of virus adjusted to achieve comparable particle concentrations based on RT activity, then with goat anti-gp70 antiserum (1: 100), and finally with donkey anti-goat conjugated to FITC (Jackson Laboratories). Propidium iodide (Sigma) was added to the binding reaction 5 minutes prior to analysis to identify live cells (negative for propidium iodide) for quantification of bound virus by flow cytometry (Epics Profile Analyzer, Coulter Cytometry). Experiments were repeated two times. No virus, nonspecific binding of antiserum in the absence of virus to 293 cells stably expressing receptor; No receptor, binding of wild-type MoMLV to parental 293 cells lacking ecotropic receptor. The mean fluorescence intensities for the no receptor and no virus peaks were 0.2 and 0.3, respectively. +, titer within 10 fold of wild type; –, titer 10,000-fold less than wild-type MoMLV.

Virions pseudotyped with envelope cleavage mutants that were highly infectious exhibited slightly greater levels of receptor binding than did virions pseudotyped with envelope cleavage mutants that were almost noninfectious. The exception was the highly infectious virions coated with the Arginine 223 to aspartate plus Arginine 225 to aspartate (R223D/R225D) mutant that exhibit very low binding comparable to that of the poorly infectious virions.

A representative experiment is shown for each of the following substitutions: R124D/126D, Arginine 124 to aspartate plus Arginine 126 to aspartate; R124D, Arginine 124 to aspartate; R124E, Arginine 124 to glutamate; K104D, Lysine 104 to aspartate; R102A, Arginine 102 to alanine; D135A, Aspartate 135 to alanine; R223D/R225D, Arginine 223 to aspartate plus Arginine 225 to aspartate; F137A/Y138A, Phenylalanine 137 to alanine plus Tyrosine 138 to alanine; Y138A, Tyrosine 138 to alanine; W142Y, Tryptophan 142 to tyrosine; W142M, Tryptophan 142 to methionine; and W142S, Tryptophan 142 to serine.

FIG. 15. Alignment of the Amino Acid Sequence of the Retroviral Envelope Sequences From Retroviruses Useful as Vectors in Human Gene Therapy Envelope sequences are as follows: Moloney, ecotropic Moloney MLV envelope protein (GenBank Accession number J02255); Friend, ecotropic Friend MLV envelope protein (GenBank Accession number M93134); 4070A, amphotropic 4070A MLV envelope protein (GenBank Accession number M33469); GALV SEATO, gibbon ape leukemia virus SEATO strain envelope protein (GenBank Accession number M26927). All sequences begin with the residue immediately following the signal peptide cleavage site. Residues are indicated by the single letter amino acid code. Numbers above the alignment indicate the residue position in the Moloney MLV sequence. Boxes indicate the structural domains as determined for the Friend MLV envelope residues 9–236 taken from the published X-ray crystal structure of Fass et. al., 1977 Science 277:1662–6. Residues that are members of the described motifs are in white with black highlighting. Sequences were aligned using Megalign program of the DNASTAR sequence analysis package followed by adjustment by visual inspection.

FIG. 16. Alignment of the Amino Acid Sequence of Representative Retroviral Envelope Proteins Envelope sequences are from: Consensus, consensus sequence derived by the Megalign program after adjustment by inspection; Moloney, ecotropic Moloney MLV (GenBank Accession number J02255); Friend, ecotropic Friend MLV (GenBank Accession number M93134); AKV, ecotropic AKV MLV (GenBank Accession number J01998); CasBrE, ecotropic CasBrE MLV (GenBank Accession number M14702); RadLV, ecotropic radiation leukemia virus Kaplan strain (GenBank Accession number K03363); 10A1, 10A1 MLV (GenBank Accession number M33470); 4070A, amphotropic 4070A MLV (GenBank Accession number M33469); MCF 1233, polytropic MLV mink cell focus forming virus strain 1233 (GenBank Accession number U13766); Xeno CWM, xenotropic MLV strain CWM-S-5X (GenBank Accession number M59793); Xeno NZB, Xenotropic MLV strain NZB-9-1 (GenBank Accession number K02730); FeLV A, feline leukemia virus subgroup A (GenBank Accession number M18248); FeLV B, feline leukemia virus subgroups B (GenBank Accession number K01209); and GALV SEATO, gibbon ape leukemia virus SEATO strain envelope protein (GenBank Accession number M26927). All sequences begin with the residue immediately following the signal peptide cleavage site. Residues are indicated by the single letter amino acid code. Numbers above the alignment indicate the residue position in the Moloney MLV sequence. Boxes indicate the structural domains as determined for the Friend MLV envelope residues 9–236 taken from the published X-ray crystal structure of Fass et. al., (1997). Gray highlighting indicates residues that are members of the described motifs.

Figure 17:
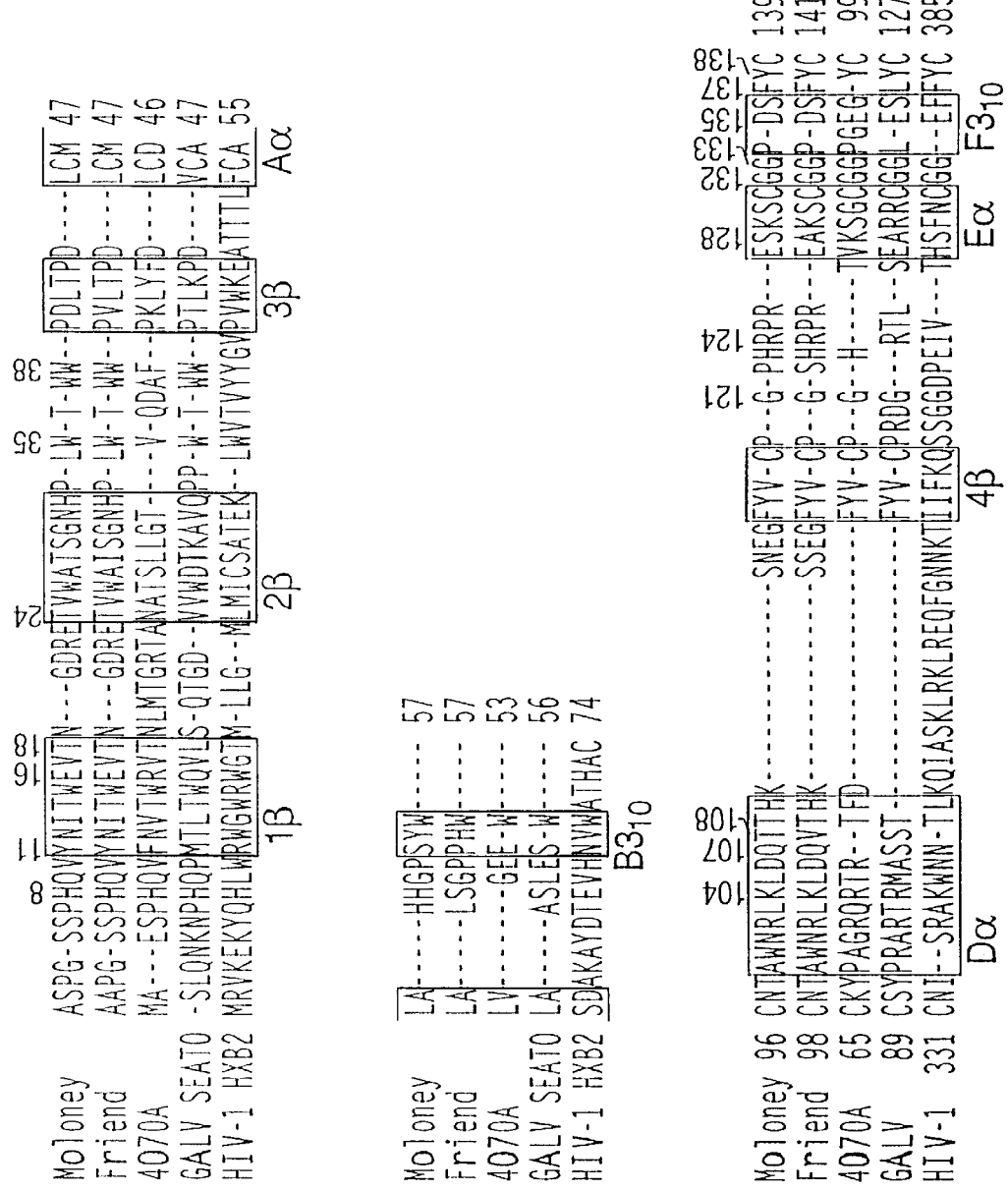

FIG. 17. Alignment of the Amino Acid Sequence of the Conserved Motifs With the HIV Envelope Protein Envelope proteins are from: Moloney, ecotropic Moloney MLV (GenBank Accession number J02255); Friend, ecotropic Friend MLV (GenBank Accession number M93134); 4070A, amphotropic 4070A MLV (GenBank Accession number M33469); GALV SEATO, gibbon ape leukemia virus SEATO strain (GenBank Accession number M26927); and HIV, human immunodeficiency virus type I isolate HXB2 (GenBank Accession number K03455). All sequences begin with the residue immediately following the signal peptide cleavage site. Residues are indicated by the single letter amino acid code. Numbers above the alignment indicate the residue position in the Moloney MLV sequence. Boxes indicate the structural domains as determined for the Friend MLV envelope residues 9–236 taken from the published X-ray crystal structure of Fass et. al., (1997).

Figure 18:
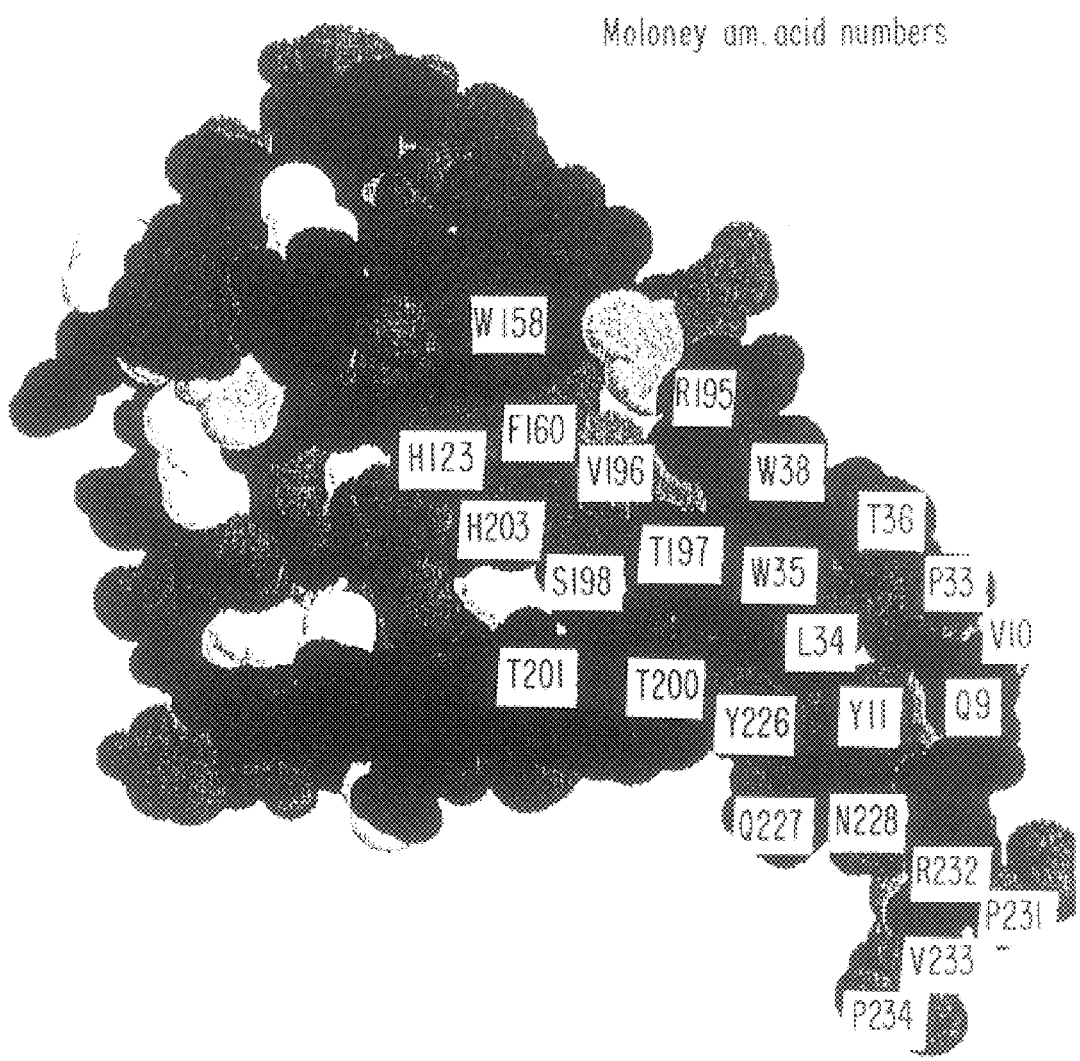
Figure 19:
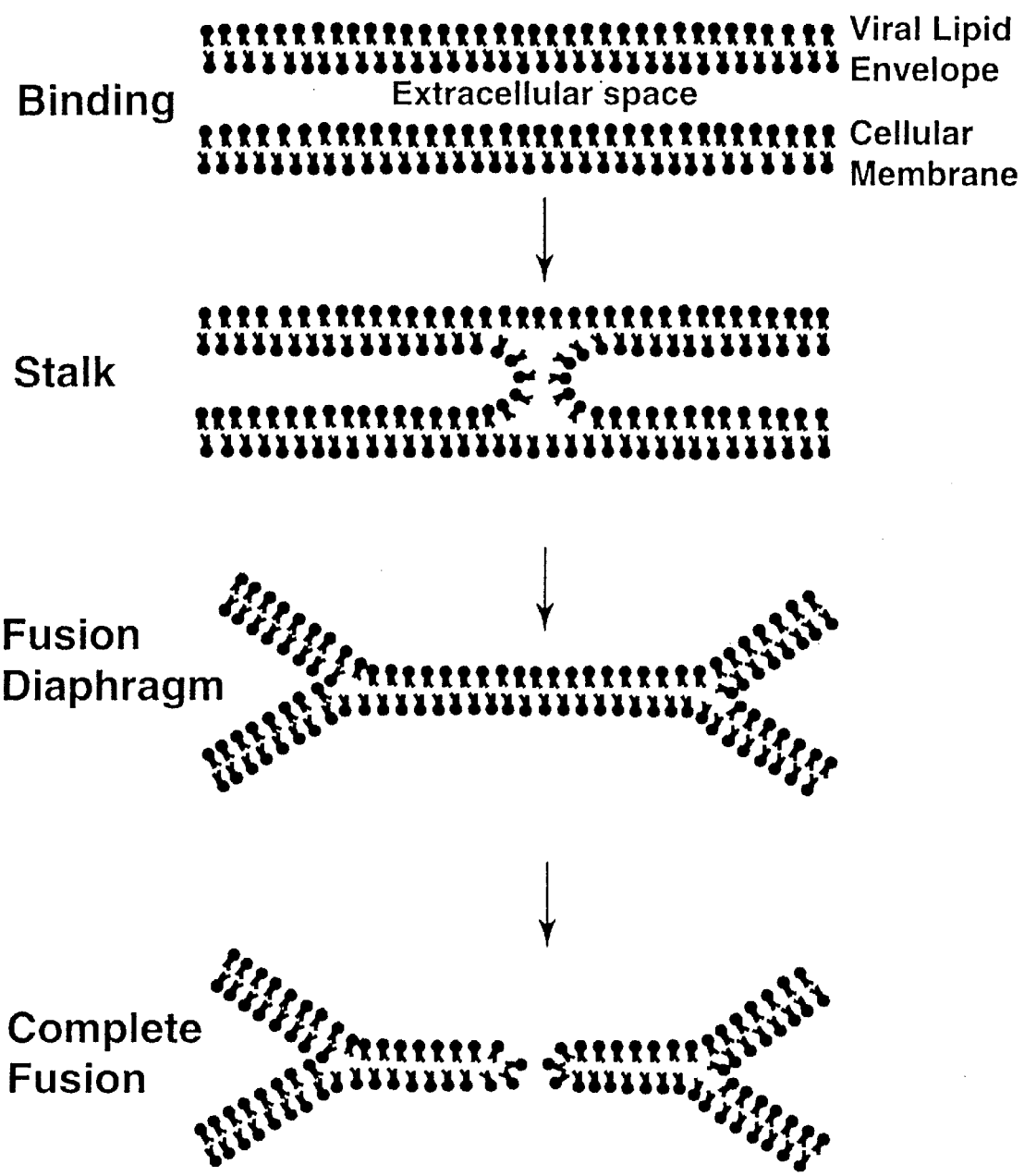

FIG. 18. Three Dimensional Model of the Structure of the Seventh Motif Comprising $^{198}$Ser, $^{11}$Tyr, $^{226}$Tyr, $^{35}$Trp, $^{38}$Trp, $^{196}$Val, $^{197}$Thr, $^{160}$Tyr, $^{158}$Trp, $^{123}$His, $^{203}$His, $^{233}$Val, $^{235}$Ile, $^{240}$Val, $^{241}$Leu and $^{8}$His The seventh described motif stabilizes the retrovirus envelope protein to maintain infectivity. The model is based on the published X-ray crystal structure of a receptor-binding fragment of the envelope surface protein of ecotropic Friend murine leukemia virus (Fr-MLV; Fass et al., 1997 *Science* 277: 1662–6). The corresponding residues of ecotropic Moloney murine leukemia virus (MoMLV) were identified by aligning the MoMLV and Fr-MLV protein sequences. The space-filled model was constructed using the RasMol 2.6 molecular structure program and replacing the residues in the motif with the corresponding residues in MoMLV. The view is a lateral one from the side of the E- and H-alpha helices in which the groove containing the motif spirals along the side of the molecule, with the receptor-binding surface on the left. Amino acids are identified by the single letter code followed by the residue number in the MoMLV surface (SU) protein.

FIG. 19. Liposome Fusion

During fusion of liposomes membrane lipids reorient from two bilayers into a single bilayer at the point of fusion. Initially the outer leaflets of the juxtaposed membranes mix to form a "stalk" structure. The "stalk" expands to form a hemifusion intermediate (i.e., a fusion diaphragm). Fusion is then completed when a pore forms within the hemifusion diaphragm that allow intermixing of the liposome contents.

FIG. 20. Induction of Complete Virus-Cell Fusion By Membrane Destabilizers

Rat XC cells were exposed to 10 fold serial dilutions of wild type (MOMLV or mutant (H8R) virus, then cells were exposed to lipid destabilizing agents (CPZ or oleic acid; (A) and (B)) buffered in DMEM/BES at the indicated pH, washed and returned to drug free medium at the same pH. Forty-eight (48) hours later cells were fixed and titers were calculated for the end point dilution (n=4). Values are the mean from two experiments. (A) CPZ effects as a function of concentration. (B) CPZ effects as a function of pH. (C) Rat XC cells were exposed as in (A) and (B) to the indicated concentration of DB and TFP.

FIG. 21. The 85 kDa Envelope Protein Species Represents a Hyperglycosylated Form of SU in F137A Virions, but Represent Uncleaved Precursor Protein in W142M Virions Digestion with glycosidase F to remove N-linked carbohydrates. Wild-type and mutant virions were incubated overnight in the absence (−) or presence (+) of excess glycosidase F, then proteins were separated on 8% SDS-polyacrylamide gels immunoblotted with anti-SU (top portion) or anti-CA (bottom portion). To determine whether glycosidase digestion had been completed, lysates of wild type MoMLV producer cells were also analyzed.

FIG. 22. The 85 kDa Envelope Protein Species Represents an Uncleaved Precursor Protein in W100M Virions (A) Infectious titers on mouse NIH3T3 cells bearing endogenous amphotropic 4070A MLV receptors (stippled bars) and human 293 expressing exogenous receptor (black bars). Titers were calculated from the endpoint dilution (n=4) after exposure to virions pseudotyped with envelope proteins containing the indicated substitution. 4070A, wild type amphotropic MLV 4070A; W100M, tryptophan 100 to methionine substitution. (B) Western blot analysis of virions containing mutant envelope proteins. Virions were purified by pelleting through 25% sucrose cushion. Then proteins were separated on 8% SDS polyacrylamide gels and transferred to nitrocellulose membranes (Protran, S&S). The membrane was cut into two parts, roughly at the 45 kDa molecular mass standard. Envelope proteins (SU and Precursor) were detected on the top portion with anti-gp70 antiserum and the structural capsid protein (CA) was detected on the bottom portion with goat anti-p30 antiserum. Subsequent incubation with mouse anti-goat antibodies were conjugated to horse radish peroxidase (HRP; 1:10,000; Sigma) was performed and immunoblots were developed using Renaissance (NEN). (C) Western blot analysis of virus producer cell lysates. 100 μg of proteins from total cell lysates were separated on 8% SDS-polyacrylamide gels, then blotted to anti-SU antiserum. (D) Digestion with glycosidase F to remove N-linked carbohydrates. Wild-type and mutant virions were incubated overnight in the absence (−) or presence (+) of excess glycosidase F, then proteins were separated on 8% SDS-polyacrylamide gels immunoblotted with anti-SU and anti-CA. To determine whether glycosidase digestion had been completed, lysates of wild type MoMLV producer cells were also analyzed.

FIG. 23. The 85 kDa Envelope Protein Species Does Not Represent Hyperglycosylated SU Wild type MoMLV producer cell lysate (last lane) or purified wild type and mutant virions were incubated with glycosidase F overnight, separated by 8% SDS-polyacrylamide gel and then Western blotted with anti-SU antiserum (top portion) and anti-CA antiserum (bottom portion).

DETAILED DESCRIPTION

I. DEFINITIONS

By "retroviral vector" is meant a retroviral particle that is used to target delivery of genes into cells. Retroviral vector targeting can be cell specific wherein only cells with the appropriate ligand for the retrovirus envelope will bind to the vector allowing penetration of the retroviral core and incorporation of the retroviral genome into the host genome.

By "retroviral particle" and "virion" is meant a retroviral structure which contains at least the gag, pol and env gene products necessary for infection to occur. An "infectious" retroviral particle or virion also contains two RNA strands encoding, at a minimum, the gag, pol and env genes necessary to support replication and assembly of new retrovirus particles capable of budding from the infected cell.

By "retrovirus envelope protein" or "env protein" is meant the retroviral protein found on the surface of the virion. The envelope proteins of retroviruses are typically encoded by the env gene. The native retroviral env gene product is generally a polyprotein precursor (in MoMLV it is referred to as "gp85", a precursor protein) that is proteolytically cleaved during transport to yield two polypeptides. These two proteolytic cleavage products are (1) the "surface protein" (also referred to as "SU protein" and "gp70") and (2) the "transmembrane protein", "TM" or "p15E". The SU protein is responsible for recognizing and binding to cellular receptors. The TM protein is involved in mediating the fusion of viral and cellular membranes necessary for virion entry and infection of the target cell.

By "mutant envelope protein" or "envelope mutants" is meant all retrovirus envelope proteins containing at least one mutation in at least one motif comprising said envelope proteins. These mutants can also contain a heterologous protein.

By "chimeric envelope proteins" or "fusion proteins" is meant envelope protein mutants fused to a non-retroviral peptide, polypeptide, or heterologous protein.

"Polypeptides" and "protein" are used interchangeably to refer to polymers of amino acids and do not refer to any specific lengths. These terms also include post-translationally modified proteins, for example glycosylated, acetylated, phosphorylated proteins and the like. Also included within the definition are, for example, proteins containing one or more analogs of an amino acid (including, for example, unnatural amino acids, etc.), proteins with substituted linkages, as well as other modifications known in the art, both naturally occurring and non-naturally occurring. Envelope peptides or polypeptides comprise at least about 2, 3, 5, 10, 15, 20, 25, 30, or 50 or more consecutive amino acid residues.

"Isolated" DNA, RNA, peptides, polypeptides, or proteins are DNA, RNA, peptides polypeptides or proteins that are isolated or purified relative to other DNA, RNA, peptides, polypeptides, or proteins in the source material. For example, "isolated DNA" encoding the envelope protein (which would include cDNA) refers to DNA purified relative to DNA which encodes polypeptides other than the envelope protein.

"Pharmaceutically acceptable" refers to molecular entities and compositions that are physiologically tolerated and do not typically produce an allergic or toxic reaction, such as gastric upset, dizziness and the like when administered to a subject or a patient; the preferred subjects of the invention are vertebrates, mammals, and humans.

By "retroviral pseudotype" or "pseudotype virus" is meant a viral vector comprising a mutated envelope protein of this invention in another retrovirus or virus (e.g., vesicular stomatitis virus or Rhabdovirus).

By "liposome" or "liposomal composition" is meant a small vesicle bound by a bilayer lipid membrane which contains a mutated envelope protein of this invention. DNA, proteins, and other materials can be enclosed within the liposome and can be introduced into animal cells by liposome fusion with the plasma membrane ("lipofection").

By "increased penetration capability" is meant an increased ability to initiate and complete fusion of the inner and outer leaflets of the vector lipid bilayer with the inner and outer leaflets of the cell membrane. The range of increase of this penetration capability is defined to be an increase of greater than 1500 fold relative to wild type envelope protein.

By "decreased shedding" is meant an envelope protein having decreased dissociation of the binding sequences from the virus membrane and/or sequences compared with wild type shedding.

"Binding sequences" herein refer to the receptor binding domain of the surface protein (SU). For example, amino acids 34–263 comprise the binding sequences of the naturally occurring envelope protein of Moloney MLV (MoMLV).

"Surface protein binding polypeptide fragment" herein refers to the minimal structural information necessary to bind to a retroviral receptor on the cell surface when said fragment is present on the surface of a liposome or expressed on the surface of a retroviral particle.

"Agent" herein refers to any chemical substance that causes a change. For example, agents include, but are not limited to, therapeutic genes, proteins, drugs, dyes, toxins, pharmaceutical compositions, labels, radioactive compounds, probes etc.

"Medicament" herein refers to an agent that promotes recovery from injury, ailment, disease or condition or reduces the symptoms associated with an injury, ailment, disease or condition.

"Producer cell lines" herein refers to engineered cell lines that do not produce a replication-competent retrovirus but can provide trans-acting factors required by a replication-defective retrovirus.

"Substitution" herein refers to changing an amino acid residue of a naturally occurring retroviral envelope protein or polypeptide fragment thereof, resulting in the mutation of the naturally occurring envelope protein sequence. For example, such replacement can be accomplished by any known method, including, but not limited to, site directed mutagenesis.

"In alignment with" herein refers to equivalent amino acid residues identified by lining-up retroviral envelope primary protein structures between various species of virus. For example, equivalent amino acid sequences comprising the primary amino acid structures of the envelope proteins comprising Friend and Moloney MLV are in alignment with each other as shown in FIGS. 15 and 16. In a related aspect, amino acid sequences identified by such alignment are predicted to form similar secondary structure motifs, such as alpha-helixes and beta-strands, resulting in virus particles having similar and predictable phenotypes.

"Alignment equivalents" herein refers to amino acids residues which when identified by lining-up primary protein structures occupy similar coordinates in folded proteins.

Alignments are determined by the Jotun Hein multiple alignment algorithm (Hein, J. J. *Methods in Enzymology* (1990) 183:626–645) using the Megalign software of DNASTAR. The algorithm builds a phylogeny represented by a graph of possible alignments by examining sequence pairs. Each sequence entered into the graph retains a relationship with the others allowing the algorithm to avoid exploration of distant pair relationships. The phylogeny created by this process is then re-examined for the best possible arrangement of ancestral branches.

The method is briefly described as follows: 1) pairwise distances are used which can be calculated by traditional pairwise methods (i.e., the method is k-tuple based. See Benson et al., *J Comput Biol* (1998) 5(1):87–100), 2) an initial tree is made, 3) the sequences are aligned following this tree and 4) the goodness of the tree is determined by switching to parsimony (i.e., the parsimony principle is the minimization of change, and when there must be changes minimal evolutionary distances, throughout all ancestral relationships. See Song et al., *Virus Genes* (1996) 12(3) :249–56).

The order of calculations is as follows: 1) The most informative distances for the tree construction process are calculated. Once a sequence has a distant relationship to a sequence within the initial phylogeny, distances to other sequences within the same neighborhood are not computed, 2) a distance tree is constructed for the sequences by adding them one by one to a growing tree, 3) rearrangements are performed on the obtained tree to improve the overall fit of the tree to the distance data. The approach used is best described as a nearest neighbor interchange, see Robinson D. F., *J Comb Theor* (1971) 11, 105, 4) the resulting tree is used to guide the alignment algorithm such that a parsimony tree is obtained that has the same topology as the distance tree, 5) the criterion for goodness of the history of the sequences is now parsimony (i.e., minimize evolutionary events. See Foulds et al., *J Mol Evol* (1979) 18:13(2) :151–66). Rearrangements are performed on the tree to improve it in an effort to make it more parsimonious, and 6) one phylogeny is chosen from a set of equally parsimonious possibilities and the result is presented. Initial data are generated by using default parameters.

II. Retroviral Vectors With Envelope Mutants

This invention includes mutant envelope proteins that possess the characteristics of increased penetration capability, increased stability, and decreased surface protein (SU) shedding. The exemplified mutations are in 7 motif domains. The domains were defined in part by mutational analysis (see for examples H. Skov et al., 1993 *J. Gen. Virol.* 74: 707–14; A. J. MacKrell et al., 1996 *J. Virol.* 70: 1768–74; and Y. Bae et al., 1997 *J. Virol.* 71: 2092–9) and in part by the three dimensional structure of the envelope protein of Friends MLV as described by D. Fass et al., 1997 *Science* 277: 1662–6. These 7 domains or motifs are described in Table I. A short hand form for delimiting said motifs 1–7 is denoted by amino acids $^{104}$Lys, $^{124}$Arg, $^{223}$Arg, $^{137}$Phe, $^{142}$Trp, $^{227}$Gln and $^{198}$Ser, respectively. Substitution of amino acids comprising other retroviral envelope proteins which are in alignment with amino acids comprising the 7 motifs are contemplated. Such an alignment of amino acids comprised in the retroviral envelope proteins for a variety of retroviruses are shown in the alignments as set forth in FIGS. 15–17. Further, separate sets of amino acids comprising the motifs may be denoted by functional classes. For example, it is contemplated that substitution of one or more amino acids which align with residues $^{16}$Glu, $^{24}$Thr, $^{90}$Thr, $^{102}$Arg, $^{104}$Lys, $^{107}$Glu, $^{108}$Thr, $^{121}$Gly, $^{124}$Arg, $^{126}$Arg, $^{128}$Ser, $^{132}$Gly, $^{133}$Gly, $^{134}$Pro, $^{135}$Asp, $^{136}$Ser, $^{137}$Phe, $^{138}$Tyr, $^{141}$Tyr, $^{142}$Trp, $^{151}$Tyr, $^{152}$Trp, $^{201}$Thr, $^{208}$Arg, $^{210}$Tyr, $^{217}$Gly, $^{223}$Arg, $^{224}$Leu and/or $^{225}$Arg of SEQ ID NO: 2 as set forth in FIGS. 15, 16 and/or 17 would comprise a class of mutations, wherein substitution of said one or more amino acids involving protein folding and structural changes which would prevent shedding of the surface protein by suppression of precursor cleavage. It is also contemplated that substitution of one or more amino acids which align with residues $^{8}$His, $^{11}$Tyr, $^{35}$Trp, $^{38}$Trp, $^{123}$His, $^{158}$Trp, $^{160}$Tyr, $^{196}$Val $^{197}$Thr, $^{198}$Ser, $^{203}$His, $^{226}$Tyr, $^{227}$Gln, $^{228}$Asn, $^{233}$Val, $^{235}$Ile, $^{240}$Val, $^{241}$Leu, and/or $^{243}$Asp of SEQ ID NO: 2 as set forth in FIGS. 15, 16 and/or 17 would comprise a class of mutations, wherein substitution of one or more said amino acids would involve protein folding and structural changes which result in increased envelope stability and fusion of retroviruses with cell membranes. For example, it is contemplated that mutations in retroviral envelope proteins which mimic fusion defective H8R mutations in MoMLV (i.e., comprising substitution of equivalent $^{8}$His to Arg substitution based on linear alignment and available modeling data, e.g., Protean program of DNASTAR) can be suppressed by the synergistic actions of substitutions at alignment equivalents comprising $^{227}$Gln and $^{243}$Asp substitution, wherein similar structural changes that bring aromatic rings at adjacent folded positions close enough to the position normally occupied by the aromatic ring of histidine 8 provide the required contribution of histidine 8 to fusion.

Alignment data can be supplemented by generation of speculative models of specific defects based on known crystal solutions for a variety of retroival envelope proteins. For example, diagrams of structures of residues of wild type SUs can be generated with crystal structure coordinates of other retroviral SUs using visualization programs based on assumptions, including conserved structures established via amino acid identity and domain specific sequence identity. Using Chou-Fasman and Garnier-Robson algorithms, secondary structures can be predicted and hypothetical structures generated for putative side chain interactions between mutated residues (see http://www.dnastar.com/products/Protean.html) for a variety of retroviral envelope proteins. Initial data are generated using default parameters.

Further, altered residues for cleavage mutants (e.g., substitution at $^{104}$Lys) are used to determine how changes in cleavage of precursor protein can influence the folding of the cleavage recognition site. For example, using alignment and protein modeling algorithms, crystal structures of known retroviral envelope proteins are generated which suggest that cleavage mutations occur at the "top" surface of the env gene product which is thought to be the cell receptor binding site. In a preferred embodiment, mutations that produce structural changes mimicking those changes occurring during interaction between the envelope protein and the cell receptor would be expected to translate through the protein to change folding of the same domains comprised in a variety of retroviral envelope proteins. For example, the envelope surface that makes initial contact with the cellular receptor transduces changes occurring upon receptor binding through the β-sandwich of the binding domain into the carboxy-terminal region of SU and then into TM to activate fusion peptide function. Further, such cleavage mutants create conformation changes which may simulate conformations induced by receptor binding. As such, said mutants are more entry-competent in that single receptor binding events are sufficient for these mutants to induce all the conformational changes required for virus entry (e.g., MoMLV mutant R223D/R225D).

Using models and alignments as guides for amino acid substitution, together with binding and infectivity assays, mutable sites on retroviral envelope proteins are disclosed which can be exploited to predictably minimize the negative aspects of vector/infective particles expressing surface N-terminal envelope-fusion proteins on cell binding and penetration.

A. Envelope Protein Synthesis and Use

The nucleic acid molecules encoding the envelope proteins may be mutated using methods commonly known in the art. See Ausubel et. al., CURRENT PROTOCOLS IN MOLECULAR BIOLOGY, (Greene Publishing Co. NY, 1995); Sambrook, Fritsch and Maniatis, MOLECULAR CLONING: A LABORATORY MANUAL (Second Ed., Cold Spring Harbor Press, Cold Spring Harbor N.Y., 1989); DNA CLONING: A PRACTICAL APPROACH, vols. 1 and 2 (D. N. Glover ed., 1985); OLIGONUCLEOTIDE SYNTHESIS (M. J. Gait ed., 1984); and NUCLEIC ACID HYBRIDIZATION (B. D. Hames and S. J. Higgins eds., 1985). Preferred retroviral sequences to be used in mutagenesis include the amphotropic type C retroviruses (Ott et al., 1990), Moloney murine leukemia virus (MoMLV) (Shinnick et al., 1981), amphotropic murine leukemia virus (MLV) 10A1 (Ott et al., 1990), amphotropic MLV 4070A, avian leukosis viruses, and gibbon ape leukemia virus (GALV) SEATO strain (S. Delassus et al., 1989). Other retroviruses which may be modified are ecotropic and xenotropic type C retroviruses, type D retroviruses, and lentiviruses.

B. Methods of Preparing Retroviral Vectors

Recombinant retroviruses can be produced by a number of methods. One method is the use of packaging cell lines. The packaging cells are provided with viral protein-coding sequences, preferably encoded on two plasmids. The plasmids encode all proteins necessary for the production of viable retroviral particles and encode a RNA viral construct which carries the desired gene (e.g., the gene encoding the mutant envelope protein or a mutant envelope fusion protein), along with a packaging signal (Ψ Psi) which directs packaging of the RNA into the retroviral particles.

Alternatively, the mutated retroviral genome can be transfected into cells using commonly known transfection methods such as calcium chloride, electroporation, or methods described in the examples. Sambrook et al., (1989).

The retroviral vector may also include an appropriate selectable marker. Examples of selectable markers which may be utilized in either eukaryotic or prokaryotic cells, include but are not limited to, the neomycin resistance marker (neo), the ampicillin resistance marker (amp), the hygromycin resistance marker (hygro), the multidrug resistance (mdr) gene, the dihydrofolate reductase (dhfr) gene, the β-galactosidase gene (lacZ), and the chloramphenicol acetyl transferase (CAT) gene.

Cells transfected with cDNAs encoding a retrovirus genome or infected with retrovirus particles can be cultured to produce virions or virus particles. Virus particle-containing supernatant can be collected. The virus particles can be concentrated by centrifuging the supernatant, pelleting the virus and by size exclusion chromatography. Pharmaceutical compositions containing virus particles can also be resuspended in pharmaceutically acceptable liquids or carriers such as saline.

C. Methods to Identify Additional Retroviral Mutants

Envelope mutants may be prepared by mutating or deleting at least one amino acid residue in a critical motif such as one or more of the seven motifs set forth in Table I. Table I also lists the preferred amino acids, if any, to be used as substitute residues in the envelope mutants created. Also listed in Table I are several examples which represent one or more preferred embodiments of the invention. The examples in no manner limit the ultimate number of changes that can be created.

Once the envelope mutants have been made, retrovirus particles coated with these mutants can be prepared. The particles can be analyzed by several different methodologies. Using simple Western analysis of extracts from virus particles, one can determine whether the envelope precursor protein ("gp85") is capable of being processed into SU and TM. See E. Harlow et al., ANTIBODIES: A LABORATORY MANUAL (Cold Spring Harbor Press, Cold Spring Harbor, N.Y. 1988) for methods. The virus particles can also be allowed to infect a target cell. After allowing a suitable period of time to elapse in which infection normally occurs, the cells can be washed and assayed for the presence of retroviral proteins. For example, in the instance of MoMLV, the presence of the gag protein precursor, $Pr65^{gag}$ can be assayed. Additional methods of assaying the (1) stability, (2) infectivity, and (3) virus titers are described in the examples below and are commonly available to skilled artisans.

Residues corresponding to those described in the motifs can be mutated in retroviruses other than Moloney MLV. Other preferred retrovirus envelope proteins contemplated include type C and type D retroviruses and lentiviruses.

TABLE I

| MoMLV Motif Amino Acids | Potential Amino Acid Substitutions | Examples |
|---|---|---|
| $^{104}$Lys, $^{107}$Glu, $^{90}$Thr, $^{102}$Arg and $^{108}$Thr | $^{104}$Lys→ any amino acid except Arg<br>$^{107}$Gln→ any amino acid except Arg and Lys<br>$^{90}$Thr→ any amino acid except Ser<br>$^{108}$Thr→any amino acid except Ser or Val<br>$^{102}$Arg → any amino acid | $^{107}$Gln → Trp<br>$^{90}$Thr → Arg<br>$^{108}$Thr → Lys |
| $^{124}$Arg, $^{126}$Arg, $^{138}$Tyr, $^{128}$Ser, $^{132}$Gly, $^{134}$Pro, $^{121}$Gly and $^{133}$Gly | $^{124}$Arg→ any amino acid<br>$^{128}$Ser→ any amino acid except Ala<br>$^{132}$Gly→ any amino acid<br>$^{138}$Tyr → any amino acid<br>$^{134}$Pro → any amino acid except Leu<br>$^{121}$Gly → any amino acid<br>$^{133}$Gly → any amino acid<br>$^{126}$Arg → any amino acid except Leu | $^{128}$Ser → Arg<br>$^{132}$Gly→Arg<br>$^{138}$Tyr → Ala<br>$^{134}$Pro→ Asp or Arg<br>$^{121}$Gly→ Arg<br>$^{133}$Gly→ Arg |
| $^{223}$Arg, $^{225}$Arg, $^{224}$Leu, $^{16}$Glu, $^{24}$Thr and $^{201}$Thr | $^{223}$Arg and $^{225}$Arg → both changed to any other amino acid<br>$^{224}$Leu → any amino acid<br>$^{16}$Glu→ any amino acid<br>$^{24}$Thr→ any amino acid except Ser<br>$^{201}$Thr→ any amino acid except Ser | $^{224}$Leu→ Asp or Ala<br>$^{16}$Glu → Lys<br>$^{16}$Glu→ Ala<br>$^{24}$Thr→ Ala<br>$^{201}$Thr → Ala |
| $^{137}$Phe, $^{135}$Asp, $^{136}$Ser, $^{208}$Arg and $^{217}$Gly | $^{137}$Phe → any amino acid<br>$^{135}$Asp → deleted from the env protein<br>$^{136}$Ser → deleted from the env protein<br>$^{208}$Arg → any amino acid<br>$^{217}$Gly → any amino acid | $^{135}$Asp → deleted from the env protein<br>$^{136}$Ser → deleted from the env protein<br>$^{208}$Arg → Asp<br>$^{217}$Gly → Trp or Ile |
| $^{142}$Trp, $^{152}$Trp, $^{210}$Tyr, $^{141}$Tyr and $^{151}$Tyr | $^{142}$Tyr → any amino acid except Tyr<br>$^{152}$Trp → any amino acid<br>$^{210}$Tyr → any amino acid<br>$^{151}$Tyr → any amino acid except Ser, Ala or Trp<br>$^{141}$Tyr→ any amino acid except Ser or Ala | $^{152}$Trp→ Asp<br>$^{142}$Trp → Asp<br>$^{210}$Tyr → Asp<br>$^{151}$Tyr → Asp<br>$^{141}$Tyr → Asp |
| $^{227}$Gln and $^{243}$Asp and $^{228}$Asn | $^{227}$Gln→ any amino acid except Thr or Leu plus $^{243}$Asp→ any hydrophobic amino acid including His<br>$^{228}$Asn → any amino acid except Asp or Thr plus $^{243}$Asp → any | $^{227}$Gln → Arg plus<br>$^{243}$Asp → deleted<br>$^{244}$Gln → Tyr<br>$^{227}$Gln → Arg plus Tyr inserted between |

TABLE I-continued

| MoMLV Motif Amino Acids | Potential Amino Acid Substitutions | Examples |
|---|---|---|
| | hydrophobic amino acid including His | $^{242}$Ala and $^{243}$Asp |
| | | $^{228}$Asn → Arg plus $^{243}$Asp → Tyr |
| $^{198}$Ser, $^{11}$Tyr, $^{226}$Tyr, $^{35}$Trp, $^{38}$Trp, $^{196}$Val, $^{197}$Thr, $^{160}$Tyr, $^{158}$Trp, $^{123}$His, $^{203}$His, $^{223}$Val, $^{235}$Ile, $^{240}$Val, $^{241}$Leu and $^{8}$His | $^{198}$Ser→ any hydrophobic amino acid including His | $^{11}$Tyr→ Trp |
| | $^{11}$Tyr → any hydrophobic amino acid including His | $^{226}$Tyr → use $^{204}$Val → Trp of amphotropic MLV |
| | $^{226}$Tyr → any hydrophobic amino acid including His | $^{35}$Trp → use $^{33}$Val → Trp of amphotropic MLV |
| | $^{35}$Trp → any hydrophobic amino acid including His | $^{38}$Trp → use $^{37}$Phe → Trp in amphotropic MLV |
| | $^{38}$Trp → any hydrophobic amino acid including His | $^{196}$Val → use $^{175}$Ala → Trp in amphotropic MLV |
| | $^{196}$Val → any hydrophobic amino acid including His | $^{197}$Thr → insert Tyr between $^{175}$Ala and $^{176}$Asp in amphotropic MLV |
| | $^{197}$Thr → any hydrophobic amino acid including His | |
| | $^{160}$Tyr → any hydrophobic amino acid including His | $^{160}$Tyr → use $^{120}$Leu → Tyr in amphotropic MLV |
| | $^{158}$Trp → any hydrophobic amino acid including His | $^{158}$Trp → use $^{146}$Leu → Trp in GALV |
| | $^{123}$His → any hydrophobic amino acid including His | $^{123}$His → His between $^{110}$Gly and $^{111}$Arg in GALV |
| | $^{203}$His → any hydrophobic amino acid including His | $^{203}$His → $^{193}$Lys → His in GALV $^{233}$Val → Ile |
| | $^{233}$Val → any hydrophobic amino acid including His | $^{235}$Ile→ Tyr |
| | $^{235}$Ile → any hydrophobic amino acid including His | $^{240}$Val → His |
| | $^{240}$Val→ any hydrophobic amino acid including His | $^{241}$Leu → His |
| | $^{241}$Leu→ any hydrophobic amino acid including His | $^{8}$His → Tyr |
| | $^{8}$His → any hydrophobic amino acid including His | |

Once the envelope mutants are created, they can be screened for envelope protein stability and virion infectivity using the following assays. The first assay comprises determining which virus particles containing an envelope protein, wherein at least one amino acid of one motif in has been substituted have the greatest stability under conditions of mechanical stress. In all examples, Western blot analysis quantitation of the amount of envelope protein (SU plus precursor) present in virions that were pelleted directly by high speed centrifugation (conditions of low viscosity and thus low mechanical stress) can be compared to the amount present in virions pelleted through sucrose (conditions of high viscosity and mechanical stress) to determine which retroviral vector is the most stable before and after repeated freeze-thawing cycles.

A second assay can be utilized to identify the virus particles exhibiting specific binding to the cognate receptor of the fused targeting sequence. The preferred virions will bind at the greatest levels to cells expressing the cognate receptor for the fused targeting sequence. The preferred virions will also maintain the lowest ratio of binding to cells lacking the cognate receptor compared to binding to cells with the cognate receptor. In embodiments that contain an envelope gene from a retrovirus that does not have a receptor on any human cells, retention of binding to the original virus receptor will not be a criterion for the preferred virus particle. For example, because human cells do not express a receptor for ecotropic MLV that could mediate retroviral vector gene delivery to nonspecific cell types, retention or loss of ecotropic MLV receptor binding will not be a criterion in embodiments containing ecotropic MLV envelope protein. In other examples using retroviral vectors containing envelope proteins from retroviruses that have receptors on human cells, the criterion of least binding to the original retrovirus receptor and maintenance of the greatest binding to the cognate receptor will be applied (see, Battini et al., *J Virol* (1998) 72(1):428–35).

A third assay may be utilized to identify which virus particles expressing a mutant envelope protein exhibit the highest level of gene delivery specifically to designated target cell populations in vitro. The preferred retrovirus vector containing at least one altered amino acid of at least one of the seven motifs will deliver a gene to the greatest number of cells expressing the cognate receptor for the fused targeting sequences and maintain the lowest ratio of gene delivery to cells lacking the cognate receptor compared to gene delivery to cells with the cognate receptor. These particles can then be assessed for their efficacy in targeting cells in vivo. The preferred retrovirus vector will deliver a gene to the greatest number of cells expressing the cognate receptor for the fused targeting sequences and maintain the lowest ratio of gene delivery in cells lacking the cognate receptor in vivo. For example, quantitation of gene delivery will indicate the retroviral vector that delivers a gene to the greatest number of tumor cells and their vascular endothelial cells and to the least number of healthy cells and established vasculature in the nude mouse model of m.f.p. implantation.

III. Fusion Proteins

Once the mutant envelope proteins and the genes encoding them are created, additional engineering of the retrovirus vector can occur. The retrovirus vector can be engineered to contain a ligand or protein that recognizes and binds to a specific cell receptor, or an antibody or antibody fragment that recognizes an antigen on a cell. The types of polypeptide molecules which may be fused to the retroviral envelope protein include immunoglobulin molecules or their fragments (e.g., scFV), lectins, polypeptides or their fragments of a ligand-receptor pair, and polypeptides or their fragments of an antibody-antigen pair (e.g., anti-human transferrin receptor antibody). Methods of preparing these chimeric targeting proteins for use in gene therapy or as a delivery vector mechanism are described by Etienne-Julan et al., (1992) *J. Gen. Virol.* 73: 3251–55; R. W. Paul et al., U.S. Pat. No. 5,736,387 (1998); and S. Kayman et al., U.S. Pat. No. 5,643,756 (1997).

IV. Use of Retroviral Envelope Proteins in Non-Viral Vectors

Non-viral compositions have also been prepared that introduce agents into targeted cells. The introduced agents include dyes, proteins, toxins and other drugs (C. R. Dass et al., 1997 *Drug Deliv.: J. Deliv. & Targeting Ther. Agents* 4: 151–65), antibodies, as well as nucleic acid molecules (V. J. Dzau et al., 1996 *Proc. Nat'l Acad. Sci. USA* 93: 11421–25; D. D. Lasic et al., 1996 *Adv. Drug Deliv. Rev.* 20: 2–3). Liposomal compositions can also be utilized as vaccines, as described by T. Okamoto et al., 1997 *Gene Ther.* 4: 969–76. This invention contemplates using the envelope protein mutants either alone or in a liposomal composition expressing a described mutant envelope protein or a fragment thereof capable of targeting a specific cell population or tissue. The mutant envelope protein may be in combination with one or more phospholipids and/or carbohydrate cryopreservatives in the liposome. Methods of preparing and administering these compositions are described in L. Li et al., U.S. Pat. No. 5,641,508 (1997); L. D. Mayer et al., U.S. Pat. No. 5,744,158 (1998); M. B. Bally et al., U.S. Pat. No. 5,736,155 (1998); J. Virtanen et al., U.S. Pat. No. 5,718,915 (1998); M. Foldvari, U.S. Pat. No. 5,718,914 (1998); N. Dattagupta et al., U.S. Pat. No. 5,711,964 (1998). Liposomal compositions containing the envelope protein may also be administered after preparation in the presence of lipid destabilizing molecules that enhance the lipid fusion ability (Melikyan et al., 1997 *J. Cell. Biol.* 136: 995–1005; and Kemble et al., 1994 *Cell* 76: 383–91). Other methods commonly known in the art may be used.

V. Retroviral Gene Transfer

The retrovirus particles described above can infect cells by the normal infection pathway as along as recognition of the target cell receptor, fusion and penetration into the cell all occur. All eukaryotic cells are contemplated for infection by the recombinant virions. Preferred cells include cells from vertebrates. Most preferred are human cells. Other preferred cells include, but are not limited to, hematopoietic cells, totipotent stem cells, bone marrow cells, endothelial cells, epithelial cells, keratinocytes, stem cells, hepatocytes, fibroblasts, mesenchymal cells, mesothelial cells and parenchymal cells. Methods for infecting cells with retrovirus particles are described in A. D. Miller et al., U.S. Pat. No. 5,219,740 (1993), which discloses methods of infecting fibroblasts; D. A. Williams et al., U.S. Pat. No. 5,686,278 (1997), which discloses methods of infecting and enhancing infection of hematopoietic cells; and generally in GENE THERAPY PROTOCOLS: METHODS IN MOLECULAR MEDICINE, Paul D. Robbins (ed.) (Humana Press 1997). Other methods of preparing and administering retroviral particles in gene therapy commonly known to the skilled artisan may be used.

The types of genes that are to be transferred into the host cell by the retrovirus particles of this invention may encode therapeutic agents, including, but not limited to, tumor necrosis factor genes (TNF); genes encoding interferons, such as interferon $\alpha$ (IFN-$\alpha$); genes encoding interleukins (IL), such as IL-2 to IL-12; genes encoding granulocyte macrophage colony stimulating factor (GM-CSF); genes encoding adenosine deaminase (ADA); genes encoding cellular growth factors; genes encoding CD4, Factor VIII, Factor IX, T cell receptors, the LDL receptor, ApoE, ApoC, the $\alpha$-1 antitrypsin gene, the ornithine transcarbamylase (OTC) gene, the DFTR gene, Fc receptors, and the insulin gene; antisense sequences which inhibit viral replication or replication of other genes; and genes encoding specific immunoglobulins or their fragments (Fv, scFv, Fab, Fab', or F(ab')$_2$). Further, these include, but are not limited to, suicide or lethal genes such as the gene encoding diptheria toxin A-chain (Gelfand et al., U.S. Pat. No. 4,830,962), *Escherichia coli* cytosine deaminse that renders cells susceptible to the drug 5-fluorocytosine (Ju et al., *J Cancer Res Clin Oncol* (1998) 124:683–689) or herpes simplex virus type-1 thymidine kinase that render cells susceptible to the drug gancyclovir (Fretag et al., *Hum Gene Ther* (1998) 9:1323–1333).

Such genes or nucleic acid molecules are under the control of a suitable promoter. Suitable promoters, which may be employed, include, but are not limited to adenoviral promoters, the cytomegalovirus promoter, the Rous sarcoma virus (RSV) promoter, the respiratory syncytial virus promoter, inducible promoters such as the metallothionein promoter, heat shock promoters, or the gene's own natural promoter. It is to be understood however, that the scope of the present invention is not to be limited to specific foreign genes or promoters.

Most gene therapy is administered to cells ex vivo. The cells receiving such gene therapy treatment may be exposed to the retrovirus particles in combination with a pharmaceutically acceptable carrier suitable for administration to a patient. The carrier may be a liquid carrier (for example, a saline solution), or a solid carrier such as an implant or microcarrier beads. In employing a liquid carrier, the cells may be introduced intravenously, subcutaneously, intramuscularly, intraperitoneally, intralesionally, etc. In yet another embodiment, the cells may be administered by transplanting or grafting the cells. Lipid destabilizers, such as thiocationic lipids, can be utilized in admixture with the viral vector or liposomal vector to increase infectivity (see examples of lipid destabilizers in C. N. Sridhar et al., 1998 U.S. Pat. No. 5,739,271 and N. Dattagupta et al., 1998 U.S. Pat. No. 5,711,964).

Although most current gene therapy protocols involve ex vivo transfection of cells, the vectors disclosed would permit in vivo treatment of a subject, such as a human patient, as well as ex vivo utilization. For example, ex vivo therapy requires that cells such as hepatocytes be removed from the patient, transduced with the retroviral particle containing the desired nucleic acid molecule, and then transplanted back into the patient. In vivo therapy would allow direct infusion of the gene therapy vector, without the intervening steps and the complications that they raise. Moreover, this will allow access to tissues that may not have been good candidates for ex vivo gene therapy.

Transduced cells may be used, for example, in the treatment of cancer in a human by transducing a vector into human primary cells, such as blood cells which specifically target the tumor cells. Other diseases contemplated for treatment include, but are not limited to: adenosine deaminase deficiency (ADA), thalassemia, hemophilia, diabetes, alpha-anti trypsin deficiency, brain and neural disorders, phenylketonuria, growth disorders, heart diseases and immune diseases.

VI. Pseudotype Virus Particles

Gene therapy vectors also include pseudotyped virus particles. Pseudotype viruses were originally created to overcome problems encountered by gene therapy vectors' natural host cell tropisms. In recent years, many gene therapy patents have issued wherein the vector contains a heterologous polypeptide used to target the vector to specific cells, such as vectors containing chimeric fusion glycoproteins (S. Kayman et al., U.S. Pat. No. 5,643,756); vectors that contain an antibody to a virus coat protein (M. Cotten et al., U.S. Pat. No. 5,693,509); viruses engineered to allow study of HIV-1 in monkeys, a species that normally cannot be infected by HIV-1, by creating hybrid viruses (J. Sodroski et al., U.S. Pat. No. 5,654,195); and pseudotype retrovirus vectors which contain the G protein of Vesicular Stomatitis Virus (VSV) (J. C. Burns et al., U.S. Pat. Nos. 5,512,421 and 5,670,354).

Pseudotyping can also be used in preparing liposomal compositions. Pseudotyped viruses are viruses where the envelope of another virus has been integrated into the virion. For example, a pseudotype Rhabdovirus expressing CXCR4/CD4 instead of the complete G protein of the Rhabdovirus has been shown to infect cells which express the HIV-1 envelope protein, the ligand pair to CXCR4/CD4 (T. Mebatsion et al., 1997 *Cell* 90: 841–7). Other examples of preparing pseudotyped viruses and chimeric envelope proteins include those described in the following publications: M. C. Galmiche et al., 1997 *J. Gen. Virol.* 78: 3019–27; Schnell et al., (1996) *Proc. Nat'l Acad. Sci. USA* 93: 11359–11365); Schnell et al., 1997 *Cell* 90: 849–857; L. Naldini et al., 1996 *Proc. Nat'l Acad. Sci. USA* 93: 11382–8; A. M. Robinson et al., 1998 *Biochim. Biophys. Acta* 1369: 278–86; D. Korpotin et al., 1997 *Biochemistry* 36: 66–75; J. Huwyler et al., 1996 *Proc. Nat'l Acad. Sci. USA* 93: 14164–9; and D. D. Spragg et al., 1997 *Proc. Nat'l Acad. Sci. USA* 94: 8795–8800. Preferred pseudotype viruses include members of the Rhabdovirus family (e.g., rabies virus, vesicular stomatitis virus) and vaccinia virus.

VII. Lipid Destabilizers

The use of the various substitutions provides a method for identifying candidate molecules on a target cell surface that have the characteristics required to function as a receptor. For example, a given ligand sequence is fused into the envelope gene sequence encoding the N-terminus of a retrovirus comprising cleavage suppression or SU stabilizing substitutions by standard PCR methods and ligation into an appropriate plasmid. Viruses are produced by transfection of these constructs alone into cells as well as by cotransfection of the constructs plus the parental wild type retroviral constructs. Virus binding and endpoint dilution titration are quantified using cells that express the cognate receptor for the fused ligand and cells that lack the cognate receptor. A selected target molecule is expected to give a high level of gene delivery specifically to the target cell population, compared to delivery to cells lacking the target molecule, using vectors containing a stable mutant envelope protein with the target molecule's ligand inserted in the N-terminus alone or co-expressed with wild type retroviral envelope protein. A target cell surface molecule whose ligand inserted into the mutant does not yield a high level of specific gene delivery alone, or when co-expressed with wild type retroviral envelope protein, would be a candidate for gene delivery using lipid destabilizers. In a preferred embodiment certain lipid and lipid analogs are used which can greatly influence the fusion process by inducing curvature in the membrane leaflets. For example, such destabilizers include, but are not limited to, chlorpromazine (CPZ), dibucaine (DB) and trifluoropyrosine (TFP). In a further preferred embodiment, said destabilizers promote leaflet curvature in a direction that favors pore formation in the membrane bilayers. Moreover, the destabilizers include other membrane permeable molecules which partition preferentially into the inner leaflet.

The following examples therefore, specifically point out preferred embodiments of the present invention, and are not to be construed as limiting in any way the remainder of the disclosure. Other generic configurations will be apparent to one skilled in the art.

EXAMPLES

Example 1

The Effect of Mutations at $^{227}$Gln and $^{243}$Asp on the Defect in Envelope Protein Rendered By $^{8}$His Substitution $^{227}$Gln, $^{243}$Asp and $^{228}$Asn residues form a motif. When the $^{8}$His residue is mutated to an arginine residue host cell fusion is substantially reduced. The combined mutations of $^{227}$Gln and $^{243}$Asp can rescue the fusion function that $^{8}$His confers to the env protein. One mutant which rescues the $^{8}$His to Arg mutation contains $^{227}$Gln to Arg and $^{243}$Asp to Tyr substitutions. Other embodiments contemplated include changing $^{227}$Gln to any amino acid except alanine, plus changing $^{243}$Asp to any hydrophobic amino acid including histidine. $^{228}$Asn can also be mutated to any amino acid except alanine, plus $^{243}$Asp to any hydrophobic residue including histidine. Other embodiments contemplated include changing $^{227}$Gln to any amino acid except alanine plus inserting Tyr between $^{242}$Ala and 243Asp, or changing $^{227}$Gln to any amino acid except alanine plus deleting $^{243}$Asp plus changing $^{227}$Gln to any hydrophobic amino acid including histidine, or any combination of deletion, insertion, or substitution of residues 228 through 244 that replaces any hydrophobic amino acid and produces a similar phenotype. The envelope proteins thus produced would have increased penetration capability through restoration of the function of residue $^{8}$His and decreased shedding of binding sequences through stabilization of SU:TM interaction.

The aligned sequences, and more importantly, the amino acid residues that align with a residue from one of the seven motifs, identifies the conserved amino acids in each of the seven motifs as found in MoMLV, Friend MLV, RadLV MLV, MLV 10A1, MCF1233, Xeno CWM, Xeno NZB, FeLV-A, FeLV-B, GALV SEATO and HIV-1. Correspondingly, one or more of these conserved residues in one or more of the seven motifs which align with the above identified MoMLV motif residues may be altered using methods described above for similar effect.

Methods

Cell lines and viruses. Mouse NIH3T3 fibroblasts and non-permissive human 293 fetal kidney cells were cultured in Dulbecco's modified Eagle's medium (DMEM) supplemented with 8% donor calf serum. 293-derived stable transfectants expressing defective ecotropic retrovirus receptors have been described elsewhere (S. Malhotra et al., 1996 *J. Virol.* 70:321–6). They were maintained in DMEM containing 200 µg/ml G418 (GIBCO). XC rat sarcoma cells (ATCC CCL-165) were cultured in DMEM supplemented with 8% fetal bovine serum and 3.5 mg/ml D-glucose. HI-BAG cells were maintained in DMEM with 8% fetal bovine serum and 250 µg/ml G418 (Sigma).

Plasmids Encoding Virus Genomes

Initially, a master plasmid, pcDNA MoMLV, was constructed encoding a virus genome derived from MoMLV which provides wild type gag and pol genes from which proteins for the virion core would be made. The plasmid also contains an env gene from which the envelope proteins for assembly into the membrane of the virions can be synthesized. The 8 kbp fragment from the BssHII restriction site to the env termination codon containing the MoMLV proviral genome that lacks the packaging signal was derived from plasmid pEM-5 (gift of V. Garcia). The env gene termination codon is followed by an artificially engineered BamHI site. The genome was inserted between HindIII and BamHI sites of the eukaryotic expression vector pcDNA3, placing transcription of the viral genome under the control of the cytomegalovirus promoter. A downstream polyadenylation site is provided by the bovine growth hormone polyA site. This genome is not incorporated into virions because it lacks the packaging sequence, Ψ. The pBAG plasmid (gift of C. Cepko) (D. L. Turner et al., 1987 Nature 328:131–6) encodes a replication-defective but packagable MoMLV genome. The structural genes have been replaced in pBAG by two genes—the E. coli lacZ gene encoding β-galactosidase (lacZ) under the control of the retroviral 5' LTR, followed by the neomycin resistance gene (neo$^r$) under the control of the SV40 promoter.

Sequence Analysis of Parental env Gene

Genomic DNA from the replication-competent ecotropic virus producer cell line was isolated as previously described (L. M. Albritton et al., 1989 Cell 57:659–66). Two overlapping fragments of the env gene were amplified using Pfu thermal polymerase (Stratagene). The amplimers were then gel-purified and sequenced using the Exo(–) Pfu Cyclist kit (Stratagene).

Isolation of env Genes From Virus Quasi Species

Genomic DNA was isolated from virus producing cells as previously described (Albritton, et al., 1989) and used as a template for PCR to amplify env genes representing quasi species acquired by virus passaging. Oligonucleotides used for PCR were: 5'-CAAAGTAGACGGCATCGCAGCTTGG-3' from the sense strand upstream of PmlI restriction site; and 5'-GGCGAATTCATCTATGGCTCGTACTCT-3' from the antisense strand including the last five codons of the env gene and an engineered EcoRI site. PCR reactions were performed in the presence of high Mg$^{++}$ concentration shown to improve the fidelity of TAQ polymerase. PCR products were digested with PmlI and EcoRI restriction enzymes and subcloned into a PmlI-EcoRI digested pcDNA3-MoMLV plasmid. The resulting plasmids were used to produce virus particles as described below. Selected plasmids were submitted to DNA sequence, analysis.

Preparation of Retroviral Vectors

Amphotropic packaging cell line PA317 (A. D. Miller et al., 1986 Mol. Cell. Biol. 6: 2895–02) was transiently transfected by calcium phosphate precipitation with the pBAG plasmid. The virus-containing supernatant was harvested and used to infect human 293 cells into which the virus transduces the lacZ and neo$^r$ genes. Infected 293 cells were selected in the medium containing 1 mg/ml of G418. Twenty four drug-resistant colonies were propagated and analyzed for β-galactosidase expression by staining with 5-bromo-4-chloro-3-indolyl-β-D-galactopyranoside (X-GAL). The five clones developing the most intense staining in the shortest period of time, indicative of high levels of transcription of the packagable virus genome, were selected as virus producers. Expression of packagable viral RNA was confirmed by Northern analysis. One of these cell clones, H1-BAG, was used in all experiments reported here.

To produce virus particles, we transiently transfected the H1-BAG cells with pcDNA-MoMLV DNA containing wild type, cloned or mutated env genes. Transfection was performed by calcium phosphate precipitation as described by Sambrook et al, (1989). 30 μg of DNA was used per 100 mm dish of 70%–80% confluent H1-BAG cells. 16 h after transfection, cells were fed with 10.5 ml of fresh medium (DMEM plus 8% fetal bovine serum without G418), virus-containing supernatant was harvested 24 h later, cells were re-fed with 10.5 ml of fresh medium, and virus was harvested again at 64 h post-transfection. Virus preparations were freed of producer cells by low speed centrifugation followed by filtration through a 0.45 micron filter. An aliquot of 3 ml was removed, stored at –80° C., and then used for virus titration. Virions produced in this manner transduce β-galactosidase activity upon infection of cells because they contain the genome encoded by the pBAG plasmid which is the only virus genome present that has a packaging signal. Virus from the remaining 7 ml were immediately pelleted as described below for immunoblotting. For each virus binding experiment, the entire virus preparations were frozen and concentrated as described below.

Site-directed Mutagenesis of env Genes

Nucleotide substitutions in the env gene were generated by the method described by Kunkel (T. A. Kunkel, 1985 Proc. Nat'l Acad. Sci. USA 82:477–492). For this purpose we subcloned the 1300 bp, HpaI-HpaI restriction fragment from the Mo-MLV-E env gene on plasmid pMOV3 (gift of H. Stuhlmann; K. Harbers et al., 1981 Proc. Nat'l Acad. Sci. USA 78:7609–13) into bacteriophage vector M13mp18 with an engineered HpaI site. Site-directed mutagenesis was performed, and the fragment was inserted back into pcDNA3-MoMLV. The entire 1300 bp fragment was sequenced using the fmol™ sequencing kit (Promega) to ensure the absence of unscheduled substitutions and to confirm the presence of desired mutations.

Table II shows all of the mutations to the nucleic acid sequence performed to produce the associated altered amino acid. The first column indicates the original amino acid (indicated by the first letter), and the second amino acid reflects the new mutated residue. The nucleic acid sequence number is from the MoMLV sequence by Shinnick et al., (1981).

TABLE II

| Amino Acid Mutation | Nucleotide Change | Nucleotide Sequence No. |
|---|---|---|
| R102D/K104D | a → g | 6179 |
|  | g → a | 6180 |
|  | a → t | 6181 |
|  | a → g | 6185 |
|  | g → t | 6187 |
| R102A | a → g | 6179 |
|  | g → c | 6180 |
| R102D | a → g | 6179 |
|  | g → a | 6180 |
|  | a → t | 6181 |
| R102E | a → g | 6179 |
|  | g → a | 6180 |
|  | g → a | 6181 |
| K104A | a → g | 6185 |
|  | a → c | 6186 |
|  | g → a | 6187 |
| K104D | a → g | 6185 |
|  | g → t | 6187 |
| K111A/E114A | a → g | 6206 |
|  | a → c | 6207 |
|  | a → c | 6216 |
| R124D/R126D | c → g | 6245 |
|  | g → a | 6246 |
|  | c → t | 6247 |
|  | c → g | 6251 |
|  | g → a | 6252 |
|  | a → t | 6253 |

TABLE II-continued

| Amino Acid Mutation | Nucleotide Change | Nucleotide Sequence No. |
|---|---|---|
| R124D | c → g | 6245 |
|  | g → a | 6246 |
|  | c → t | 6247 |
| R124E | c → g | 6245 |
|  | g → a | 6246 |
|  | c → a | 6247 |
| R126D | c → g | 6251 |
|  | g → a | 6252 |
|  | a → c | 6253 |
| R126E | c → g | 6251 |
|  | g → a | 6252 |
|  | a → g | 6253 |
| D135A | a → g | 6279 |
|  | c → g | 6280 |
| D135K | g → a | 6278 |
|  | c → g | 6280 |
| D135R | g → a | 6278 |
|  | a → g | 6279 |
|  | c → g | 6280 |
| P134A | c → g | 6275 |
| F137A/Y138A | t → g | 6284 |
|  | t → c | 6285 |
|  | c → a | 6286 |
|  | t → g | 6287 |
|  | a → c | 6288 |
|  | c → a | 6289 |
| F137E/Y138E | t → g | 6284 |
|  | t → a | 6285 |
|  | c → a | 6286 |
|  | t → g | 6287 |
|  | c → a | 6289 |
| F137A | t → g | 6284 |
|  | t → c | 6285 |
|  | c → a | 6286 |
| Y138A | t → g | 6287 |
|  | a → c | 6288 |
|  | c → a | 6289 |
| R223D/R225D | c → g | 6542 |
|  | g → a | 6543 |
|  | a → t | 6544 |
|  | a → g | 6548 |
|  | g → a | 6549 |
|  | a → t | 6550 |
| Y141A/W142A | t → g | 6296 |
|  | a → c | 6297 |
|  | t → a | 6298 |
|  | t → g | 6299 |
|  | g → c | 6270 |
| Y141A | t → g | 6296 |
|  | a → c | 6297 |
|  | t → a | 6298 |
| W142A | t → g | 6299 |
|  | g → c | 6270 |
| W142S | g → c | 6330 |
|  | g → a | 6331 |
| W142M | t → a | 6329 |
|  | g → t | 6330 |
|  | g → g | 6331 |
| W142Y | g → a | 6330 |
|  | g → c | 6331 |
| K153D | a → g | 6332 |
|  | g → t | 6334 |
| R149D/K153D | a → g | 6320 |
|  | g → a | 6321 |
|  | a → t | 6322 |
|  | a → g | 6332 |
|  | g → t | 6334 |

Reverse Transcriptase Assay and Virus Titers

Reverse transcriptase assays were performed exactly as described by S. Goff (S. Goff et al:, 1981 *T. Virol.* 38:239–48). End-point dilution titration of all virus stocks was performed essentially as previously described for MLV-E with modifications as follows (S. Malhotra et al., 1996). Briefly, $2 \times 10^4$ cells were seeded in each well of a 24-well culture plate. Quadruplicate wells were exposed to 10 fold serial dilutions of virus stock in medium containing polybrene (20 µg/ml; Sigma). For cells exposed to stocks of DHFR-5HE* virus, the medium was replaced two days later with medium containing 150 µM methotrexate (Sigma) and 8% dialyzed donor calf serum. Selection in methotrexate-containing medium was maintained for two weeks, and infected cells were identified and scored as methotrexate-resistant colonies following fixation and staining using 2% crystal violet, 90% ethanol. In the case of exposure to stocks of β-galactosidase transducing virus, cells were fixed and stained with X-GAL for β-galactosidase activity. Titers were calculated for the end-point dilution.

Western Blot Analysis

Virus particles were pelleted from 7 ml of cell-free virus supernatant through 3 ml of 25% sucrose in TNE (10 mM Tris pH 8.0, 1 mM EDTA, 100 mM NaCl) in a Beckman SW41 rotor (30,000 rpm, 2 h, 4° C.). Pellets were resuspended in 40 µl of PBS and stored at –80° C. Virus producer cells were lysed immediately after the second virus harvest in 300 µl of RIPA buffer (20 mM Tris pH 7.0, 1% Triton X-100, 0.05% SDS, 0.5% Na deoxycholate, 150 mM NaCl, 2.5 mM PMSF) and incubated for 30 min on ice. Cell lysates were centrifuged for 10 min at 10,000 rpm to pellet nuclei and supernatants were frozen at –80° C. Total protein concentration in cell lysates was determined by Bradford assay (BioRad). 10 µl of virus pellets or 100 µg of total protein from cell lysates was diluted 1:1 in 2× gel loading buffer (J. Sambrook et al., 1989) boiled for 10 min, chilled on ice and subjected to SDS-polyacrylamide gel electrophoresis. The separated proteins were transferred onto nitrocellulose membranes (Protran, S&S) in 48 mM Tris, 39 mM glycine, 0.037% SDS, and 20% methanol overnight. Filters were blocked in 6% powdered milk and Tris Buffered Saline (TBS) pH 7.4 containing 0.2% Tween 20 for 1 h at room temperature. Envelope proteins (SU and Precursor) were detected with goat anti-Rauscher-gp70 (1:100); structural capsid protein (CA) was detected with goat anti-Rauscher-p30 (1:10,000) (Quality Biotech Inc.). Envelope TM protein was detected with monoclonal mouse anti-p15E antisera (Hybridoma 372; ATCC). Incubations were done at 4° C. for 1 h. Subsequent incubation with secondary antibodies, mouse anti-goat or mouse anti-rabbit conjugated to horse radish peroxidase (HRP) (1:10,000) (Sigma) was performed at room temperature for 1 h. Immunoblots were developed using detection of HRP with SuperSignal™ (Pierce).

Virus Binding Assays

Binding assays were performed essentially as described (F. L. Cosset et al., 1995 *J. Virol.* 69:6314–22; and M. J. Kadan et al., 1992 *J. Virol.* 66:2281–7) with the following modifications. Virus-containing supernatants were concentrated 10- to 15-fold on Centricon-100 concentrators (Amicon). This concentration eliminates most of the SU protein not associated with virions so that virus binding can be quantitated in the absence of monomer SU shed from virions or the producer cell surface. This concentration also promotes binding of multiple virions to a single cell and increases the mean fluorescence per cell detected by flow cytometry. To ensure that equal numbers of particles from each of the virus stocks were incubated with cells during the assay, the concentration of virus stocks was adjusted to achieve comparable particle concentrations based on the reverse transcriptase activity and Western blot quantitation of capsid protein. 293 cells expressing wild type virus receptor or parental 293 cells were detached from culture plates with PBS containing 0.02% EDTA. $10^6$ cells were then incubated with 1 ml of concentrated virus stocks containing equal amounts of virions in the presence of polybrene (5 μg/ml) for 1 h at 4° C. Cells were then washed with PBA (PBS, 2% fetal bovine serum, and 0.02% sodium azide) and incubated in 500 μl of PBA containing goat anti-gp70 antisera (1:100) for 30 min at 4° C. After two washes, cells were incubated with 500 μl of secondary antibody, donkey anti-goat conjugated to FITC (Jackson Laboratories) diluted in PBA (1:200) for 30 min at 4° C. Propidium iodide (Sigma) was added to the binding reaction for 5 min at a final concentration of 20 μg/ml. Cells were washed twice, taken up in 500 μl of PBA, and the fluorescence of the live cells (negative for propidium iodide) was analyzed by flow cytometry (Epics Profile Analyzer, Coulter Cytometry). Experiments were repeated three times.

Cell-cell Fusion Assays

XC fusion assays were performed as described by A. Rein et al., (1978 *J. Virol.* 25:146–56) with modification as follows. XC cells were exposed to virus stock containing 20 μg/ml polybrene or to medium containing 20 μg/ml polybrene and incubated for continuous exposure at 37° C. for 16 h, then they were fixed and stained as described by Rein and coworkers (A. J. Rein et al., 1994 *J. Virol.* 68: 1773–81). Cell-cell fusion was quantitated by counting the total number of nuclei with the total number of nuclei in syncytia (a syncytium was defined as a cell containing at least three nuclei with a diffuse, disperse cytoplasm.) under the light microscope in at least three representative fields containing at least 300 total nuclei. The percentage of cell-cell fusion was calculated as: (the total number of nuclei in syncytium/ the total number of nuclei) multiplied by 100.

Envelope fusion function was also assessed using a modification of the method described by G. W. Kemble et al., (1992 *J. Virol.* 66:4940–50). cDNA plasmids encoding the wild type or mutant env genes were transiently transfected into human 293 cells. 24 hr later, the transfected cells, as well as naive XC cells, were labeled with membrane permeable viable fluorescent dyes, CellTracker Green CMFDA and CellTracker Orange CMTMR (Molecular Probes) following the manufacturer's instructions. Upon dye entry into the cells, cellular esterases cleave the acetate moieties to release their fluorescent derivatives and weak interactions with intracellular proteins containing thiol groups, particularly glutathione, result in adducts that are membrane impermeable and retained in the cell long term. Labeled 293 cells expressing envelope protein were overlaid on the labeled cultures of XC cells and incubated at 37° C. for various times. Cells were then examined by epifluorescent microscope using a FITC filter set for the fluorescent adduct of CellTracker Green CMFDA and a filter set for the adduct of CellTracker Orange CMTMR. Cell images were captured using a Kodak digital camera (Eastman Kodak). Files were transferred into Adobe Photoshop, and the contrast and brightness was adjusted to allow reproduction.

Results

Replication-competent ecotropic virus possessing a wild type env gene sequence was passaged on human 293 cells expressing defective receptors. After three rounds of passaging, genomic DNA of virus-producing cells was isolated and the env genes from the quasi-species present were amplified and subcloned into plasmid pcDNA MoMLV. Twenty-four representative env clones were selected for analysis.

Clones 838 and 839 were identical in sequence; they encoded the same three substitutions of Histidine 8 to arginine (H8R; a→g at nucleotide 5898), Glutamine 227 to arginine (Q227R; a→g at nucleotide 6555), and Aspartate 243 to tyrosine (D243Y; g→t at nucleotide 6602). To determine which of the three mutations found in clones 838 and 839 was responsible for the decrease in envelope function, these nucleotide changes were inserted in the wild type env sequences in plasmid pcDNA MoMLV, either as a single mutation or as all combinations of multiple substitutions. FIG. 5 shows the results of the characterization of the encoded proteins. A single H8R substitution almost completely abolished infection, while single and double mutations at the other two positions did not affect infection. These results indicate that the change in $^8$His is responsible for the defect in infection found with clones 838 and 839. Interestingly, the triple mutation corresponding to the original 838 and 839 clones remained only 100-fold less infectious than wild type virus, suggesting that one or both of the other two mutations can compensate for the defect introduced by the H8R substitution. However, neither a Q227R in combination with a H8R mutation nor a D243Y mutation in combination with a H8R mutation improved infectivity appreciably. Therefore, both changes are required, and they exert a synergistic effect to overcome the H8R mutation.

The next step was to determine whether the observed defect in the H8R mutant could be rescued by changes in the residues at 227 and 243. All of the mutant envelope proteins were efficiently incorporated into virions (FIG. 5B) and processed normally (FIG. 5C). These results indicate that the reduction in infectivity of viruses carrying the H8R mutation was not due to lack of expression of producer cells nor to failure of cells to incorporate into virions. Therefore, it was likely that mutation of $^8$His abolished a function of the envelope involved in virus entry. Binding and fusion assays were performed to determine if virus binding or virus penetration of the host cell membrane is affected by the substitution of $^8$His. Viruses pseudotyped with envelope proteins containing the H8R mutation bound human cells expressing receptor as proficiently as did viruses coated with wild type envelope proteins (FIG. 6A), indicating that $^8$His is not involved in virus attachment. To determine if $^8$His is involved in virus-cell fusion, rat XC cells were incubated with each of the mutant viruses. XC cells express the ecotropic retrovirus receptor on their surface and are susceptible to MLV-E. In addition, XC cells exhibit an extraordinary propensity to undergo cell fusion when exposed to wild type MLV-E, a phenomenon called syncytium induction (A. Rein et al., 1978). This ability to induce syncytium on XC cells correlates with the fusion properties of the envelope proteins on the virus (R. Weiss et al., RNA TUMOR VIRUSES 1984 Cold Spring Harbor Laboratory Press). Viruses pseudotyped in envelope containing the H8R mutation failed to induce XC cell fusion as compared to wild type virus which induced extensive fusion in the same assay (FIG. 6B). In contrast, complementation of the H8R mutation with both the Q227R and D243Y mutations restored the syncytium-inducing capability. These results indicate that the histidine in position 8 of MoMLV SU plays an essential role in virus-cell fusion that can be replaced by substitution of Glutamine 227 plus Aspartate 243.

Example 2

Use of the $^{227}$Gln and $^{243}$Asp Mutations to Maintain Infectivity and Stability in a Fusion Envelope Protein $^{227}$Gln and $^{243}$Asp residues form a motif along with $^{228}$Asn wherein if a heterologous binding peptide or glycopeptide is linked to the envelope protein and viral fusion or penetration is reduced as a result, then the combined mutations of $^{227}$Gln and $^{243}$Asp can rescue the target cell penetration and stabilize the envelope protein. Viral vectors have been designed to allow infection of the specific type of cell that is the target for delivery of a nucleic acid but not of any other cells. The method of overcoming the retrovirus' natural tropism by expressing an envelope fusion protein that contains the SU linked to a selected peptide or glycopeptide has encountered problems. The pseudotype vectors of the prior art were very poorly infectious or completely noninfectious in the target cell due to failure of a post-binding event that is essential to penetration (N. Kasahara et al., 1994 *Science* 266: 1373–76). The prior art disclosed the following: The defect in penetration is the failure to complete fusion of the vector lipid bilayer with the bilayer of the target (Y. Zhao et al., 1997 *J. Virol.* 71: 6967–72; A. Rein et al., 1998 *J. Virol.* 72: 3432–35; and W. F. Anderson, 1998, *Nature (Suppl)* 392: 25–30). Fusion envelope proteins constructed by this method linked the peptide sequence between Serine 6 and Proline 7 (F.-L. Cossett et al., 1995 *J. Virol.* 69: 6314–22; and M. Marin et al., 1996 *J. Virol.* 70: 2957–62), before Valine 17 (N. V. Somia et al., 1995 *Proc. Nat'l Acad. Sci. USA* 92: 7570–74), and in place of Threonine 18 through Glycine 221 (N. Kasahara et al., 1994; and X. Han et. al., 1995 *Proc. Nat'l Acad. Sci. USA* 92: 9747–51) in the Moloney MLV envelope protein. Fusion envelope proteins have also been constructed by linking the peptide sequence in similar positions of the Rous sarcoma virus (RSV) (J. A. T. Young et al., 1990 *Science* 250: 1421–23) and in the middle of the Rous-associated virus type 1 (RAV-1) envelope proteins (S. Valsesia-Wittman et al., 1994 *J. Virol.* 68: 4609–19). Further limitations of these fusion envelope proteins included unstable association with virions and poor incorporation into virions (F.-L. Cossett et al., 1995; and M. Marin et al., 1996), or in two instances, the requirement for co-expression of the wild type MoMLV envelope protein for virion incorporation (N. Kasahara et al., 1994; and X. Han et. al., 1995 *Proc. Nat'l Acad. Sci. USA* 92: 9747–51). In fusion envelope proteins in which the heterologous peptide is linked to sequences in the N-terminus of SU, the penetration defect is thought to be due to loss of function of a domain on the MoMLV SU consisting of residues 1 through 8, including Histidine 8, and the instability to be due to changes in the envelope conformation (Y. Bae et al., 1997 *J. Virol.* 71: 2092–99; and W. F. Anderson, 1998, *Nature (Suppl)* 392: 25–30). We propose the defective penetration phenotype exhibited by the fusion targeting envelope proteins is equivalent to the penetration defect found in the Histidine 8 changed to arginine envelope mutant, e.g., inability to complete fusion of the virus membrane with the membrane of the cell, that we identified in a genetic selection (see Example 1). Furthermore, we show that the Glutamine 227 to arginine and Aspartate 243 to tyrosine changes can restore the ability to penetrate to the fusion envelope proteins in the same manner in which they rescue the penetration defect rendered by Histidine 8 to arginine substitution.

Methods

Construction of Plasmids Encoding a Virus Genome With a Fusion env

We previously described the construction of plasmid pcDNA MoMLV, encoding a virus genome derived from ecotropic Moloney MLV that provides wild type gag and pol genes encoding proteins for the virion core and an env gene encoding the envelope proteins for assembly into the membrane of the virions but lacks an encapsidation sequence for inclusion of this genome into virions. Refer to Example 1 for this construct. From this plasmid, additional plasmids were constructed that provide cloning vectors for insertion of sequences encoding targeting peptides to enable examples of our invention: (1) Plasmid pcDNA MoMLV NotI was constructed by removing the adjacent NotI recognition site in the MultiCloningSite of the pcDNA3 sequences in plasmid pcDNA MoMLV using NotI digestion, followed by Klenow fragment filling of the resulting cohesive ends and religation of these blunted ends, and then by placing a unique NotI restriction enzyme recognition site between the codons for Serine 6 and Proline 7 of the ecotropic Moloney MLV envelope gene using PCR mutagenesis as follows: A DNA fragment containing a NotI recognition site inserted between nucleotides 5893 and 5894 of the envelope gene was amplified using the sense strand oligonucleotide 5'-GGTCAGTACTGCTTCGCCCGGCTCCAGTGCGG CCGCACCTCATCAAGTCTAT-3' and anti-sense strand oligonucleotide 5'-TGTTGGTCTGCCAGAACG-3', digested with ScaI and BspE1, and ligated into the corresponding ScaI and BspE1 sites of the wild type Moloney MLV env gene. The presence of the NotI recognition site and maintenance of the correct reading frame in the PCR-generated DNA fragment were confirmed by DNA sequence analysis of the final construct, pcDNA MoMLV NotI. (2) Fragment encoding amino-terminal 208 amino acids (Methionine 1 through Glycine 208) of the mature amphotropic virus (4070A) envelope protein was amplified by PCR using oligonucleotides: sense 5'-ACTACTCTAGCGGCCGCAATGGCAGAGAGCC CCCAT-3'; and antisense 5'-CTACTAACTTGCGGCCGCTCCCACATTAAGGAC-3'. Each oligonucleotide contains NotI restriction site flanking nucleotides coding for the amphotropic envelope peptide. PCR products were digested with NotI and ligated to the NotI digested pcDNA MoMLV NotI. Inserted fragment was sequenced to verify the presence of the designated substitutions and the absence of unscheduled mutations. This construct was called pcMLV ampho-eco. (3) Plasmid pcMLVampho-eco+Q227R/D243Y was constructed by replacing BspEII-EcoRI restriction fragment in plasmid pcMLV ampho-eco for BspEII-EcoRI restriction fragment of pcDNA-MoMLV encoding Q227R and D243Y substitutions.

Envelope Protein Stability Assay 20 ml of virus-containing supernatant was divided into 3 aliquots: 6 ml were frozen to use in the infection experiment, 7 ml were used immediately to pellet virions through sucrose cushion (3 ml of 25% of sucrose in 10 mM Tris-HCl pH 7.5, 100 mM NaCl, 10 mM EDTA) in SW41 Beckman Rotor for 30,000 r.p.m., 2 h at 4° C. Virions from another 7 ml were pelleted without sucrose (SW41 rotor, 30,000 r.p.m. for 75 min at 4° C.). Pellets were taken up in 40 ml of phosphate buffered saline (PBS) and frozen. Later, they were subjected to the Western blot analysis as described in Example 1.

Virus production and virus titers were performed as described in Example 1.

Results

We constructed a fusion envelope protein in which the receptor-binding peptide from amphotropic 4070A MLV envelope protein was linked to the N-termiinus of the wild type MoMLV envelope as described by F.-L. Cossett et al., 1995 *J. Virol.* 69: 6314–22. We also constructed a fusion envelope in which the same peptide was linked in the same manner to the N-terninus of the Q227R/D243Y mutant envelope protein. The heterologous peptide from the 4070A envelope protein directs binding to targets expressing the amphotropic retrovirus receptor on their surface. These fusion envelopes retain the ecotropic receptor-binding sequences. The infectivity of viruses pseudotyped with these fusion envelope proteins was determined on mouse NIH3T3 cells that express both ecotropic and amphotropic MLV receptors, on human 293 cells that express amphotropic MLV receptors but not ecotropic receptors, and on human 293 expressing exogenous ecotropic receptors in addition to their endogenous amphotropic receptors. Virions coated with the amphotropic receptor-binding peptide linked to the Q227R/D243Y mutant envelope protein (ampho/eco+ Q227R/D243Y) were at least 1,000-fold more capable of delivery of the lacZ gene to human 293 cells expressing the amphotropic receptor but not the ecotropic receptor (FIG. 7, last column) than were virions coated with the peptide linked to the wild type MoMLV envelope protein (ampho/ eco). Infection by ampho/eco+Q227R/D243Y envelope pseudotype virus was comparable to infection by the wild type amphotropic envelope pseudotype virus. Moreover, the ampho/eco+Q227R/D243Y envelope pseudotype virions were more infectious on cells that expressed both amphotropic and ecotropic receptors than were ampho/eco envelope pseudotype virus, suggesting that the penetration defect due to the fused peptide extended to penetration via interaction with the ecotropic receptor.

Because unstable association with virions and poor incorporation into virions had been reported for other fusion proteins (F.-L. Cossett et al., 1995; and M. Marin et al., 1996 *J. Virol.* 70: 2957–62), we assessed the stability of the fusion envelope protein association with the virions (e.g., SU:TM association) by comparing the amount of SU present in virions that had been pelleted from virus-containing supernatants by direct high speed centrifugation to the amount in virions that had been pelleted through a 25% sucrose cushion. Retention of SU after pelleting through sucrose in amounts comparable to that retained after direct centrifugation indicates that the stability of the fusion SU:TM association is comparable to that of the wild type MoMLV and 4070A SU:TM association. Under conditions of low mechanical stress (direct centrifugation followed by one cycle of freezing and thawing), wild type and fusion envelope proteins remain associated with virions (FIGS. 8A and D). In contrast, only wild type envelope proteins and fusion envelope proteins containing the Q227R/D243Y substitutions retained association with virions under conditions of high mechanical stress (centrifugation through sucrose cushion followed by one cycle of freezing and thawing) (FIGS. 8B and D). Ampho-eco fusion envelope protein that lacked the substitutions at ecotropic SU residues 227 and 243, dissociated from virions under these conditions, in spite of comparable incorporation of that fusion SU in the virions as evidenced by the presence of amounts of TM comparable to that in wild type virions (FIG. 8D). Envelope protein cleavage was not altered by the presence of inserted peptide or of the Q227R/D243Y substitutions (FIG. 8C). These results provide further evidence that weak SU:TM interaction results in shedding of fusion SU protein from the virion surface, suggesting that the decreased infectivity of fusion envelope proteins constructed from wild type retrovirus envelope proteins is due not only to the failure to complete penetration but also to decreased stability of the SU:TM interaction. Further, construction of fusion envelope proteins in the Q227R/D243Y mutant envelope protein increases both the penetration and stability of the pseudotyped virus.

Example 3
Production and Characterization of a $^{198}$Ser Mutant

The nucleic acid encoding $^{198}$Ser, of the motif group comprising: $^{198}$Ser, $^{11}$Tyr, $^{226}$Ty, $^{35}$Trp, $^{38}$Trp, $^{196}$Val, $^{197}$Thr, $^{160}$Tyr, $^{158}$Trp, $^{123}$His, $^{203}$His, $^{233}$Val, $^{235}$Ile, $^{240}$Val $^{241}$Leu, and $^{8}$His, was engineered to the hydrophobic amino acid phenylalanine (S198F) and $^{223}$Val was changed to the more hydrophobic amino acid isoleucine. Other mutants including one or more of amino acids of this group of residues can be mutated. All the potential mutants contemplated with each of these residues would substitute any hydrophobic amino acid residue. Preferred envelope proteins (and polypeptide fragments thereof) would have increased penetration capability.

Methods
The methods and assays utilized in creating and analyzing these mutants are the same as those described in Example 1. Serine 198 was mutated to phenylalanine using a C→T change at nucleotide 6468. Valine 233 was changed to isoleucine using a G→A change at nucleotide 6572.

Replication-competent ecotropic virus was passaged on human 293 cells expressing mutant receptors previously described by us (S. Malhotra et al., 1996 *J. Virol.* 70: 321–26). After three rounds of passaging, genomic DNA of virus-producing cells was isolated and representative env genes from quasi-species were amplified and subcloned into plasmid pcDNA MoMLV, as described in Example 1. One of the representative clones selected for analysis was clone 855. It encoded three amino acid substitutions in the envelope protein: Serine to tyrosine (S198Y, C→T change at nucleotide 6468); Valine 233 to isoleucine (V233I, G→A change at nucleotide 6572); and Serine 337 to proline (S337P, T→C change at nucleotide 6884). Virus pseudotyped with this mutant envelope protein were surprisingly infectious (comparable to wild type virion infection), in spite of poor incorporation of envelope protein into virions (FIGS. 9A and B).

Results
Interestingly, the Serine 198 ($^{198}$Ser) and the Valine 233 ($^{233}$Val) reside on the same surface as Glutamine 9 in the crystal structure analyzed by X-ray crystallography (see FIG. 18), indicating that they are also near $^{8}$His. The substitution of Phe for $^{198}$Ser provides an additional hydrophobic side chain group that increases the hydrophobicity of the fusion domain which includes the critical $^{8}$His. The resulting increase in the fusion function of that domain creates a "superfusion" mutant. This superfusion mutant is able to compensate for the reduced binding caused by the scarcity of SU on clone 855 virions by shortening the delay between the binding and completion of viral and cellular membrane fusion. Replacement of Ile for $^{233}$Val also might enhance this effect. The Serine 337 to proline change found in this env gene might be innocuous. A serine occupies the corresponding position in most other retroviral envelope proteins except in the feline leukemia viruses (FeLV), wherein a proline occupies this site. However, in the context of an ecotropic virus envelope sequence, the bend of the peptide chain introduced by the proline might produce structural alterations that interfere with envelope protein processing in producer cells, depressing steady state levels of mature SU to below the levels capable of detection by Western blots.

Example 4
Production and Characterization of Two $^{104}$Lys Mutants and Three $^{102}$Arg Mutants The nucleic acid molecule encoding $^{104}$Lys was changed to produce two different mutants. One was an $^{104}$Lys→Asp and the other was $^{104}$Lys→Ala. $^{104}$Lys and $^{102}$Arg are part of the motif comprising: $^{102}$Arg, $^{104}$Lys, 107Gln, $^{90}$Thr, $^{102}$Arg and $^{108}$Thr. The nucleic acid sequence encoding $^{102}$Arg was changed to produce three different mutants. One was an $^{102}$Arg→Ala; another was $^{102}$Arg→Asp, and the third was $^{102}$Arg→Glu. Other envelope embodiments include: (1) mutating $^{104}$Lys to any amino acid, including alanine or aspartate; (2) $^{102}$Arg to any amino acid including alanine, aspartate or glutamate; (3) $^{107}$Gln altered to any amino acid; and (4) $^{90}$Thr and $^{108}$Thr which can be engineered into any other residues except serine, either individually or combined. Additional embodiments include combinations of one or more of these mutations. Preferred envelope proteins would have decreased shedding of binding sequences through the suppression of envelope protein cleavage comprising an amino acid substitution in at least one of the amino acids comprising this motif.

In this experiment, the function of $^{104}$Lys and $^{102}$Arg were investigated. Residues important to ecotropic retrovirus receptor function include Tyrosine 235 ($^{235}$Tyr) and Glutamate 237 ($^{237}$Glu), which are discussed in the examples below. On the ecotropic retrovirus receptor protein, it is believed that the negatively-charged carboxyl group on the side chain of $^{237}$Glu may participate in a salt bridge with a positively-charged side chain of a lysine or arginine residue on the ecotropic virus SU protein (S. Malhotra et al., 1996). To test this hypothesis, the effect of replacing positively-charged residues in SU with amino acids having negatively-charged side chains or with alanine was examined. We focused on Lysine 111, Arginine 149, and Lysine 153 and on the three pairs of arginines and lysines previously identified by Skov and Andersen as critical for virus infection (H. Skov et al., 1993).

In the experiments shown in Examples 7 and 8, we propose that the side chain of $^{235}$Tyr on the wild type virus receptor binds inside a hydrophobic pocket on SU (S. Malhotra et al., 1996). Because a hydrophobic amino acid is an essential residue in the receptors of a number of different retroviruses, we suspected that the binding pocket is in a highly conserved region of SU. A candidate hydrophobic segment was identified as lying between residues 131 and 143 in the Mo MLV surface protein. It contains four hydrophobic residues Phenylalanine 137, Tyrosines 141 and 138, and Tryptophan 142 (Example 8). These last two residues are present in all the known retroviral envelope protein sequences, except possibly the human immunodeficiency virus (HIV) surface protein. Moreover, this region of SU is constrained by two conserved disulfide bridges, suggesting that an important special relationship must be maintained between them (M. Linder et al., 1994 *J. Virol.* 68:5133–41). The same two disulfide bridges also constrain the ends of the segment containing two positively-charged residues, Lysines 124 and 126, either of which might provide an adjacent binding site for Glutamate 237 on the receptor. We were also interested in a negatively-charged residue (Aspartate 135) that is common to the envelope proteins of all retroviruses (Example 7). Also, interesting is the adjacent conserved proline (Proline 134) as the $^{135}$Asp might confer receptor specificity and $^{134}$Pro might provide flexibility. Initially, the four aromatic residues were replaced with alanine or with charged residues, Aspartate 135 with alanine, lysine or arginine, and Proline 134 with alanine. The infectious titer of virus containing each of the altered envelope proteins was determined and envelope incorporation and processing assessed.

Methods

Cell Lines and Viruses

Mouse NIH3T3 fibroblasts and non-permissive human 293 fetal kidney cells (gift of M. Quinlan) were cultured in Dulbecco's modified Eagle's medium (DMEM) supplemented with 8% donor calf serum. The 293 derived stable transfectant expressing the receptor cDNA has been described elsewhere (S. Malhotra et al., 1996). They were maintained in DMEM containing 200 µg/ml G418 (GIBCO). HI-BAG cells were maintained in DMEM with 8% fetal bovine serum and 250 µg/ml G418 (Sigma).

Plasmids Encoding Virus Genomes

Initially, we constructed a master plasmid, pcDNA-MoMLV, encoding a virus genome derived from Mo-MLV-E that provides wild type gag and pol genes from which proteins for the virion core would be made and an env gene from which the envelope proteins for assembly into the membrane of the virions would be synthesized. The 8 kbp fragment from the BssHII restriction site to the env termination codon containing the Mo-MLV-E proviral genome that lacks the packaging signal was derived from plasmid pEM-5 (gift of V. Garcia). The env gene termination codon is followed by artificially engineered BamHI site. The genome was inserted between HindIII and BamHI sites of the eukaryotic expression vector pcDNA3, placing transcription of the viral genome under the control of the cytomegalovirus promoter, with a downstream polyadenylation site provided by the bovine growth hormone polyA. This genome is not incorporated into virions, because it lacks the psi packaging sequence, Ψ. The pBAG plasmid (gift of C. Cepko) (D. L. Turner et al., 1987 *Nature* 328:131–6), encodes a replication-defective but packagable Mo MLV genome, in which the structural genes have been replaced by two genes—the *E. coli* lacZ gene encoding ,β-galactosidase under the control of the retroviral 5' LTR, followed by the neomycin resistance gene (neo$^r$) under the control of the SV40 promoter.

Preparation of Retroviral Vectors

Amphotropic packaging cell line PA317 (A. D. Miller et al., 1986 *Mol. Cell. Biol.* 6:2895–02) was transiently transfected by calcium phosphate precipitation with the pBAG plasmid. The virus-containing supernatant was harvested and used to infect human 293 cells into which the virus transduces the lacZ and neo genes. Infected 293 cells were selected in the medium containing 1 mg/ml of G418. Twenty four drug-resistant colonies were propagated and analyzed for β-galactosidase expression by staining with 5-bromo-4-chloro-3-indolyl-p-D-galactopyranoside (X-GAL). The five clones developing the most intense staining in the shortest period of time, indicative of high levels of transcription of the virus genome, were selected as virus producers. Expression of packagable viral RNA was confirmed by Northern analysis. One of these cell clones, H1-BAG, was used in all experiments.

To produce virus particles, the H1-BAG cells were transiently transfected with pcDNA-MoMLV DNA containing wild type or mutated env genes. Transfection was performed by calcium phosphate precipitation as described by Sambrook et al., (1989). 30 µg of DNA was used per 100 mm dish of 70%–80% confluent H1-BAG cells. 16 h after transfection cells were fed with 10.5 ml of fresh medium (DMEM plus 8% fetal bovine serum without G418). Virus-containing supernatant was harvested 24 h later. Then fresh medium was added to cells and 24 h later virus was harvested again. Virus preparations removed producer cells by low speed centrifugation followed by filtration through a 0.45 micron filter. An aliquot of 3 ml was removed, stored at −80° C., and then used for virus titration. Virions produced in this manner transduced β-galactosidase activity upon infection of cells, because they contain the genome encoded by the pBAG plasmid which is the only virus genome present that has the Ψ packaging signal. Viruses from the remaining 7 ml were immediately pelleted as described below for immunoblotting. For each virus binding experiment, the entire virus preparations were frozen and concentrated as described below.

Site-directed Mutagenesis of env Genes

Nucleotide substitutions in the env gene were generated by the method described by Kunkel (T. A. Kunkel, 1985).

For this purpose we subcloned the 1300 bp HpaI-HpaI restriction fragment from the Mo-MLV-E env gene on plasmid pMOV3 (gift of H. Stuhlmann) (K. Harbers et al., 1981) into the bacteriophage vector M13mp18 with an engineered HpaI site. Site-directed mutagenesis was performed and the fragment was transferred back to pcDNA3-MoMLV. The entire 1300 bp fragment was sequenced using the fmol™ sequencing kit (Promega) to ensure the absence of unscheduled substitutions and to confirm the presence of desired mutations.

Virus Titers

End-point dilution titration of all virus stocks was performed essentially as previously described for MLV-E (S. Malhotra et al., 1996) with modifications as follows. Briefly, $2 \times 10^4$ cells were seeded in each well of 24-well culture plates. Quadruplicate wells were exposed to 10-fold serial dilutions of virus stock in medium containing polybrene (20 µg/ml; Sigma). Forty-eight hours after exposure, cells were fixed and stained with X-GAL for β-galactosidase activity. Titers were calculated for the end-point dilution.

Western Blot Analysis

Virus particles were pelleted from 7 ml of cell-free virus supernatant through 3 ml of 25% sucrose in TNE (10 mM Tris pH 8.0, 1 mM EDTA, 100 mM NaCl) in a Beckman SW41 rotor at 30,000 rpm for 2 h at 4° C. Pellets were taken up in 40 µl of PBS and stored at −80° C. Virus producer cells were lysed immediately after the second virus harvest in 300 µl of RIPA buffer (20 mM Tris pH 7.0; 1% Triton X-100; 0.05% SDS; 0.5% Na deoxycholate; 150 mM NaCl; and 2.5 mM PMSF) by incubation for 30 min on ice. Cell lysates were centrifuged for 10 min at 10,000 rpm to pellet nuclei and supernatants were frozen at −80° C. Total protein concentration in cell lysates was determined by Bradford assay (BioRad). 10 µl of virus pellets or 100 µg of total protein from cell lysates were diluted 1:1 in 2× gel loading buffer (J. Sambrook et al., 1989) boiled for 10 min, then chilled on ice. Proteins were separated via SDS-polyacrylamide gel electrophoresis. The separated proteins were transferred onto nitrocellulose membranes (Protran, S&S) using 48 mM Tris, 39 mM glycine, 0.037% SDS, 20% methanol overnight. Filters were blocked in 6% powdered milk and Tris Buffered Saline pH 7.4 containing 0.2% Tween 20 for 1 h at room temperature. Envelope proteins (SU, and precursor, gp80) were detected with goat anti-Rauscher-gp70 (1: 100); structural capsid protein (CA) was detected with goat anti-Rauscher-p30 (1: 10,000) (Quality Biotech Inc.); and envelope TM protein was detected with rabbit anti-p15E antisera (1: 1000) (gift of Alan Rein). Incubations were done at 4° C. for 1 h. Subsequent incubation with secondary antibodies, mouse anti-goat or mouse anti-rabbit conjugated to horse radish peroxidase (HRP) (1: 10,000) (Sigma) was performed at room temperature for 1 h. Immunoblots were developed using detection of horse radish peroxidase with SuperSignal™ (Pierce).

Virus Binding Assays

Binding assays were performed essentially as described (F. L. Cosset et al., 1995; and M. J. Kadan et al., 1992) with the following modifications. Virus-containing supernatants were concentrated 10- to 15-fold on Centricon-100 concentrators (Amicon). This concentration eliminates most of the SU protein not associated with virions so that virus binding can be quantitated in the absence of monomer SU shed from virions or the producer cell surface. Concentration also promotes binding of multiple virions to a single cell and increases the mean fluorescence per cell detected by flow cytometry. To ensure that equal numbers of particles from each of the virus stocks were incubated with cells during the assay, the concentration of virus stocks was adjusted to achieve comparable particle concentrations based on the reverse transcriptase activity and Western blot quantitation of capsid protein. 293 cells expressing wild type virus receptor or parental 293 cells were detached from culture plates with PBS containing 0.02% EDTA. $10^6$ cells were then incubated with 1 ml of concentrated virus stocks containing equal amounts of virions in the presence of polybrene (5 µg/ml) for 1 h at 4° C. Cells were then washed with PBA (PBS, 2% fetal bovine serum, and 0.02% sodium azide) and incubated in 500 µl of PBA containing goat anti-gp70 antisera (1: 100) for 30 min at 4° C. After two washes, cells were incubated with 500 µl of secondary antibody, donkey anti-goat conjugated to FITC (Jackson Laboratories) diluted in PBA (1:200) and incubated for 30 min at 4° C. Propidium iodide (Sigma) was added to the binding reaction for 5 min at a final concentration of 20 µg/ml. Cells were washed twice, taken up in 500 µl of PBA. The fluorescence of the live cells (negative for propidium iodide) was analyzed by flow cytometry (Epics Profile Analyzer, Coulter Cytometry). Experiments were repeated three times.

Results

In the experiment wherein $^{104}$Lys was substituted with an aspartate or alanine, the $^{104}$Lys substitution suppressed envelope precursor cleavage, but did not prevent incorporation of precursor envelope protein into virus particles, which were highly infectious. Replacement of $^{104}$Lys on SU with alanine or with aspartate did not alter infection of human 293 cells stably expressing the virus receptor. Cells were as susceptible to virions coated with envelope molecules containing a $^{104}$Lys to aspartate (KI04D) or to alanine (K104A) change, as they were to virions coated with wild type envelope protein (FIG. 10A). Mouse fibroblasts NIH3T3 cells were slightly less susceptible to these viruses (FIG. 10A).

The incorporation of the K104D and K104A mutants into virions was then assessed by Western blot analysis. Surprisingly, the virions contained two protein species reacted with anti-SU antisera—one species the size of SU (70 kDa) and a second species the size of envelope precursor (85 kDa) (FIG. 10B)—demonstrating that uncleaved envelope protein can be assembled into virions, and importantly, that the virions carrying precursor can be highly infectious.

K104D virions consistently contained more uncleaved envelope protein and less mature SU than did K104A virions (data not shown). More than likely this difference is a stoichiometric one, that is, the K104D mutation suppresses cleavage to a greater degree than does the K104A mutation such that greater amounts of K104D precursor are available for assembly into virions. However, it is also possible that cleavage was only slightly suppressed in both mutants and the K104D precursor was preferentially incorporated. To determine which was the case, the envelope protein forms present in the producer cells from which the virus had been harvested were analyzed. Mature SU was not detectable in cells producing K104D viruses, although precursor was present (FIG. 10C). In contrast, K104A producers contained steady-state levels of mature SU that were comparable to levels in cells producing wild type MoMLV virus (FIG. 10C), suggesting that the K104D mutation is a more potent suppressor of envelope cleavage than is the K104A mutation. Interestingly, K104D virions contained appreciable amounts of mature SU even though steady state levels of mature SU were too low to be detected in the K104D producer cells. These results suggest that although precursor can be incorporated, the cleaved envelope proteins are the preferred substrate for assembly into virions. Alternately, the suppression of precursor cleavage may be somewhat relieved during or after virion assembly so that secreted cellular proteases can perform the cleavage that normally occurs in the Golgi. Substitution of $^{102}$Arg with alanine (R102A), aspartate (R102D) or glutamate (R102E) almost completely abolished infectivity and cleavage of the envelope precursor into SU and TM was suppressed (FIG. 10). Envelope precursor was incorporated into virions, albeit poorly. No mature SU was detectable in virions or in producer cells (FIG. 10).

Example 5
Production and Characterization of Two $^{124}$Arg Mutants

The nucleic acid molecule encoding $^{124}$Arg was changed to produce two different mutants. One was an $^{124}$Arg→Asp and the other was $^{124}$Arg→Glu. $^{124}$Arg is part of the motif comprising $^{124}$Arg, $^{126}$Arg $^{138}$Tyr, $^{128}$Ser, $^{132}$Gly, $^{134}$Pro, $^{121}$Gly, and $^{133}$Gly. Other embodiments include: (1) mutating $^{124}$Arg to any amino acid; (2) $^{128}$Ser altered to any amino acid except an alanine; (3) $^{132}$Gly, $^{138}$Tyr, $^{121}$Gly and $^{133}$Gly mutated to any amino acid residue; (4) $^{134}$Pro changed to any amino acid except alanine or leucine; and (5) $^{126}$Arg altered to any amino acid except leucine. Additional embodiments include combinations of one or more of these mutations. Preferred envelope proteins would have decreased shedding of binding sequences through the suppression of envelope protein cleavage comprising an amino acid substitution in at least one of the amino acids comprising this motif.

Methods

The methods and assays utilized in creating and analyzing these mutants are the same as those described in Example 4.

Results

Infection was dramatically decreased and precursor cleavage was almost completely abolished by an $^{124}$Arg to glutamate (R124E) substitution (FIG. 11). Envelope precursor was incorporated into virions, albeit poorly. No mature SU was detectable in virions or in producer cells. Surprisingly, virions containing an $^{124}$Arg to aspartate (R124D) substitution were only slightly less infectious than were wild type viruses, a 10,000-fold improvement over that observed for the glutamate change (FIG. 11). Both precursor and mature SU were incorporated into the highly infectious R124D virions. As with mutant K104A, virions contained a surprising amount of mature SU considering that none was detectable in producer cells. Moreover, virions from the double mutant with an R124D and an R126D substitution consistently contained more precursor molecules than mature SU (FIG. 11), suggesting that the addition of the seemingly innocuous R126D substitution somehow enhances precursor incorporation into virions.

Example 6
Production and Characterization of $^{223}$Arg and $^{225}$Arg Double Mutant Nucleic acids encoding $^{223}$Arg and $^{225}$Arg were both altered to yield $^{223}$Asp and $^{225}$Asp. The double mutant was prepared and characterized, as described below. The $^{223}$Arg and $^{225}$Arg residues are members of the motif comprising: $^{223}$Arg, $^{225}$Arg, $^{224}$Leu, $^{16}$Glu, $^{24}$Thr, and $^{201}$Thr. Other envelope protein embodiments include mutations involving at least one or more residues in this motif. The preferred mutations would include mutations: (1) $^{201}$Thr changed to any other amino acid except serine; (2) $^{24}$Thr engineered into any amino acid except serine; and (3) $^{16}$Glu, $^{224}$Leu, $^{225}$Arg, and $^{223}$Arg changed to any amino acid either individually or in combination. Preferred envelope proteins would have decreased shedding of surface protein through the suppression of envelope protein cleavage comprising an amino acid substitution in at least one of the amino acids comprising this motif.

Methods

The methods and assays utilized in creating and analyzing these mutants are the same as those described in Example 4.

Results

Substitution of $^{225}$Arg and $^{223}$Arg with aspartate (R223D and R225D) also suppressed cleavage of the envelope precursor (FIG. 12). Here too, the envelope precursor was incorporated into highly infectious virions (FIG. 12). A number of other substitutions led to mutants with reduced infectivity. Substitution of Arginine 102 ($^{102}$Arg) with alanine (R102A), aspartate (R104D) or glutamate (R104E) almost completely abolished infectivity, and cleavage of the envelope precursor into SU and TM was suppressed (FIG. 10). Envelope precursor was incorporated into virions, albeit poorly. No mature SU was detectable in virions (FIG. 12B) or in producer cells (FIG. 12C). Replacement of Arginine 124 ($^{124}$Arg) with glutamate (R124E), Tyrosine 138 ($^{138}$Tyr) with alanine (Y138A) or glutamate (Y138E), or Tryptophan 142 ($^{142}$Trp) with alanine (W142A), serine (W142S) or methionine (W142M) gave similar phenotypes (FIGS. 11–13).

Example 7
Production and Characterization of a $^{137}$Phe Mutant

The nucleic acid encoding $^{137}$Phe of the motif group comprising $^{137}$Phe, $^{135}$Asp, $^{136}$Ser, $^{208}$Arg, and $^{217}$Gly was engineered to an alanine (F137A). Other envelope embodiments contemplated include: (1) mutating $^{137}$Phe to any amino acid residue including alanine; (2) changing $^{208}$Arg or $^{217}$Gly to any amino acid; and (3) deleting $^{135}$Asp or $^{136}$Ser from the envelope polypeptide sequence; or any combination of these mutations. Preferred envelope proteins would have decreased shedding of surface protein through the suppression of envelope protein cleavage comprising an amino acid substitution in at least one of the amino acids comprising this motif.

Methods

The methods and assays utilized in creating and analyzing these mutants are the same as those described in Example 4.

Results

Substitution of Phenylalanine 137 ($^{137}$Phe) with alanine (F137A) also suppressed cleavage of the envelope precursor (FIG. 12). Here too, envelope precursor was incorporated into highly infectious virions.

Example 8
Production and Characterization of Three $^{142}$Trp Mutants

The nucleic acid encoding $^{142}$Trp of the motif group comprising $^{142}$Trp, $^{152}$Trp, $^{210}$Tyr, $^{141}$Tyr and $^{151}$Tyr was engineered to either an alanine, a serine or a methionine. Other envelope mutants, including mutations in one or more of the residues of this motif, are also contemplated. The mutations contemplated include: (1) $^{142}$Trp mutated into any amino acid except tyrosine; (2) $^{151}$Tyr changed to any amino acid; (3) $^{152}$Trp mutated into any amino acid; (4) $^{141}$Tyr changed to any amino acid; and (5) $^{210}$Tyr changed to any amino acid. Preferred envelope proteins would have decreased shedding of binding sequences through the suppression of envelope protein cleavage comprising an amino acid substitution in at least one of the amino acids comprising this motif.

Methods

The methods and assays utilized in creating and analyzing these mutants are the same as those described in Example 4.

Results

Replacement of Tryptophan 142 ($^{142}$Trp) with alanine (W142A), serine (W142S) or methionine (W142M) gave similar phenotypes to those of Example 7 and are depicted in FIG. 13. Notably, replacement of $^{142}$Trp with tyrosine (W142Y) resulted in infection, cleavage, and receptor binding comparable to wild type envelope protein (FIG. 13). These results indicate the requirement for an aromatic side chain in position 142 for proper envelope protein folding.

The phenotype of a number of substitutions was indistinguishable from that of the wild type envelope protein. Substitution of Lysine 111 (K111A), Glutamate 114 (E114A), Proline 134 (P134A), Aspartate 135 (D135A) or Tyrosine 141 with alanine (Y141A) did not alter infection or envelope precursor cleavage (FIGS. 10–13). Virions coated with envelope protein containing Aspartate 135 to lysine (D135K) or arginine (D135R), Arginine 126 to aspartate (R126D) or glutamate (R126E), or Arginine 149 to aspartate and Lysine 153 to aspartate (R149D K1531) also gave a wild type phenotype (FIGS. 10–13). These results suggest that those residues are not essential to productive virus-receptor interaction or to envelope protein folding.

FIG. 14 depicts the reduction of infectivity for each of the mutations described in this example and in the preceding examples.

Example 9

Alignment of Retrovirus Sequences

In order to view the motifs as described in Table I in a linear fashion, Moloney MLV (MoMLV), Friend MLV, amphotropic MLV 4070A (4070A), AKV MLV, CasBrE MLV, RadLV MLV, MLV 10A1 (10A1), MCF1233, Xenotropic CWM (Xeno CWM), Xenotropic NZB (Xeno NZB), feline leukemia virus strains A and B (FeLV-A and FeLV-B), and gibbon ape leukemia virus SEATO strain (GALV SEATO), and HIV-1 were aligned. All the retroviruses except HIV-1 are aligned in FIG. 16. FIG. 15 aligns the MoMLV, Friend MLV, 4070A and GALV SEATO envelope protein sequences. FIG. 17 is a hand alignment of residues of HIV-1. Because of the length of the HIV-1 envelope protein, computer programs have not been as helpful in aligning the motifs. FIG. 18 shows the three dimensional arrangement of amino acid residues in the MoMLV envelope protein which comprise the seventh motif. The seventh motif consists of: $^{198}$Ser, $^{11}$Tyr, $^{226}$Tyr, $^{35}$Trp, $^{38}$Trp, $^{196}$Val, $^{197}$Thr, $^{160}$Tyr, $^{158}$Trp, $^{123}$His $^{203}$His, $^{233}$Val, $^{235}$Ile, $^{240}$Val, $^{241}$Leu and $^{8}$His.

Example 10

Use of Mutant Envelope Proteins As Gene Therapy Vectors

One example of using the mutant retroviral envelope proteins described above is as a vector that can target specific cells. For example, substitutions in two of the motifs stabilize a retroviral vector for targeted gene delivery to highly metastatic human breast carcinoma cells. A human breast carcinoma line, MDA-MB-435 cells, implanted in the mammary fat pad (m.f.p.) of nude mice grows vigorously and metastasizes to several organs (Price et. al., 1990 *Cancer Res.* 50: 717–721), providing a methodology for a xenograft animal model of human breast carcinoma growth and metastasis. MDA-MB-435 carcinoma cells express the alphaVβ3 integrin on their cell surface (Pasqualini et. al., 1997 *Nature Biotechnology* 15: 542–546). Implantation of MDA-MB-435 cells in the m.f.p. of nude mice induces expression of alphaVβ3 integrin on the proliferating endothelial cells forming blood vessels supplying the developing tumor, but not on healthy tissues at other sites or on endothelial cells in established blood vessels (Pasqualini et. al., 1997). The cyclic nonapeptide, CDCRGDCFC, has been shown to bind specifically and tightly to alphaVβ3 integrin (Koivunen et. al., 1995 *Bio/Technology* 13: 265–270). Thus, the alphaVβ3 integrin provides an attractive receptor for virus- or liposome-mediated human gene and drug therapy of breast carcinoma cells using this nonapeptide as a targeting sequence. The targeted virus or liposome will deliver a gene not only to the tumor cells but also to the endothelial cells of the tumor vasculature, thereby killing tumor cells both directly and by destruction of their blood supply. Destruction of the blood vessels also blocks the primary route of metastasis for tumor cells. Because many types of metastatic tumors induce angiogenesis (Folkman, 1995 *Nature Med.* 1: 27–31) during which newly proliferating endothelial cells begin expressing alphaV integrins, including alphaVβ3, that are not expressed in established vasculature (Pasquilini et. al., 1997; and Wadih et. al., 1998 *Science* 279: 377–380), retroviral vectors targeted by fused peptides specific for the members of this integrin family will be effective in therapy of a wide spectrum of highly metastatic human tumors.

Methods

Construction of the Basic Plasmids Encoding the Recombinant Virus Genomes

We previously described the construction of plasmid pcDNA MoMLV, encoding a virus genome derived from ecotropic Moloney MLV that provides wild type gag and pol genes encoding proteins for the virion core and an env gene encoding the envelope proteins for assembly into the membrane of the virions but lacking an encapsidation sequence for inclusion of this genome into virions. Refer to Example 1 for this construct.

From this plasmid, four additional plasmids can be constructed that provide cloning vectors for insertion of sequences encoding targeting ligands to enable examples of our invention: (1) Plasmid pcDNA MoMLV Not I is constructed by removing the adjacent Not I recognition site in the MultiCloningSite of the pcDNA3 sequences in plasmid pcDNA MoMLV using Not I digestion, followed by Klenow fragment filling of the resulting cohesive ends and religation of these blunted ends. A unique Not I restriction enzyme recognition site is placed between the codons for Serine 6 and Proline 7 of the ecotropic Moloney MLV envelope gene using PCR mutagenesis as follows: A DNA fragment containing a Not I recognition site is inserted between nucleotides 5893 and 5894 of the envelope gene and is amplified using the sense strand oligonucleotide 5'-GGTCAGTACTGCTTCGCCCGGCTCCAGTGCGG CCGCACCTCATCAAGTCTAT-3' and anti-sense strand oligonucleotide 5'-TGTTGGTCTGCCAGAACG-3', digested with Sca I and BspE1, and ligated into the corresponding Sca I and BspE1 sites of the wild type Moloney MLV envelope gene. The presence of the Not I recognition site and maintenance of the correct reading frame in the PCR-generated DNA fragment is confirmed by DNA sequence analysis of the final construct, pcDNA MoMLV Not I. We constructed this plasmid in Example 2. (2) Plasmid pcDNA MoMLV Not I Q227R D243Y is constructed by replacing the BspEI-EcoRI restriction fragment encoding Serine 212 through the carboxy-terminal termination codon of the envelope gene in pcDNA MoMLV Not I with the corresponding restriction fragment from a plasmid that contains the $^{227}$Gln→Arg mutation and the $^{243}$Asp→Tyr mutation in the envelope gene of pcDNA MoMLV, described in the Examples above. We constructed this plasmid in Example 2. (3) Plasmid pcDNA MoMLV Not I K104D is constructed by replacing the BstEII-BspEI restriction fragment encoding Valine 17 through Glycine 213 of the envelope gene in pcDNA MoMLV Not I with the corresponding restriction fragment from a plasmid that contains an the $^{104}$Lys→Asp (K104D) mutation in the envelope gene of pcDNA MoMLV, described above. (4) Plasmid pcDNA MoMLV Not I Q227R D243Y K104D is constructed by replacing the BstEII-BspEI restriction fragment encoding Valine 17 through Glycine 213 of the envelope gene in pcDNA MoMLV Not I Q227R D243Y with the corresponding restriction fragment from a plasmid that contains the $^{104}$Lys→Asp mutation in the envelope gene of pcDNA MoMLV, described above.

The presence of the inserted Not I recognition site and of the correct codon substitutions within each construct were verified by DNA sequence analysis. Constructions containing other motifs and other combinations of motifs can be made in a similar manner. We constructed the recombinant viral genome encoding the chimeric envelope protein for the retroviral vectors. The sequence encoding the alphaVβ3-binding nonapeptide, CDCRGDCFC, was placed in the envelope genes of each of the four basic plasmids as follows: Two synthetic oligonucleotides encoding the nonapeptide flanked on the 5' end by sequences corresponding to the cohesive ends of Not I digested DNA, 5'-GGCCGCATGCGACTGTCGGGGCGATTGTTTCT GTGC-3', and 5'-GGCCGCACAGAAACAATCGCCCCGACAGTCG CATG-3', are annealed, phosphorylated on their 5' ends using T4 polynucleotide kinase, and the double-stranded products purified by agarose gel electrophoresis as described by Sambrook et al., (1989). Plasmids pcDNA MoMLV Not I, pcDNA MoMLV Not I Q227R D243Y, pcDNA MoMLV Not I K104D, and pcDNA MoMLV Not I Q227R D243Y K104D are digested with Not I restriction enzyme, dephosphorylated with calf intestinal phosphatase, and purified by agarose gel electrophoresis as described by Sambrook et aL, (1989). The purified, annealed oligonucleotides are ligated to each of the purified Not I-digested dephosphorylated plasmids by standard methods to construct four recombinant retroviral genomes encoding chimeric envelope proteins: (1) pcDNA RGD MoMLV; (2) pcDNA RGD MoMLV Q227R D243Y; (3) pcDNA RGD MoMLV K104D; and (4) pcDNA RGD MoMLV Q227R D243Y K104D. Each construction encodes the peptide sequence AAACDCRGDCFCAAA fused between Serine 6 and Proline 7 of the envelope protein. The viral genomes contained in these plasmids are not incorporated into virions because all lack the encapsidation sequence, Psi(Ψ). The presence of the inserted nonapeptide encoding sequence and of the correct codon substitutions within each construct was verified by DNA sequence analysis.

Production of Retroviral Vectors

We previously described the generation of the H1-BAG cell line (see Example 1), stably expressing the pBAG plasmid (gift of C. Cepko; Turner, 1987), that encodes a replication-defective but packagable ecotropic Moloney MLV genome, in which the gag, pol and env structural genes have been replaced by two other genes—the E. coli lacZ gene encoding β-galactosidase under the control of the retroviral 5' LTR, followed by the neomycin resistance gene (neo') under the control of the SV40 promoter.

To produce virus particles, H1-BAG cells are transiently transfected with pcDNA MoMLV, pcDNA RGD MoMLV, pcDNA RGD MoMLV Q227R D243Y, pcDNA RGD MoMLV K104D, or pcDNA RGD MoMLV Q227R D243Y K104D. Transfection is performed by calcium phosphate precipitation as described by Sambrook, et al., (1989). 30 μg of DNA is used per 100 mm dish of 70%–80% confluent H1-BAG cells. 16 h after transfection, cells are fed with 10.5 ml of fresh medium (DMEM plus 8% fetal bovine serum), virus-containing supernatant is harvested 24 h later. Fresh medium is then added to cells and 24 h later virus is again harvested. Virus preparations are freed of producer cells by low speed centrifugation (1000×g) for 5 min at 4° C. followed by filtration through a 0.45 μm filter. An aliquot of 3 ml is removed, stored at –80° C., and is later used for virus titration. Virions produced in this manner transduce β-galactosidase activity upon infection of cells, because they contain the genome encoded by the pBAG plasmid as the only virus genome present that has an encapsidation signal. Viruses from the remaining 7 ml were immediately pelleted as described below for immunoblotting. For each virus binding assay, the entire virus preparations were frozen and concentrated as described below.

Cell Lines

Mouse NIH3T3 fibroblasts and nonpermissive human 293 fetal kidney cells (gift of M. Quinlan) are cultured in Dulbecco's modified Eagle's medium (DMEM) supplemented with 8% donor calf serum. H1-BAG cells are maintained in DMEM with 8% fetal bovine serum and 250 μg/ml G418 (Sigma), except during virus production when they are maintained in DMEM with 8% fetal bovine serum without G418. Human breast carcinoma cell lines MDA-MB-435 (ATCC HTB-129) and MDA-MB-468 (ATCC HTB-132) are cultured in DMEM plus 20% fetal bovine serum. Human endothelial umbilical cord cell line HUV-EC-C (ATCC CRL-1730) is cultured in F12K medium containing 10% fetal bovine serum, 10% heparin, and 30 μg/ml endothelial growth supplement.

Western Blot Analysis to Quantify Envelope Protein Stability

Virus particles are pelleted from duplicate aliquots of 7 ml of cell-free virus supernatant by high speed centrifugation. One aliquot is pelleted directly from the supernatant in a Beckman SW41 rotor (30,000 rpm) for 75 min at 4° C. The other aliquot is pelleted through 3 ml of 25% sucrose in TNE (10 mM Tris pH 8.0, 1 mM EDTA, 100 mM NaCl) in a Beckman SW41 rotor at 30,000 rpm, for 2 h at 4° C. Both types of pellets are resuspended in 40 μl of PBS—and stored at –80° C. Transfected H1-BAG cells are lysed immediately after the second virus harvest in 300 μl of RIPA buffer (20 mM Tris pH 7.0, 1% Triton X-100, 0.05% SDS, 0.5% Na deoxycholate, 150 mM NaCl, 2.5 mM PMSF) by incubation for 30 min on ice. Cell lysates are centrifuged for 10 min at 10,000 rpm to pellet nuclei and supernatants are frozen at –80° C. Total protein concentration in cell lysates are determined by Bradford assay (BioRad). 10 ml of virus pellets or 100 μg of total protein from cell lysates is diluted 1:1 in 2× gel loading buffer (Sambrook et. al., 1989) boiled for 10 min and chilled on ice. Proteins are separated using SDS-polyacrylamide gel electrophoresis. The separated proteins are transferred onto nitrocellulose membranes (Protran, S&S) in 48 mM Tris, 39 mM glycine, 0.037% SDS, and 20% methanol overnight. Nitrocellulose filters are blocked in 6% powdered milk and Tris Buffered Saline pH 7.4 containing 0.2% Tween 20 for 1 h at room temperature. Envelope proteins (SU and Precursor) are detected with goat anti-Rauscher-gp70 (1:100) (Quality Biotech Inc.); structural capsid protein (CA) are detected with goat anti-Rauscher-p30 (1:10,000) (Quality Biotech Inc.), and envelope TM protein are detected with undiluted supernatant from mouse anti-p15E hybridoma 372 (ATCC CRL-1893). Incubations are performed at 4° C. for 1 h. Subsequent incubation with secondary antibodies, mouse anti-goat or rabbit anti-mouse conjugated to horse radish peroxidase (HRP) (1:10,000)

(Sigma), is performed at room temperature for 1 h. Immunoblots are developed using detection of HRP with SuperSignal™ (Pierce) following manufacturer's suggestions. This assay is repeated on virus-containing supernatants that have been stored at −80° C., warmed to 37° C., refrozen and stored for greater than 24 h at −80° C., then thawed and frozen once more for a total of three freeze-thaw cycles prior to Western blot analysis.

Virus Binding Assays

Virus binding to the wild type receptor of the parental retrovirus envelope protein and to the cognate receptor of the fused targeting sequence is quantitated as previously described (Cosset, 1995; Kadan, 1992; and as described in Example 2). Essentially, virus-containing supernatants are concentrated 10- to 15-fold using Centricon-100 concentrators (Amicon). This concentration eliminates most of the SU protein not associated with virions so that virus binding can be quantitated in the absence of monomer SU shed from virions or the producer cell surface. Concentration also promotes binding of multiple virions to a single cell and increases the sensitivity of the assay by increasing the mean fluorescence per cell detected by flow cytometry. To ensure that equal numbers of particles from each of the virus stocks are incubated with cells during the assay, the concentration of virus stocks is adjusted to achieve comparable particle concentrations based on the reverse transcriptase activity performed exactly as described by S. Goff (Goff et. al., 1981) and Western blot quantitation of capsid protein performed as described above. Cells are detached from culture plates with PBS containing 0.02% EDTA. $10^6$ cells are then incubated with 1 ml of concentrated virus stocks containing equal amounts of virions in the presence of polybrene (5 µg/ml) for 1 h at 4° C. A second set of cells is incubated with 1 ml of concentrated cell medium containing polybrene (5 µg/ml) but lacking virus, for 1 h at 4° C. (Mock binding). Cells are then washed with PBA (PBS, 2% fetal bovine serum, and 0.02% sodium azide) and incubated in 500 µl of PBA containing goat anti-gp70 antisera (1:100) for 30 min at 4° C. After two washings, cells are incubated with 500 µl of secondary antibody, donkey anti-goat conjugated to FITC (Jackson Laboratories) diluted in PBA (1:200) for 30 min at 4° C. Propidium iodide (Sigma) is added to the binding reaction for 5 min at a final concentration of 20 µg/ml. Cells are washed twice, taken up in 500 µl of PBA and the mean FITC-emitted fluorescence of the live cells (negative for propidium iodide) is analyzed by flow cytometry (Epics Profile Analyzer, Coulter Cytometry or comparable apparatus). Experiments are repeated twice.

In this example, virus binding is quantitated on mouse NIH3T3, human 293 expressing wild type ecotropic MLV virus receptor, parental human kidney 293, human breast carcinoma MDA-MB-435 and MDA-MB-468 cells, and human endothelial umbilical cord HUV-EC-C cells. The increase in mean FITC-emitted fluorescence of live cells incubated with virus over live cells incubated in the absence of virus is a measure of the virus binding to cell surface receptors. Nonspecific background binding of virus is measured as the increase obtained for human 293 and HUV-EC-C cells that lack alphaVβ3 integrin and the ecotropic MLV receptor. Binding to the ecotropic MLV receptor is measured as the increase obtained for NIH3T3 and human 293 cells expressing wild type ecotropic MLV virus receptor but no alphaVβ3 integrin. Virus binding to alphaVβ3 integrin, the cognate receptor for the fused nonapeptide, is measured as the increase on human MDA-MB-435 breast carcinoma cells that express alphaVβ3 integrin but lack the ecotropic MLV receptor. In this example, virus binding to a second human breast carcinoma cell line, MDA-MB468, is measured to demonstrate the use of this assay in identifying other potential target cells not previously characterized for expression of the cognate receptor of the fused targeting sequence.

Specific binding of virus to the cognate receptor of the fused targeting sequence is quantitated. In this example, the virus binding assay is performed on human MDA-MB-435, MDA-MB-468, 293, and HUV-EC-C cells as described above except for the following modifications. Quantitation is performed on four sets of each cell line. The first set is incubated with concentrated virus stock plus polybrene; the second set is incubated with concentrated virus stock plus polybrene and 500 µg of HPLC-purified, cyclized synthetic peptide ACDCRGDCFCG described by Pasqualini et. al. as specifically inhibiting attachment to alphaVβ3 integrin; the third set is incubated with concentrated virus stock plus polybrene and 500 µg of the nonspecific synthetic peptide GRGESP described by Paqualini et. al.; and the fourth set is incubated with concentrated medium plus polybrene but lacking virus. The increase in mean FITC-emitted fluorescence in the presence of virus and polybrene over that in the absence of virus is a measure of virus binding. Specific virus binding is measured as the decrease in mean fluorescence observed in the presence of virus and the ACDCRGDCFCG peptide over the mean fluorescence observed in the presence of virus but absence of the peptide, minus any nonspecific decrease observed in the presence of virus and the GRGESP peptide..

Virus Titers to Quantitate Gene Delivery By Retroviral Vectors

End-point dilution titration of all virus stocks is performed as previously described for replication-defective ecotropic MLV transducing the pBAG viral genome (Malhotra et al., 1996) with modifications as follows. Briefly, $2×10^4$ cells are seeded in each well of 24-well culture plates and quadruplicate wells were exposed to 10-fold serial dilutions of virus stock in medium containing polybrene (20 µg/ml; Sigma). Forty-eight hours after exposure, cells are fixed and stained with X-GAL for β-galactosidase activity. Titers are calculated for the end-point dilution. Virus titration is performed on NIH3T3 and human 293 cells expressing wild type ecotropic MLV receptor, and on parental 293 cells lacking the ecotropic MLV receptor to quantitate infection using the ecotropic MLV receptor. Titration is also performed on cell lines expressing the cognate receptor for the fused targeting sequences and on cell lines lacking its cognate receptor. For this example, human breast carcinoma cell lines MDA-MB-435 and MDA-MB-468 which express alphaVβ3 integrin, the cognate nonapeptide receptor, and HUV-EC-C which lack alphaVβ3 integrin, are used.

Quantitation of Targeted Retroviral Vector Gene Delivery in vivo

M.f.p. implantation of MDA-MD-435 breast carcinoma cells are performed on 6–8 week old nude mice as described by Price et. al., (1990). Virus stocks are injected into these mice intravenously about 40 days post-m.f.p. implantation when tumors have grown to 1.5 cm in diameter as described by Pasqualini et. al. for injection of recombinant bacteriophage bearing the CDCRGDCFC nonapeptide fused to their coat proteins (1997). Tissue from lungs, brain, heart, kidney, lymph nodes and tumors is excised 48 to 72 hours after virus injection. Sections of each tissue are fixed, then stained for β-galactosidase activity indicative of gene delivery by retroviral vectors as described by Closs et. al. (*J. Virol.*, 67: 2097–2102).

Example 11
Tumor Cell Targeting Using Mutant Envelope Proteins

In another example, the use of two motifs in stabilizing a retroviral vector for targeted gene delivery to human colon adenocarcinoma, epidermoid carcinoma, prostate carcinomas and glioblastoma cells is used. It has recently been shown that these tumor cells express high levels of the receptors for human interleukin-13 (IL-13) (Puri et. al., 1996 *Blood* 87: 4333; Debinski et. al., 1995 *Clin. Cancer Res.,* 1: 1253; Debinski et. al., 1995 *J. Biol. Chem.* 270: 16775; and Maini et. al., 1997 *J. Urology* 158: 948). Thus, the IL-13 receptor provides an attractive receptor for virus- or liposome-mediated human gene and drug therapy of a wide range of cancer cells using the IL-13 protein as a targeting sequence. The criteria for the preferred embodiment of the invention for this use will be determined as described above for envelope protein stability, and with the following exceptions to that described above for virus binding and gene delivery.

The recombinant retroviral vector genomes for this example are constructed by inserting the nucleotide sequence encoding the 114 amino acids of human IL-13 into the unique Not I site of the four basic retroviral vectors described above using standard PCR techniques. Virus binding is quantitated on mouse NIH3T3, human 293, human colon adenocarcinoma cell line Colo201 (ATCC CCL-224), human epidermoid carcinoma cell line A-431 (ATCC CRL-1555), human glioblastoma, astrocytoma cell lines SW1088 (ATCC HTB-12) and U-373 MG (ATCC HTB-17), and human endothelial umbilical cord cell line HUV-EC-C (ATCC CRL-1730). In this example, specific binding of virus to the cognate receptor (IL-13 receptor) of the fused targeting sequence (IL-13) is quantitated by measuring the decrease in mean fluorescence observed when virus and cells are incubated in the presence of recombinant human IL-13 or in the presence of antibody specific for either the fused targeting sequence or for the binding site on the cognate receptor. The preferred vector is expected to bind specifically to Colo201, A-431, SW1088, and U-373 MG cells, all of which express high levels of the IL-13 receptor and lack the ecotropic MLV receptor, but not to 293 cells which lack the IL-13 receptor and the ecotropic MLV receptor, regardless of binding to NIH3T3 cells. Binding to HUV-EC-C cells is expected to be low as these have less than 200 IL-13 binding sites per cell. Titration of all virus stocks is performed on the same cell lines. The preferred vector is expected to deliver the β-galactosidase gene to the greatest number of Colo201, A-431, SW1088 and U-373 MG cells lacking the ecotropic MLV receptor, with the least ratio of gene delivery to 293 cells compared to delivery to the tumor cells. β-galactosidase gene delivery to HUV-EC-C cells will indicate the best mode for gene delivery to cells expressing very low numbers of the target receptor. A preferred retrovirus vector is also expected to deliver the β-galactosidase gene to the greatest number of tumor cells with the least ratio of gene delivery in healthy tissues compared to tumor cells when virus stocks are injected into nude mice carrying xenografts of the carcinoma cells.

In another example, we will enable the use of two motifs in stabilizing a retroviral vector for targeted gene delivery to human Hodgkin's lymphoma cells and other human malignancies of hematopoietic origin. Hodgkin's lymphoma cells and cells of other human hematopoietic malignancies express high levels of CD30, the receptor for human CD30Ligand (CD30L) (Durkop et. al., 1992 *Cell* 68: 421–427; Smith et. al., 1993 *Cell* 73: 1349–1360; and Gattei et. al., 1997 *Blood* 89: 2048–2059). Thus, CD30 provides a particularly attractive receptor for virus- or liposome-mediated human gene and drug therapy of a wide range of hematopoietic malignancies using the CD30L as a targeting sequence because cancer cell killing will result from retroviral vector binding, as the interaction of CD30L with CD30 initiates a signal transduction cascade that causes programmed cell death, as well as from delivery of a lethal gene or drug. The recombinant retroviral vector genomes for this example are constructed by inserting the nucleotide sequence encoding the 360 amino acid receptor-binding ectodomain of human CD30L in-frame into the unique Not I site of the four basic retroviral vectors described above using standard PCR techniques. Virus binding is quantitated on mouse NIH3T3, African green monkey COS-1, human 293, human cutaneous T cell lymphoma HUT-102 (ATCC TIB-162) from which a CD30 cDNA is isolated, and human 293 cells expressing the CD30 cDNA. In this example, specific binding of virus to the cognate receptor (CD30) of the fused targeting sequence (CD30L) is quantitated by measuring the decrease in mean fluorescence observed when virus and cells are incubated in the presence of antibody specific for the fused CD30L targeting sequence as well as for the CD30L binding site on CD30, its cognate receptor. The preferred vector is expected to bind specifically to HUT-102 and 293 cells expressing high levels of CD30 and lacking the ecotropic MLV receptor, but not to 293 and COS-1 cells which lack CD30 and the ecotropic MLV receptor, regardless of binding to NIH3T3 cells. Titration of all virus stocks are performed on the same cell lines. The preferred vector is expected to deliver the β-galactosidase gene to the greatest number of HUT-102 and 293 cells expressing high levels of CD30, with the lowest ratio of gene delivery to 293 and COS-1 cells compared to delivery to the CD30-expressing cells. The preferred vector to be used for gene delivery in vivo is expected to deliver the β-galactosidase gene to the greatest number of HUT-102 cells upon inspection of the bone marrow of SCID mice injected with HUT-102 prior to retroviral vector administration, with the lowest ratio of gene delivery to mouse tissues.

In another example, the nucleotide sequence encoding a single chain antibody that specifically recognizes CD7 is inserted in-frame into the Not I site of the four basic retroviral vector genomes. Almost all T cell acute lymphoblastic leukemia (T-ALL) cells express high levels of CD7 on their surface and bind single chain antibodies constructed from two monoclonal anti-CD7 antibody genes (Pauza et. al., 1997 *J. Immunol.* 158: 3259–69).

The preferred means of gene delivery in vivo will be expected to deliver the β-galactosidase gene to the greatest number of human T-ALL cells upon inspection of the bone marrow of SCID mice injected with T-ALLs prior to retroviral vector administration, with the lowest ratio of gene delivery to mouse tissues.

Example 12

Effect of Destablizers on H8R Mutant Viruses

Chlorpromazine (CPZ), dibucaine (DB), trifluoropyrosine (TFP), and oleic acid were purchased from Sigma. Stock solutions (200 mM CPZ, DB and TFP and 50 mM oleic acid) were made in ethanol and prepared fresh for each experiment. Cell culture medium at pH 6, 6.5, 7, or 7.5 was prepared from DMEM powdered medium (GIBCO) by adding BES buffer (Sigma) to a final concentration of 50 mM and adjusted to the desired pH by addition of HCl. Ecotropic receptor-bearing rat XC cells were seeded on 24-well plates 24 hours prior to each experiment. Quadruplicate wells were exposed to 10 fold serial dilutions of wild type or mutant virus stocks in medium containing polybrene (20 μg/ml) for 1 hour at 37° C. Cells were then washed with DMEM and exposed to the lipid destabilizing agents (CPZ or oleic acid) in DMEM/BES at the indicated pH for 1 minute (CPZ, DB or TFP) or 5 minutes (oleic acid). The cells were quickly washed with DMEM and returned to drug free medium at the same pH. Forty-eight (48) hours later cells were fixed, stained with X-GAL and titers were calculated for end point dilution (n=4).

Wild type or mutant viruses carrying lacZ gene were produced from H1-BAG cells and then used to expose replicate wells of rat XC cells for 1 hour at 37° C. During that time virus binding and its initial fusion with host cells occur. The virus-cell complexes were then treated with lipid destabilizing agents for a period of time sufficient for intercalation of the drugs into the membranes (1 to 5 minutes). Forty-eight (48) hours later, the virus titers were determined.

Figure 20A:
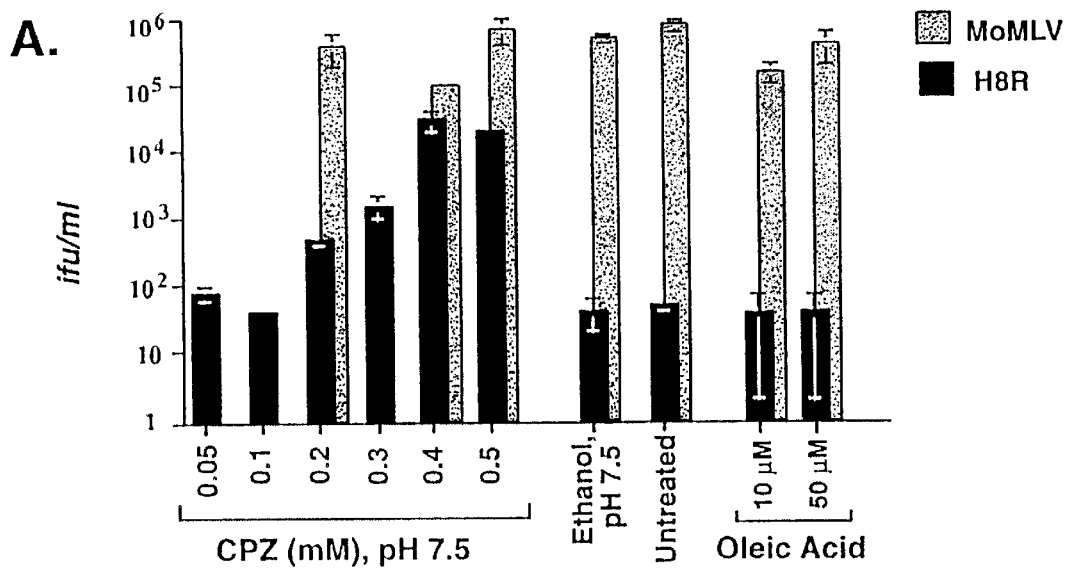
Figure 20B:
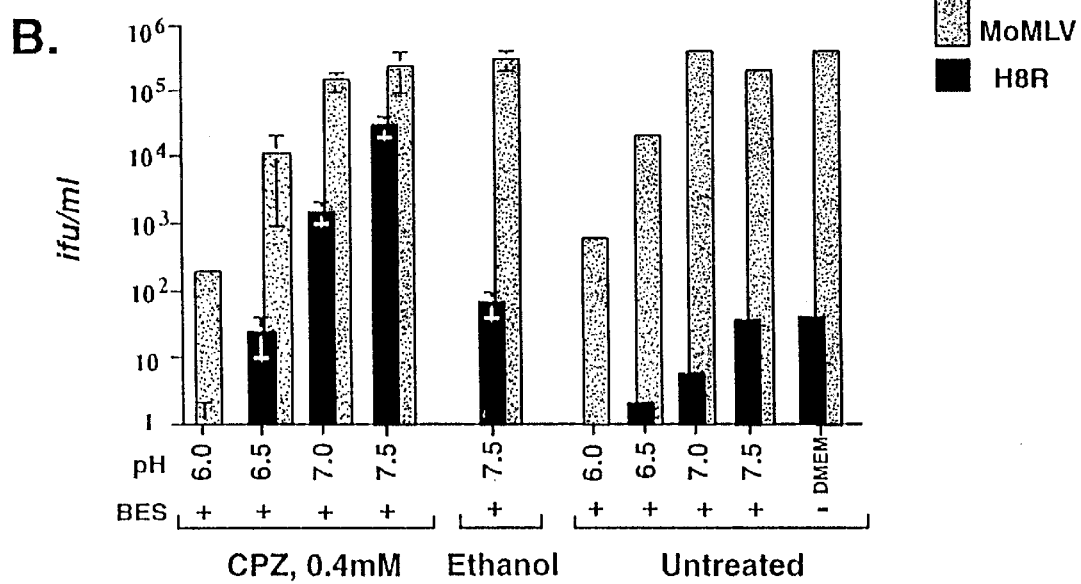
Figure 20C:
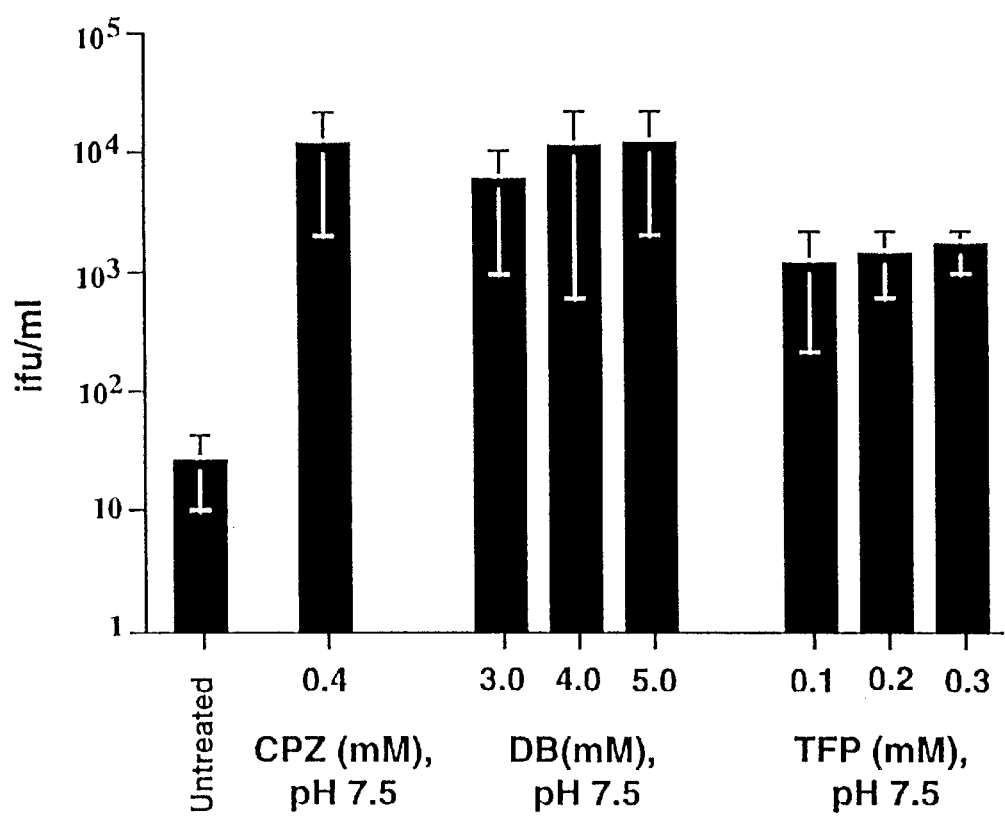

Treatment of virus-cell complexes with the outer leaflet destabilizing agent, oleic acid, at concentrations reported to enhance outer leaflet fusion did not increase the infectivity of the mutant viruses (FIG. 20A), FIG. 20 shows the effect of CPZ treatment on H8R virus infection. In the absence of any treatment or upon treatment with ethanol at concentrations used to solubilize CPZ, the titer of H8R virus on XC cells did not exceed 100 ifu/ml. A brief exposure of H9R virus-cell complexes to CPZ at concentrations as low as 0.2 mM increases infectivity of H8R virus by several fold. Moreover, the enhancement of H8R virus infection was concentration dependent. Entry-defective H8R virus became 500 to 100 fold more infectious upon treatment with 0.4 mM CPZ (FIG. 20A and B). The inner leaflet destabilizers DB and TFP produce similar increases in H8R virion infection (FIG. 20C).

The action of CPZ has been shown to be dependent on its ability to partition into the inner leaflet of fusing membranes. This ability is greatly compromised at acidic pH. Extent of CPZ induced H8R virus infection correlated with the fraction of neutral non-protonated form of CPZ. When virus-cell complexes were treated with CPZ at a pH that favors protonation and disfavors intercalation of the drug into the inner membrane monolayer, no increase in infection by the H8R virus was observed (FIG. 20B). Even at pH 7.0 the effect of CPZ was not as profound as it was at pH 7.5.

Example 13

Liposome Compositions

Abbreviations used in this example include the following: DOPC, dioleoylphosphotidylcholine; DOPE, dioleoyl-phosphatidylethanolamine; MPB-PE, dioleoylphosphotidylethanolamine-N-[4-(maleimidophenyl)butyrate]; PEG, disteroylphosphatidylethanolamine-polyethylene glycol-2000; and CHEMS, cholesteryl 4,4-difluoro-5,7-dimethyl-4-bora-3a,4a-diaza-s-indacene-3-dodecanoate.

Liposomes are composed of 62.5:2.5 mol % DOPC/MPB-PE (classic liposome), or 57.5:5:2.5 mol % DOPC/PEG/MPB-PE (sterically stabilized liposomes) or 20:27.5:50:2.5 mol % DOTAP/DOPC/DOPE/MPB-PE (cationic liposomes) or 65.4:32.1:2.5 mol % DOPE/CHEMS/MPB-PE (pH sensitive liposomes) conjugated to mutant retroviral envelope proteins. Briefly, liposomes are prepared by mixing the ratio of lipids as outlined above in chloroform. Chloroform is removed under argon stream and the lipids are lyophilized from spectral grade cyclohexane. The lipid mixtures are hydrated in 10 mM Hepes, 150 mM NaCl, and 0.1 mM EDTA (HBSE buffer). All hydrating solutions are prepared at pH 7.5 and ≈290 mmol/kg osmolality. Hydrated lipids are frozen and thawed four (4) times, then extruded for 15 cycles through two stacked 0.08 μm polycarbonate membranes using a hand-held extruder. Liposome diameter is determined by quasi-elastic light scattering with an N4 Plus Submicron Particle Sizer (Coulter).

Envelope proteins are purified and incubated with succinimidyl-S-acetylthioacetate (SATA) [solubilized in dimethylformamide at 1:10 and 100:1 volume ratios (protein/SATA)] for 30 minutes at room temperature, dialyzed against 50–100 volumes of HBSE buffer, with two (2) changes, deacetylated with a 10% (vol/vol) addition of 50 mM sodium phosphate, 25 mM EDTA and 0.5 M Hydroxylamine (pH 7.5) for two (2) hours and then immediately added to liposomes. The liposome/protein mixture is gently shaken at 4° C. overnight, and proteoliposomes are separated from free protein and deacetylation solution by chromatography. Lipid mass is determined by phosphate assay: protein content is quantified by SDS-PAGE.

Example 14

Figure 22:
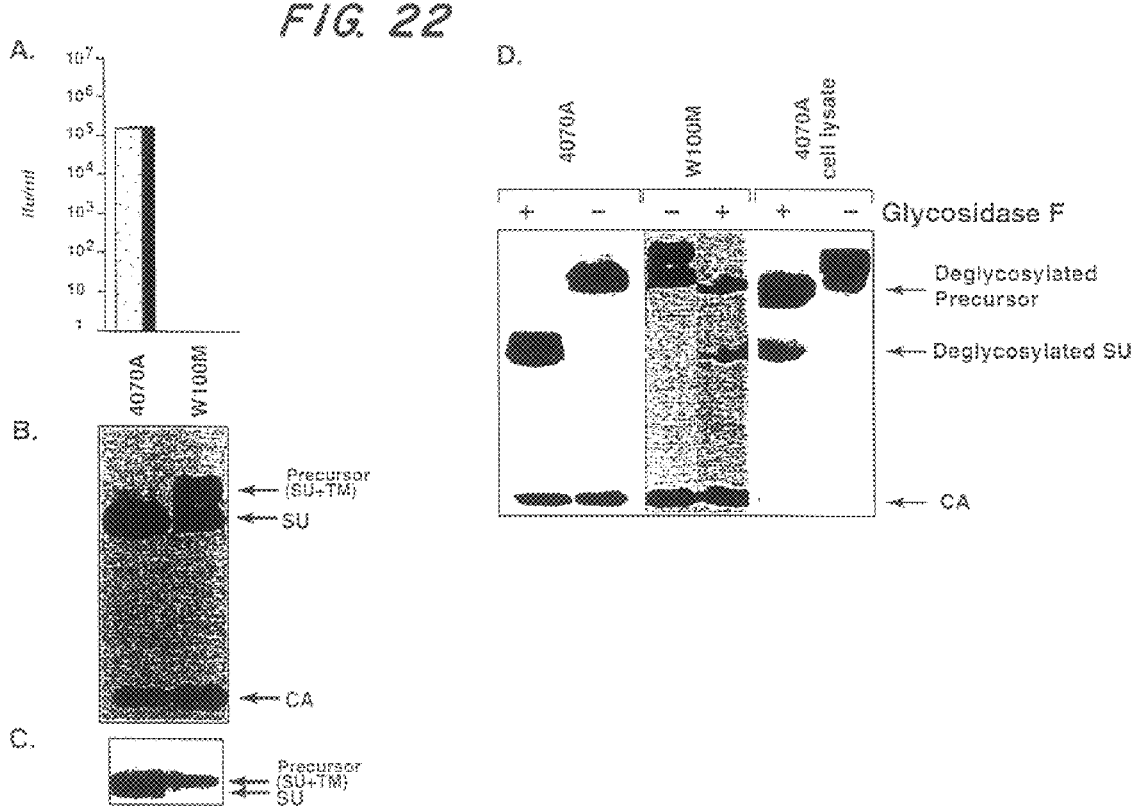
Figure 23:
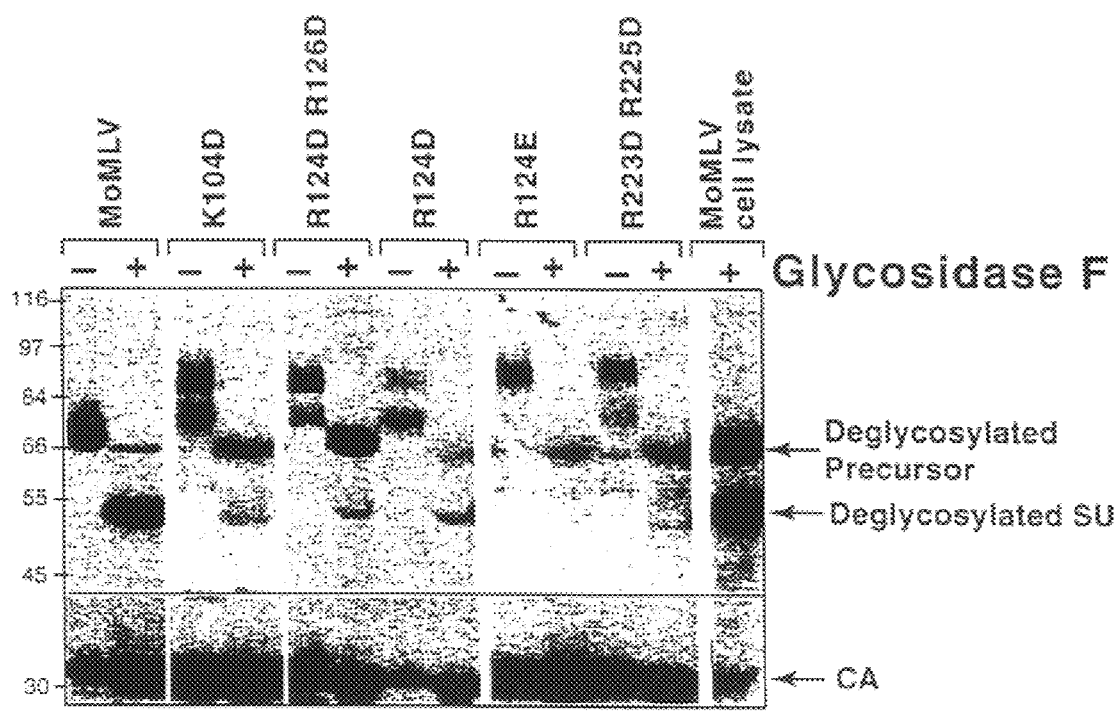

Comparison of Alignment Equivalent Mutations at W142M of MoMLV and W100M of 4070A MLV According to MegAlign alignment and analysis of Friend MLV crystal coordinates, the alignment equivalent for tryptophan 100 of amphotropic 4070A MLV is tryptophan 142 of ecotropic MoMLV (see FIG. 16). FIG. 22A shows infectious titers on mouse NIH3T3 cells bearing endogenous amphotropic 4070A MLV receptors (stippled bars) and human 293 expressing exogenous receptor (black bars). Viruses containing a Tryptophan$^{100}$($^{100}$Trp) to methionine substitution (W100M) contained appreciable amounts of cleaved SU, but the presence of this mature SU did not rescue their infectivity. Titers were calculated from the endpoint dilution (n=4) after exposure to virions pseudotyped with envelope proteins containing the indicated substitution. 4070A, wild type amphotropic MLV 4070A; W100M, tryptophan 100 to methionine substitution (See FIG. 22A).

FIG. 13A demonstrates the viruses containing a Tryptophan$^{142}$ ($^{142}$Trp) to methionine substitution (W142M) contained appreciable amounts of cleaved SU, and again the presence of this mature SU did not rescue their infectivity. FIG. 13 shows irus titers on NIH3T3 cells (stippled bars) and human 293 expressing exogenous wild type receptor (black bars). Titers were calculated from the end-point dilution (n=4) after exposure to virions pseudotyped with envelope proteins containing the indicated substitutions. Each value is the average of five independent experiments.

Figure 21:
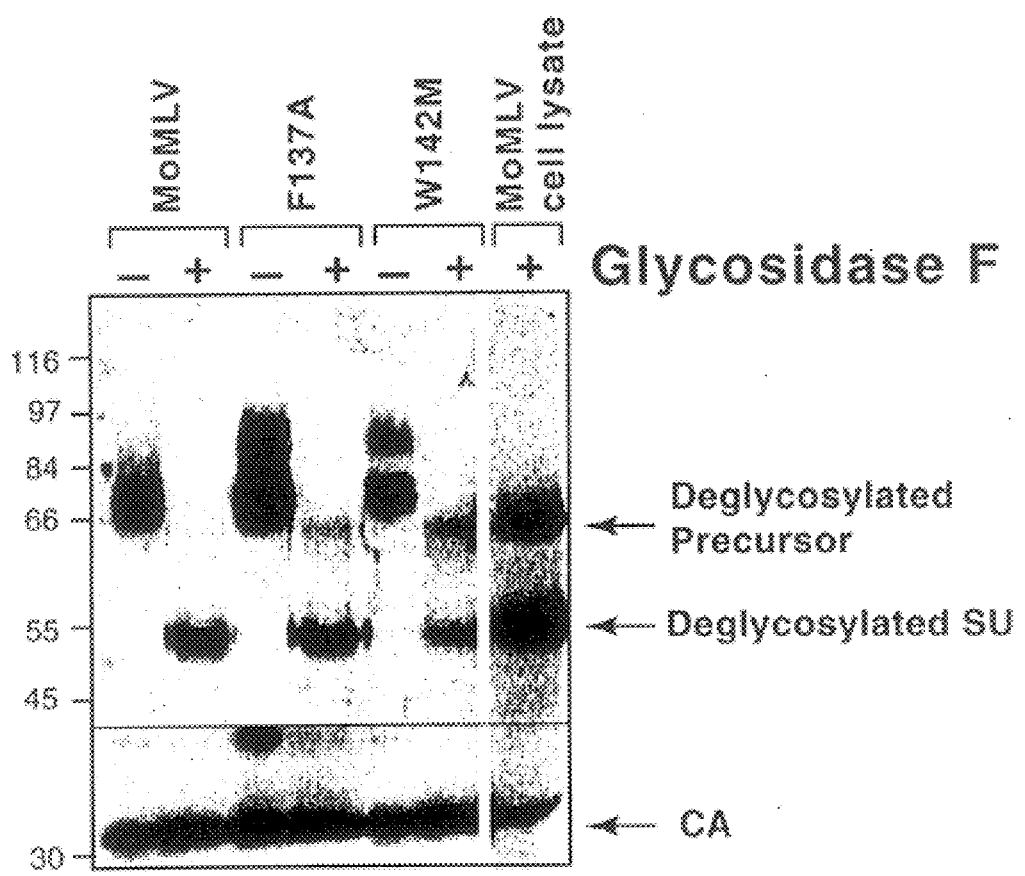

Further, digestion overnight with glycosidase F demonstrates that the 85 kDa envelope protein species for these mutants represents an uncleaved precursor protein (compare FIGS. 21 and 22B). Taken together, the Western blot and titer show that W100M substitution in the amphotropic 4070A envelope SU give cleavage/envelope protein stabilization and loss of natural host range. These results were identically demonstrated for ecotropic MoMLV SU W142M substitution. These data provide material evidence that a similar motif exists in ecotropic and amphotropic SU as predicted by the alignment of envelope proteins. Similar predictions for secondary structure motifs, alpha-helexes and beta-strands based on the alignments as set forth in FIG. 17 have been demonstrated for HIV.

Although the present invention has been described in detail with reference to examples above, it is understood that various modifications can be made without departing from the spirit of the invention. For example, envelope proteins can be engineered that contain one or more mutations in one motif, or the protein can contain mutations in one or more of the motifs. These mutations can be utilized to augment the ability of the virus to fuse to its target and to enhance the stability of the envelope protein to avoid envelope protein shedding from the virion. Accordingly, the invention is limited only by the following claims. All references, articles, texts and other documents referred to above, and the references contained therein, are hereby incorporated by reference in their entirety, as is U.S. Provisional Application Ser. No. 60/086,149, filed May 20, 1998.

We claim:

1. An isolated nucleic acid encoding a mutant retrovirus envelope protein comprising the substitution of one or more amino acids in at least one motif of the seven motifs listed in Table I, wherein said mutant protein allows for decreased shedding of the surface protein by suppressing precursor cleavage, while maintaining mutant envelope protein incorporation into a virion.

2. An isolated nucleic acid encoding a mutant retrovirus envelope protein comprising the substitution of one or more amino acids in at least one motif of the seven motifs listed in Table I, wherein said mutant protein allows for decreased shedding of the surface protein by increasing envelope stability and for increased fusion of retroviruses with cell membranes, while maintaining mutant envelope protein incorporation into a virion.

3. The nucleic acid of claim 1, wherein said substitution of one or more amino acids corresponds to at least one mutation of at least one residue in alignment with $^{16}$Glu, 24Thr, $^{90}$Thr, $^{102}$Arg, $^{104}$Lys, $^{107}$Glu, $^{108}$Thr, $^{121}$Gly, $^{124}$Arg, $^{126}$Arg, $^{128}$Ser, $^{132}$Gly, $^{133}$Gly, $^{134}$Pro, $^{135}$Asp, $^{136}$Ser, $^{137}$Phe, $^{138}$Tyr, $^{141}$Tyr, $^{142}$Trp, $^{151}$Tyr, $^{152}$Trp, $^{201}$Thr, $^{208}$Arg, $^{210}$Tyr, $^{217}$Gly, $^{223}$Arg, $^{224}$Leu or $^{225}$Arg of SEQ ID NO: 2.

4. The nucleic acid claim of claim 2, wherein said substitution of one or more amino acids corresponds to at least one mutation of at least one residue in alignment with $^{8}$His, $^{11}$Tyr, $^{35}$Trp, $^{38}$Trp, $^{123}$His, $^{158}$Trp, $^{160}$Tyr, $^{196}$Val, $^{197}$Thr, 198Ser, $^{203}$His, $^{226}$Tyr, $^{227}$Gln, $^{228}$Asn, $^{233}$Val, $^{235}$Ile, $^{240}$Val, $^{241}$Leu, or $^{243}$Asp of SEQ ID NO: 2.

5. The nucleic acid of claim 4, wherein said substitution of one or more amino acids corresponds to mutations in residues in alignment with $^{8}$His, $^{227}$Gln and $^{243}$Asp of SEQ ID NO: 2.

6. A nucleic acid encoding a mutant retroviral protein comprising at least one substitution of one or more amino acids, wherein said substitution of one or more amino acids corresponds to at least one mutation of at least one residue in alignment with $^{8}$His, $^{11}$Tyr, $^{16}$Glu, $^{24}$Thr, $^{35}$Trp, 38Trp, $^{102}$Arg, $^{104}$Lys, $^{107}$Glu, 108Thr, $^{109}$Thr, $^{121}$Gly, $^{123}$His, $^{124}$Arg, $^{128}$Ser, $^{132}$Gly, $^{133}$Gly, $^{134}$Pro, $^{135}$Asp, $^{136}$Ser, $^{137}$Phe, $^{138}$Tyr, $^{141}$Tyr, $^{142}$Trp, $^{151}$Tyr, $^{152}$Trp, $^{158}$Trp, $^{160}$Tyr, $^{196}$Val, $^{197}$Thr, $^{198}$Ser, $^{201}$Thr, $^{203}$His, $^{208}$Arg, $^{210}$Tyr, $^{217}$Gly, $^{223}$Arg, $^{224}$Leu, $^{225}$Arg, $^{226}$Tyr, $^{227}$Gln, $^{228}$Asn, $^{233}$Val, $^{235}$Ile, $^{240}$Val, $^{241}$Leu, and/or $^{243}$Asp of SEQ ID NO: 2.

7. The nucleic acid of claims 1 or 2, wherein said mutant retroviral envelope protein is derived from the env gene of a virus selected from the group consisting of Moloney MLV, Friend MLV, MLV 10A1, AKV MLV, CasBrE, RadLV, MCF1233, Xenotrophic NZB, FelV-A, FeLV-B, avian leukosis retrovirus, GALV SEATO strain, HIV-1, HIV-2 and SIV.

8. A nucleic acid encoding a mutant retroviral protein comprising one or more amino acid substitutions, wherein said one or more substitutions at residues $^{8}$His, $^{11}$Tyr, $^{16}$Glu, $^{24}$Thr, $^{35}$Trp, $^{38}$Trp, $^{102}$Arg, $^{104}$Lys, $^{107}$Glu, $^{108}$Thr, $^{109}$Thr, $^{121}$Gly, $^{123}$His, $^{124}$Arg, $^{128}$Ser, $^{132}$Gly, $^{133}$Gly, $^{134}$Pro, $^{135}$Asp, $^{136}$Ser, $^{137}$Phe, $^{138}$Tyr, $^{141}$Tyr, $^{142}$Trp, $^{151}$Tyr, $^{152}$Trp, $^{158}$Trp, $^{160}$Tyr, $^{196}$Val, $^{197}$Thr, $^{198}$Ser, $^{201}$Thr, $^{203}$His, $^{208}$Arg, $^{210}$Tyr, $^{217}$Gly, $^{223}$Arg, $^{224}$Leu, $^{225}$Arg, $^{226}$Tyr, $^{227}$Gln, $^{228}$Asn, $^{233}$Val, $^{235}$Ile, $^{240}$Val, $^{241}$Leu, or $^{243}$Asp as set forth in SEQ ID NO: 2, and wherein said mutant protein allows for decreased shedding of the surface protein by suppressing precursor cleavage or increased envelope stability and fusion of retroviruses with cell membranes when said protein is expressed on the surface of a retroviral particle.

9. The nucleic acid of claim 8, wherein said nucleic acid comprises SEQ ID NO: 1.

10. The nucleic acid of any one of claims 1, 2, 6, or 8, wherein said mutant retroviral envelope protein further comprises a heterologous protein, polypeptide or peptide fragment.

11. An isolated nucleic acid encoding a mutant retrovirus envelope protein comprising the substitution of one or more amino acids in at least one motif of the receptor binding domain, wherein said mutant protein allows for decreased shedding of the surface protein by suppressing precursor cleavage, while maintaining mutant envelope protein incorporation into a virion.

12. An isolated nucleic acid encoding a mutant retrovirus envelope protein comprising the substitution of one or more amino acids in at least one motif of the receptor binding domain, wherein said mutant protein allows for decreased shedding of the surface protein by increasing envelope protein stability and for increased envelope stability and fusion of retroviruses with cell membranes, while maintaining mutant envelope protein incorporation into a virion.

13. A nucleic acid encoding a mutant retroviral protein comprising one or more amino acid substitutions, wherein said one or more substitutions at residues $^{8}$His, $^{11}$Tyr, $^{16}$Glu, $^{24}$Thr, $^{35}$Trp, $^{38}$Trp, $^{102}$Arg, $^{104}$Lys, $^{107}$Glu, $^{108}$Thr, $^{109}$Thr, $^{121}$Gly, $^{123}$His, $^{124}$Arg, $^{128}$Ser, $^{132}$Gly, $^{133}$Gly, $^{134}$Pro, $^{135}$Asp, $^{136}$Ser, $^{137}$Phe; $^{138}$Tyr, $^{141}$Tyr, $^{142}$Trp, $^{151}$Tyr, $^{152}$Trp, $^{158}$Trp, $^{160}$Tyr, $^{196}$Val, $^{197}$Thr, $^{198}$Ser, $^{201}$Thr, $^{203}$His, $^{208}$Arg, $^{210}$Tyr, $^{217}$Gly, $^{223}$Arg, $^{224}$Leu, $^{225}$Arg, $^{226}$Tyr, $^{227}$Gln, $^{228}$Asn, $^{233}$Val, $^{235}$Ile, $^{240}$Val, $^{241}$Leu, or $^{243}$Asp asset forth in SEQ ID NO: 2, and wherein said mutant protein allows for decreased shedding of the surface protein by suppressing precursor cleavage or increased envelope stability and fusion of retroviruses with cell membranes when said protein is expressed on the surface of a retroviral particle.

* * * * *

SEQUENCE LISTING

```
<160> NUMBER OF SEQ ID NOS: 23

<210> SEQ ID NO 1
<211> LENGTH: 8332
<212> TYPE: DNA
<213> ORGANISM: Artificial Sequence
<220> FEATURE:
<223> OTHER INFORMATION: Description of Artificial Sequence:  SEQ. ID
      NO. 1, retroviral vector
<220> FEATURE:
<221> NAME/KEY: CDS
<222> LOCATION: (5876)..(7771)

<400> SEQUENCE: 1
gcgccagtcc tccgattgac tgagtcgccc gggtacccgt gtatccaata aaccctcttg     60
cagttgcatc cgacttgtgg tctcgctgtt ccttgggagg gtctcctctg agtgattgac    120
tacccgtcag cgggggtctt tcatttgggg gctcgtccgg gatcgggaga cccctgccca    180
gggaccaccg acccaccacc gggaggtaag ctggccagca acttatctgt gtctgtccga    240
ttgtctagtg tctatgactg attttatgcg cctgcgtcgg tactagttag ctaactagct    300
ctgtatctgg cggacccgtg gtggaactga cgagttcgga acacccggcc gcaaccctgg    360
gagacgtccc agggacttcg ggggccgttt ttgtggcccg acctgagtcc aaaaatcccg    420
atcgttttgg actctttggt gcaccccct tagaggaggg atatgtggtt ctggtaggag     480
acgagaacct aaaacagttc ccgcctccgt ctgaattttt gctttcggtt tgggaccgaa    540
gccgcgccgc gcgtcttgtc tgctgcagca tcgttctgtg ttgtctctgt ctgactgtgt    600
ttctgtattt gtctgagaat atgggccaga ctgttaccac tcccttaagt ttgaccttag    660
gtcactggaa agatgtcgag cggatcgctc acaaccagtc ggtagatgtc aagaagagac    720
gttgggttac cttctgctct gcagaatggc caacctttaa cgtcggatgg ccgcgagacg    780
gcacctttaa ccgagacctc atcacccagg ttaagatcaa ggtcttttca cctggcccgc    840
atggacaccc agaccaggtc ccctacatcg tgacctggga agccttggct tttgaccccc    900
ctccctgggt caagcccttt gtacacccta agcctccgcc tcctcttcct ccatccgccc    960
cgtctctccc ccttgaacct cctcgttcga ccccgcctcg atcctccctt tatccagccc   1020
tcactccttc tctaggcgcc aaacctaaac ctcaagttct ttctgacagt ggggggccgc   1080
tcatcgacct acttacagaa gaccccccgc cttataggga cccaagacca cccccttccg   1140
acagggacgg aaatggtgga gaagcgaccc ctgcgggaga ggcaccggac ccctccccaa   1200
tggcatctcg cctacgtggg agacgggagc cccctgtggc cgactccact acctcgcagg   1260 cattcccct ccgcgcagga ggaaacggac agcttcaata ctggccgttc tcctcttctg    1320
acctttacaa ctggaaaaat aataaccctt ctttttctga agatccaggt aaactgacag   1380
ctctgatcga gtctgttctc atcacccatc agcccacctg ggacgactgt cagcagctgt   1440
tggggactct gctgaccgga gaagaaaaac aacgggtgct cttagaggct agaaaggcgg   1500
tgcggggcga tgatgggcgc cccactcaac tgcccaatga agtcgatgcc gcttttcccc   1560
```

-continued

```
tcgagcgccc agactgggat tacaccaccc aggcaggtag gaaccaccta gtccactatc    1620
gccagttgct cctagcgggt ctccaaaacg cgggcagaag ccccaccaat ttggccaagg    1680
taaaaggaat aacacaaggg cccaatgagt ctccctcggc cttcctagag agacttaagg    1740
aagcctatcg caggtacact ccttatgacc ctgaggaccc agggcaagaa actaatgtgt    1800
ctatgtcttt catttggcag tctgccccag acattgggag aaagttagag aggttagaag    1860
atttaaaaaa caagacgctt ggagatttgg ttagagaggc agaaaagatc tttaataaac    1920
gagaaacccc ggaagaaaga gaggaacgta tcaggagaga aacagaggaa aaagaagaac    1980
gccgtaggac agaggatgag cagaaagaga agaaagaga tcgtaggaga catagagaga    2040
tgagcaagct attggccact gtcgttagtg gacagaaaca ggatagacag ggaggagaac    2100
gaaggaggtc ccaactcgat cgcgaccagt gtgcctactg caaagaaaag gggcactggg    2160
ctaaagattg tcccaagaaa ccacgaggac ctcgggacc aagacccag acctccctcc    2220 tgaccctaga tgactaggga ggtcagggtc aggagccccc ccctgaaccc aggataaccc    2280
tcaaagtcgg ggggcaaccc gtcaccttcc tggtagatac tggggcccaa cactccgtgc    2340
tgacccaaaa tcctggaccc ctaagtgata agtctgcctg gtccaaggg gctactggag    2400 gaaagcggta tcgctggacc acggatcgca aagtacatct agctaccggt aaggtcaccc    2460
actctttcct ccatgtacca gactgtccct atcctctgtt aggaagagat ttgctgacta    2520
aactaaaagc ccaaatccac tttgagggat caggagctca ggttatggga ccaatggggc    2580
agcccctgca agtgttgacc ctaaatatag aagatgagca tcggctacat gagacctcaa    2640
aagagccaga tgtttctcta gggtccacat ggctgtctga ttttcctcag gcctgggcgg    2700
aaaccggggg catgggactg gcagttcgcc aagctcctct gatcatacct ctgaaagcaa    2760
cctctacccc cgtgtccata aaacaatacc ccatgtcaca agaagccaga ctggggatca    2820
agccccacat acagagactg ttggaccagg gaatactggt accctgccag tcccctggaa    2880
acacgcccct gctacccgtt aagaaaccag ggactaatga ttataggcct gtccaggatc    2940
tgagagaagt caacaagcgg gtggaagaca tccaccccac cgtgcccaac ccttacaacc    3000
tcttgagcgg gctcccaccg tcccaccagt ggtacactgt gcttgattta aaggatgcct    3060
ttttctgcct gagactccac cccaccagtc agcctctctt cgcctttgag tggagagatc    3120
cagagatggg aatctcagga caattgacct ggaccagact cccacagggt ttcaaaaaca    3180
gtcccaccct gtttgatgag gcactgcaca gagacctagc agacttccgg atccagcacc    3240
cagacttgat cctgctacag tacgtggatg acttactgct ggccgccact tctgagctag    3300
actgccaaca aggtactcgg gccctgttac aaacccagg gaacctcggg tatcgggcct    3360
cggccaagaa agcccaaatt tgccagaaac aggtcaagta tctggggtat cttctaaaag    3420
agggtcagag atggctgact gaggccagaa aagagactgt gatggggcag cctactccga    3480
agacccctcg acaactaagg gagttcctag ggacggcagg cttctgtcgc tctggatcc    3540 ctgggtttgc agaaatggca gcccccttgt accctctcac caaaacgggg actctgttta    3600
attgggggcc agaccaacaa aaggcctatc aagaaatcaa gcaagctctt ctaactgccc    3660
cagccctggg gttgcagat ttgactaagc ccttttgaact cttttgtcgac gagaagcagg    3720 gctacgccaa aggtgtccta acgcaaaaac tgggaccttg gcgtcggccg gtggcctacc    3780
tgtccaaaaa gctagaccca gtagcagctg ggtggccccc ttgcctacgg atggtagcag    3840
ccattgccgt actgacaaag gatgcaggca agctaaccat gggacagcca ctagtcattc    3900
tggcccccca tgcagtagag gcactagtca acaacccccc cgaccgctgg ctttccaacg    3960
```

-continued

```
cccggatgac tcactatcag gccttgcttt tggacacgga ccgggtccag ttcggaccgg    4020
tggtagccct gaacccggct acgctgctcc cactgcctga ggaagggctg caacacaact    4080
gccttgatat cctggccgaa gcccacggaa cccgacccga cctaacggac cagccgctcc    4140
cagacgccga ccacctggta cacggatg gaagcagtct cttacaagag ggacagcgta     4200
aggcgggagc tgcggtgacc accgagaccg aggtaatctg gctaaagcc ctgccagccg     4260 ggacatccgc tcagcgggct gaactgatag cactcaccca ggccctaaag atggcagaag    4320
gtaagaagct aaatgtttat actgatagcc gttatgcttt tgctactgcc catatccatg    4380
gagaaatata cagaaggcgt gggttgctca catcagaagg caaagagatc aaaaataaag    4440
acgagatctt ggccctacta aagccctct ttctgcccaa aagacttagc ataatccatt     4500
gtccaggaca tcaaaaggga cacagcgccg aggctagagg caaccggatg gctgaccaag    4560
cggcccgaaa ggcagccatc acagagactc cagacacctc taccctcctc atagaaaatt    4620
catcacccta cacctcagaa cattttcatt acacagtgac tgatataaag gacctaacca    4680
agttgggggc catttatgat aaaacaaaga agtattgggt ctaccaagga aaacctgtga    4740
tgcctgacca gtttactttt gaattattag actttcttca tcagctgact cacctcagct    4800
tctcaaaaat gaaggctctc ctagagagaa gccacagtcc ctactacatg ctgaaccggg    4860
atcgaacact caaaaatatc actgagacct gcaaagcttg tgcacaagtc aacgccagca    4920
agtctgccgt taaacaggga actagggtcc gcgggcatcg gcccggcact cattgggaga    4980
tcgatttcac cgagataaag cccggattgt atggctataa atatcttcta gttttttatag   5040 atacctttc tggctggata gaagccttcc caaccaagaa agaaaccgcc aagtcgtaa     5100 ccaagaagct actagaggag atcttcccca ggttcggcat gcctcaggta ttgggaactg    5160
acaatgggcc tgccttcgtc tccaaggtga gtcagacagt ggccgatctg ttggggattg    5220
attggaaatt acattgtgca tacagacccc aaagctcagg ccagtagaa agaatgaata     5280 gaaccatcaa ggagacttta actaaattaa cgcttgcaac tggctctaga gactgggtgc    5340
tcctactccc cttagccctg taccgagccc gcaacacgcc gggcccccat ggcctcaccc    5400
catatgagat cttatatggg gcaccccgc cccttgtaaa cttccctgac cctgacatga     5460
caagagttac taacagcccc tctctccaag ctcacttaca ggctctctac ttagtccagc    5520
acgaagtctg gagacctctg gcggcagcct accaagaaca actggaccga ccggtggtac    5580 ctcacccttaa ccgagtcggc gacacagtgt gggtccgccg acaccagact aagaacctag    5640
aacctcgctg gaaaggacct tacacagtcc tgctgaccac ccccaccgcc ctcaaagtag    5700
acggcatcgc agcttggata cacgccgccc acgtgaaggc tgccgacccc ggggtggac     5760 catcctctag actgacatgg cgcgttcaac gctctcaaaa ccccttaaaa ataaggttaa    5820
cccgcgaggc ccctaatcc ccttaattct tctgatgctc agagggtca gtact gct      5878
                                                                Ala
                                                                 1 tcg ccc ggc tcc agt cct cat caa gtc tat aat atc acc tgg gag gta    5926
Ser Pro Gly Ser Ser Pro His Gln Val Tyr Asn Ile Thr Trp Glu Val
         5                  10                 15 acc aat gga gat cgg gag acg gta tgg gca act tct ggc aac cac cct    5974
Thr Asn Gly Asp Arg Glu Thr Val Trp Ala Thr Ser Gly Asn His Pro
 20                  25                  30 ctg tgg acc tgg tgg cct gac ctt acc cca gat tta tgt atg tta gcc    6022
Leu Trp Thr Trp Trp Pro Asp Leu Thr Pro Asp Leu Cys Met Leu Ala
 35                  40                  45
```

```
cac cat gga cca tct tat tgg ggg cta gaa tat caa tcc cct ttt tct    6070
His His Gly Pro Ser Tyr Trp Gly Leu Glu Tyr Gln Ser Pro Phe Ser
 50              55                  60                  65 tct ccc ccg ggg ccc cct tgt tgc tca ggg ggc agc agc cca ggc tgt    6118
Ser Pro Pro Gly Pro Pro Cys Cys Ser Gly Gly Ser Ser Pro Gly Cys
             70                  75                  80 tcc aga gac tgc gaa gaa cct tta acc tcc ctc acc cct cgg tgc aac    6166
Ser Arg Asp Cys Glu Glu Pro Leu Thr Ser Leu Thr Pro Arg Cys Asn
                 85                  90                  95 act gcc tgg aac aga ctc aag cta gac cag aca act cat aaa tca aat    6214
Thr Ala Trp Asn Arg Leu Lys Leu Asp Gln Thr Thr His Lys Ser Asn
            100                 105                 110 gag gga ttt tat gtt tgc ccc ggg ccc cac cgc ccc cga gaa tcc aag    6262
Glu Gly Phe Tyr Val Cys Pro Gly Pro His Arg Pro Arg Glu Ser Lys
        115                 120                 125 tca tgt ggg ggt cca gac tcc ttc tac tgt gcc tat tgg ggc tgt gag    6310
Ser Cys Gly Gly Pro Asp Ser Phe Tyr Cys Ala Tyr Trp Gly Cys Glu
130                 135                 140                 145 aca acc ggt aga gct tac tgg aag ccc tcc tca tca tgg gat ttc atc    6358
Thr Thr Gly Arg Ala Tyr Trp Lys Pro Ser Ser Ser Trp Asp Phe Ile
                150                 155                 160 aca gta aac aac aat ctc acc tct gac cag gct gtc cag gta tgc aaa    6406
Thr Val Asn Asn Asn Leu Thr Ser Asp Gln Ala Val Gln Val Cys Lys
            165                 170                 175 gat aat aag tgg tgc aac ccc tta gtt att cgg ttt aca gac gcc ggg    6454
Asp Asn Lys Trp Cys Asn Pro Leu Val Ile Arg Phe Thr Asp Ala Gly
        180                 185                 190 aga cgg gtt act tcc tgg acc aca gga cat tac tgg ggc tta cgt ttg    6502
Arg Arg Val Thr Ser Trp Thr Thr Gly His Tyr Trp Gly Leu Arg Leu
195                 200                 205 tat gtc tcc gga caa gat cca ggg ctt aca ttt ggg atc cga ctc aga    6550
Tyr Val Ser Gly Gln Asp Pro Gly Leu Thr Phe Gly Ile Arg Leu Arg
210                 215                 220                 225 tac caa aat cta gga ccc cgc gtc cca ata ggg cca aac ccc gtt ctg    6598
Tyr Gln Asn Leu Gly Pro Arg Val Pro Ile Gly Pro Asn Pro Val Leu
                230                 235                 240 gca gac caa cag cca ctc tcc aag ccc aaa cct gtt aag tcg cct tca    6646
Ala Asp Gln Gln Pro Leu Ser Lys Pro Lys Pro Val Lys Ser Pro Ser
            245                 250                 255 gtc acc aaa cca ccc agt ggg act cct ctc tcc cct acc caa ctt cca    6694
Val Thr Lys Pro Pro Ser Gly Thr Pro Leu Ser Pro Thr Gln Leu Pro
        260                 265                 270 ccg gcg gga acg gaa aat agg ctg cta aac tta gta gac gga gcc tac    6742
Pro Ala Gly Thr Glu Asn Arg Leu Leu Asn Leu Val Asp Gly Ala Tyr
275                 280                 285 caa gcc ctc aac ctc acc agt cct gac aaa acc caa gag tgc tgg ttg    6790
Gln Ala Leu Asn Leu Thr Ser Pro Asp Lys Thr Gln Glu Cys Trp Leu
290                 295                 300                 305 tgt cta gta gcg gga ccc ccc tac tac gaa ggg gtt gcc gtc ctg ggt    6838
Cys Leu Val Ala Gly Pro Pro Tyr Tyr Glu Gly Val Ala Val Leu Gly
                310                 315                 320 acc tac tcc aac cat acc tct gct cca gcc aac tgc tcc gtg gcc tcc    6886
Thr Tyr Ser Asn His Thr Ser Ala Pro Ala Asn Cys Ser Val Ala Ser
            325                 330                 335 caa cac aag ttg acc ctg tcc gaa gtg acc gga cag gga ctc tgc ata    6934
Gln His Lys Leu Thr Leu Ser Glu Val Thr Gly Gln Gly Leu Cys Ile
        340                 345                 350 gga gca gtt ccc aaa aca cat cag gcc cta tgt aat acc acc cag aca    6982
Gly Ala Val Pro Lys Thr His Gln Ala Leu Cys Asn Thr Thr Gln Thr
355                 360                 365
```

```
agc agt cga ggg tcc tat tat cta gtt gcc cct aca ggt acc atg tgg    7030
Ser Ser Arg Gly Ser Tyr Tyr Leu Val Ala Pro Thr Gly Thr Met Trp
370             375                 380                 385 gct tgt agt acc ggg ctt act cca tgc atc tcc acc aca ata ctg aac    7078
Ala Cys Ser Thr Gly Leu Thr Pro Cys Ile Ser Thr Thr Ile Leu Asn
                390                 395                 400 ctt acc act gat tat tgt gtt ctt gtc gaa ctc tgg cca aga gtc acc    7126
Leu Thr Thr Asp Tyr Cys Val Leu Val Glu Leu Trp Pro Arg Val Thr
            405                 410                 415 tat cat tcc ccc agc tat gtt tac ggc ctg ttt gag aga tcc aac cga    7174
Tyr His Ser Pro Ser Tyr Val Tyr Gly Leu Phe Glu Arg Ser Asn Arg
        420                 425                 430 cac aaa aga gaa ccg gtg tcg tta acc ctg gcc cta tta ttg ggt gga    7222
His Lys Arg Glu Pro Val Ser Leu Thr Leu Ala Leu Leu Leu Gly Gly
    435                 440                 445 cta acc atg ggg gga att gcc gct gga ata gga aca ggg act act gct    7270
Leu Thr Met Gly Gly Ile Ala Ala Gly Ile Gly Thr Gly Thr Thr Ala
450                 455                 460                 465 cta atg gcc act cag caa ttc cag cag ctc caa gcc gca gta cag gat    7318
Leu Met Ala Thr Gln Gln Phe Gln Gln Leu Gln Ala Ala Val Gln Asp
                470                 475                 480 gat ctc agg gag gtt gaa aaa tca atc tct aac cta gaa aag tct ctc    7366
Asp Leu Arg Glu Val Glu Lys Ser Ile Ser Asn Leu Glu Lys Ser Leu
            485                 490                 495 act tcc ctg tct gaa gtt gtc cta cag aat cga agg ggc cta gac ttg    7414
Thr Ser Leu Ser Glu Val Val Leu Gln Asn Arg Arg Gly Leu Asp Leu
        500                 505                 510 tta ttt cta aaa gaa gga ggg ctg tgt gct gct cta aaa gaa gaa tgt    7462
Leu Phe Leu Lys Glu Gly Gly Leu Cys Ala Ala Leu Lys Glu Glu Cys
    515                 520                 525 tgc ttc tat gcg gac cac aca gga cta gtg aga gac agc atg gcc aaa    7510
Cys Phe Tyr Ala Asp His Thr Gly Leu Val Arg Asp Ser Met Ala Lys
530                 535                 540                 545 ttg aga gag agg ctt aat cag aga cag aaa ctg ttt gag tca act caa    7558
Leu Arg Glu Arg Leu Asn Gln Arg Gln Lys Leu Phe Glu Ser Thr Gln
                550                 555                 560 gga tgg ttt gag gga ctg ttt aac aga tcc cct tgg ttt acc acc ttg    7606
Gly Trp Phe Glu Gly Leu Phe Asn Arg Ser Pro Trp Phe Thr Thr Leu
            565                 570                 575 ata tct acc att atg gga ccc ctc att gta ctc cta atg att ttg ctc    7654
Ile Ser Thr Ile Met Gly Pro Leu Ile Val Leu Leu Met Ile Leu Leu
        580                 585                 590 ttc gga ccc tgc att ctt aat cga tta gtc caa ttt gtt aaa gac agg    7702
Phe Gly Pro Cys Ile Leu Asn Arg Leu Val Gln Phe Val Lys Asp Arg
    595                 600                 605 ata tca gtg gtc cag gct cta gtt ttg act caa caa tat cac cag ctg    7750
Ile Ser Val Val Gln Ala Leu Val Leu Thr Gln Gln Tyr His Gln Leu
610                 615                 620                 625 aag cct ata gag tac gag cca tagataaaat aaaagatttt atttagtctc       7801
Lys Pro Ile Glu Tyr Glu Pro
                630 cagaaaaagg ggggaatgaa agaccccacc tgtaggtttg gcaagctagc ttaagtaacg   7861 ccatttttgca aggcatggaa aaatacataa ctgagaatag agaagttcag atcaaggtca  7921 ggaacagatg gaacagctga atatgggcca aacaggatat ctgtggtaag cagttcctgc   7981 cccggctcag ggccaagaac agatggaaca gctgaatatg gccaaacag gatatctgtg    8041 gtaagcagtt cctgccccgg ctcagggcca agaacagatg gtccccagat gcggtccagc   8101
```

-continued

```
cctcagcagt tctagagaa ccatcagatg tttccagggt gccccaagga cctgaaatga    8161
ccctgtgcct tatttgaact aaccaatcag ttcgcttctc gcttctgttc gcgcgcttct    8221
gctccccgag ctcaataaaa gagcccacaa cccctcactc ggggcgccag tcctccgatt    8281
gactgagtcg cccgggtacc cgtgtatcca ataaaccctc ttgcagttgc a             8332
```

<210> SEQ ID NO 2
<211> LENGTH: 632
<212> TYPE: PRT
<213> ORGANISM: Artificial Sequence

<400> SEQUENCE: 2

```
Ala Ser Pro Gly Ser Ser Pro His Gln Val Tyr Asn Ile Thr Trp Glu
  1               5                  10                  15

Val Thr Asn Gly Asp Arg Glu Thr Val Trp Ala Thr Ser Gly Asn His
                 20                  25                  30

Pro Leu Trp Thr Trp Trp Pro Asp Leu Thr Pro Asp Leu Cys Met Leu
             35                  40                  45

Ala His His Gly Pro Ser Tyr Trp Gly Leu Glu Tyr Gln Ser Pro Phe
         50                  55                  60

Ser Ser Pro Pro Gly Pro Pro Cys Cys Ser Gly Ser Ser Pro Gly
 65                  70                  75                  80

Cys Ser Arg Asp Cys Glu Glu Pro Leu Thr Ser Leu Thr Pro Arg Cys
                 85                  90                  95

Asn Thr Ala Trp Asn Arg Leu Lys Leu Asp Gln Thr Thr His Lys Ser
                100                 105                 110

Asn Glu Gly Phe Tyr Val Cys Pro Gly Pro His Arg Pro Arg Glu Ser
            115                 120                 125

Lys Ser Cys Gly Gly Pro Asp Ser Phe Tyr Cys Ala Tyr Trp Gly Cys
        130                 135                 140

Glu Thr Thr Gly Arg Ala Tyr Trp Lys Pro Ser Ser Ser Trp Asp Phe
145                 150                 155                 160

Ile Thr Val Asn Asn Asn Leu Thr Ser Asp Gln Ala Val Gln Val Cys
                165                 170                 175

Lys Asp Asn Lys Trp Cys Asn Pro Leu Val Ile Arg Phe Thr Asp Ala
            180                 185                 190

Gly Arg Arg Val Thr Ser Trp Thr Thr Gly His Tyr Trp Gly Leu Arg
        195                 200                 205

Leu Tyr Val Ser Gly Gln Asp Pro Gly Leu Thr Phe Gly Ile Arg Leu
    210                 215                 220

Arg Tyr Gln Asn Leu Gly Pro Arg Val Pro Ile Gly Pro Asn Pro Val
225                 230                 235                 240

Leu Ala Asp Gln Gln Pro Leu Ser Lys Pro Lys Pro Val Lys Ser Pro
                245                 250                 255

Ser Val Thr Lys Pro Pro Ser Gly Thr Pro Leu Ser Pro Thr Gln Leu
            260                 265                 270

Pro Pro Ala Gly Thr Glu Asn Arg Leu Leu Asn Leu Val Asp Gly Ala
        275                 280                 285

Tyr Gln Ala Leu Asn Leu Thr Ser Pro Asp Lys Thr Gln Glu Cys Trp
    290                 295                 300

Leu Cys Leu Val Ala Gly Pro Pro Tyr Tyr Glu Gly Val Ala Val Leu
305                 310                 315                 320

Gly Thr Tyr Ser Asn His Thr Ser Ala Pro Ala Asn Cys Ser Val Ala
                325                 330                 335
```

```
Ser Gln His Lys Leu Thr Leu Ser Glu Val Thr Gly Gln Gly Leu Cys
        340             345             350

Ile Gly Ala Val Pro Lys Thr His Gln Ala Leu Cys Asn Thr Thr Gln
        355             360             365

Thr Ser Ser Arg Gly Ser Tyr Tyr Leu Val Ala Pro Thr Gly Thr Met
        370             375             380

Trp Ala Cys Ser Thr Gly Leu Thr Pro Cys Ile Ser Thr Thr Ile Leu
385             390             395             400

Asn Leu Thr Thr Asp Tyr Cys Val Leu Val Glu Leu Trp Pro Arg Val
                405             410             415

Thr Tyr His Ser Pro Ser Tyr Val Tyr Gly Leu Phe Glu Arg Ser Asn
            420             425             430

Arg His Lys Arg Glu Pro Val Ser Leu Thr Leu Ala Leu Leu Leu Gly
        435             440             445

Gly Leu Thr Met Gly Gly Ile Ala Ala Gly Ile Gly Thr Gly Thr Thr
        450             455             460

Ala Leu Met Ala Thr Gln Gln Phe Gln Gln Leu Gln Ala Ala Val Gln
465             470             475             480

Asp Asp Leu Arg Glu Val Glu Lys Ser Ile Ser Asn Leu Glu Lys Ser
                485             490             495

Leu Thr Ser Leu Ser Glu Val Val Leu Gln Asn Arg Arg Gly Leu Asp
            500             505             510

Leu Leu Phe Leu Lys Glu Gly Gly Leu Cys Ala Ala Leu Lys Glu Glu
        515             520             525

Cys Cys Phe Tyr Ala Asp His Thr Gly Leu Val Arg Asp Ser Met Ala
        530             535             540

Lys Leu Arg Glu Arg Leu Asn Gln Arg Gln Lys Leu Phe Glu Ser Thr
545             550             555             560

Gln Gly Trp Phe Glu Gly Leu Phe Asn Arg Ser Pro Trp Phe Thr Thr
                565             570             575

Leu Ile Ser Thr Ile Met Gly Pro Leu Ile Val Leu Leu Met Ile Leu
            580             585             590

Leu Phe Gly Pro Cys Ile Leu Asn Arg Leu Val Gln Phe Val Lys Asp
        595             600             605

Arg Ile Ser Val Val Gln Ala Leu Val Leu Thr Gln Gln Tyr His Gln
    610             615             620

Leu Lys Pro Ile Glu Tyr Glu Pro
625             630

<210> SEQ ID NO 3
<211> LENGTH: 632
<212> TYPE: PRT
<213> ORGANISM: Artificial Sequence
<220> FEATURE:
<223> OTHER INFORMATION: Description of Artificial Sequence:  SEQ ID NO.
      2, envelope protein produced by retroviral vector of seq. id no.1

<400> SEQUENCE: 3

Ala Ser Pro Gly Ser Ser Pro His Gln Val Tyr Asn Ile Thr Trp Glu
  1               5                  10                  15

Val Thr Asn Gly Asp Arg Glu Thr Val Trp Ala Thr Ser Gly Asn His
                 20                  25                  30

Pro Leu Trp Thr Trp Trp Pro Asp Leu Thr Pro Asp Leu Cys Met Leu
            35                  40                  45

Ala His His Gly Pro Ser Tyr Trp Gly Leu Glu Tyr Gln Ser Pro Phe
        50                  55                  60
```

```
Ser Ser Pro Pro Gly Pro Cys Cys Ser Gly Ser Ser Pro Gly
 65                  70                  75                  80

Cys Ser Arg Asp Cys Glu Glu Pro Leu Thr Ser Leu Thr Pro Arg Cys
                 85                  90                  95

Asn Thr Ala Trp Asn Arg Leu Lys Leu Asp Gln Thr Thr His Lys Ser
            100                 105                 110

Asn Glu Gly Phe Tyr Val Cys Pro Gly Pro His Arg Pro Arg Glu Ser
            115                 120                 125

Lys Ser Cys Gly Gly Pro Asp Ser Phe Tyr Cys Ala Tyr Trp Gly Cys
130                 135                 140

Glu Thr Thr Gly Arg Ala Tyr Trp Lys Pro Ser Ser Ser Trp Asp Phe
145                 150                 155                 160

Ile Thr Val Asn Asn Asn Leu Thr Ser Asp Gln Ala Val Gln Val Cys
                165                 170                 175

Lys Asp Asn Lys Trp Cys Asn Pro Leu Val Ile Arg Phe Thr Asp Ala
            180                 185                 190

Gly Arg Arg Val Thr Ser Trp Thr Thr Gly His Tyr Trp Gly Leu Arg
            195                 200                 205

Leu Tyr Val Ser Gly Gln Asp Pro Gly Leu Thr Phe Gly Ile Arg Leu
    210                 215                 220

Arg Tyr Gln Asn Leu Gly Pro Arg Val Pro Ile Gly Pro Asn Pro Val
225                 230                 235                 240

Leu Ala Asp Gln Gln Pro Leu Ser Lys Pro Lys Pro Val Lys Ser Pro
                245                 250                 255

Ser Val Thr Lys Pro Pro Ser Gly Thr Pro Leu Ser Pro Thr Gln Leu
            260                 265                 270

Pro Pro Ala Gly Thr Glu Asn Arg Leu Leu Asn Leu Val Asp Gly Ala
            275                 280                 285

Tyr Gln Ala Leu Asn Leu Thr Ser Pro Asp Lys Thr Gln Glu Cys Trp
    290                 295                 300

Leu Cys Leu Val Ala Gly Pro Pro Tyr Tyr Glu Gly Val Ala Val Leu
305                 310                 315                 320

Gly Thr Tyr Ser Asn His Thr Ser Ala Pro Ala Asn Cys Ser Val Ala
                325                 330                 335

Ser Gln His Lys Leu Thr Leu Ser Glu Val Thr Gly Gln Gly Leu Cys
            340                 345                 350

Ile Gly Ala Val Pro Lys Thr His Gln Ala Leu Cys Asn Thr Thr Gln
            355                 360                 365

Thr Ser Ser Arg Gly Ser Tyr Tyr Leu Val Ala Pro Thr Gly Thr Met
    370                 375                 380

Trp Ala Cys Ser Thr Gly Leu Thr Pro Cys Ile Ser Thr Thr Ile Leu
385                 390                 395                 400

Asn Leu Thr Thr Asp Tyr Cys Val Leu Val Glu Leu Trp Pro Arg Val
                405                 410                 415

Thr Tyr His Ser Pro Ser Tyr Val Tyr Gly Leu Phe Glu Arg Ser Asn
            420                 425                 430

Arg His Lys Arg Glu Pro Val Ser Leu Thr Leu Ala Leu Leu Leu Gly
            435                 440                 445

Gly Leu Thr Met Gly Gly Ile Ala Ala Gly Ile Gly Thr Gly Thr Thr
    450                 455                 460

Ala Leu Met Ala Thr Gln Gln Phe Gln Gln Leu Gln Ala Ala Val Gln
465                 470                 475                 480
```

```
Asp Asp Leu Arg Glu Val Glu Lys Ser Ile Ser Asn Leu Glu Lys Ser
            485                 490                 495
Leu Thr Ser Leu Ser Glu Val Val Leu Gln Asn Arg Arg Gly Leu Asp
        500                 505                 510
Leu Leu Phe Leu Lys Glu Gly Leu Cys Ala Ala Leu Lys Glu Glu
        515                 520                 525
Cys Cys Phe Tyr Ala Asp His Thr Gly Leu Val Arg Asp Ser Met Ala
        530                 535                 540
Lys Leu Arg Glu Arg Leu Asn Gln Arg Gln Lys Leu Phe Glu Ser Thr
545                 550                 555                 560
Gln Gly Trp Phe Glu Gly Leu Phe Asn Arg Ser Pro Trp Phe Thr Thr
                565                 570                 575
Leu Ile Ser Thr Ile Met Gly Pro Leu Ile Val Leu Leu Met Ile Leu
                580                 585                 590
Leu Phe Gly Pro Cys Ile Leu Asn Arg Leu Val Gln Phe Val Lys Asp
            595                 600                 605
Arg Ile Ser Val Val Gln Ala Leu Val Leu Thr Gln Gln Tyr His Gln
        610                 615                 620
Leu Lys Pro Ile Glu Tyr Glu Pro
625                 630

<210> SEQ ID NO 4
<211> LENGTH: 8088
<212> TYPE: DNA
<213> ORGANISM: Artificial Sequence
<220> FEATURE:
<223> OTHER INFORMATION: Description of Artificial Sequence:SEQ. ID NO.
      3, retroviral vector
<220> FEATURE:
<221> NAME/KEY: CDS
<222> LOCATION: (5552)..(7552)

<400> SEQUENCE: 4
gcgccagtcc ttagagagac tgagccgccc gggtacccgt gtgtccaata aaacctcttg     60
ctgattgcat ccggagccgt ggtctcgttg ttccttggga gggtttctcc taactattga    120
ccgcccactt cggggggtctc acatttgggg gctcgtccgg gatcggaaac cccacccagg    180
gaccaccgac ccaccaacgg gaggtaagct ggccagcgac cgttgtgtgt ctcgcttctg    240
tgtctaagtc cgtaattctg actgtccttg tgtgtctcgc ttctgtgtct gagaccgtaa    300
ctctgactgc ccttgtaagt gcgcgcattt ttttggtttc agtctgttcc gggtgaatca    360
ctctgcgagt gacgtgtgag tagcgaacag acgtgttcgg ggctcaccgc ctggtaatcc    420
agggagacgt cccaggatca ggggaggacc agggacgcct ggtggacccc tcggtaacgg    480
gtcgttgtga cccgatttca tcgcccgtct ggtaagacgc gctctgaatc tgattctctc    540
tctcggtcgc ctcgccgccg tctctggttt cttttttgttt cgtttctgga agcctctgt    600
gtcacagtct ttctctccca aatcatcaat atgggacaag ataattctac ccctatctcc    660
ctcactctaa atcactggag agatgtgaga acaagggctc acaatctatc cgtggaaatc    720
aaaaagggaa aatggcagac tttctgttcc tccgagtggc ccacattcgg cgtggggtgg    780
ccaccggagg gaacttttaa tctctctgtc atttttgcag ttaaaaagat tgtcttttcag    840
gagaacgggg gacatccgga ccaagttcca tatatcgtgg tatggcagga cctcgcccag    900
aatcccccac catgggtgcc agcctccgcc aaggtcgctg ttgtctctga tacccgaaga    960
ccagttgcgg ggaggccatc agctcctccc cgacccccca tctacccggc aacagacgac   1020
ttactcctcc tctctgaacc cacgccccg ccctatccgg cggcactgcc accccctctg   1080
```

-continued

```
gccccctcagg cgatcggacc gccgtcaggc cagatgcccg atagtagcga tcctgagggg   1140
ccagccgctg ggaccaggag tcgccgtgcc cgcagtccag cagacaactc gggtcctgac   1200
tccactgtga ttttgcccct ccgagccata ggaccccggg ccgagcccaa tggcctggtc   1260
cctctacaat attggccttt ttcctcagca gatctttata attggaaatc taatcatccc   1320 tcttttctg aaacccagc aggtctcacg gggctccttg agtctcttat gttctcccat    1380
cagcccactt gggacgattg ccaacagctc ctacagattc ttttcaccac tgaggaacgg   1440
gaaagaattc tcctggaggc ccgcaaaaat gtccttgggg acaatggggc cctacacag    1500 ctcgagaacc tcattaatga ggccttcccc ctcaatcgac ctcactggga ttacaacaca   1560
gccgcaggta gggagcgtct tctggtctac cgccggactc tagtggcagg tctcaaaggg   1620
gcagctcggc gtcctaccaa tttggctaag gtaagagagg tcttgcaggg accggcagaa   1680 ccccttcgg ttttcttaga acgcctgatg gaggcctata ggagatacac tccgtttgat   1740
ccctcttctg agggacaaca ggctgcggtc gccatggcct ttatcggaca gtcagcccca   1800
gatatcaaga aaagttaca gaggctagag gggctccagg actattcctt acaagattta    1860 gtaaagagg cagaaaaggt gtaccataag agagagacag aagaagaaag acaagaaaga    1920
gaaaaaaagg aggcagaaga aaggagagg cggcgcgata ggccgaagaa aaaaaacttg    1980
actaaaattc tggccgcagt agtaagtaga aagggtcca caggtaggca gacagggaac    2040
ctgagcaacc aggcaaagaa gacacctagg gatggaagac ctccactaga caagaccag    2100 tgcgcatact gtaaagagaa gggccattgg gcaagagaat gtccccgaaa aaaacacgtc   2160
agagaagcca aggttctagc cctagataac taggggagtc agggttcgga ccccctcccc   2220
gaacctaggg taacactgac tgtggagggg accccccattg agttcctggt cgacaccgga   2280
gctgaacatt cagtattgac ccaacccatg ggaaaagtag ggtccagacg gacggtcgtg    2340
gaaggagcga caggcagcaa ggtctacccc tggaccacaa aaagactttt aaaaattgga   2400
cataaacaag tgacccactc cttcctggtc atacccgagt gccctgctcc tctgttgggc   2460
agggacctcc taaccaaact aaaggcccag atccagtttt ccgctgaggg cccacaggta   2520
acatggggag aacgccctac tatgtgcctg gtcctaaacc tggaagaaga ataccgacta   2580
catgaaaagc cagtaccctc ctctatcgac ccatcctggc tccagctttt ccccactgta   2640
tgggcagaaa gagccggcat gggactagcc aatcaagtcc caccagtggt agtagagcta   2700
agatcaggtg cctcaccagt ggctgttcga caatatccaa tgagcaaaga agctcgggaa   2760
ggtatcagac cccacatcca gaagttccta gacctagggg tcttggtgcc ctgtcggtcg   2820
ccctggaata ccccctctgct acctgtaaaa agccagggga ccaatgacta tcggccagtt   2880
caagacctga gagaaattaa taaagggta caggatattc atcccacagt cccaaaccct   2940
tacaatcttc tgagttccct tccgcctagc tatacttggt actcagtctt agatctcaag   3000
gatgcctttt tctgcctcag gctacatccc aacagccagc cgctgttcgc gttcgagtgg   3060
aaagacccag aaaaggtaa cacaggtcag ctgacctgga cgcggctacc acaagggttc   3120
aagaactctc ccactctctt cgacgaggcc ctccaccgag atttggctcc ctttagggcc   3180
ctcaaccccc agtggtgtt actccaatat gtggacgacc tcttggtggc cgccccaca    3240 tatgaagact gcaaaaaagg aacacagaag ctcttacagg agttaagtaa gttggggtac   3300
cgggtatcgg ctaagaaggc ccagctctgc cagagagaag tcacctatct ggggtaccta   3360
ctcaaggaag gaaaaagatg gctaaccca gcccgaaagg ctactgttat gaaaatccct   3420
```

```
gttcctacga cccccagaca ggtccgtgaa tttctaggca ctgccggatt ctgcaggctc    3480
tggatccctg ggtttgcttc cctggctgca cccttgtacc ccctaacaaa agagagcatc    3540
ccttttattt ggactgagga acatcagcag gcttttgacc ataaaaaaa agccttgctg    3600 tcagcccctg cattggccct cccagacctc accaagccat tcactctata tatagatgag    3660
agagccggcg tggcccgggg agtgctcact cagactttag gaccctggcg gcggccagta    3720
gcatatctat caaaaaaact ggatccggtg gccagcgggt ggccaacctg cctgaaagcg    3780
gttgcagcag tagcactcct tctcaaagac gctgataagt taaccttggg acaaaatgtg    3840
actgtgattg cttcccatag cctcgaaagc atcgtgcggc aaccccccga ccggtggatg    3900
accaatgcca gaatgactca ttaccagagc ctgctgttaa atgaaagggt atcgtttgcg    3960 cccctgctg tcctaaaccc agctacccta cttccagtcg agtcggaagc cacccccagtg    4020 cacaggtgct cagaaatcct cgccgaagaa actggaactc gacgagacct agaagaccaa    4080
ccattgcccg gggtgccaac ctggtataca gacggtagca gtttcatcac ggaaggtaaa    4140
cggagagcag gggcccccgat cgtagatggc aagcggacgg tatgggctag cagcctgcca    4200
gaaggtacgt cagcccagaa ggctgaacta gtagccttga cgcaggcatt acgcctggcc    4260
gaaggaaaaa acatcaacat ctacacggac agcaggtatg cttttgccac tgctcatatt    4320
catggggcaa tatataagca gagggggctg ctcacttctg ctggaaaaga tatcaaaaac    4380
aaagaggaaa ttttggccct gctagaggcc atccatctcc ctaggcgggt cgccattatc    4440
cactgtcctg gccaccagag gggaagtaac cctgtggcca ctgggaaccg gagggccgac    4500
gaggctgcaa agcaagccgc cctgtcgacc agagtgctgg caggaactac aaaacctcaa    4560
gagccaatcg agcccgctca agaaaagacc aggccgaggg agctcacccc tgaccgggga    4620
aaagaattca ttaagcggtt acatcagtta actcacttag gaccagaaaa gcttctccaa    4680
ctagtgaacc gtaccagcct cctcatcccg aacctccaat ctgcagttcg cgaagtcacc    4740
agtcagtgtc aggcttgtgc catgactaat gcggtcacca cctacagaga gaccggaaaa    4800
aggcaacgag gagatcgacc cggcgtgtac tgggaggtag acttcacaga aataaagcct    4860
ggtcggtatg gaaacaagta tctgttagta ttcatagata cttttctccgg atgggtagaa    4920 gcttttccta ccaaaactga aacggcccta atcgtctgta aaaaaatatt agaagaaatt    4980
ctaccccgct tcgggatccc taaggtactc gggtcagaca atggcccggc ctttgttgct    5040
caggtaagtc agggactggc cactcaactg gggataaatt ggaagttaca ttgtgcgtat    5100
agaccccaga gctcaggtca ggtagaaaga atgaacagaa caattaaaga gaccttgacc    5160
aaattagcct tagagaccgg tggaaaagac tgggtgaccc tccttccctt agcgctgctt    5220
agggccagga ataccctgg ccggtttggt ttaactcctt atgaaattct ctatggagga    5280 ccaccccca tacttgagtc tggagaaact ttgggtcccg atgatagatt tctccctgtc    5340
ttatttactc acttaaaggc tttagaaatt gtaaggaccc aaatctggga ccagatcaaa    5400
gaggtgtata gcctggtac cgtaacaatc cctcacccgt tccaggtcgg ggatcaagtg    5460
cttgtcagac gccatcgacc cagcagcctt gagcctcggt ggaaaggccc ataccctggtg   5520
```

| | | |
|---|---|---|
| ttgctgacta ccccgaccgc ggtaaaagtc g atg gta ttg ctg cct ggg tcc | 5572 |
|                                                       Met Val Leu Leu Pro Gly Ser | |
|                                                           1               5 | |

```
atg ctt ctc acc tca aac ctg cac cac ctt cgg cac cag atg agt cct    5620
Met Leu Leu Thr Ser Asn Leu His His Leu Arg His Gln Met Ser Pro
         10                  15                  20 ggg agc tgg aaa aga ctg atc atc ctc tta agc tgc gta ttc ggc ggc    5668
```

```
                                                              -continued

Gly Ser Trp Lys Arg Leu Ile Ile Leu Leu Ser Cys Val Phe Gly Gly
     25                  30                  35 ggc ggg acg agt ctg caa aat aag aac ccc cac cag ccc atg acc ctc    5716
Gly Gly Thr Ser Leu Gln Asn Lys Asn Pro His Gln Pro Met Thr Leu
 40                  45                  50                  55 act tgg cag gta ctg tcc caa act gga gac gtt gtc tgg gat aca aag    5764
Thr Trp Gln Val Leu Ser Gln Thr Gly Asp Val Val Trp Asp Thr Lys
                 60                  65                  70 gca gtc cag ccc cct tgg act tgg tgg ccc aca ctt aaa cct gat gta    5812
Ala Val Gln Pro Pro Trp Thr Trp Trp Pro Thr Leu Lys Pro Asp Val
             75                  80                  85 tgt gcc ttg gcg gct agt ctt gag tcc tgg gat atc ccg gga acc gat    5860
Cys Ala Leu Ala Ala Ser Leu Glu Ser Trp Asp Ile Pro Gly Thr Asp
         90                  95                 100 gtc tcg tcc tct aaa cga gtc aga cct ccg gac tca gac tat act gcc    5908
Val Ser Ser Ser Lys Arg Val Arg Pro Pro Asp Ser Asp Tyr Thr Ala
    105                 110                 115 gct tat aag caa atc acc tgg gga gcc ata ggg tgc agc tac cct cgg    5956
Ala Tyr Lys Gln Ile Thr Trp Gly Ala Ile Gly Cys Ser Tyr Pro Arg
120                 125                 130                 135 gct agg act aga atg gca agc tct acc ttc tac gta tgt ccc cgg gat    6004
Ala Arg Thr Arg Met Ala Ser Ser Thr Phe Tyr Val Cys Pro Arg Asp
                140                 145                 150 ggc cgg acc ctt tca gaa gct aga agg tgc ggg ggg cta gaa tcc cta    6052
Gly Arg Thr Leu Ser Glu Ala Arg Arg Cys Gly Gly Leu Glu Ser Leu
            155                 160                 165 tac tgt aaa gaa tgg gat tgt gag acc acg ggg acc ggt tat tgg cta    6100
Tyr Cys Lys Glu Trp Asp Cys Glu Thr Thr Gly Thr Gly Tyr Trp Leu
        170                 175                 180 tct aaa tcc tca aaa gac ctc ata act gta aaa tgg gac caa aat agc    6148
Ser Lys Ser Ser Lys Asp Leu Ile Thr Val Lys Trp Asp Gln Asn Ser
    185                 190                 195 gaa tgg act caa aaa ttt caa cag tgt cac cag acc ggc tgg tgt aac    6196
Glu Trp Thr Gln Lys Phe Gln Gln Cys His Gln Thr Gly Trp Cys Asn
200                 205                 210                 215 ccc ctt aaa ata gat ttc aca gac aaa gga aaa tta tcc aag gac tgg    6244
Pro Leu Lys Ile Asp Phe Thr Asp Lys Gly Lys Leu Ser Lys Asp Trp
                220                 225                 230 ata acg gga aaa acc tgg gga tta aga ttc tat gtg tct gga cat cca    6292
Ile Thr Gly Lys Thr Trp Gly Leu Arg Phe Tyr Val Ser Gly His Pro
            235                 240                 245 ggc gta cag ttc acc att cgc tta aaa atc acc aac atg cca gct gtg    6340
Gly Val Gln Phe Thr Ile Arg Leu Lys Ile Thr Asn Met Pro Ala Val
        250                 255                 260 gca gta ggt cct gac ctc gtc ctt gtg gaa caa gga cct cct aga acg    6388
Ala Val Gly Pro Asp Leu Val Leu Val Glu Gln Gly Pro Pro Arg Thr
    265                 270                 275 tcc ctc gct ctc cca cct cct ctt ccc cca agg gaa gcg cca ccg cca    6436
Ser Leu Ala Leu Pro Pro Pro Leu Pro Pro Arg Glu Ala Pro Pro Pro
280                 285                 290                 295 tct ctc ccc gac tct aac tcc aca gcc ctg gcg act agt gca caa act    6484
Ser Leu Pro Asp Ser Asn Ser Thr Ala Leu Ala Thr Ser Ala Gln Thr
                300                 305                 310 ccc acg gtg aga aaa aca att gtt acc cta aac act ccg cct ccc acc    6532
Pro Thr Val Arg Lys Thr Ile Val Thr Leu Asn Thr Pro Pro Pro Thr
            315                 320                 325 aca ggc gac aga ctt ttt gat ctt gtg cag ggg gcc ttc cta acc tta    6580
Thr Gly Asp Arg Leu Phe Asp Leu Val Gln Gly Ala Phe Leu Thr Leu
        330                 335                 340
```

```
aat gct acc aac cca ggg gcc act gag tct tgc tgg ctt tgt ttg gcc      6628
Asn Ala Thr Asn Pro Gly Ala Thr Glu Ser Cys Trp Leu Cys Leu Ala
    345                 350                 355 atg ggc ccc cct tat tat gaa gca ata gcc tca tca gga gag gtc gcc      6676
Met Gly Pro Pro Tyr Tyr Glu Ala Ile Ala Ser Ser Gly Glu Val Ala
360                 365                 370                 375 tac tcc acc gac ctt gac cgg tgc cgc tgg ggg acc caa gga aag ctc      6724
Tyr Ser Thr Asp Leu Asp Arg Cys Arg Trp Gly Thr Gln Gly Lys Leu
                380                 385                 390 acc ctc act gag gtc tca gga cac ggg ttg tgc ata gga aag gtg ccc      6772
Thr Leu Thr Glu Val Ser Gly His Gly Leu Cys Ile Gly Lys Val Pro
    395                 400                 405 ttt acc cat cag cat ctc tgc aat cag acc cta tcc atc aat tcc tcc      6820
Phe Thr His Gln His Leu Cys Asn Gln Thr Leu Ser Ile Asn Ser Ser
    410                 415                 420 gga gac cat cag tat ctg ctc ccc tcc aac cat agc tgg tgg gct tgc      6868
Gly Asp His Gln Tyr Leu Leu Pro Ser Asn His Ser Trp Trp Ala Cys
    425                 430                 435 agc act ggc ctc acc cct tgc ctc tcc acc tca gtt ttt aat cag act      6916
Ser Thr Gly Leu Thr Pro Cys Leu Ser Thr Ser Val Phe Asn Gln Thr
440                 445                 450                 455 aga gat ttc tgt atc cag gtc cag ctg att cct cgc atc tat tac tat      6964
Arg Asp Phe Cys Ile Gln Val Gln Leu Ile Pro Arg Ile Tyr Tyr Tyr
                460                 465                 470 cct gaa gaa gtt ttg tta cag gcc tat gac aat tct cac ccc agg act      7012
Pro Glu Glu Val Leu Leu Gln Ala Tyr Asp Asn Ser His Pro Arg Thr
    475                 480                 485 aaa aga gag gct gtc tca ctt acc cta gct gtt tta ctg ggg ttg gga      7060
Lys Arg Glu Ala Val Ser Leu Thr Leu Ala Val Leu Leu Gly Leu Gly
    490                 495                 500 atc acg gcg gga ata ggt act ggt tca act gcc tta att aaa gga cct      7108
Ile Thr Ala Gly Ile Gly Thr Gly Ser Thr Ala Leu Ile Lys Gly Pro
505                 510                 515 ata gac ctc cag caa ggc ctg aca agc ctc cag atc gcc ata gat gct      7156
Ile Asp Leu Gln Gln Gly Leu Thr Ser Leu Gln Ile Ala Ile Asp Ala
520                 525                 530                 535 gac ctc cgg gcc ctc caa gac tca gtc agc aag tta gag gac tca ctg      7204
Asp Leu Arg Ala Leu Gln Asp Ser Val Ser Lys Leu Glu Asp Ser Leu
                540                 545                 550 act tcc ctg tcc gag gta gtg ctc caa aat agg aga ggc ctt gac ttg      7252
Thr Ser Leu Ser Glu Val Val Leu Gln Asn Arg Arg Gly Leu Asp Leu
    555                 560                 565 ctg ttt cta aaa gaa ggt ggc ctc tgt gcg gcc cta aag gaa gag tgc      7300
Leu Phe Leu Lys Glu Gly Gly Leu Cys Ala Ala Leu Lys Glu Glu Cys
    570                 575                 580 tgt ttt tac ata gac cac tca ggt gca gta cgg gac tcc atg aaa aaa      7348
Cys Phe Tyr Ile Asp His Ser Gly Ala Val Arg Asp Ser Met Lys Lys
    585                 590                 595 ctc aaa gaa aaa ctg gat aaa aga cag tta gag cgc cag aaa agc caa      7396
Leu Lys Glu Lys Leu Asp Lys Arg Gln Leu Glu Arg Gln Lys Ser Gln
600                 605                 610                 615 aac tgg tat gaa gga tgg ttc aat aac tcc cct tgg ttc act acc ctg      7444
Asn Trp Tyr Glu Gly Trp Phe Asn Asn Ser Pro Trp Phe Thr Thr Leu
                620                 625                 630 cta tca acc atc gct ggg ccc cta tta ctc ctc ctt ctg ttg ctc atc      7492
Leu Ser Thr Ile Ala Gly Pro Leu Leu Leu Leu Leu Leu Leu Leu Ile
    635                 640                 645 ctc ggg cca tgc atc atc aat aag tta gtt caa ttc atc aat gat agg      7540
Leu Gly Pro Cys Ile Ile Asn Lys Leu Val Gln Phe Ile Asn Asp Arg
    650                 655                 660
```

-continued

```
ata agt gca tgt taaaattctg gtccttagac aaaatatcag gccctagaga        7592
Ile Ser Ala Cys
        665 acgaaggtaa cctttaattt tgctctaaga ttagagctat tcacaagaga aatgggggaa   7652 tgaaagaagt gtttttttt agccaactgc agtaacgcca ttttgctagg cacacctaaa   7712 ggataggaaa aatacagcta agaacagggc caaacaggat atctgtggtc atgcacctgg   7772 gccccggccc aggccaagga cagagggttc ccagaaatag atgagtcaac agcagtttcc   7832 agcaaggaca gagggttccc agaaatagat gagtcaacag cagtttccag ggtgcccctc   7892 aaccgtttca aggactccca tgaccgggaa ttcacccctg gccttatttg aactaaccaa   7952 ttaccttgcc tctcgcttct gtacccgcgc ttttgctat aaaataagct cagaaactcc   8012 acccggagcg ccagtcctta gagagactga gccgcccggg tacccgtgtg tccaataaaa   8072 cctcttgctg attgca                                                   8088
```

<210> SEQ ID NO 5
<211> LENGTH: 667
<212> TYPE: PRT
<213> ORGANISM: Artificial Sequence

<400> SEQUENCE: 5

```
Met Val Leu Leu Pro Gly Ser Met Leu Leu Thr Ser Asn Leu His His
  1               5                  10                  15

Leu Arg His Gln Met Ser Pro Gly Ser Trp Lys Arg Leu Ile Ile Leu
             20                  25                  30

Leu Ser Cys Val Phe Gly Gly Gly Thr Ser Leu Gln Asn Lys Asn
         35                  40                  45

Pro His Gln Pro Met Thr Leu Thr Trp Gln Val Leu Ser Gln Thr Gly
     50                  55                  60

Asp Val Val Trp Asp Thr Lys Ala Val Gln Pro Pro Trp Thr Trp Trp
 65                  70                  75                  80

Pro Thr Leu Lys Pro Asp Val Cys Ala Leu Ala Ala Ser Leu Glu Ser
                 85                  90                  95

Trp Asp Ile Pro Gly Thr Asp Val Ser Ser Lys Arg Val Arg Pro
            100                 105                 110

Pro Asp Ser Asp Tyr Thr Ala Ala Tyr Lys Gln Ile Thr Trp Gly Ala
        115                 120                 125

Ile Gly Cys Ser Tyr Pro Arg Ala Arg Thr Arg Met Ala Ser Ser Thr
    130                 135                 140

Phe Tyr Val Cys Pro Arg Asp Gly Arg Thr Leu Ser Glu Ala Arg Arg
145                 150                 155                 160

Cys Gly Gly Leu Glu Ser Leu Tyr Cys Lys Glu Trp Asp Cys Glu Thr
                165                 170                 175

Thr Gly Thr Gly Tyr Trp Leu Ser Lys Ser Ser Lys Asp Leu Ile Thr
            180                 185                 190

Val Lys Trp Asp Gln Asn Ser Glu Trp Thr Gln Lys Phe Gln Gln Cys
        195                 200                 205

His Gln Thr Gly Trp Cys Asn Pro Leu Lys Ile Asp Phe Thr Asp Lys
    210                 215                 220

Gly Lys Leu Ser Lys Asp Trp Ile Thr Gly Lys Thr Trp Gly Leu Arg
225                 230                 235                 240

Phe Tyr Val Ser Gly His Pro Gly Val Gln Phe Thr Ile Arg Leu Lys
                245                 250                 255
```

-continued

```
Ile Thr Asn Met Pro Ala Val Ala Val Gly Pro Asp Leu Val Leu Val
            260                 265                 270
Glu Gln Gly Pro Pro Arg Thr Ser Leu Ala Leu Pro Pro Pro Leu Pro
            275                 280                 285
Pro Arg Glu Ala Pro Pro Ser Leu Pro Asp Ser Asn Ser Thr Ala
            290                 295                 300
Leu Ala Thr Ser Ala Gln Thr Pro Thr Val Arg Lys Thr Ile Val Thr
305                 310                 315                 320
Leu Asn Thr Pro Pro Thr Thr Gly Asp Arg Leu Phe Asp Leu Val
                325                 330                 335
Gln Gly Ala Phe Leu Thr Leu Asn Ala Thr Asn Pro Gly Ala Thr Glu
            340                 345                 350
Ser Cys Trp Leu Cys Leu Ala Met Gly Pro Pro Tyr Tyr Glu Ala Ile
            355                 360                 365
Ala Ser Ser Gly Glu Val Ala Tyr Ser Thr Asp Leu Asp Arg Cys Arg
            370                 375                 380
Trp Gly Thr Gln Gly Lys Leu Thr Leu Thr Glu Val Ser Gly His Gly
385                 390                 395                 400
Leu Cys Ile Gly Lys Val Pro Phe Thr His Gln His Leu Cys Asn Gln
                405                 410                 415
Thr Leu Ser Ile Asn Ser Ser Gly Asp His Gln Tyr Leu Leu Pro Ser
            420                 425                 430
Asn His Ser Trp Trp Ala Cys Ser Thr Gly Leu Thr Pro Cys Leu Ser
            435                 440                 445
Thr Ser Val Phe Asn Gln Thr Arg Asp Phe Cys Ile Gln Val Gln Leu
            450                 455                 460
Ile Pro Arg Ile Tyr Tyr Tyr Pro Glu Glu Val Leu Leu Gln Ala Tyr
465                 470                 475                 480
Asp Asn Ser His Pro Arg Thr Lys Arg Glu Ala Val Ser Leu Thr Leu
                485                 490                 495
Ala Val Leu Leu Gly Leu Gly Ile Thr Ala Gly Ile Gly Thr Gly Ser
            500                 505                 510
Thr Ala Leu Ile Lys Gly Pro Ile Asp Leu Gln Gln Gly Leu Thr Ser
            515                 520                 525
Leu Gln Ile Ala Ile Asp Ala Asp Leu Arg Ala Leu Gln Asp Ser Val
            530                 535                 540
Ser Lys Leu Glu Asp Ser Leu Thr Ser Leu Ser Glu Val Val Leu Gln
545                 550                 555                 560
Asn Arg Arg Gly Leu Asp Leu Leu Phe Leu Lys Glu Gly Gly Leu Cys
                565                 570                 575
Ala Ala Leu Lys Glu Glu Cys Cys Phe Tyr Ile Asp His Ser Gly Ala
            580                 585                 590
Val Arg Asp Ser Met Lys Lys Leu Lys Glu Lys Leu Asp Lys Arg Gln
            595                 600                 605
Leu Glu Arg Gln Lys Ser Gln Asn Trp Tyr Glu Gly Trp Phe Asn Asn
            610                 615                 620
Ser Pro Trp Phe Thr Thr Leu Leu Ser Thr Ile Ala Gly Pro Leu Leu
625                 630                 635                 640
Leu Leu Leu Leu Leu Ile Leu Gly Pro Cys Ile Ile Asn Lys Leu
                645                 650                 655
Val Gln Phe Ile Asn Asp Arg Ile Ser Ala Cys
            660                 665
```

-continued

```
<210> SEQ ID NO 6
<211> LENGTH: 667
<212> TYPE: PRT
<213> ORGANISM: Artificial Sequence
<220> FEATURE:
<223> OTHER INFORMATION: Description of Artificial Sequence:  SEQ ID NO.
      4, envelope protein produced by retroviral vector of seq. id no. 3

<400> SEQUENCE: 6

Met Val Leu Leu Pro Gly Ser Met Leu Leu Thr Ser Asn Leu His His
 1               5                  10                  15

Leu Arg His Gln Met Ser Pro Gly Ser Trp Lys Arg Leu Ile Ile Leu
                20                  25                  30

Leu Ser Cys Val Phe Gly Gly Gly Thr Ser Leu Gln Asn Lys Asn
             35                 40                  45

Pro His Gln Pro Met Thr Leu Thr Trp Gln Val Leu Ser Gln Thr Gly
         50                  55                  60

Asp Val Val Trp Asp Thr Lys Ala Val Gln Pro Pro Trp Thr Trp Trp
 65                  70                  75                  80

Pro Thr Leu Lys Pro Asp Val Cys Ala Leu Ala Ala Ser Leu Glu Ser
                 85                  90                  95

Trp Asp Ile Pro Gly Thr Asp Val Ser Ser Lys Arg Val Arg Pro
                100                 105                 110

Pro Asp Ser Asp Tyr Thr Ala Ala Tyr Lys Gln Ile Thr Trp Gly Ala
            115                 120                 125

Ile Gly Cys Ser Tyr Pro Arg Ala Arg Thr Arg Met Ala Ser Ser Thr
        130                 135                 140

Phe Tyr Val Cys Pro Arg Asp Gly Arg Thr Leu Ser Glu Ala Arg Arg
145                 150                 155                 160

Cys Gly Gly Leu Glu Ser Leu Tyr Cys Lys Glu Trp Asp Cys Glu Thr
                165                 170                 175

Thr Gly Thr Gly Tyr Trp Leu Ser Lys Ser Ser Lys Asp Leu Ile Thr
            180                 185                 190

Val Lys Trp Asp Gln Asn Ser Glu Trp Thr Gln Lys Phe Gln Gln Cys
        195                 200                 205

His Gln Thr Gly Trp Cys Asn Pro Leu Lys Ile Asp Phe Thr Asp Lys
    210                 215                 220

Gly Lys Leu Ser Lys Asp Trp Ile Thr Gly Lys Thr Trp Gly Leu Arg
225                 230                 235                 240

Phe Tyr Val Ser Gly His Pro Gly Val Gln Phe Thr Ile Arg Leu Lys
                245                 250                 255

Ile Thr Asn Met Pro Ala Val Ala Val Gly Pro Asp Leu Val Leu Val
            260                 265                 270

Glu Gln Gly Pro Pro Arg Thr Ser Leu Ala Leu Pro Pro Pro Leu Pro
        275                 280                 285

Pro Arg Glu Ala Pro Pro Ser Leu Pro Asp Ser Asn Ser Thr Ala
    290                 295                 300

Leu Ala Thr Ser Ala Gln Thr Pro Thr Val Arg Lys Thr Ile Val Thr
305                 310                 315                 320

Leu Asn Thr Pro Pro Thr Thr Gly Asp Arg Leu Phe Asp Leu Val
                325                 330                 335

Gln Gly Ala Phe Leu Thr Leu Asn Ala Thr Asn Pro Gly Ala Thr Glu
            340                 345                 350

Ser Cys Trp Leu Cys Leu Ala Met Gly Pro Pro Tyr Tyr Glu Ala Ile
        355                 360                 365
```

```
Ala Ser Ser Gly Glu Val Ala Tyr Ser Thr Asp Leu Asp Arg Cys Arg
    370                 375                 380

Trp Gly Thr Gln Gly Lys Leu Thr Leu Thr Glu Val Ser Gly His Gly
385                 390                 395                 400

Leu Cys Ile Gly Lys Val Pro Phe Thr His Gln His Leu Cys Asn Gln
                405                 410                 415

Thr Leu Ser Ile Asn Ser Ser Gly Asp His Gln Tyr Leu Leu Pro Ser
            420                 425                 430

Asn His Ser Trp Trp Ala Cys Ser Thr Gly Leu Thr Pro Cys Leu Ser
        435                 440                 445

Thr Ser Val Phe Asn Gln Thr Arg Asp Phe Cys Ile Gln Val Gln Leu
    450                 455                 460

Ile Pro Arg Ile Tyr Tyr Pro Glu Glu Val Leu Leu Gln Ala Tyr
465                 470                 475                 480

Asp Asn Ser His Pro Arg Thr Lys Arg Glu Ala Val Ser Leu Thr Leu
                485                 490                 495

Ala Val Leu Leu Gly Leu Gly Ile Thr Ala Gly Ile Gly Thr Gly Ser
            500                 505                 510

Thr Ala Leu Ile Lys Gly Pro Ile Asp Leu Gln Gln Gly Leu Thr Ser
        515                 520                 525

Leu Gln Ile Ala Ile Asp Ala Asp Leu Arg Ala Leu Gln Asp Ser Val
    530                 535                 540

Ser Lys Leu Glu Asp Ser Leu Thr Ser Leu Ser Glu Val Val Leu Gln
545                 550                 555                 560

Asn Arg Arg Gly Leu Asp Leu Leu Phe Leu Lys Glu Gly Gly Leu Cys
                565                 570                 575

Ala Ala Leu Lys Glu Glu Cys Cys Phe Tyr Ile Asp His Ser Gly Ala
            580                 585                 590

Val Arg Asp Ser Met Lys Lys Leu Lys Glu Lys Leu Asp Lys Arg Gln
        595                 600                 605

Leu Glu Arg Gln Lys Ser Gln Asn Trp Tyr Glu Gly Trp Phe Asn Asn
    610                 615                 620

Ser Pro Trp Phe Thr Thr Leu Leu Ser Thr Ile Ala Gly Pro Leu Leu
625                 630                 635                 640

Leu Leu Leu Leu Leu Leu Ile Leu Gly Pro Cys Ile Ile Asn Lys Leu
                645                 650                 655

Val Gln Phe Ile Asn Asp Arg Ile Ser Ala Cys
            660                 665

<210> SEQ ID NO 7
<211> LENGTH: 2002
<212> TYPE: DNA
<213> ORGANISM: Artificial Sequence
<220> FEATURE:
<223> OTHER INFORMATION: Description of Artificial Sequence: SEQ. ID
      NO. 5, retroviral vector
<220> FEATURE:
<221> NAME/KEY: CDS
<222> LOCATION: (65)..(1999)

<400> SEQUENCE: 7
ggatccacgc cgctcacgta aaggcggcga caaccccctcc ggccggaaca gcatcaggac    60 cgac atg gaa ggt cca gcg ttc tca aaa ccc ctt aaa gat aag att aac    109
     Met Glu Gly Pro Ala Phe Ser Lys Pro Leu Lys Asp Lys Ile Asn
      1               5                  10                  15 ccg tgg aag tcc tta atg gtc atg ggg gtc tat tta aga gta ggg atg    157
Pro Trp Lys Ser Leu Met Val Met Gly Val Tyr Leu Arg Val Gly Met
```

-continued

```
                    20                  25                  30
gca gag agc ccc cat cag gtc ttt aat gta acc tgg aga gtc acc aac    205
Ala Glu Ser Pro His Gln Val Phe Asn Val Thr Trp Arg Val Thr Asn
             35                  40                  45 ctg atg act ggg cgt acc gcc aat gcc acc tcc ctt tta gga act gta    253
Leu Met Thr Gly Arg Thr Ala Asn Ala Thr Ser Leu Leu Gly Thr Val
         50                  55                  60 caa gat gcc ttc cca aga tta tat ttt gat cta tgt gat ctg gtc gga    301
Gln Asp Ala Phe Pro Arg Leu Tyr Phe Asp Leu Cys Asp Leu Val Gly
 65                  70                  75 gaa gag tgg gac cct tca gac cag gaa cca tat gtc ggg tat ggc tgc    349
Glu Glu Trp Asp Pro Ser Asp Gln Glu Pro Tyr Val Gly Tyr Gly Cys
 80                  85                  90                  95 aaa tac ccc gga ggg aga aag cgg acc cgg act ttt gac ttt tac gtg    397
Lys Tyr Pro Gly Gly Arg Lys Arg Thr Arg Thr Phe Asp Phe Tyr Val
                100                 105                 110 tgc cct ggg cat acc gta aaa tcg ggg tgt ggg ggg cca aga gag ggc    445
Cys Pro Gly His Thr Val Lys Ser Gly Cys Gly Gly Pro Arg Glu Gly
            115                 120                 125 tac tgt ggt gaa tgg ggt tgt gaa acc acc gga cag gct tac tgg aag    493
Tyr Cys Gly Glu Trp Gly Cys Glu Thr Thr Gly Gln Ala Tyr Trp Lys
        130                 135                 140 ccc aca tca tca tgg gac cta atc tcc ctt aag cgc ggt aac acc ccc    541
Pro Thr Ser Ser Trp Asp Leu Ile Ser Leu Lys Arg Gly Asn Thr Pro
    145                 150                 155 tgg gac acg gga tgc tcc aaa atg gct tgt ggc ccc tgc tac gac ctc    589
Trp Asp Thr Gly Cys Ser Lys Met Ala Cys Gly Pro Cys Tyr Asp Leu
160                 165                 170                 175 tcc aaa gta tcc aat tcc ttc caa ggg gct act cga ggg ggc aga tgc    637
Ser Lys Val Ser Asn Ser Phe Gln Gly Ala Thr Arg Gly Gly Arg Cys
                180                 185                 190 aac cct cta gtc cta gaa ttc act gat gca gga aaa aag gct aat tgg    685
Asn Pro Leu Val Leu Glu Phe Thr Asp Ala Gly Lys Lys Ala Asn Trp
            195                 200                 205 gac ggg ccc aaa tcg tgg gga ctg aga ctg tac cgg aca gga aca gat    733
Asp Gly Pro Lys Ser Trp Gly Leu Arg Leu Tyr Arg Thr Gly Thr Asp
        210                 215                 220 cct att acc atg ttc tcc ctg acc cgc cag gtc ctc aat ata ggg ccc    781
Pro Ile Thr Met Phe Ser Leu Thr Arg Gln Val Leu Asn Ile Gly Pro
    225                 230                 235 cgc atc ccc att ggg cct aat ccc gtg atc act ggt caa cta ccc ccc    829
Arg Ile Pro Ile Gly Pro Asn Pro Val Ile Thr Gly Gln Leu Pro Pro
240                 245                 250                 255 tcc cga ccc gtg cag atc agg ctc ccc agg cct cct cag cct cct cct    877
Ser Arg Pro Val Gln Ile Arg Leu Pro Arg Pro Pro Gln Pro Pro Pro
                260                 265                 270 aca ggc gca gcc tct ata gtc cct gag act gcc cca cct tct caa caa    925
Thr Gly Ala Ala Ser Ile Val Pro Glu Thr Ala Pro Pro Ser Gln Gln
            275                 280                 285 cct ggg acg gga gac agg ctg cta aac ctg gta gaa gga gcc tat cag    973
Pro Gly Thr Gly Asp Arg Leu Leu Asn Leu Val Glu Gly Ala Tyr Gln
        290                 295                 300 gcg ctt aac ctc acc aat ccc gac aag acc caa gaa tgt tgg ctg tgc   1021
Ala Leu Asn Leu Thr Asn Pro Asp Lys Thr Gln Glu Cys Trp Leu Cys
    305                 310                 315 tta gtg tcg gga cct cct tat tac gaa gga gta gcg gtc gtg ggc act   1069
Leu Val Ser Gly Pro Pro Tyr Tyr Glu Gly Val Ala Val Val Gly Thr
320                 325                 330                 335 tat acc aat cat tct acc gcc ccg gcc agc tgt acg gcc act tcc caa   1117
```

```
                Tyr Thr Asn His Ser Thr Ala Pro Ala Ser Cys Thr Ala Thr Ser Gln
                                340                 345                 350 cat aag ctt acc cta tct gaa gtg aca gga cag ggc cta tgc atg gga            1165
His Lys Leu Thr Leu Ser Glu Val Thr Gly Gln Gly Leu Cys Met Gly
            355                 360                 365 gca cta cct aaa act cac cag gcc tta tgt aac acc acc caa agt gcc            1213
Ala Leu Pro Lys Thr His Gln Ala Leu Cys Asn Thr Thr Gln Ser Ala
370                 375                 380 ggc tca gga tcc tac tac ctt gca gca ccc gct gga aca atg tgg gct            1261
Gly Ser Gly Ser Tyr Tyr Leu Ala Ala Pro Ala Gly Thr Met Trp Ala
        385                 390                 395 tgt agc act gga ttg act ccc tgc ttg tcc acc acg atg ctc aat cta            1309
Cys Ser Thr Gly Leu Thr Pro Cys Leu Ser Thr Thr Met Leu Asn Leu
400                 405                 410                 415 acc aca gac tat tgt gta tta gtt gag ctc tgg ccc aga ata att tac            1357
Thr Thr Asp Tyr Cys Val Leu Val Glu Leu Trp Pro Arg Ile Ile Tyr
                420                 425                 430 cac tcc ccc gat tat atg tat ggt cag ctt gaa cag cgt acc aaa tat            1405
His Ser Pro Asp Tyr Met Tyr Gly Gln Leu Glu Gln Arg Thr Lys Tyr
            435                 440                 445 aag agg gag cca gta tcg ttg acc ctg gcc ctt ctg cta gga gga tta            1453
Lys Arg Glu Pro Val Ser Leu Thr Leu Ala Leu Leu Leu Gly Gly Leu
        450                 455                 460 acc atg gga ggg att gca gct gga ata ggg acg ggg acc act gcc cta            1501
Thr Met Gly Gly Ile Ala Ala Gly Ile Gly Thr Gly Thr Thr Ala Leu
    465                 470                 475 atc aaa acc cag cag ttt gag cag ctt cac gcc gct atc cag aca gac            1549
Ile Lys Thr Gln Gln Phe Glu Gln Leu His Ala Ala Ile Gln Thr Asp
480                 485                 490                 495 ctc aac gaa gtc gaa aaa tca att acc aac cta gaa aag tca ctg acc            1597
Leu Asn Glu Val Glu Lys Ser Ile Thr Asn Leu Glu Lys Ser Leu Thr
                500                 505                 510 tcg ttg tct gaa gta gtc cta cag aac cga aga ggc cta gat ttg ctc            1645
Ser Leu Ser Glu Val Val Leu Gln Asn Arg Arg Gly Leu Asp Leu Leu
            515                 520                 525 ttc cta aaa gag gga ggt ctc tgc gca gcc cta aaa gaa gaa tgt tgt            1693
Phe Leu Lys Glu Gly Gly Leu Cys Ala Ala Leu Lys Glu Glu Cys Cys
        530                 535                 540 ttt tat gca gac cac acg gga cta gtg aga gac agc atg gcc aaa cta            1741
Phe Tyr Ala Asp His Thr Gly Leu Val Arg Asp Ser Met Ala Lys Leu
545                 550                 555 agg gaa agg ctt aat cag aga caa aaa cta ttt gag tca ggc caa ggt            1789
Arg Glu Arg Leu Asn Gln Arg Gln Lys Leu Phe Glu Ser Gly Gln Gly
560                 565                 570                 575 tgg ttc gaa ggg cag ttt aat aga tcc ccc tgg ttt acc acc tta atc            1837
Trp Phe Glu Gly Gln Phe Asn Arg Ser Pro Trp Phe Thr Thr Leu Ile
                580                 585                 590 tcc acc atc atg gga cct cta ata gta ctc tta ctg atc tta ctc ttt            1885
Ser Thr Ile Met Gly Pro Leu Ile Val Leu Leu Leu Ile Leu Leu Phe
            595                 600                 605 gga ccc tgc att ctc aat cga ttg gtc caa ttt gtt aaa gac agg atc            1933
Gly Pro Cys Ile Leu Asn Arg Leu Val Gln Phe Val Lys Asp Arg Ile
        610                 615                 620 tca gtg gtc cag gct ctg gtt ttg act caa caa tat cac cag cta aaa            1981
Ser Val Val Gln Ala Leu Val Leu Thr Gln Gln Tyr His Gln Leu Lys
625                 630                 635 cct ata gag tac gag cca tga                                                2002
Pro Ile Glu Tyr Glu Pro
640                 645
```

```
<210> SEQ ID NO 8
<211> LENGTH: 645
<212> TYPE: PRT
<213> ORGANISM: Artificial Sequence

<400> SEQUENCE: 8
```

| | | | | | | | | | | | | | | |
|---|---|---|---|---|---|---|---|---|---|---|---|---|---|---|
| Met | Glu | Gly | Pro | Ala | Phe | Ser | Lys | Pro | Leu | Lys | Asp | Lys | Ile | Asn | Pro |
| 1 | | | | 5 | | | | | 10 | | | | | 15 | |
| Trp | Lys | Ser | Leu | Met | Val | Met | Gly | Val | Tyr | Leu | Arg | Val | Gly | Met | Ala |
| | | | 20 | | | | | 25 | | | | | 30 | | |
| Glu | Ser | Pro | His | Gln | Val | Phe | Asn | Val | Thr | Trp | Arg | Val | Thr | Asn | Leu |
| | | 35 | | | | | 40 | | | | | 45 | | | |
| Met | Thr | Gly | Arg | Thr | Ala | Asn | Ala | Thr | Ser | Leu | Leu | Gly | Thr | Val | Gln |
| | 50 | | | | | 55 | | | | | 60 | | | | |
| Asp | Ala | Phe | Pro | Arg | Leu | Tyr | Phe | Asp | Leu | Cys | Asp | Leu | Val | Gly | Glu |
| 65 | | | | | 70 | | | | | 75 | | | | | 80 |
| Glu | Trp | Asp | Pro | Ser | Asp | Gln | Glu | Pro | Tyr | Val | Gly | Tyr | Gly | Cys | Lys |
| | | | | 85 | | | | | 90 | | | | | 95 | |
| Tyr | Pro | Gly | Gly | Arg | Lys | Arg | Thr | Arg | Thr | Phe | Asp | Phe | Tyr | Val | Cys |
| | | | 100 | | | | | 105 | | | | | 110 | | |
| Pro | Gly | His | Thr | Val | Lys | Ser | Gly | Cys | Gly | Gly | Pro | Arg | Glu | Gly | Tyr |
| | | 115 | | | | | 120 | | | | | 125 | | | |
| Cys | Gly | Glu | Trp | Gly | Cys | Glu | Thr | Thr | Gly | Gln | Ala | Tyr | Trp | Lys | Pro |
| | 130 | | | | | 135 | | | | | 140 | | | | |
| Thr | Ser | Ser | Trp | Asp | Leu | Ile | Ser | Leu | Lys | Arg | Gly | Asn | Thr | Pro | Trp |
| 145 | | | | | 150 | | | | | 155 | | | | | 160 |
| Asp | Thr | Gly | Cys | Ser | Lys | Met | Ala | Cys | Gly | Pro | Cys | Tyr | Asp | Leu | Ser |
| | | | | 165 | | | | | 170 | | | | | 175 | |
| Lys | Val | Ser | Asn | Ser | Phe | Gln | Gly | Ala | Thr | Arg | Gly | Gly | Arg | Cys | Asn |
| | | | 180 | | | | | 185 | | | | | 190 | | |
| Pro | Leu | Val | Leu | Glu | Phe | Thr | Asp | Ala | Gly | Lys | Lys | Ala | Asn | Trp | Asp |
| | | 195 | | | | | 200 | | | | | 205 | | | |
| Gly | Pro | Lys | Ser | Trp | Gly | Leu | Arg | Leu | Tyr | Arg | Thr | Gly | Thr | Asp | Pro |
| | 210 | | | | | 215 | | | | | 220 | | | | |
| Ile | Thr | Met | Phe | Ser | Leu | Thr | Arg | Gln | Val | Leu | Asn | Ile | Gly | Pro | Arg |
| 225 | | | | | 230 | | | | | 235 | | | | | 240 |
| Ile | Pro | Ile | Gly | Pro | Asn | Pro | Val | Ile | Thr | Gly | Gln | Leu | Pro | Pro | Ser |
| | | | | 245 | | | | | 250 | | | | | 255 | |
| Arg | Pro | Val | Gln | Ile | Arg | Leu | Pro | Arg | Pro | Gln | Pro | Pro | Pro | Pro | Thr |
| | | | 260 | | | | | 265 | | | | | 270 | | |
| Gly | Ala | Ala | Ser | Ile | Val | Pro | Glu | Thr | Ala | Pro | Pro | Ser | Gln | Gln | Pro |
| | | 275 | | | | | 280 | | | | | 285 | | | |
| Gly | Thr | Gly | Asp | Arg | Leu | Leu | Asn | Leu | Val | Glu | Gly | Ala | Tyr | Gln | Ala |
| | 290 | | | | | 295 | | | | | 300 | | | | |
| Leu | Asn | Leu | Thr | Asn | Pro | Asp | Lys | Thr | Gln | Glu | Cys | Trp | Leu | Cys | Leu |
| 305 | | | | | 310 | | | | | 315 | | | | | 320 |
| Val | Ser | Gly | Pro | Pro | Tyr | Tyr | Glu | Gly | Val | Ala | Val | Gly | Thr | Tyr |
| | | | | 325 | | | | | 330 | | | | | 335 | |
| Thr | Asn | His | Ser | Thr | Ala | Pro | Ala | Ser | Cys | Thr | Ala | Thr | Ser | Gln | His |
| | | | 340 | | | | | 345 | | | | | 350 | | |
| Lys | Leu | Thr | Leu | Ser | Glu | Val | Thr | Gly | Gln | Gly | Leu | Cys | Met | Gly | Ala |
| | | 355 | | | | | 360 | | | | | 365 | | | |
| Leu | Pro | Lys | Thr | His | Gln | Ala | Leu | Cys | Asn | Thr | Thr | Gln | Ser | Ala | Gly |
| | 370 | | | | | 375 | | | | | 380 | | | | |

-continued

```
Ser Gly Ser Tyr Tyr Leu Ala Ala Pro Ala Gly Thr Met Trp Ala Cys
385                 390                 395                 400

Ser Thr Gly Leu Thr Pro Cys Leu Ser Thr Thr Met Leu Asn Leu Thr
            405                 410                 415

Thr Asp Tyr Cys Val Leu Val Glu Leu Trp Pro Arg Ile Ile Tyr His
        420                 425                 430

Ser Pro Asp Tyr Met Tyr Gly Gln Leu Glu Gln Arg Thr Lys Tyr Lys
            435                 440                 445

Arg Glu Pro Val Ser Leu Thr Leu Ala Leu Leu Gly Gly Leu Thr
    450                 455                 460

Met Gly Gly Ile Ala Ala Gly Ile Gly Thr Gly Thr Thr Ala Leu Ile
465                 470                 475                 480

Lys Thr Gln Gln Phe Glu Gln Leu His Ala Ala Ile Gln Thr Asp Leu
                485                 490                 495

Asn Glu Val Glu Lys Ser Ile Thr Asn Leu Glu Lys Ser Leu Thr Ser
                500                 505                 510

Leu Ser Glu Val Val Leu Gln Asn Arg Arg Gly Leu Asp Leu Leu Phe
            515                 520                 525

Leu Lys Glu Gly Gly Leu Cys Ala Ala Leu Lys Glu Glu Cys Cys Phe
    530                 535                 540

Tyr Ala Asp His Thr Gly Leu Val Arg Asp Ser Met Ala Lys Leu Arg
545                 550                 555                 560

Glu Arg Leu Asn Gln Arg Gln Lys Leu Phe Glu Ser Gly Gln Gly Trp
                565                 570                 575

Phe Glu Gly Gln Phe Asn Arg Ser Pro Trp Phe Thr Thr Leu Ile Ser
            580                 585                 590

Thr Ile Met Gly Pro Leu Ile Val Leu Leu Leu Ile Leu Leu Phe Gly
        595                 600                 605

Pro Cys Ile Leu Asn Arg Leu Val Gln Phe Val Lys Asp Arg Ile Ser
        610                 615                 620

Val Val Gln Ala Leu Val Leu Thr Gln Gln Tyr His Gln Leu Lys Pro
625                 630                 635                 640

Ile Glu Tyr Glu Pro
                645

<210> SEQ ID NO 9
<211> LENGTH: 645
<212> TYPE: PRT
<213> ORGANISM: Artificial Sequence
<220> FEATURE:
<223> OTHER INFORMATION: Description of Artificial Sequence: SEQ. ID
      NO. 6, envelope protein produced by retroviral vector of seq. id
      no. 5

<400> SEQUENCE: 9

Met Glu Gly Pro Ala Phe Ser Lys Pro Leu Lys Asp Lys Ile Asn Pro
1               5                   10                  15

Trp Lys Ser Leu Met Val Met Gly Val Tyr Leu Arg Val Gly Met Ala
            20                  25                  30

Glu Ser Pro His Gln Val Phe Asn Val Thr Trp Arg Val Thr Asn Leu
        35                  40                  45

Met Thr Gly Arg Thr Ala Asn Ala Thr Ser Leu Leu Gly Thr Val Gln
    50                  55                  60

Asp Ala Phe Pro Arg Leu Tyr Phe Asp Leu Cys Asp Leu Val Gly Glu
65                  70                  75                  80
```

-continued

```
Glu Trp Asp Pro Ser Asp Gln Glu Pro Tyr Val Gly Tyr Gly Cys Lys
                 85                  90                  95

Tyr Pro Gly Gly Arg Lys Arg Thr Arg Thr Phe Asp Phe Tyr Val Cys
            100                 105                 110

Pro Gly His Thr Val Lys Ser Gly Cys Gly Pro Arg Glu Gly Tyr
        115                 120                 125

Cys Gly Glu Trp Gly Cys Glu Thr Thr Gly Gln Ala Tyr Trp Lys Pro
130                 135                 140

Thr Ser Ser Trp Asp Leu Ile Ser Leu Lys Arg Gly Asn Thr Pro Trp
145                 150                 155                 160

Asp Thr Gly Cys Ser Lys Met Ala Cys Gly Pro Cys Tyr Asp Leu Ser
                165                 170                 175

Lys Val Ser Asn Ser Phe Gln Gly Ala Thr Arg Gly Arg Cys Asn
            180                 185                 190

Pro Leu Val Leu Glu Phe Thr Asp Ala Gly Lys Lys Ala Asn Trp Asp
            195                 200                 205

Gly Pro Lys Ser Trp Gly Leu Arg Leu Tyr Arg Thr Gly Thr Asp Pro
    210                 215                 220

Ile Thr Met Phe Ser Leu Thr Arg Gln Val Leu Asn Ile Gly Pro Arg
225                 230                 235                 240

Ile Pro Ile Gly Pro Asn Pro Val Ile Thr Gly Gln Leu Pro Pro Ser
                245                 250                 255

Arg Pro Val Gln Ile Arg Leu Pro Arg Pro Gln Pro Pro Thr
            260                 265                 270

Gly Ala Ala Ser Ile Val Pro Glu Thr Ala Pro Pro Ser Gln Gln Pro
        275                 280                 285

Gly Thr Gly Asp Arg Leu Leu Asn Leu Val Glu Gly Ala Tyr Gln Ala
    290                 295                 300

Leu Asn Leu Thr Asn Pro Asp Lys Thr Gln Glu Cys Trp Leu Cys Leu
305                 310                 315                 320

Val Ser Gly Pro Pro Tyr Tyr Glu Gly Val Ala Val Gly Thr Tyr
                325                 330                 335

Thr Asn His Ser Thr Ala Pro Ala Ser Cys Thr Ala Thr Ser Gln His
            340                 345                 350

Lys Leu Thr Leu Ser Glu Val Thr Gly Gln Gly Leu Cys Met Gly Ala
        355                 360                 365

Leu Pro Lys Thr His Gln Ala Leu Cys Asn Thr Thr Gln Ser Ala Gly
    370                 375                 380

Ser Gly Ser Tyr Tyr Leu Ala Ala Pro Ala Gly Thr Met Trp Ala Cys
385                 390                 395                 400

Ser Thr Gly Leu Thr Pro Cys Leu Ser Thr Met Leu Asn Leu Thr
                405                 410                 415

Thr Asp Tyr Cys Val Leu Val Glu Leu Trp Pro Arg Ile Ile Tyr His
            420                 425                 430

Ser Pro Asp Tyr Met Tyr Gly Gln Leu Glu Gln Arg Thr Lys Tyr Lys
        435                 440                 445

Arg Glu Pro Val Ser Leu Thr Leu Ala Leu Leu Leu Gly Gly Leu Thr
    450                 455                 460

Met Gly Gly Ile Ala Ala Gly Ile Gly Thr Gly Thr Thr Ala Leu Ile
465                 470                 475                 480

Lys Thr Gln Gln Phe Glu Gln Leu His Ala Ala Ile Gln Thr Asp Leu
                485                 490                 495

Asn Glu Val Glu Lys Ser Ile Thr Asn Leu Glu Lys Ser Leu Thr Ser
```

-continued

```
                500             505             510
Leu Ser Glu Val Val Leu Gln Asn Arg Arg Gly Leu Asp Leu Leu Phe
        515                 520                 525

Leu Lys Glu Gly Gly Leu Cys Ala Ala Leu Lys Glu Glu Cys Cys Phe
    530                 535                 540

Tyr Ala Asp His Thr Gly Leu Val Arg Asp Ser Met Ala Lys Leu Arg
545                 550                 555                 560

Glu Arg Leu Asn Gln Arg Gln Lys Leu Phe Glu Ser Gly Gln Gly Trp
                565                 570                 575

Phe Glu Gly Gln Phe Asn Arg Ser Pro Trp Phe Thr Thr Leu Ile Ser
            580                 585                 590

Thr Ile Met Gly Pro Leu Ile Val Leu Leu Ile Leu Leu Phe Gly
            595                 600                 605

Pro Cys Ile Leu Asn Arg Leu Val Gln Phe Val Lys Asp Arg Ile Ser
        610                 615                 620

Val Val Gln Ala Leu Val Leu Thr Gln Gln Tyr His Gln Leu Lys Pro
625                 630                 635                 640

Ile Glu Tyr Glu Pro
                645

<210> SEQ ID NO 10
<211> LENGTH: 2001
<212> TYPE: DNA
<213> ORGANISM: Artificial Sequence
<220> FEATURE:
<223> OTHER INFORMATION: Description of Artificial Sequence:  SEQ. ID
      NO. 7, retroviral vector
<220> FEATURE:
<221> NAME/KEY: CDS
<222> LOCATION: (37)..(1998)

<400> SEQUENCE: 10
ggccgacacc cagagtggac catcctctgg acggac atg gcg cgt tca acg ctc        54
                                       Met Ala Arg Ser Thr Leu
                                       1               5 tca aaa ccc cct caa gat aag att aac ccg tgg aag ccc tta ata gtc      102
Ser Lys Pro Pro Gln Asp Lys Ile Asn Pro Trp Lys Pro Leu Ile Val
            10                  15                  20 atg gga gtc ctg tta gga gta ggg atg gca gag agc ccc cat cag gtc      150
Met Gly Val Leu Leu Gly Val Gly Met Ala Glu Ser Pro His Gln Val
        25                  30                  35 ttt aat gta acc tgg aga gtc acc aac ctg atg act ggg cgt acc gcc      198
Phe Asn Val Thr Trp Arg Val Thr Asn Leu Met Thr Gly Arg Thr Ala
    40                  45                  50 aat gcc acc tcc ctc ctg gga act gta caa gat gcc ttc cca aaa tta      246
Asn Ala Thr Ser Leu Leu Gly Thr Val Gln Asp Ala Phe Pro Lys Leu
55                  60                  65                  70 tat ttt gat cta tgt gat ctg gtc gga gag gag tgg gac cct tca gac      294
Tyr Phe Asp Leu Cys Asp Leu Val Gly Glu Glu Trp Asp Pro Ser Asp
                75                  80                  85 cag gaa ccg tat gtc ggg tat ggc tgc aag tac ccc gca ggg aga cag      342
Gln Glu Pro Tyr Val Gly Tyr Gly Cys Lys Tyr Pro Ala Gly Arg Gln
            90                  95                  100 cgg acc cgg act ttt gac ttt tac gtg tgc cct ggg cat acc gta aag      390
Arg Thr Arg Thr Phe Asp Phe Tyr Val Cys Pro Gly His Thr Val Lys
        105                 110                 115 tcg ggg tgt ggg gga cca gga gag ggc tac tgt ggt aaa tgg ggg tgt      438
Ser Gly Cys Gly Gly Pro Gly Glu Gly Tyr Cys Gly Lys Trp Gly Cys
    120                 125                 130
```

```
gaa acc acc gga cag gct tac tgg aag ccc aca tca tcg tgg gac cta      486
Glu Thr Thr Gly Gln Ala Tyr Trp Lys Pro Thr Ser Ser Trp Asp Leu
135                 140                 145                 150 atc tcc ctt aag cgc ggt aac acc ccc tgg gac acg gga tgc tct aaa      534
Ile Ser Leu Lys Arg Gly Asn Thr Pro Trp Asp Thr Gly Cys Ser Lys
                155                 160                 165 gtt gcc tgt ggc ccc tgc tac gac ctc tcc aaa gta tcc aat tcc ttc      582
Val Ala Cys Gly Pro Cys Tyr Asp Leu Ser Lys Val Ser Asn Ser Phe
            170                 175                 180 caa ggg gct act cga ggg gga aga tgc aac cct cta gtc cta gaa ttc      630
Gln Gly Ala Thr Arg Gly Gly Arg Cys Asn Pro Leu Val Leu Glu Phe
        185                 190                 195 act gat gca gga aaa aag gct aac tgg gac ggg ccc aaa tcg tgg gga      678
Thr Asp Ala Gly Lys Lys Ala Asn Trp Asp Gly Pro Lys Ser Trp Gly
    200                 205                 210 ctg aga ctg tac cgg aca gga aca gat cct att acc atg ttc tcc ctg      726
Leu Arg Leu Tyr Arg Thr Gly Thr Asp Pro Ile Thr Met Phe Ser Leu
215                 220                 225                 230 acc cgg cag gtc ctt aat gtg gga ccc cga gtc ccc ata ggg ccc aac      774
Thr Arg Gln Val Leu Asn Val Gly Pro Arg Val Pro Ile Gly Pro Asn
                235                 240                 245 cca gta tta ccc gac caa aga ctc cct tcc tca cca ata gag att gta      822
Pro Val Leu Pro Asp Gln Arg Leu Pro Ser Ser Pro Ile Glu Ile Val
            250                 255                 260 ccg gct cca cag cca cct agc ccc ctc aat acc agt tac ccc cct tcc      870
Pro Ala Pro Gln Pro Pro Ser Pro Leu Asn Thr Ser Tyr Pro Pro Ser
        265                 270                 275 act acc agt aca ccc tca acc tcc cct aca agt cca agt gtc cca cag      918
Thr Thr Ser Thr Pro Ser Thr Ser Pro Thr Ser Pro Ser Val Pro Gln
    280                 285                 290 cca ccc cca gga act gga gat aga cta cta gct cta gtc aaa gga gcc      966
Pro Pro Pro Gly Thr Gly Asp Arg Leu Leu Ala Leu Val Lys Gly Ala
295                 300                 305                 310 tat cag gcg ctt aac ctc acc aat ccc gac aag acc caa gaa tgt tgg     1014
Tyr Gln Ala Leu Asn Leu Thr Asn Pro Asp Lys Thr Gln Glu Cys Trp
                315                 320                 325 ctg tgc tta gtg tcg gga cct cct tat tac gaa gga gta gcg gtc gtg     1062
Leu Cys Leu Val Ser Gly Pro Pro Tyr Tyr Glu Gly Val Ala Val Val
            330                 335                 340 ggc act tat acc aat cat tcc acc gct ccg gcc aac tgt acg gcc act     1110
Gly Thr Tyr Thr Asn His Ser Thr Ala Pro Ala Asn Cys Thr Ala Thr
        345                 350                 355 tcc caa cat aag ctt acc cta tct gaa gtg aca gga cag ggc cta tgc     1158
Ser Gln His Lys Leu Thr Leu Ser Glu Val Thr Gly Gln Gly Leu Cys
    360                 365                 370 atg ggg gca gta cct aaa act cac cag gcc tta tgt aac acc acc caa     1206
Met Gly Ala Val Pro Lys Thr His Gln Ala Leu Cys Asn Thr Thr Gln
375                 380                 385                 390 agc gcc ggc tca gga tcc tac tac ctt gca gca ccc gcc gga aca atg     1254
Ser Ala Gly Ser Gly Ser Tyr Tyr Leu Ala Ala Pro Ala Gly Thr Met
                395                 400                 405 tgg gct tgc agc act gga ttg act ccc tgc ttg tcc acc acg gtg ctc     1302
Trp Ala Cys Ser Thr Gly Leu Thr Pro Cys Leu Ser Thr Thr Val Leu
            410                 415                 420 aat cta acc aca gat tat tgt gta tta gtt gaa ctc tgg ccc aga gta     1350
Asn Leu Thr Thr Asp Tyr Cys Val Leu Val Glu Leu Trp Pro Arg Val
        425                 430                 435 att tac cac tcc ccc gat tat atg tat ggt cag ctt gaa cag cgt acc     1398
Ile Tyr His Ser Pro Asp Tyr Met Tyr Gly Gln Leu Glu Gln Arg Thr
    440                 445                 450
```

```
aaa tat aaa aga gag cca gta tca ttg acc ctg gcc ctt cta cta gga    1446
Lys Tyr Lys Arg Glu Pro Val Ser Leu Thr Leu Ala Leu Leu Leu Gly
455                 460                 465                 470 gga tta acc atg gga ggg att gca gct gga ata ggg acg ggg acc act    1494
Gly Leu Thr Met Gly Gly Ile Ala Ala Gly Ile Gly Thr Gly Thr Thr
                475                 480                 485 gcc tta att aaa acc cag cag ttt gag cag ctt cat gcc gct atc cag    1542
Ala Leu Ile Lys Thr Gln Gln Phe Glu Gln Leu His Ala Ala Ile Gln
            490                 495                 500 aca gac ctc aac gaa gtc gaa aag tca att acc aac cta gaa aag tca    1590
Thr Asp Leu Asn Glu Val Glu Lys Ser Ile Thr Asn Leu Glu Lys Ser
        505                 510                 515 ctg acc tcg ttg tct gaa gta gtc cta cag aac cgc aga ggc cta gat    1638
Leu Thr Ser Leu Ser Glu Val Val Leu Gln Asn Arg Arg Gly Leu Asp
    520                 525                 530 ttg cta ttc cta aag gag gga ggt ctc tgc gca gcc cta aaa gaa gaa    1686
Leu Leu Phe Leu Lys Glu Gly Gly Leu Cys Ala Ala Leu Lys Glu Glu
535                 540                 545                 550 tgt tgt ttt tat gca gac cac acg ggg cta gtg aga gac agc atg gcc    1734
Cys Cys Phe Tyr Ala Asp His Thr Gly Leu Val Arg Asp Ser Met Ala
                555                 560                 565 aaa tta aga gaa agg ctt aat cag aga caa aaa cta ttt gag aca ggc    1782
Lys Leu Arg Glu Arg Leu Asn Gln Arg Gln Lys Leu Phe Glu Thr Gly
            570                 575                 580 caa gga tgg ttc gaa ggg ctg ttt aat aga tcc ccc tgg ttt acc acc    1830
Gln Gly Trp Phe Glu Gly Leu Phe Asn Arg Ser Pro Trp Phe Thr Thr
        585                 590                 595 tta atc tcc acc atc atg gga cct cta ata gta ctc tta ctg atc tta    1878
Leu Ile Ser Thr Ile Met Gly Pro Leu Ile Val Leu Leu Leu Ile Leu
    600                 605                 610 ctc ttt gga cct tgc att ctc aat cga ttg gtc caa ttt gtt aaa gac    1926
Leu Phe Gly Pro Cys Ile Leu Asn Arg Leu Val Gln Phe Val Lys Asp
615                 620                 625                 630 agg atc tca gtg gtc cag gct ctg gtt ttg act cag caa tat cac cag    1974
Arg Ile Ser Val Val Gln Ala Leu Val Leu Thr Gln Gln Tyr His Gln
                635                 640                 645 cta aaa ccc ata gag tac gag cca tga                                2001
Leu Lys Pro Ile Glu Tyr Glu Pro
                650

<210> SEQ ID NO 11
<211> LENGTH: 654
<212> TYPE: PRT
<213> ORGANISM: Artificial Sequence

<400> SEQUENCE: 11

Met Ala Arg Ser Thr Leu Ser Lys Pro Pro Gln Asp Lys Ile Asn Pro
1               5                   10                  15

Trp Lys Pro Leu Ile Val Met Gly Val Leu Gly Val Gly Met Ala
                20                  25                  30

Glu Ser Pro His Gln Val Phe Asn Val Thr Trp Arg Val Thr Asn Leu
                35                  40                  45

Met Thr Gly Arg Thr Ala Asn Ala Thr Ser Leu Leu Gly Thr Val Gln
            50                  55                  60

Asp Ala Phe Pro Lys Leu Tyr Phe Asp Leu Cys Asp Leu Val Gly Glu
65                  70                  75                  80

Glu Trp Asp Pro Ser Asp Gln Glu Pro Tyr Val Gly Tyr Gly Cys Lys
                85                  90                  95
```

-continued

```
Tyr Pro Ala Gly Arg Gln Arg Thr Arg Thr Phe Asp Phe Tyr Val Cys
            100                 105                 110

Pro Gly His Thr Val Lys Ser Gly Cys Gly Pro Gly Glu Gly Tyr
            115                 120                 125

Cys Gly Lys Trp Gly Cys Glu Thr Thr Gly Gln Ala Tyr Trp Lys Pro
            130                 135                 140

Thr Ser Ser Trp Asp Leu Ile Ser Leu Lys Arg Gly Asn Thr Pro Trp
145                 150                 155                 160

Asp Thr Gly Cys Ser Lys Val Ala Cys Gly Pro Cys Tyr Asp Leu Ser
                165                 170                 175

Lys Val Ser Asn Ser Phe Gln Gly Ala Thr Arg Gly Arg Cys Asn
                180                 185                 190

Pro Leu Val Leu Glu Phe Thr Asp Ala Gly Lys Lys Ala Asn Trp Asp
            195                 200                 205

Gly Pro Lys Ser Trp Gly Leu Arg Leu Tyr Arg Thr Gly Thr Asp Pro
            210                 215                 220

Ile Thr Met Phe Ser Leu Thr Arg Gln Val Leu Asn Val Gly Pro Arg
225                 230                 235                 240

Val Pro Ile Gly Pro Asn Pro Val Leu Pro Asp Gln Arg Leu Pro Ser
                245                 250                 255

Ser Pro Ile Glu Ile Val Pro Ala Pro Gln Pro Ser Pro Leu Asn
                260                 265                 270

Thr Ser Tyr Pro Pro Ser Thr Thr Ser Thr Pro Ser Thr Ser Pro Thr
            275                 280                 285

Ser Pro Ser Val Pro Gln Pro Pro Gly Thr Gly Asp Arg Leu Leu
            290                 295                 300

Ala Leu Val Lys Gly Ala Tyr Gln Ala Leu Asn Leu Thr Asn Pro Asp
305                 310                 315                 320

Lys Thr Gln Glu Cys Trp Leu Cys Leu Val Ser Gly Pro Pro Tyr Tyr
                325                 330                 335

Glu Gly Val Ala Val Val Gly Thr Tyr Thr Asn His Ser Thr Ala Pro
            340                 345                 350

Ala Asn Cys Thr Ala Thr Ser Gln His Lys Leu Thr Leu Ser Glu Val
            355                 360                 365

Thr Gly Gln Gly Leu Cys Met Gly Ala Val Pro Lys Thr His Gln Ala
            370                 375                 380

Leu Cys Asn Thr Thr Gln Ser Ala Gly Ser Gly Ser Tyr Tyr Leu Ala
385                 390                 395                 400

Ala Pro Ala Gly Thr Met Trp Ala Cys Ser Thr Gly Leu Thr Pro Cys
                405                 410                 415

Leu Ser Thr Thr Val Leu Asn Leu Thr Thr Asp Tyr Cys Val Leu Val
                420                 425                 430

Glu Leu Trp Pro Arg Val Ile Tyr His Ser Pro Asp Tyr Met Tyr Gly
            435                 440                 445

Gln Leu Glu Gln Arg Thr Lys Tyr Lys Arg Glu Pro Val Ser Leu Thr
            450                 455                 460

Leu Ala Leu Leu Leu Gly Gly Leu Thr Met Gly Gly Ile Ala Ala Gly
465                 470                 475                 480

Ile Gly Thr Gly Thr Thr Ala Leu Ile Lys Thr Gln Gln Phe Glu Gln
                485                 490                 495

Leu His Ala Ala Ile Gln Thr Asp Leu Asn Glu Val Glu Lys Ser Ile
                500                 505                 510

Thr Asn Leu Glu Lys Ser Leu Thr Ser Leu Ser Glu Val Val Leu Gln
```

```
                515                 520                 525
Asn Arg Arg Gly Leu Asp Leu Leu Phe Leu Lys Glu Gly Gly Leu Cys
        530                 535                 540

Ala Ala Leu Lys Glu Glu Cys Cys Phe Tyr Ala Asp His Thr Gly Leu
545                 550                 555                 560

Val Arg Asp Ser Met Ala Lys Leu Arg Glu Arg Leu Asn Gln Arg Gln
                565                 570                 575

Lys Leu Phe Glu Thr Gly Gln Gly Trp Phe Glu Gly Leu Phe Asn Arg
        580                 585                 590

Ser Pro Trp Phe Thr Thr Leu Ile Ser Thr Ile Met Gly Pro Leu Ile
        595                 600                 605

Val Leu Leu Leu Ile Leu Leu Phe Gly Pro Cys Ile Leu Asn Arg Leu
        610                 615                 620

Val Gln Phe Val Lys Asp Arg Ile Ser Val Val Gln Ala Leu Val Leu
625                 630                 635                 640

Thr Gln Gln Tyr His Gln Leu Lys Pro Ile Glu Tyr Glu Pro
                645                 650

<210> SEQ ID NO 12
<211> LENGTH: 654
<212> TYPE: PRT
<213> ORGANISM: Artificial Sequence
<220> FEATURE:
<223> OTHER INFORMATION: Description of Artificial Sequence:  SEQ. ID
      NO. 8, envelope protein produced by retroviral vector of seq. id
      no. 7

<400> SEQUENCE: 12

Met Ala Arg Ser Thr Leu Ser Lys Pro Pro Gln Asp Lys Ile Asn Pro
1               5                   10                  15

Trp Lys Pro Leu Ile Val Met Gly Val Leu Gly Val Gly Met Ala
                20                  25                  30

Glu Ser Pro His Gln Val Phe Asn Val Thr Trp Arg Val Thr Asn Leu
        35                  40                  45

Met Thr Gly Arg Thr Ala Asn Ala Thr Ser Leu Leu Gly Thr Val Gln
    50                  55                  60

Asp Ala Phe Pro Lys Leu Tyr Phe Asp Leu Cys Asp Leu Val Gly Glu
65                  70                  75                  80

Glu Trp Asp Pro Ser Asp Gln Glu Pro Tyr Val Gly Tyr Gly Cys Lys
                85                  90                  95

Tyr Pro Ala Gly Arg Gln Arg Thr Arg Thr Phe Asp Phe Tyr Val Cys
            100                 105                 110

Pro Gly His Thr Val Lys Ser Gly Cys Gly Gly Pro Gly Glu Gly Tyr
        115                 120                 125

Cys Gly Lys Trp Gly Cys Glu Thr Thr Gly Gln Ala Tyr Trp Lys Pro
130                 135                 140

Thr Ser Ser Trp Asp Leu Ile Ser Leu Lys Arg Gly Asn Thr Pro Trp
145                 150                 155                 160

Asp Thr Gly Cys Ser Lys Val Ala Cys Gly Pro Cys Tyr Asp Leu Ser
                165                 170                 175

Lys Val Ser Asn Ser Phe Gln Gly Ala Thr Arg Gly Gly Arg Cys Asn
            180                 185                 190

Pro Leu Val Leu Glu Phe Thr Asp Ala Gly Lys Lys Ala Asn Trp Asp
        195                 200                 205

Gly Pro Lys Ser Trp Gly Leu Arg Leu Tyr Arg Thr Gly Thr Asp Pro
    210                 215                 220
```

-continued

```
Ile Thr Met Phe Ser Leu Thr Arg Gln Val Leu Asn Val Gly Pro Arg
225                 230                 235                 240

Val Pro Ile Gly Pro Asn Pro Val Leu Pro Asp Gln Arg Leu Pro Ser
                245                 250                 255

Ser Pro Ile Glu Ile Val Pro Ala Pro Gln Pro Ser Pro Leu Asn
            260                 265                 270

Thr Ser Tyr Pro Pro Ser Thr Ser Thr Pro Ser Thr Ser Pro Thr
        275                 280                 285

Ser Pro Ser Val Pro Gln Pro Pro Gly Thr Gly Asp Arg Leu Leu
    290                 295                 300

Ala Leu Val Lys Gly Ala Tyr Gln Ala Leu Asn Leu Thr Asn Pro Asp
305                 310                 315                 320

Lys Thr Gln Glu Cys Trp Leu Cys Leu Val Ser Gly Pro Pro Tyr Tyr
                325                 330                 335

Glu Gly Val Ala Val Val Gly Thr Tyr Thr Asn His Ser Thr Ala Pro
                340                 345                 350

Ala Asn Cys Thr Ala Thr Ser Gln His Lys Leu Thr Leu Ser Glu Val
            355                 360                 365

Thr Gly Gln Gly Leu Cys Met Gly Ala Val Pro Lys Thr His Gln Ala
370                 375                 380

Leu Cys Asn Thr Thr Gln Ser Ala Gly Ser Gly Ser Tyr Tyr Leu Ala
385                 390                 395                 400

Ala Pro Ala Gly Thr Met Trp Ala Cys Ser Thr Gly Leu Thr Pro Cys
                405                 410                 415

Leu Ser Thr Thr Val Leu Asn Leu Thr Thr Asp Tyr Cys Val Leu Val
                420                 425                 430

Glu Leu Trp Pro Arg Val Ile Tyr His Ser Pro Asp Tyr Met Tyr Gly
                435                 440                 445

Gln Leu Glu Gln Arg Thr Lys Tyr Lys Arg Glu Pro Val Ser Leu Thr
            450                 455                 460

Leu Ala Leu Leu Leu Gly Gly Leu Thr Met Gly Gly Ile Ala Ala Gly
465                 470                 475                 480

Ile Gly Thr Gly Thr Thr Ala Leu Ile Lys Thr Gln Gln Phe Glu Gln
                485                 490                 495

Leu His Ala Ala Ile Gln Thr Asp Leu Asn Glu Val Glu Lys Ser Ile
            500                 505                 510

Thr Asn Leu Glu Lys Ser Leu Thr Ser Leu Ser Glu Val Val Leu Gln
            515                 520                 525

Asn Arg Arg Gly Leu Asp Leu Leu Phe Leu Lys Glu Gly Gly Leu Cys
530                 535                 540

Ala Ala Leu Lys Glu Glu Cys Cys Phe Tyr Ala Asp His Thr Gly Leu
545                 550                 555                 560

Val Arg Asp Ser Met Ala Lys Leu Arg Glu Arg Leu Asn Gln Arg Gln
                565                 570                 575

Lys Leu Phe Glu Thr Gly Gln Gly Trp Phe Glu Gly Leu Phe Asn Arg
            580                 585                 590

Ser Pro Trp Phe Thr Thr Leu Ile Ser Thr Ile Met Gly Pro Leu Ile
            595                 600                 605

Val Leu Leu Leu Ile Leu Leu Phe Gly Pro Cys Ile Leu Asn Arg Leu
        610                 615                 620

Val Gln Phe Val Lys Asp Arg Ile Ser Val Val Gln Ala Leu Val Leu
625                 630                 635                 640
```

Thr Gln Gln Tyr His Gln Leu Lys Pro Ile Glu Tyr Glu Pro
            645                 650

<210> SEQ ID NO 13
<211> LENGTH: 52
<212> TYPE: DNA
<213> ORGANISM: Artificial Sequence
<220> FEATURE:
<223> OTHER INFORMATION: Description of Artificial Sequence: SEQ ID NO.
      9, sense strand oligonucleotide for vector construction

<400> SEQUENCE: 13
ggtcagtact gcttcgcccg gctccagtgc ggccgcacct catcaagtct at          52

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: SEQ. ID
      NO. 10, anti-sense oligonucleotide for vector construction

<400> SEQUENCE: 14
tgttggtctg ccagaacg                                                18

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: SEQ. ID
      NO. 11, sense strand oligonucleotide for vector construction

<400> SEQUENCE: 15
actactctag cggccgcaat ggcagagagc ccccat                            36

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: SEQ. ID
      NO. 12, anti-sense oligonucleotide for vector construction

<400> SEQUENCE: 16
ctactaactt gcggccgctc ccacattaag gac                               33

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence: SEQ. ID
      NO. 13, sense strand oligonucleotide for vector construction

<400> SEQUENCE: 17
ggtcagtact gcttcgcccg gctccagtgc ggccgcacct catcaagtct             50

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: SEQ. ID
      NO. 14, alpha Vbeta3-binding pe
<400> SEQUENCE: 18

Cys Asp Cys Arg Gly Asp Cys Phe Cys

-continued

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: SEQ. ID
      NO. 15, oligonucleotide encoding peptide of  seq. id no. 14

<400> SEQUENCE: 19
ggccgcatgc gactgtcggg gcgattgttt ctgtgc                                36

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: SEQ. ID
      NO. 16, oligonucleotide encoding peptide of seq. id no. 14

<400> SEQUENCE: 20
ggccgcacag aaacaatcgc cccgacagtc gcatg                                 35

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: SEQ. ID
      NO. 17, peptide encoded by cDNA between Ser6 and Pro7 of envelope
      protein

<400> SEQUENCE: 21

Ala Ala Ala Cys Asp Cys Arg Gly Asp Cys Phe Cys Ala Ala Ala
  1               5                  10                  15

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: SEQ. ID
      NO. 18, peptide inhibiting attachment of envelope protein to
      alphaVbeta3 integrin

<400> SEQUENCE: 22

Ala Cys Asp Cys Arg Gly Asp Cys Phe Cys Gly
  1               5                  10

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: SEQ. ID
      NO. 19, peptide that non-specifically inhibits binding of envelope
      protein

<400> SEQUENCE: 23

Gly Arg Gly Glu Ser Pro
  1               5